US008329179B2

(12) United States Patent
Ni et al.

(10) Patent No.: US 8,329,179 B2
(45) Date of Patent: *Dec. 11, 2012

(54) DEATH DOMAIN CONTAINING RECEPTOR 4 ANTIBODIES AND METHODS

(75) Inventors: Jian Ni, Germantown, MD (US); Craig A. Rosen, Laytonsville, MD (US); James G. Pan, Toronto (CA); Reiner L. Gentz, Belo Horizonte-MG (BR); Vishva M. Dixit, Los Altos Hills, CA (US)

(73) Assignees: Human Genome Sciences, Inc., Rockville, MD (US); The Regents of the University of Michigan, Ann Arbor, MI (US)

( * ) Notice: Subject to any disclaimer, the term of this patent is extended or adjusted under 35 U.S.C. 154(b) by 579 days.

This patent is subject to a terminal disclaimer.

(21) Appl. No.: 12/010,108
(22) Filed: Jan. 18, 2008
(65) Prior Publication Data

US 2008/0241155 A1 Oct. 2, 2008

Related U.S. Application Data

(63) Continuation-in-part of application No. 11/076,187, filed on Mar. 10, 2005, now Pat. No. 7,476,384, and a continuation-in-part of application No. 10/648,786, filed on Aug. 27, 2003, now Pat. No. 7,452,538, and a continuation-in-part of application No. 09/565,918, filed on May 5, 2000, now Pat. No. 6,433,147, and a continuation-in-part of application No. 09/013,895, filed on Jan. 27, 1998, now Pat. No. 6,342,363.

(60) Provisional application No. 60/990,687, filed on Nov. 28, 2007, provisional application No. 60/885,971, filed on Jan. 22, 2007, provisional application No. 60/551,768, filed on Mar. 11, 2004, provisional application No. 60/608,469, filed on Sep. 10, 2004, provisional application No. 60/413,861, filed on Sep. 27, 2002, provisional application No. 60/406,922, filed on Aug. 30, 2002, provisional application No. 60/132,922, filed on May 6, 1999, provisional application No. 60/035,722, filed on Jan. 28, 1997, provisional application No. 60/037,829, filed on Feb. 5, 1997.

(51) Int. Cl.
*A61K 39/395* (2006.01)
*A61K 31/00* (2006.01)
*C07K 16/30* (2006.01)

(52) U.S. Cl. ............... 424/143.1; 424/133.1; 424/138.1; 424/142.1; 424/135.1; 424/141.1; 424/155.1; 424/174.1; 424/178.1; 530/350; 514/1.1; 514/2.3; 514/7.5; 514/18.9; 514/19.3; 540/478

(58) Field of Classification Search .................. None
See application file for complete search history.

(56) References Cited

U.S. PATENT DOCUMENTS

| | | | |
|---|---|---|---|
| 4,002,531 A | 1/1977 | Royer | |
| 4,179,337 A | 12/1979 | Davis et al. | |
| 4,946,778 A | 8/1990 | Ladner et al. | |
| 5,349,053 A | 9/1994 | Landolfi | |
| 5,447,851 A | 9/1995 | Beutler et al. | |
| 5,478,925 A | 12/1995 | Wallach et al. | |
| 5,530,101 A | 6/1996 | Queen et al. | |
| 5,565,332 A | 10/1996 | Hoogenboom et al. | |
| 5,763,223 A | 6/1998 | Wiley et al. | |
| 5,807,715 A | 9/1998 | Morrison et al. | |
| 6,342,363 B1 | 1/2002 | Ni et al. | |
| 6,433,147 B1 | 8/2002 | Ni et al. | |
| 6,461,823 B1 | 10/2002 | Ni et al. | |
| 6,902,910 B2 | 6/2005 | Ni et al. | |
| 6,943,020 B2 | 9/2005 | Ni et al. | |
| 7,060,272 B2 | 6/2006 | Ni et al. | |
| 2002/0048566 A1 | 4/2002 | El-Deiry et al. | |
| 2002/0155109 A1 | 10/2002 | Lynch | |
| 2005/0112090 A9 | 5/2005 | Ni et al. | |
| 2005/0244857 A1 | 11/2005 | Ni et al. | |

FOREIGN PATENT DOCUMENTS

| | | |
|---|---|---|
| CA | 2045869 | 12/1991 |
| EP | 0 239 400 B1 | 8/1994 |
| EP | 0 401 384 B1 | 3/1996 |
| EP | 0 857 782 A2 | 8/1998 |
| WO | WO 91/06570 | 5/1991 |
| WO | WO 91/09967 | 7/1991 |
| WO | WO 95/06058 | 3/1995 |
| WO | WO 97/01633 | 1/1997 |
| WO | WO 98/30693 | 7/1998 |
| WO | WO 98/32856 | 7/1998 |
| WO | WO 98/41629 | 9/1998 |
| WO | WO 99/02653 | 1/1999 |
| WO | WO 99/11791 | 3/1999 |
| WO | WO 99/37684 | 7/1999 |
| WO | WO 00/67793 A1 | 11/2000 |

OTHER PUBLICATIONS

Ishioka et al., An autopsy case of diffuse panbronchiolitis associated with lung cancer, Internal Med. 39(5):404-406, May 2000.*
Mirhosseini et al., The role of antiboiotics in the management of infection-related symptoms in advanced cancer patients, J. Palliative Care, 22(2):69-74, 2006.*
Delgi-Esposti, M.A. et al., "Cloning and Characterization of TRAIL-R3, a Novel Member of the Emerging TRAIL Receptor Family," *J. Exp. Med.* 186:1165-1170, Rockefeller University Press (Oct. 1997).
Locksley, R.M., et al., "The TNF and TNF Receptor Superfamilies: Integrating Mammalian Biology," *Cell* 104:487-501, Cell Press (Feb. 2001).
MacFarlane, M., "Identification and Molecular Cloning of Two Novel Receptors for the Cytotoxic Ligand TRAIL," *J. Biol. Chem.* 272:25417-25420, American Society for Biochemistry and Molecular Biology (Oct. 1997).
Marsters, S.A., et al., "A novel receptor for Apo2L/TRAIL contains a truncated death domain," *Curr. Biol.* 7:1003-1006, Cell Press (Dec. 1997).

(Continued)

*Primary Examiner* — Claire Kaufman

(74) *Attorney, Agent, or Firm* — Human Genome Sciences, Inc.

(57) ABSTRACT

The present invention relates to novel Death Domain Containing Receptor-4 (DR4) proteins which are members of the tumor necrosis factor (TNF) receptor family. In particular, isolated nucleic acid molecules are provided encoding the human DR4 proteins. DR4 polypeptides are also provided as are vectors, host cells and recombinant methods for producing the same. The invention further relates to screening methods for identifying agonists and antagonists of DR4 activity and methods for using DR4 polynucleotides and polypeptides. The invention also relates to the treatment of diseases associated with reduced or increased levels of apoptosis using antibodies specific for DR4, which may be agonists and/or antagonists of DR4 activity.

64 Claims, 10 Drawing Sheets

OTHER PUBLICATIONS

Pan, G., et al., "An Antagonist Decoy Receptor and a Death Domain-Containing Receptor for TRAIL," *Science* 277:815-818, American Association for the Advancement of Science (Aug. 1997).
Schneider, P., et al., "Characterization of two recpetors for TRAIL," *FEBS Lett.* 416:329-334, Elsevier Science B.V. (Oct. 1997).
Screaton, G.R., et al., "TRICK2, a new alternatively spliced receptor that transduces the cytotoxic signal from TRAIL," *Curr. Biol.* 7:693-696, Cell Press (Sep. 1997).
Sheridan, J.P., et al., "Control of TRAIL-Induced Apoptosis by a Family of Signaling and Decoy Receptors," *Science* 277:818-821, American Association for the Advancement of Science (Aug. 1997).
Simonet, W.S., et al., "Osteoprotegerin: A Novel Secreted Protein Involved in the Regulation of Bone Density," *Cell* 89:309-319, Cell Press (Apr. 1997).
Tsuda, E., et al., "Isolation of a Novel Cytokine from Human Fibroblasts That Specifically Inhibits Osteoclastogenesis," *Biochem. Biophys. Res. Commun.* 234:137-142, Academic Press (May 1997).
Wallach, D., et al., "Tumor Necrosis Factor Recpetor and *Fas* Signaling Mechanims," *Annu. Rev. Immunol.* 17:331-367, Annual Reviews (Apr. 1999).
Ware, C.F., et al., "Apoptosis Mediated by the TNF-Related Cytokine and Receptor Families," *J. Cell. Biochem.* 60:47-55, Wiley-Liss (Jan. 1996).
European Opposition Document for European Patent No. 1 012 274, Communication of a notice of opposition, 1 page, dated Mar. 28, 2008.
European Opposition Document for European Patent No. 1 012 274, Communication of a notice of opposition, 1 page, dated Mar. 7, 2008.
Opposition to European Patent No. 1 012 274 B, filed by Genentech, Inc. in the European Patent Office, 23 pages, dated Feb. 27, 2008.
Chantry, D., "Tumour necrosis factor antagonists," *Exp. Opin. Emerging Drugs* 4:5-13, Ashley Publications Ltd (Jan. 1999).
Chinnaiyan, A.M., et al., "Signal Transduction by DR3, a Death Domain-Containing Receptor Related to TNFR-1 and CD95," *Science* 24:990-992, American Association for the Advancement of Science (Nov. 1996).
Delgado, C., et al., "The Uses and Properties of PEG-Linked Proteins," *Crit. Rev. Thera. Drug Carrier Sys.* 9:249-304, Begell House (1992).
Delgado, C., et al., "Quantitative analysis of polyethylene glycol (PEG) in PEG-modifed proteins/cytokines by aqueous two-phase systems," *J. Biochem. Biophys. Methods* 29:237-250, Elsevier Science B.V. (1994).
Dillman, R.O., "Monoclonal Antibodies for Treating Cancer," *Ann. Internal Med.* 111:592-603, American College of Physicians (1989).
Goodman, J.W., "Immunogens & Antigens," in *Basic & Clinical Immunology*, Stites et al., eds., Appleton & Lange, Norwalk, CT, pp. 20-27 (1988).
Griffith, T.S., et al., "Monocyte-mediated Tumoricidal Activity via the Tumor Necrosis Factor-related Cytokine, TRAIL," *J. Exp. Med.* 189:1343-1353, The Rockefeller University Press (Apr. 1999).
Huston, J.S., et al., "Protein Engineering of Single-Chain Fv Analogs and Fusion Proteins," *Methods in Enzymology* 203:46-88, Academic Press (1991).
Kayagaki, N., et al., "Type I Interferons (IFNs) Regulate Tumor Necrosis Factor-related Apoptosis-inducing Ligand (TRAIL) Expression on Human T Cells: A Novel Mechanism for the Antitumor Effects of Type I IFNs," *J. Exp. Med.* 189:1451-1460, The Rockefeller University Press (May 1999).
Kim, K., et. al., "Molecular determinants of response to TRAIL combined with chemotherapy in killing of normal cancer cells," Proceedings of the American Association for Cancer Research Annual Meeting 40:486, 90th Annual Meeting of the American Association for Cancer Research (Apr. 1999).
Lerner, R.A., "Antibodies of Predetermined Specificity in Biology and Medicine," *Adv. Immunol.* 36:1-44, Academic Press, Inc. (1984).
Marsters, S.A., et. al., "Control of Apoptosis Signaling by Apo2 Ligand," *Recent Progress in Hormone Research* 54:225-234, The Endocrine Society (Jan. 1999).

Morpurgo, M., et al., "Covalent Modification of Mushroom Tyrosinase with Different Amphiphic Polymers for Pharmaceutical and Biocatalysis Applications," *Appl. Biochem. Biotechnol.* 56:59-72, Humana Press (Jan. 1996).
Morrison, S.L. "Transfectomas Provide Novel Chimeric Antibodies," *Science* 229:1202-1207, American Association for the Advancement of Science (1985).
Pan, G., et al., "The Receptor for the Cytotoxic Ligand Trail," *Science* 276:111-113, American Association for Advancement of Science (Apr. 1997).
Roguska, M.A., et al., "Humanization of murine monoclonal antibodies through variable domain resurfacing," *Proc. Natl. Acad. Sci. USA* 91:969-973, National Academy of Science (1994).
Ruf, M. and Kossel, H., "Structure and Expression of the Gene Coding for the Alpha-Subunit of DNA-Dependent RNA Polymerase from the Chloroplast Genome of *Zea mays*," *Nucl. Acids Res.* 16:5741-5754, IRL Press (1988).
Sedger, L.M., et al., "IFN-γ Mediates a Novel Antiviral Activity Through Dynamic Modulation of TRAIL and TRAIL Receptor Expression," *J. Immunol.* 163:920-926, The American Association of Immunologists (Jul. 1999).
Shaw, J.P., et al., "Cytotoxic properties DAB486EGF and DAB389EGF, epidermal growth factor (EGF) receptor-targeted fusion toxins," *J. Biol. Chem.* 266:21118-21124, The American Society for Biochemistry and Molecular Biology, Inc. (1991).
Shin, E.-C., et al., "IFN-γ Induces Cell Death in Human Hepatoma Cells Through a TRAIL/Death Receptor-Mediated Apoptotic Pathway," *Int. J. Cancer* 93:262-268, Wiley-Liss, Inc. (Jul. 2001).
Strader, C.D., et al., "Structural basis of β-adrenergic receptor function," *FASEB J.* 3:1825-1832, Federation of American Societies for Experimental Biology (1989).
Walczak, H., et al., "TRAIL-R2: a novel apoptosis-mediating receptor for TRAIL," *EMBO J.* 16:5386-5397, Oxford University Press (1997).
Wiley, S.R., et al., "Identification and Characterization of a New Member of the TNF Family that Induces Apoptosis," *Immunity* 3:673-682, Cell Press (1995).
Database, EMBL Nucleic Acid DB EBI, Accession No. AA100865, Hillier et al., Entry Date Oct. 1996.
GenBank Accession No. W65310, zd33e01.r1 Soares fetal heart NbHH19W *Homo sapiens* cDNA clone 342456 5' similar to contains Alu repetitive element, NCBI National Library of Medicine Database, Bethesda, MD, USA, accessed Jan. 8, 1999, (Oct. 1996).
NCBI Entrez, GenBank Report, Accession No. AA150849, from Hillier, L., et al., Entry Date Dec. 1996.
NCBI Entrez, GenBank Report, Accession No. AA102745, from Hillier, L., et al., Entry Date Oct. 1996.
NCBI Entrez, GenBank Report, Accession No. AA102746, from Hillier, L., et al., Entry Date Oct. 1996.
NCBI Entrez, GenBank Report, Accession No. AA102383, from Hillier, L., et al., Entry Date Oct. 1996.
NBCI Entrez, Genbank Report, Accession No. U90875, Pan, G., et al., Entry Date Apr. 1997.
NCBI Entrez, GenBank Report, Accession No. AA639619, Strausberg, R., National Center for Biotechnolgy Information (1997).
U.S. Appl. No. 09/912,292, filed Jul. 26, 2001, Not Published: pp. 1-75 (pp. 1+2 partially redacted); portion of Table 2; and SEQ ID Nos. 7950 and 52011.
Alderson, et al., "Fas transduces activation signals in normal human T lymphocytes," J. Exp. Med., 178:2231-2235 (Dec. 1993).
Alderson, et al., "Regulation of apoptosis and T cell activation by Fas-sepcific mAb," International Immunology, 6(11):1799-1806 (Aug. 1994).
Boldin, et al., "A novel protein that interacts with the death domain of Fas/APO1 contains a sequence motif related to the death domain," J. Biol. Chem., 270(14):7795-7798 (Apr. 7, 1995).
Brockhaus, et al., "Identification of two types of tumor necrosis factor receptors on human cell lines by monoclonal antibodies," Proc. Natl. Acad. Sci. USA, 87:3127-3131 (Apr. 1990).
Chinnaiyan, et al., "FADD/MORT1 is a common mediator of CD95 (Fas/APO-1) and tumor necrosis factor receptor-induced apoptosis," J. Biol. Chem., 271(9):4961-4965 (Mar. 1, 1996).

Chinnaiyan, et al., "FADD, a novel death domain-containing protein, interacts with the death domain of Fas and initiates apoptosis," *Cell*, 81:505-512 (May 19, 1995).

Chuntharapai, et al., "Isotype-dependent inhibition of tumor growth in vivo by monoclonal antibodies to death receptor 4," *J. Immunol.*, 166(8):4891-4898 (Apr. 15, 2001).

Cifone, et al., "Apoptotic signaling through CD95 (Fas/Apo-1) activates an acidic sphingomyelinase," *J. Exp. Med.*, 177:1547-1552 (Oct. 1993).

Cifone, et al., "Multiple pathways originate at the Fas/APO-1 (CD95) receptor: sequential involvement of phosphatidylcholine-specific phospholipase C and acidic sphingomyelinase in the propagation of the apoptotic signal," *EMBO J.*, 14:5859-5868 (Dec. 1995).

Engelmann, et al., "Antibodies to a soluble form of a tumor necrosis factor (TNF) receptor have TNF-like activity," *J. Biol. Chem.*, 265(24):14497-14504 (Aug. 25, 1990).

Espevik, et al., "Characterization of binding and biological effects of monoclonal antibodies against a human tumor necrosis factor receptor," *J. Exp. Med.*, 171:415-426 (Feb. 1990).

Fadeel, et al., "Anti-Fas IgG1 antibodies recognizing the same epitope of Fas/APO-1 mediate different biological effects in vitro," *International Immunology*, 9(2):201-209 (Feb. 1997).

Isaacs, J., "Role of programmed cell death in carcinogenesis," *Environmental Health Perspectives*, 101 (Suppl 5):27-34 (1993).

Janeway and Travers, In: *Immunobiology*, Current Biology, Ltd./Garland Publishing, Inc., pp. 2:3 et seq. (1994).

Keane, et al., "Fas expression and function in normal and malignant breast cell lines," *Cancer Research*, 56:4791-4798 (Oct. 15, 1996).

Kischkel, et al., "Cytotoxicity-dependent APO-1 (Fas/CD95)-associated proteins form a death-inducing signaling complex (DISC) with the receptor," *EMBO J*, 14(22):5579-5588 (1995).

Mühlenbeck, et al., "The tumor necrosis factor-related apoptosis-inducing ligand receptors TRAIL-R1 and TRAIL-R2 have distinct cross-linking requirements for initiation of apoptosis and are non-redundant in JNK activation," *J. Biol. Chem.*, 275(41):32208-32213 (Oct. 13, 2000).

Sheehan, et al., "Monoclonal antibodies specific for murine p55 and p75 tumor necrosis factor receptors: identification of a novel in vivo role for p75," *J. Exp. Med.*, 181:607-617 (Feb. 1995).

Tartaglia, et al., "The two different receptors for tumor necrosis factor mediate distinct cellular responses," *Proc. Natl. Acad. Sci. USA*, 88:9292-9296 (Oct. 1991).

Tartaglia, et al., "Tumor necrosis factor receptor signaling," *J. Biol. Chem.*, 267(7):4304-4307 (Mar. 1992).

Yonehara, et al., "A cell-killing monoclonal antibody (ANTI-Fas) to a cell surface antigen co-downregulated with the receptor of tumor necrosis factor," *J. Exp. Med.*, 169:1747-1756 (May 1, 1989).

European Opposition Document for European Patent No. 1 012 274, Summons to Attend Oral Proceedings, dated Jul. 7, 2009.

European Opposition Document for European Patent No. 1 012 274, Patentee's observations to Genentech's opposition of Patentee's patent, 20 pages, dated Oct. 6, 2008.

European Opposition Document for European Patent No. 1 012 274 B, filed by Genentech, Inc. in the European Patent Office, 20 pages, dated Feb. 22, 2008.

European Opposition Document for European Patent No. 1 012 274, Patentee's response to European Patent Office Communication dated Jul. 19, 2005, 14 pages, dated Jan. 13, 2006.

European Opposition Document for European Patent No. 1 012 274, Declaration of Werner Lesslauer, MD, Ph.D., 5 pages, dated Jan. 12, 2006.

European Opposition Document for European Patent No. 1 012 274, Declaration of David H. Lynch, Ph.D., 6 pages, dated Jan. 11, 2006.

European Opposition Document for European Patent No. 1 012 274, Declaration of Robin C. Humphreys, Ph.D., 5 pages, dated Jan. 12, 2006.

European Opposition document for EP Patent No. 1 012 274—Patentee's submission in preparation for oral proceedings dated Apr. 15, 2010.

European Opposition document for EP Patent No. 1 012 274—Minutes from the oral proceedings dated Jun. 22, 2010.

Human Genome Sciences press release, "Human Genome Sciences Advances Anti-cancer Drug to Phase 2 Clinical Development" (Sep. 8, 2004).

Human Genome Sciences press release, "Human Genome Sciences Completes Patient Enrollment in a Phase 2 Clinical Trial of HGS-ETR1 for the Treatment of Non-small Cell Lung Cancer" (Nov. 30, 2004).

Human Genome Sciences press release, "Human Genome Sciences Completes Patient Enrollment in a Phase 2 Clinical Trial of HGS-ETR1 for the Treatment of Colorectal Cancer" (Feb. 23, 2005).

Human Genome Sciences press release, "Human Genome Sciences Completes Patient Enrollment in a Phase 2 Clinical Trial of HGS-ETR1 for the Treatment of Non-Hodgkin's Lymphoma" (Mar. 3, 2005).

Human Genome Sciences press release, "Human Genome Sciences Reports Results of Phase 2 Clinical Trial of HGS-ETR1 in Patients with Non-small Cell Lung Cancer" (Jul. 5, 2005).

Human Genome Sciences press release, "Human Genome Sciences Reports Results of Phase 2 Clinical Trial of HGS-ETR1 in Patients with Advanced Colorectal Cancer" (Nov. 1, 2005).

Human Genome Sciences press release, "Human Genome Sciences Reports Interim Results of Phase 1B Clinical Trials of HGS-ETR1 in Combination with Chemotherapy in Patients with Advanced Solid Tumors" (Nov. 17, 2005).

Human Genome Sciences press release, "Human Genome Sciences Reports Results of Phase 2 Clinical Trial of HGS-ETR1 in Patients with Advanced Non-Hodgkin's Lymphoma" (Dec. 13, 2005).

Human Genome Sciences press release, "Human Genome Sciences Reports Interim Results of Phase 1B Clinical Trial of HGS-ETR1 with Gemcitabine and Cisplatin in Patients with Advanced Solid Tumors" (Nov. 8, 2006).

Human Genome Sciences press release, "Human Genome Sciences Reports Growing Evidence That its Trail Receptor Antibodies have Significant Potential in the Treatment of a Broad Range of Cancers" (Apr. 27, 2007).

Human Genome Sciences press release, "Human Genome Sciences Presents New Data Showing Anti-tumor Activity and Safety of TRAIL receptor Antibodies in Combination with Chemotherapy" (Oct. 24, 2007).

Human Genome Sciences press release, "Human Genome Sciences Reports Initial Results of Randomized Phase 2 Trial of HGS-ETR1 in Combination with Bortezomib in Advanced Multiple Myeloma" (Sep. 2, 2008)

Human Genome Sciences press release, "Human Genome Sciences Announces Results of Randomized Phase 2 Trial of Mapatumumab in Non-Small Cell Lung Cancer" (Mar. 17, 2010).

Human Genome Sciences press release, "Human Genome Sciences Announces Results of Randomized Phase 2 Trial of Mapatumumab in Multiple Myeloma" (Jun. 9, 2010).

\* cited by examiner

```
         10                    30                    50
TTCGGGCACGAGGGCAGGATGGCGCCACCACCAGCTAGAGTACATCTAGGTGCGTTCCTG
                   M  A  P  P  P  A  R  V  H  L  G  A  F  L
         70                    90                   110
GCAGTGACTCCGAATCCCGGGAGCGCAGCGAGTGGGACAGAGGCAGCCGCGGCCACACCC
 A  V  T  P  N  P  G  S  A  A  S  G  T  E  A  A  A  A  T  P
        130                   150                   170
AGCAAAGTGTGGGGCTCTTCCGCGGGGAGGATTGAACCACGAGGCGGGGGCCGAGGAGCG
 S  K  V  W  G  S  S  A  G  R  I  E  P  R  G  G  G  R  G  A
        190                   210                   230
CTCCCTACCTCCATGGGACAGCACGGACCCAGTGCCCGGGCCCGGGCAGGGCGCGCCCCA
 L  P  T  S  M  G  Q  H  G  P  S  A  R  A  R  A  G  R  A  P
        250                   270                   290
GGACCCAGGCCGGCGCGGGAAGCCAGCCCTCGGCTCCGGGTCCACAAGACCTTCAAGTTT
 G  P  R  P  A  R  E  A  S  P  R  L  R  V  H  K  T  F  K  F
        310                   330                   350
GTCGTCGTCGGGGTCCTGCTGCAGGTCGTACCTAGCTCAGCTGCAACCATCAAACTTCAT
 V  V  V  G  V  L  L  Q  V  V  P  S  S  A  A  T  I  K  L  H
        370                   390                   410
GATCAATCAATTGGCACACAGCAATGGGAACATAGCCCTTTGGGAGAGTTGTGTCCACCA
 D  Q  S  I  G  T  Q  Q  W  E  H  S  P  L  G  E  L  C  P  P
        430                   450                   470
GGATCTCATAGATCAGAACGTCCTGGAGCCTGTAACCGGTGCACAGAGGGTGTGGGTTAC
 G  S  H  R  S  E  R  P  G  A  C  N  R  C  T  E  G  V  G  Y
        490                   510                   530
ACCAATGCTTCCAACAATTTGTTTGCTTGCCTCCCATGTACAGCTTGTAAATCAGATGAA
 T  N  A  S  N  N  L  F  A  C  L  P  C  T  A  C  K  S  D  E
        550                   570                   590
GAAGAGAGAAGTCCCTGCACCACGACCAGGAACACAGCATGTCAGTGCAAACCAGGAACT
 E  E  R  S  P  C  T  T  T  R  N  T  A  C  Q  C  K  P  G  T
        610                   630                   650
TTCCGGAATGACAATTCTGCTGAGATGTGCCGGAAGTGCAGCACAGGGTGCCCCAGAGGG
 F  R  N  D  N  S  A  E  M  C  R  K  C  S  T  G  C  P  R  G
        670                   690                   710
ATGGTCAAGGTCAAGGATTGTACGCCCTGGAGTGACATCGAGTGTGTCCACAAAGAATCA
 M  V  K  V  K  D  C  T  P  W  S  D  I  E  C  V  H  K  E  S
```

FIG.1A

```
              730                  750                  770
GGCAATGGACATAATATATGGGTGATTTTGGTTGTGACTTTGGTTGTTCCGTTGCTGTTG
 G  N  G  H  N  I  W  V  I  L  V  V  T  L  V  V  P  L  L  L
    ********************************************************
              790                  810                  830
GTGGCTGTGCTGATTGTCTGTTGTTGCATCGGCTCAGGTTGTGGAGGGGACCCCAAGTGC
 V  A  V  L  I  V  C  C  I  G  S  G  C  G  G  D  P  K  C
*******************************************
              850                  870                  890
ATGGACAGGGTGTGTTTCTGGCGCTTGGGTCTCCTACGAGGGCCTGGGGCTGAGGACAAT
 M  D  R  V  C  F  W  R  L  G  L  L  R  G  P  G  A  E  D  N
              910                  930                  950
GCTCACAACGAGATTCTGAGCAACGCAGACTCGCTGTCCACTTTCGTCTCTGAGCAGCAA
 A  H  N  E  I  L  S  N  A  D  S  L  S  T  F  V  S  E  Q  Q
              970                  990                  1010
ATGGAAAGCCAGGAGCCGGCAGATTTGACAGGTGTCACTGTACAGTCCCCAGGGGAGGCA
 M  E  S  Q  E  P  A  E  L  T  G  V  T  V  Q  S  P  G  E  A
              1030                 1050                 1070
CAGTGTCTGCTGGGACCGGCAGAAGCTGAAGGGTCTCAGAGGAGGAGGCTGCTGGTTCCA
 Q  C  L  L  G  P  A  E  A  E  G  S  Q  R  R  R  L  L  V  P
              1090                 1110                 1130
GCAAATGGTGCTGACCCCACTGAGACTCTGATGCTGTTCTTTGACAAGTTTGCAAACATC
 A  N  G  A  D  P  T  E  T  L  M  L  F  F  D  K  F  A  N  I
              1150                 1170                 1190
GTGCCCTTTGACTCCTGGGACCAGCTCATGAGGCAGCTGGACCTCACGAAAAATGAGATC
 V  P  F  D  S  W  D  Q  L  M  R  Q  L  D  L  T  K  N  E  I
              1210                 1230                 1250
GATGTGGTCAGAGCTGGTACAGCAGGCCCAGGGGATGCCTTGTATGCAATGCTGATGAAA
 D  V  V  R  A  G  T  A  G  P  G  D  A  L  Y  A  M  L  M  K
              1270                 1290                 1310
TGGGTCAACAAAACTGGACGGAACGCCTCGATCCACACCCTGCTGGATGCCTTGGAGAGG
 W  V  N  K  T  G  R  N  A  S  I  H  T  L  L  D  A  L  E  R
              1330                 1350                 1370
ATGGAAGAGAGACATGCAAAAGAGAAGATTCAGGACCTCTTGGTGGACTCTGGAAAGTTC
 M  E  E  R  H  A  K  E  K  I  Q  D  L  L  V  D  S  G  K  F
```

FIG.1B

```
            1390              1410              1430
ATCTACTTAGAAGATGGCACAGGCTCTGCCGTGTCCTTGGAGTGAAAGACTCTTTTTACC
  I  Y  L  E  D  G  T  G  S  A  V  S  L  E
            1450              1470              1490
AGAGGTTTCCTCTTAGGTGTTAGGAGTTAATACATATTAGGTTTTTTTTTTTTTTAACAT
            1510              1530              1550
GTATACAAAGTAAATTCTTAGCCACGTGTATTGGCTCCTGCCTGTAATCCCATCACTTTG
            1570              1590              1610
GGAGGCTGACGCCGGTGGATCCACTTGAGGTCCGAAGTTCCAAGACCAGCCCTGAACCAA
            1630              1650              1670
CATCGTGGAAATGCCCGTCTTTTACAAAAAAATACCAAAAATTCAACTGGAATGTGCATG
            1690              1710              1730
GTGTGTGCCATCATTTCCTCGGCTAACTACGGGAGGTCTGAGGCCAGGAGAATCCACTTG
            1750              1770              1790
AACCCCACGAAGGACAGTGTAGACTGCAGATTGCACCACTGCACTCCCAGCCTGGGAACA
            1810              1830              1850
CAGAGCAAGACTCTGTCTCAAGATAAAATAAAATAAACTTGAAAGAATTATTGCCCGACT
            1870              1890              1910
GAGGCTCACATGCCAAAGGAAAATCTGGTTCTCCCCTGAGCTGGCCTCCGTGTGTTTCCT
            1930              1950              1970
TATCATGGTGGTCAATTGGAGGTGTTAATTTGAATGGATTAAGGAACACCTAGAACACTG
            1990              2010              2030
GTAAGGCATTATTTCTGGGACATTATTTCTGGGCATGTCTTCGAGGGTGTTTCCAGAGGG
            2050              2070              2090
GATTGGCATGCGATCGGGTGGACTGAGTGGAAAAGACCTACCCTTAATTTGGGGGGGCAC
            2110              2130              2150
CGTCCGACAGACTGGGGAGCAAGATAGAAGAAAACAAAAAAAAAAAAAAAAA
```

HTOIY07R

```
  1  GGCANAGGTN CGTACCTAGC TCACCTGCAA CCATCAAACT TNATGATCAA
 51  TCAATTGGCA CACAGCAATG GGAAACATAG CCCTTTGGAA GANTTGTNTC
101  CACCAGGATC TCATAGATCA AAACATCCTG GGAGCCTGTT AACCGGTGCC
151  CCAAAGGNTG GTCAAGGTCA AGGAATTGTT NCGCCCTGGA AGTGAACATC
201  GAGTGTNTCC ACAAAGGATT CAGGCAATGG GACATAAATA TATGGGTGAA
251  TTTTGGTTGT GAACTTTGGT TGNTCCCGTT GNTGTTGNTG GCTGTGCTGA
301  TTGTTTGTTG TTGCATCGGC TTCAGGTTNT GGAGGGGGAC CCAAGTGCAT
351  GGACAGGGTG TGTTTCTGGG GTTTGGGTCT CTTAGAGGGC NTGGGTTANG
401  GCANGTTCAC AAGGGTTTTA GCAANG
```

HTXEY80R

```
  1  TGGGGCTGAG GACAATGCTG ACNACGAGAT TCTGAGCAAC GCAGNACTNG
 51  CTGTCCACTT TCGTCTNTGN GCAGCAAATG GAAAGCCAGG AGCCGGCAGA
101  TTTGACAGGT GTCACTGTAC AGTCCCCAGG GGAGGCACAG TGTCTGCTGG
151  TGAGTTGGGG ACAGGCCCTT GCAAGACCTT GTGAGGCAGG GGGTGAAGGC
201  CATGNCTCGG CTTCNNNTGG TCAAGGGGA AGTGGAGCCT GAGGGAGATG
251  GGACTTNAGG GGGACGGNGC TGCGTGGGGA AAAAGCAGCC ACCNTTTGAC
301  AAGGGGGACA GGCATTTTTN CAAATGTGTG CTTNTTGGT
```

FIG.4

DEATH DOMAIN CONTAINING RECEPTOR 4 ANTIBODIES AND METHODS

CROSS-REFERENCE TO RELATED APPLICATIONS

This application claims the benefit of priority under 35 U.S.C. §119(e) of provisional Application Nos. 60/990,687 and 60/885,971, filed Nov. 28, 2007 and Jan. 22, 2007, respectively. This application is also a Continuation-in-Part and claims benefit of priority under 35 U.S.C. §120 of non-provisional application Ser. No. 11/076,187, filed Mar. 10, 2005 (now U.S. Pat. No. 7,476,384), which claims the benefit of priority under 35 U.S.C. §119(e) of provisional Application Nos. 60/551,768 and 60/608,469, filed Mar. 11, 2004 and Sep. 10, 2004, respectively. This application is also a Continuation-in-Part and claims benefit of priority under 35 U.S.C. §120 of non-provisional application Ser. No. 10/648,786, filed Aug. 27, 2003 (now U.S. Pat. No. 7,452,538), which claims the benefit of priority under 35 U.S.C. §119(e) of provisional Application Nos. 60/413,861 and 60/406,922, filed Sep. 27, 2002 and Aug. 30, 2002 respectively. Application Ser. No. 10/648,786 is in turn a Continuation-In-Part and claims benefit of priority under 35 U.S.C. §120 of non-provisional application Ser. No. 09/565,918, filed on May 5, 2000 (now U.S. Pat. No. 6,433,147), which in turn claims the benefit of priority under 35 U.S.C. §119(e) of provisional Application No. 60/132,922, filed May 6, 1999, and is a Continuation-In-Part claiming benefit of priority under 35 U.S.C. §120 of non-provisional application Ser. No. 09/013,895, filed on Jan. 27, 1998 (now U.S. Pat. No. 6,342,363), which in turn claims the benefit of priority under 35 U.S.C. §119(e) of provisional Application Nos. 60/037,829 and 60/035,722, filed Feb. 5, 1997 and Jan. 28, 1997 respectively. Each of the above-cited applications is hereby incorporated by reference in its entirety.

FIELD OF THE INVENTION

The present invention relates to a novel member of the tumor necrosis factor family of receptors. More specifically, isolated nucleic acid molecules are provided encoding human Death Domain Containing Receptor 4, sometimes herein "DR4". DR4 polypeptides are also provided, as are vectors, host cells and recombinant methods for producing the same. The invention relates to the treatment of diseases associated with reduced or increased levels of apoptosis using antibodies specific for DR4, which may be agonists and/or antagonists of DR4 activity. The invention further relates to screening methods for identifying agonists and antagonists of DR4 activity and methods for using DR4 polynucleotides and polypeptides.

RELATED ART

Many biological actions, for instance, response to certain stimuli and natural biological processes, are controlled by factors, such as cytokines. Many cytokines act through receptors by engaging the receptor and producing an intra-cellular response.

For example, tumor necrosis factors (TNF) alpha and beta are cytokines which act through TNF receptors to regulate numerous biological processes, including protection against infection and induction of shock and inflammatory disease. The TNF molecules belong to the "TNF-ligand" superfamily, and act together with their receptors or counter-ligands, the "TNF-receptor" superfamily. So far, nine members of the TNF ligand superfamily have been identified and ten members of the TNF-receptor superfamily have been characterized.

Among the ligands there are included TNF-α, lymphotoxin-α (LT-α, also known as TNF-β), LT-β (found in complex heterotrimer LT-α2-β), FasL, CD40L, CD27L, CD30L, 4-IBBL, OX40L and nerve growth factor (NGF). The superfamily of TNF receptors includes the p55TNF receptor, p75TNF receptor, TNF receptor-related protein, FAS antigen or APO-1, CD40, CD27, CD30, 4-IBB, OX40, low affinity p75 and NGF-receptor (Meager, A., *Biologicals,* 22:291-295 (1994)).

Many members of the TNF-ligand superfamily are expressed by activated T-cells, implying that they are necessary for T-cell interactions with other cell types which underlie cell ontogeny and functions. (Meager, A., supra).

Considerable insight into the essential functions of several members of the TNF receptor family has been gained from the identification and creation of mutants that abolish the expression of these proteins. For example, naturally occurring mutations in the FAS antigen and its ligand cause lymphoproliferative disease (Watanabe-Fukunaga, R., et al., *Nature* 356:314 (1992)), perhaps reflecting a failure of programmed cell death. Mutations of the CD40 ligand cause an X-linked immunodeficiency state characterized by high levels of immunoglobulin M and low levels of immunoglobulin G in plasma, indicating faulty T-cell-dependent B-cell activation (Allen, R. C. et al., *Science* 259:990 (1993)). Targeted mutations of the low affinity nerve growth factor receptor cause a disorder characterized by faulty sensory innovation of peripheral structures (Lee, K. F. et al., *Cell* 69:737 (1992)).

TNF and LT-α are capable of binding to two TNF receptors (the 55- and 75-kd TNF receptors). A large number of biological effects elicited by TNF and LT-α, acting through their receptors, include hemorrhagic necrosis of transplanted tumors, cytotoxicity, a role in endotoxic shock, inflammation, immunoregulation, proliferation and anti-viral responses, as well as protection against the deleterious effects of ionizing radiation. TNF and LT-α are involved in the pathogenesis of a wide range of diseases, including endotoxic shock, cerebral malaria, tumors, autoimmune disease, AIDS and graft-host rejection (Beutler, B. and Von Huffel, C., *Science* 264:667-668 (1994)). Mutations in the p55 Receptor cause increased susceptibility to microbial infection.

Moreover, an about 80 amino acid domain near the C-terminus of TNFR1 (p55) and Fas was reported as the "death domain," which is responsible for transducing signals for programmed cell death (Tartaglia et al., *Cell* 74:845 (1993)).

Apoptosis, or programmed cell death, is a physiologic process essential to the normal development and homeostasis of multicellular organisms (H. Steller, *Science* 267, 1445-1449 (1995)). Derangements of apoptosis contribute to the pathogenesis of several human diseases including cancer, neurodegenerative disorders, and acquired immune deficiency syndrome (C. B. Thompson, *Science* 267, 1456-1462 (1995)). Recently, much attention has focused on the signal transduction and biological function of two cell surface death receptors, Fas/APO-1 and TNFR-1 (J. L. Cleveland, et al., *Cell* 81, 479-482 (1995); A. Fraser, et al., *Cell* 85, 781-784 (1996); S, Nagata, et al., *Science* 267, 1449-56 (1995)). Both are members of the TNF receptor family which also include TNFR-2, low affinity NGFR, CD40, and CD30, among others (C. A. Smith, et al., *Science* 248, 1019-23 (1990); M. Tewari, et al., in *Modular Texts in Molecular and Cell Biology* M. Purton, Heldin, Carl, Ed. (Chapman and Hall, London, 1995). While family members are defined by the presence of cysteine-rich repeats in their extracellular domains, Fas/APO-1 and TNFR-1 also share a region of intracellular homology, appropriately designated the "death domain", which is distantly related to the *Drosophila* suicide gene, reaper (P. Golstein, et al., *Cell* 81, 185-6 (1995); K. White et al., *Science* 264, 677-83 (1994)). This shared death domain suggests that both receptors interact with a related set of signal transducing molecules that, until recently, remained unidentified. Activation of Fas/APO-1 recruits the death domain-containing adapter molecule, FADD/MORT1 (A. M. Chinnaiyan, et al., *Cell* 81, 505-12 (1995); M. P. Boldin, et al., *J. Biol Chem* 270, 7795-8 (1995); F. C. Kischkel, et al., *EMBO* 14, 5579-5588 (1995)), which in turn binds and presumably activates FLICE/MACH1, a member of the ICE/CED-3 family of pro-apoptotic proteases (M. Muzio et al., *Cell* 85, 817-827 (1996); M. P. Boldin, et al., *Cell* 85, 803-815 (1996)). While the central role of Fas/APO-1 is to trigger cell death, TNFR-1 can signal an array of diverse biological activities-many of which stem from its ability to activate NF-kB (L. A. Tartaglia, et al., *Immunol Today* 13, 151-3 (1992)). Accordingly, TNFR-1 recruits the multivalent adapter molecule TRADD, which like FADD, also contains a death domain (H. Hsu, et al., *Cell* 81, 495-504 (1995); H. Hsu, et al., *Cell* 84, 299-308 (1996)). Through its associations with a number of signaling molecules including FADD, TRAF2, and RIP, TRADD can signal both apoptosis and NF-kB activation (H. Hsu, et al., *Cell* 84, 299-308 (1996); H. Hsu, et al., *Immunity* 4, 387-396 (1996)).

Recently a new apoptosis inducing ligand was discovered. Wiley, S. R. et al., refer to the new molecule as TNF-related apoptosis-inducing ligand or ("TRAIL") (*Immunity* 3:673-682 (1995)). Pitti, R. M. et al., refer to the new molecule as Apo-2 ligand or ("Apo-2L"). For convenience, it will be referred to herein as TRAIL.

Unlike FAS ligand whose transcripts appear to be largely restricted to stimulated T-cells, significant levels of TRAIL are seen in many tissues, and it is constitutively transcribed by some cell lines. It has been shown that TRAIL acts independently from FAS ligand (Wiley, S. R., et al. (1995)), supra). Studies by Marsters, S. A. et al., have indicated that TRAIL activates apoptosis rapidly, within a time frame that is similar to death signaling by FAS/Apo-1L but much faster than TNF-induced apoptosis (*Current Biology*, 6:750-752 (1996)). All work to date suggest that the receptor for TRAIL is not one of the many known TNF-receptors.

The effects of TNF family ligands and TNF family receptors are varied and influence numerous functions, both normal and abnormal, in the biological processes of the mammalian system. There is a clear need, therefore, for identification and characterization of such receptors and ligands that influence biological activity, both normally and in disease states. In particular, there is a need to isolate and characterize the receptor for the newly discovered TRAIL ligand.

SUMMARY OF THE INVENTION

The present invention provides for isolated nucleic acid molecules comprising, or alternatively consisting of, nucleic acid sequences encoding the amino acid sequence shown in SEQ ID NO:2 or the amino acid sequence encoding the cDNA clone deposited as ATCC Deposit No. 97853 on Jan. 21, 1997.

The present invention also provides vectors and host cells for recombinant expression of the nucleic acid molecules described herein, as well as to methods of making such vectors and host cells and for using them for production of DR4 polypeptides or peptides by recombinant techniques.

The invention further provides an isolated DR4 polypeptide having an amino acid sequence encoded by a polynucleotide described herein.

The present invention also provides diagnostic assays such as quantitative and diagnostic assays for detecting levels of DR4 protein. Thus, for instance, a diagnostic assay in accordance with the invention for detecting over-expression of DR4, or soluble form thereof, compared to normal control tissue samples may be used to detect the presence of tumors. See, for example, the assays described in Example 29.

Tumor Necrosis Factor (TNF) family ligands are known to be among the most pleiotropic cytokines, inducing a large number of cellular responses, including cytotoxicity, anti-viral activity, immunoregulatory activities, and the transcriptional regulation of several genes. Cellular response to TNF-family ligands include not only normal physiological responses, but also diseases associated with increased apoptosis or the inhibition of apoptosis. Apoptosis-programmed cell death-is a physiological mechanism involved in the deletion of peripheral T lymphocytes of the immune system, and its dysregulation can lead to a number of different pathogenic processes. Diseases associated with increased cell survival, or the inhibition of apoptosis, include cancers, autoimmune disorders, viral infections, inflammation, graft v. host disease, acute graft rejection, and chronic graft rejection. Diseases associated with increased apoptosis include AIDS, neurodegenerative disorders, myelodysplastic syndromes, ischemic injury, toxin-induced liver disease, septic shock, cachexia and anorexia.

Thus, the invention further provides a method for enhancing apoptosis induced by a TNF-family ligand, which involves administering to a cell which expresses the DR4 polypeptide an effective amount of an agonist capable of increasing DR4 mediated signaling. Preferably, DR4 mediated signaling is increased to treat and/or prevent a disease wherein decreased apoptosis is exhibited.

In a further aspect, the present invention is directed to a method for inhibiting apoptosis induced by a TNF-family ligand, which involves administering to a cell which expresses the DR4 polypeptide an effective amount of an antagonist capable of decreasing DR4 mediated signaling. Preferably, DR4 mediated signaling is decreased to treat and/or prevent a disease wherein increased apoptosis is exhibited.

The present invention relates to the detection, diagnosis, prognosis and/or treatment of diseases and disorders of cell death, including but not limited to cancers, using compositions comprising polynucleotides encoding DR4, the polypeptides encoded by these polynucleotides and antibodies that immunospecifically bind these polypeptides. The invention further relates to diagnostic and therapeutic methods useful for diagnosing, treating, preventing and/or prognosing disorders of cell death, and therapeutic methods for treating such disorders. The invention further relates to screening methods for identifying agonists and antagonists of polynucleotides and polypeptides of the invention. The invention further relates to methods and/or compositions for inhibiting or promoting the production and/or function of the polypeptides of the invention. The invention is based in part on the ability of DR4 to stimulate apoptosis and thus prevent tumor progression, as demonstrated in Examples 5 and 6, below.

In accordance with one embodiment of the present invention, there is provided an isolated antibody that binds specifically to a DR4 polypeptide, as well as biologically active fragments, analogs and derivatives thereof, together with fragments, analogs and derivatives thereof which may be useful in the diagnosis or treatment of diseases or disorders associated with decreased levels of cell death.

In one preferred embodiment of the present invention is presented an isolated antibody which is an agonist of DR4 activity and therefore may be useful in the treatment of diseases or disorders associated with decreased levels of cell death including, for example, prostate, pancreatic, hepatic, lung, breast, ovarian, colorectal and hematological cancers.

In accordance with another embodiment of the present invention, there is provided an isolated antibody that binds specifically to a DR4 polypeptide, as well as biologically active fragments, analogs and derivatives thereof, together with fragments, analogs and derivatives thereof which may be useful in the diagnosis or treatment of diseases or disorders associated with increased levels of cell death.

In another preferred embodiment of the present invention is presented an isolated antibody which is an antagonist of DR4 activity and therefore may be useful in the treatment of diseases or disorders associated with increased levels of cell death including, for example, myelodysplastic syndrome.

The present invention also provides pharmaceutical compositions comprising DR4 antibodies, as described above, which may be used for instance, to treat, prevent, prognose and/or diagnose diseases or disorders associated with abnormal levels of cell death and/or conditions associated with such diseases or disorders.

In preferred embodiments the present invention provides pharmaceutical compositions comprising DR4 agonistic antibodies, which may be used for instance to treat, prevent, prognose and/or diagnose diseases or disorders associated with increased or decreased levels of cell death as well as conditions associated with such diseases or disorders.

Whether any candidate "agonist" or "antagonist" of the present invention can enhance or inhibit apoptosis can be determined using art-known TNF-family ligand/receptor cellular response assays, including those described in more detail below. Thus, in a further aspect, a screening method is provided for determining whether a candidate agonist or antagonist is capable of enhancing or inhibiting a cellular response to a TNF-family ligand. The method involves contacting cells which express the DR4 polypeptide with a candidate compound and a TNF-family ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By the invention, a cell expressing the DR4 polypeptide can be contacted with either an endogenous or exogenously administered TNF-family ligand.

BRIEF DESCRIPTION OF THE FIGURES

FIG. 1 shows the nucleotide and deduced amino acid sequence of DR4 (SEQ ID NOS: 1 and 2, respectively). It is predicted that amino acids from about 1 to about 23 constitute the signal peptide, amino acids from about 24 to about 238 constitute the extracellular domain, amino acids from about 131 to about 229 constitute the cysteine rich domain, amino acids from about 239 to about 264 constitute the transmembrane domain, and amino acids from about 265 to about 468 constitute the intracellular domain of which amino acids from about 379 to about 422 constitute the death domain.

FIG. 2 shows the regions of similarity between the amino acid sequences of DR4 (SEQ ID NO:2), human tumor necrosis factor receptor 1 (SEQ ID NO:3), human Fas protein (SEQ ID NO:4), and the death domain containing receptor 3 (DR3) (SEQ ID NO:5). Residues that match the consensus are shaded.

FIG. 4 shows the nucleotide sequences of related nucleic acid fragments HTOIY07R (SEQ ID NO:6) and HTXEY80R (SEQ ID NO:7).

DETAILED DESCRIPTION OF THE PREFERRED EMBODIMENTS

Figure 2A:
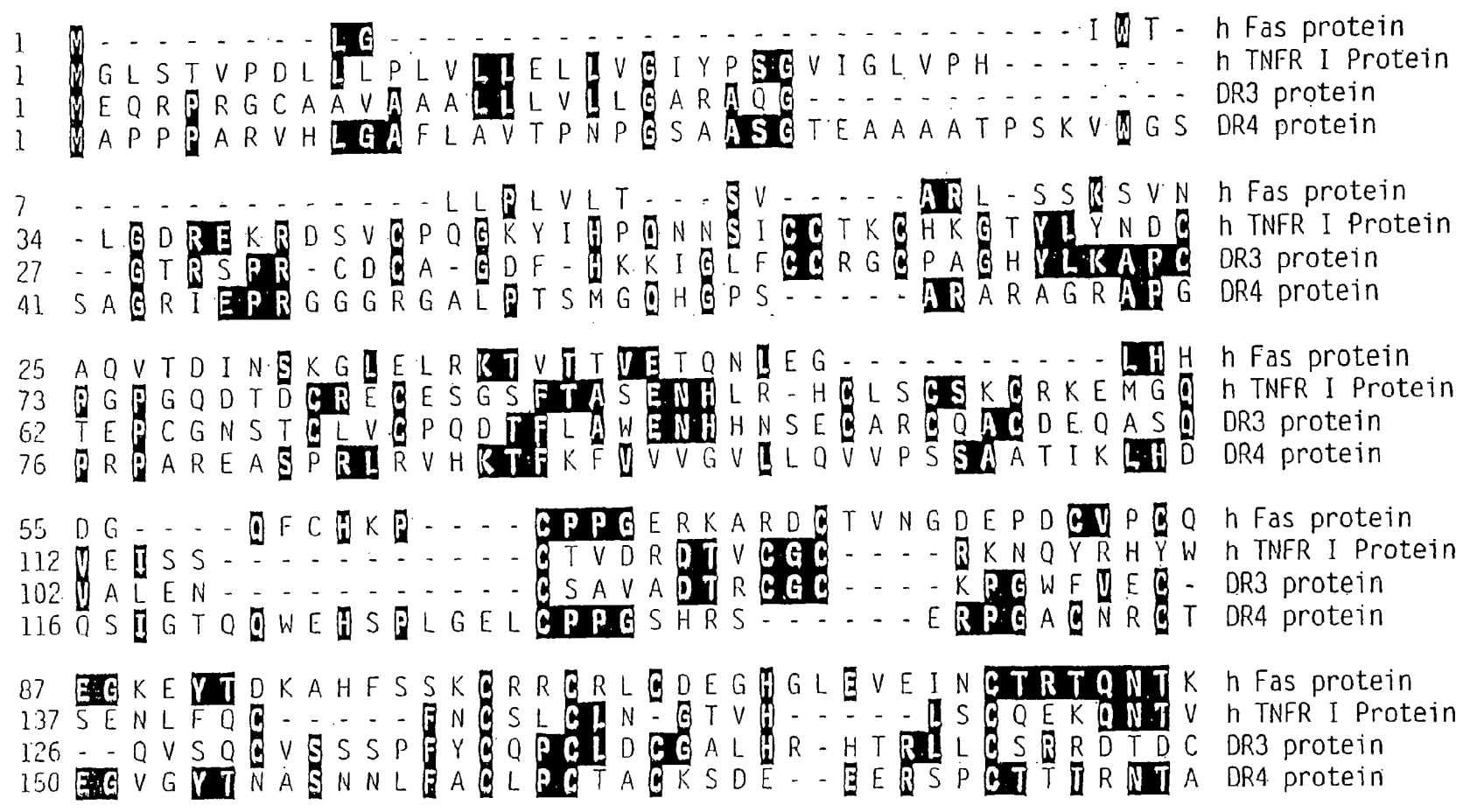
Figure 2B:
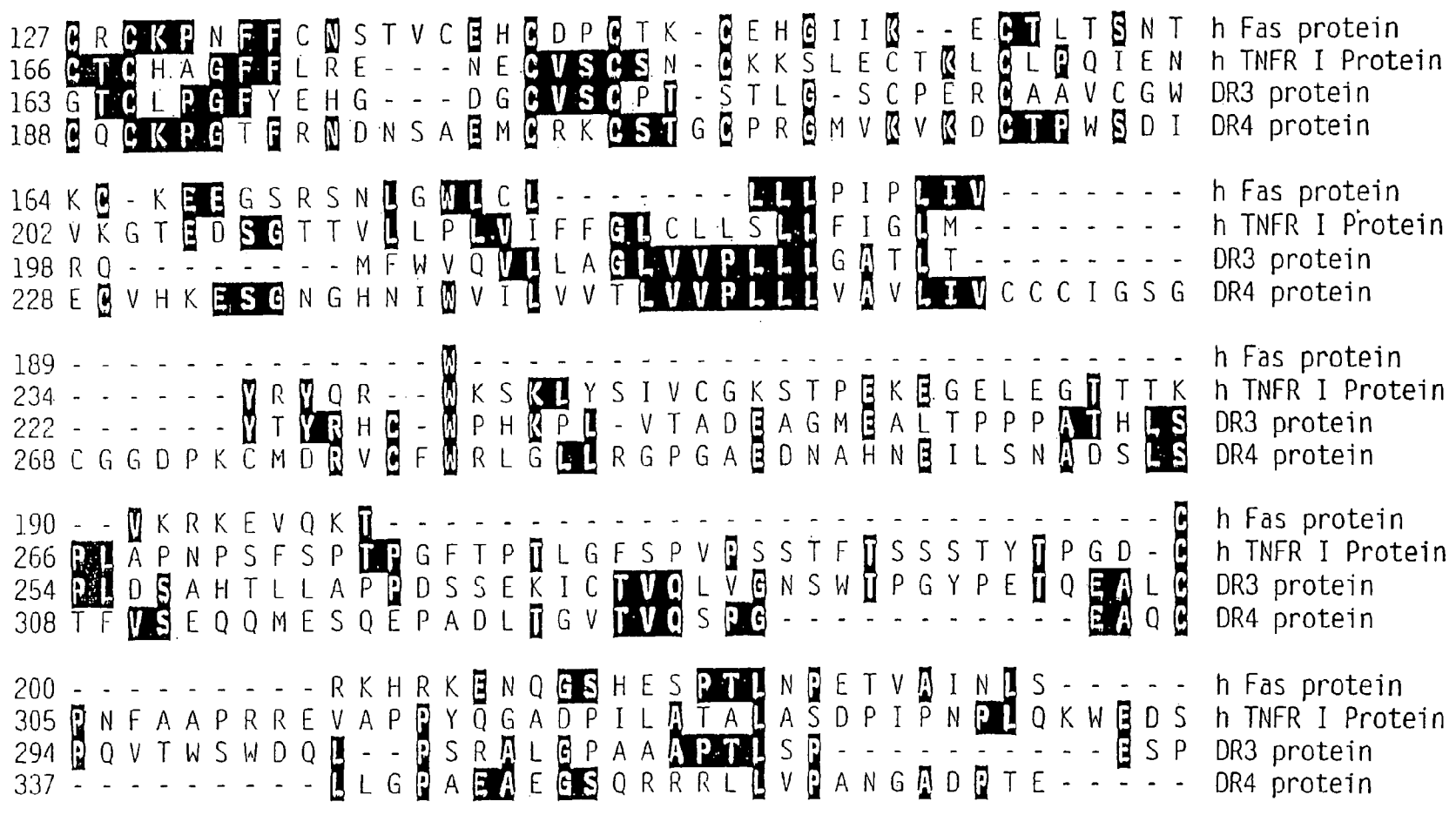
Figure 2C:
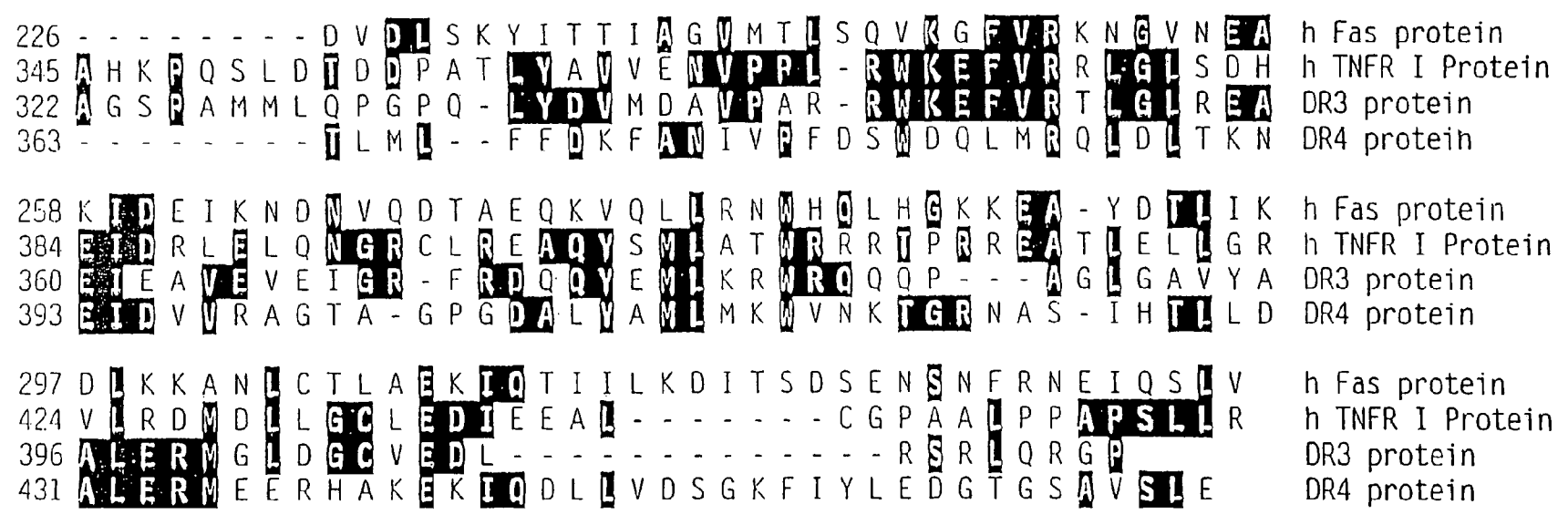
Figure 3:
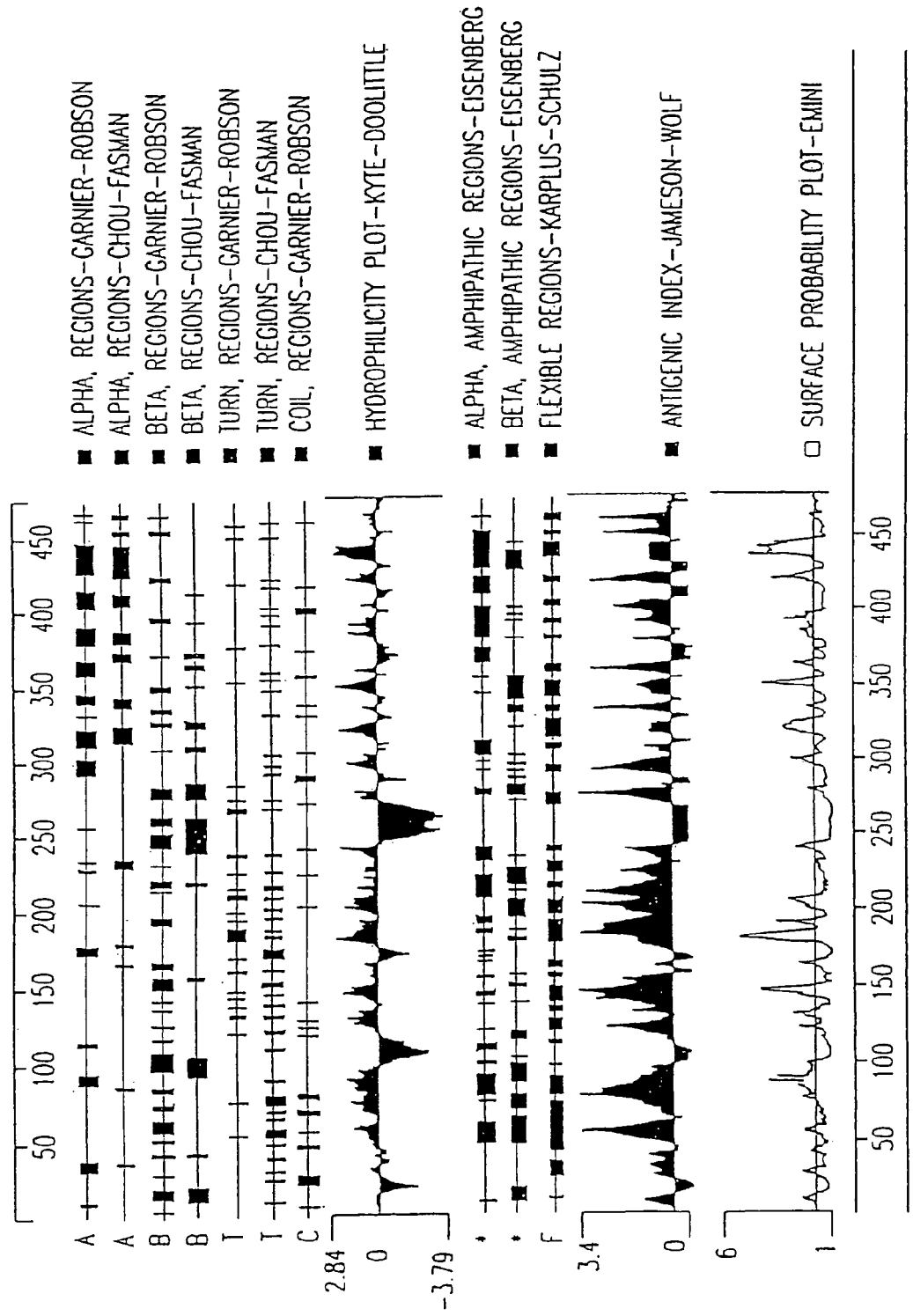
FIG. 3 shows an analysis of the DR4 amino acid sequence. Alpha, beta, turn and coil regions; hydrophilicity and hydrophobicity; amphipathic regions; flexible regions; antigenic index and surface probability are shown, as predicted for the amino acid sequence depicted in FIG. 1 (SEQ ID NO:2) using the default parameters of the recited computer programs. In the "Antigenic Index—Jameson-Wolf" graph, amino acid residues 35-92, 114-160, 169-240, 267-298, 330-364, 391-404, and 418-465 in FIG. 1 (SEQ ID NO:2) correspond to the shown highly antigenic regions of the DR4 protein.

The present invention provides isolated nucleic acid molecules comprising/, or alternatively consisting of, a nucleic acid sequence encoding the DR4 polypeptide whose amino acid sequence is shown in SEQ ID NO:2, or a fragment of the polypeptide. The DR4 polypeptide of the present invention shares sequence homology with human TNFR-I, DR3 and Fas ligand (FIG. 2). The nucleotide sequence shown in SEQ ID NO:1 was obtained by sequencing cDNA clones such as HCUDS60, which was deposited on Jan. 21, 1997 at the American Type Culture Collection, 10801 University Boulevard, Manassas, Va., 20110-2209, and given Accession Number 97853. The deposited clone is contained in the pBK plasmid (Stratagene, La Jolla, Calif.).

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "isolated" polypeptide or protein is intended a polypeptide or protein removed from its native environment. For example, recombinantly produced polypeptides and proteins expressed in host cells are considered isolated for purposed of the invention, as are native or recombinant polypeptides which have been substantially purified by any suitable technique such as, for example, the single-step purification method disclosed in Smith and Johnson, *Gene* 67:31-40 (1988).

Using the information provided herein, such as the nucleic acid sequence set out in SEQ ID NO: 1, a nucleic acid molecule of the present invention encoding a DR4 polypeptide may be obtained using standard cloning and screening procedures, such as those for cloning cDNAs using mRNA as starting material. Illustrative of the invention, the gene of the present invention has also been identified in cDNA libraries of the following tissues: amniotic cells, heart, liver cancer, kidney, leukocyte, activated T-cell, K562 plus PMA, W138 cells, Th2 cells, human tonsils, and CD34 depleted buffy coat (cord blood).

The DR4 gene contains an open reading frame encoding a mature protein of about 445 amino acid residues whose initiation codon is at position 19-21 of the nucleotide sequence shown in SEQ ID NO.1, with a leader sequence of about 23 amino acid residues (i.e., a total protein length of 468 amino acids), and a deduced molecular weight of about 50 kDa. In this context "about" includes the particularly recited size, larger or smaller by several (5, 4, 3, 2, or 1) amino acid residues, at either terminus or at both termini.

Of known members of the TNF receptor family, the DR4 polypeptide of the invention shares the greatest degree of homology with human TNFR1 and DR3 polypeptides shown in FIG. 2, including significant sequence homology over the multiple Cysteine Rich domains.

Figure 5A:
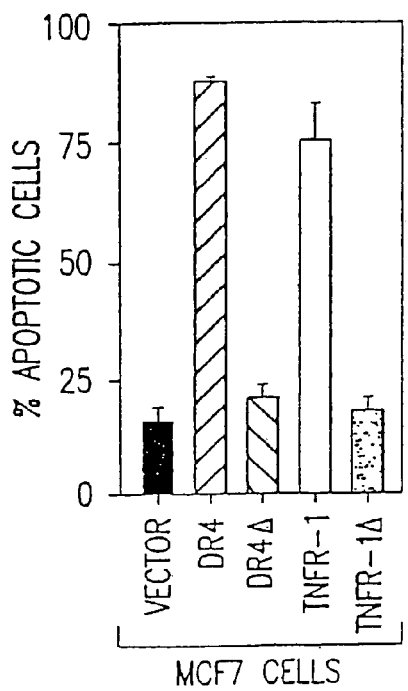
FIGS. 5A and 5B show the ability of DR4 to induce apoptosis in the cell lines MCF7 and 293.
Figure 5B:
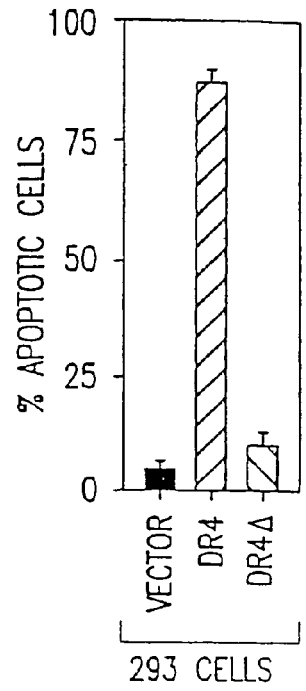
Figure 5C:
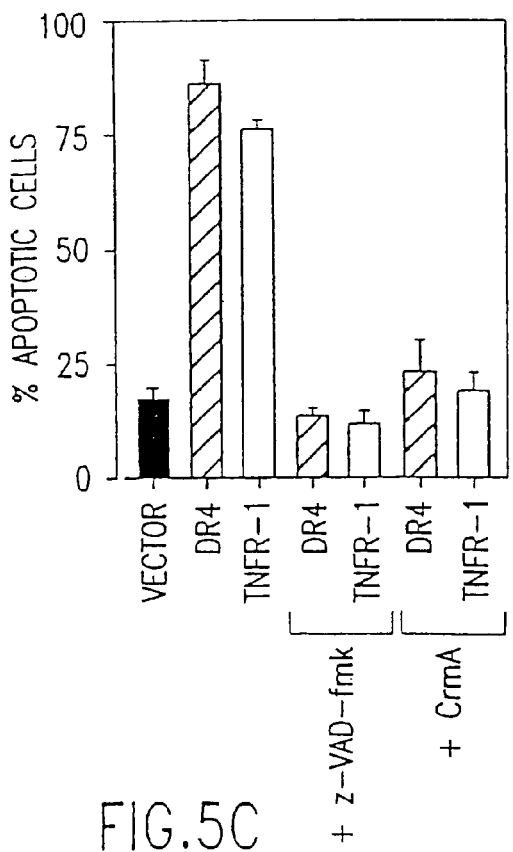
FIG. 5C shows the ability of death protease inhibitors z-VAD-fmk and CrmA to inhibit the apoptotic action of DR4.

In addition to the sequence homology exhibited between DR4 and other death domain containing receptors, DR4 has been shown to bind to TRAIL and to induce apoptosis when transiently expressed. MCF7 human breast carcinoma cells and 293 cells were transiently transfected with a DR4 expressing construct, as described in Example 5. As shown in FIGS. 5A and 5B a substantial proportion of transfected cells underwent the morphological changes characteristic of apoptosis. As anticipated, deletion of the death domain abolished the ability of DR4 to engage the death pathway. As can be seen in FIG. 5C, DR4-induced apoptosis was efficiently blocked by inhibitors of death proteases including z-VAD-fmk, an irreversible broad spectrum caspase inhibitor and CrmA, a cowpox virus encoded serpin that preferentially inhibits apical caspases such as FLICE/MACH-1 (caspase-8). Since TNFR-1, CD-95 and DR3-induced apoptosis is also attenuated by these same inhibitors, it is likely that the downstream death effector molecules are similar in nature.

To determine if DR4 was capable of binding TRAIL, the extracellular ligand binding domain of DR4 was expressed as a fusion to the Fc region of human IgG (DR4-Fc). TRAIL selectively bound to DR4-Fc but not to corresponding extracellular domains of TNFR-1 or CD-95, also expressed as Fc fusions, data not shown. Additionally, DR4-Fc did not bind either TNF alpha or Fas ligand under conditions where both of these ligands bound their cognate receptors.

Figure 6A:
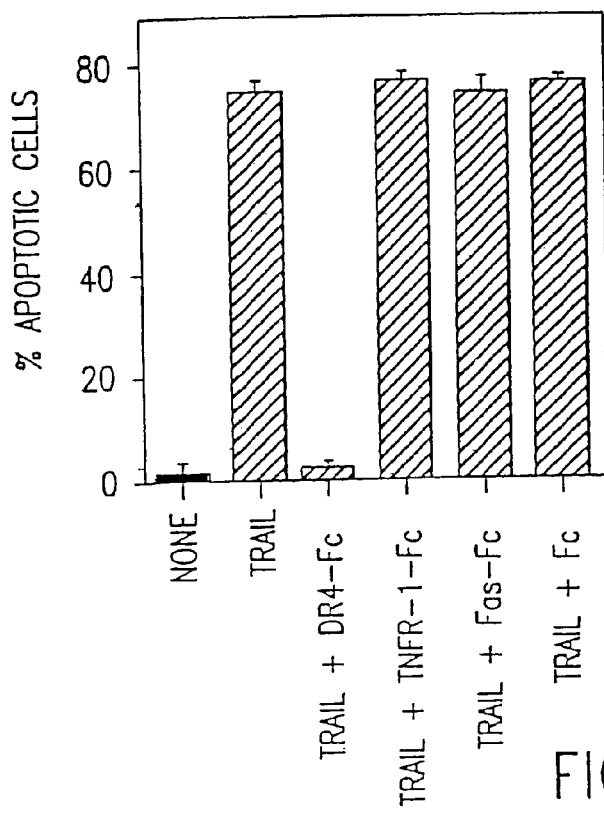
FIG. 6A shows the ability of a soluble extracellular DR4-Fc fusion to block the apoptotic inducing ability of TRAIL.
Figure 6B:
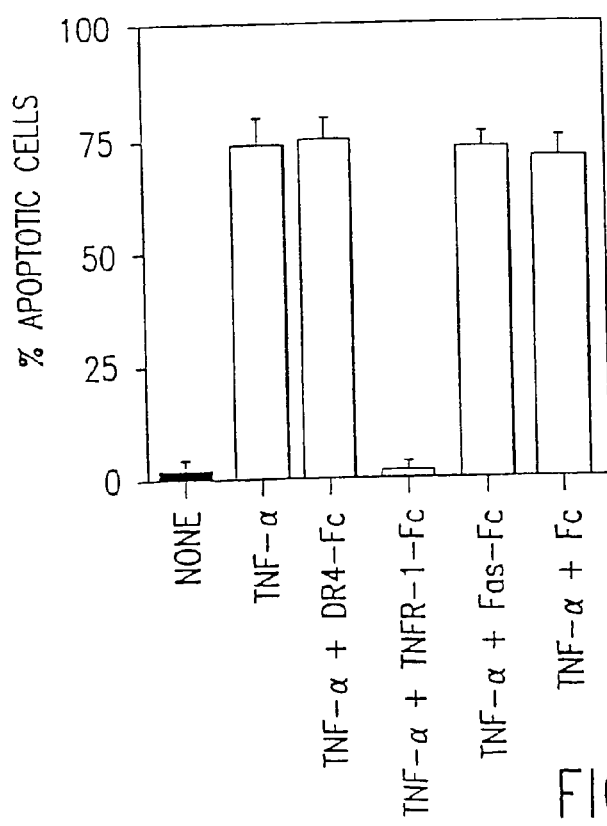
FIG. 6B shows the inability of soluble extracellular DR4-Fc fusion to block the apoptotic inducing ability of TNF-alpha.

The ability of TRAIL to induce apoptosis in MCF7 cells was specifically blocked by DR4-Fc but not influenced by TNFR1-Fc, CD95-Fc or Fc alone (FIG. 6A). Further, as expected, TNF alpha-induced apoptosis was inhibited by TNFR-1-Fc but not by DR4-Fc, CD95-Fc or Fc alone (FIG. 6B).

Taken together, the data described above indicate that DR4 is a death domain containing receptor with the ability to induce apoptosis and is a receptor for TRAIL a known apoptosis inducing ligand.

As indicated, the present invention also provides the mature form(s) of the DR4 protein of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature DR4 polypeptide having the amino acid sequence encoded by the cDNA contained in the host identified as ATCC Deposit No. 97853, and as shown in SEQ ID NO:2. By the mature DR4 protein having the amino acid sequence encoded by the cDNA contained in the host identified as ATCC Deposit No. 97853, is meant the mature form(s) of the DR4 protein produced by expression in a mammalian cell (e.g., COS cells, as described below) of the complete open reading frame encoded by the human cDNA contained in the vector in the deposited host. As indicated below, the mature DR4 having the amino acid sequence encoded by the cDNA contained in ATCC Deposit No. 97853, may or may not differ from the predicted "mature" DR4 protein shown in SEQ ID NO:2 (amino acids from about 24 to about 468 in SEQ ID NO:2) depending on the accuracy of the predicted cleavage site based on computer analysis. In this context "about" includes the particularly recited size, larger or smaller by several (5, 4, 3, 2, or 1) amino acid residues, at either terminus or at both termini.

Methods for predicting whether a protein has a secretory leader as well as the cleavage point for that leader sequence are available. For instance, the method of McGeoch (*Virus Res.* 3:271-286 (1985)) and von Heinje (*Nucleic Acids Res.* 14:4683-4690 (1986)) can be used. The accuracy of predicting the cleavage points of known mammalian secretory proteins for each of these methods is in the range of 75-80%. von Heinje, supra. However, the two methods do not always produce the same predicted cleavage point(s) for a given protein.

In the present case, the predicted amino acid sequence of the complete DR4 polypeptide of the present invention was analyzed by a computer program ("PSORT"). (See K. Nakai and M. Kanehisa, *Genomics* 14:897-911 (1992)), which is an expert system for predicting the cellular location of a protein based on the amino acid sequence. As part of this computational prediction of localization, the methods of McGeoch and von Heinje are incorporated. The analysis by the PSORT program predicted the cleavage sites between amino acids 23 and 24 in SEQ ID NO:2. Thereafter, the complete amino acid sequences were further analyzed by visual inspection, applying a simple form of the (−1, −3) rule of von Heine. von Heinje, supra. Thus, the leader sequence for the DR4 protein is predicted to consist of amino acid residues 1-23, underlined in SEQ ID NO:2, while the predicted mature DR4 protein consists of about residues 24-468.

As one of ordinary skill would appreciate, due to the possibility of sequencing errors, as well as the variability of cleavage sites for leaders in different known proteins, the predicted DR4 receptor polypeptide encoded by the deposited cDNA comprises about 468 amino acids, but may be anywhere in the range of 458478 amino acids; and the predicted leader sequence of this protein is about 40 amino acids, but may be anywhere in the range of about 30 to about 50 amino acids. It will further be appreciated that, the domains described herein have been predicted by computer analysis, and accordingly, that depending on the analytical criteria used for identifying various functional domains, the exact "address" of, for example, the extracelluar domain, intracellular domain, death domain, cysteine-rich motifs, and transmembrane domain of DR4 may differ slightly. For example, the exact location of the DR4 extracellular domain in SEQ ID NO:2 may vary slightly (e.g., the address may "shift" by about 1 to about 20 residues, more likely about 1 to about 5 residues) depending on the criteria used to define the domain. In this context "about" includes the particularly recited size, larger or smaller by several (5, 4, 3, 2, or 1) amino acid residues, at either terminus or at both termini. In any event, as discussed further below, the invention further provides polypeptides having various residues deleted from the N-terminus and/or C-terminus of the complete DR4, including polypeptides lacking one or more amino acids from the N-termini of the extracellular domain described herein, which constitute soluble forms of the extracellular domain of the DR4 polypeptides.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA may be the coding strand, also known as the sense strand, or it may be the non-coding strand, also referred to as the antisense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution.

However, a nucleic acid molecule contained in a clone that is a member of a mixed clone library (e.g., a genomic or cDNA library) and that has not been isolated from other clones of the library (e.g., in the form of a homogeneous solution containing the clone without other members of the library) or a chromosome isolated or removed from a cell or a cell lysate (e.g., a "chromosome spread", as in a karyotype), is not "isolated" for the purposes of this invention. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DR4 DNA molecules comprising, or alternatively consisting of, an open reading frame (ORF) shown in SEQ ID NO:1 and further include DNA molecules which comprise, or alternatively consist of, a sequence substantially different than all or part of the ORF whose initiation codon is at position 19-21 of the nucleotide sequence shown in SEQ ID NO:1 but which, due to the degeneracy of the genetic code, still encode the DR4 polypeptide or a fragment thereof. Of course, the genetic code is well known in the art. Thus, it would be routine for one skilled in the art to generate such degenerate variants.

In another aspect, the invention provides isolated nucleic acid molecules encoding the DR4 polypeptide having an amino acid sequence encoded by the cDNA contained in the plasmid deposited as ATCC Deposit No. 97853 on Jan. 21, 1997. Preferably, these nucleic acid molecules will encode the mature polypeptide encoded by the above-described deposited cDNA. The invention further provides an isolated nucleic acid molecule having the nucleotide sequence shown in SEQ ID NO:1 or the nucleotide sequence of the DR4 cDNA contained in the above-described deposited plasmid, or a nucleic acid molecule having a sequence complementary to one of the above sequences. Such isolated DNA molecules and fragments thereof, have uses which include, but are not limited to, as DNA probes for gene mapping by in situ hybridization of the DR4 gene in human tissue by Northern blot analysis.

The present invention is further directed to fragments of the isolated nucleic acid molecules described herein. By fragments of an isolated DNA molecule having the nucleotide sequence shown in SEQ ID NO:1 or having the nucleotide sequence of the deposited cDNA (the cDNA contained in the plasmid deposited as ATCC Deposit No. 97853) are intended DNA fragments at least 20 nt, and more preferably at least 30 nt in length, and even more preferably, at least about 40, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, or 1500 nt in length, which are useful as DNA probes as discussed above. Of course, DNA fragments corresponding to most, if not all, of the nucleotide sequence shown in SEQ ID NO:1 are also useful as DNA probes. By a fragment about 20 nt in length, for example, is intended fragments which include 20 or more bases from the nucleotide sequence in SEQ ID NO:1. In this context "about" includes the particularly recited size, larger or smaller by several (5, 4, 3, 2, or 1) nucleotides, at either terminus or at both termini.

Representative examples of DR4 polynucleotide fragments of the invention include, for example, fragments that comprise, or alternatively consist of, a sequence from about nucleotide 19 to 87, 88 to 732, 88 to 138, 139 to 189, 190 to 240, 241 to 291, 292 to 342, 343 to 705, 343 to 393, 394 to 444, 445 to 495, 496 to 546, 547 to 597, 598 to 648, 649 to 699, 700 to 732, 733 to 810, 733 to 771, 772 to 810, 811 to 1422, 811 to 861, 862 to 912, 913 to 963, 964 to 1014, 1015 to 1065, 1066 to 1116, 1117 to 1167, 1153 to 1284, 1153 to 1203, 1204 to 1254, 1255 to 1284, 1168 to 1218, 1219 to 1269, 1270 to 1320, 1321 to 1371, and 1372 to 1422 of SEQ ID NO:1, or the complementary strand thereto, or the cDNA contained in the deposited plasmid. In this context "about" includes the particularly recited ranges, larger or smaller by several (5, 4, 3, 2, or 1) nucleotides, at either terminus or at both termini.

The present invention is further directed to polynucleotides comprising, or alternatively consisting of, isolated nucleic acid molecules which encode domains of DR4. In one aspect, the invention provides polynucleotides comprising, or alternatively consisting of, nucleic acid molecules which encode beta-sheet regions of DR4 protein set out in Table 1. Representative examples of such polynucleotides include nucleic acid molecules which encode a polypeptide comprising, or alternatively consisting of, one, two, three, four, five or more amino acid sequences selected from the group consisting of amino acid residues from about 8 to about 17, amino acid residues from about 53 to about 60, amino acid residues from about 87 to about 103, amino acid residues from about 146 to about 155, amino acid residues from about 161 to about 166, amino acid residues from about 214 to about 221, amino acid residues from about 240 to about 252, amino acid residues from about 257 to about 264, amino acid residues from about 274 to about 283, amino acid residues from about 324 to about 329, amino acid residues from about 349 to about 354, amino acid residues from about 363 to about 369, amino acid residues from about 371 to about 376, amino acid residues from about 394 to about 399, and amino acid residues from about 453 to about 458 in SEQ ID NO:2. In this context "about" includes the particularly recited value and values larger or smaller by several (5, 4, 3, 2, or 1) amino acids. Polypeptides encoded by these polynucleotides are also encompassed by the invention.

In specific embodiments, the polynucleotide fragments of the invention encode a polypeptide which demonstrates a DR4 functional activity. By a polypeptide demonstrating a DR4 "functional activity" is meant, a polypeptide capable of displaying one or more known functional activities associated with a complete (full-length) or mature DR4 polypeptide. Such functional activities include, but are not limited to, biological activity (e.g., ability to induce apoptosis in cells expressing the polypeptide (see, e.g., Example 5), antigenicity (ability to bind (or compete with a DR4 polypeptide for binding) to an anti-DR4 antibody), immunogenicity (ability to generate antibody which binds to a DR4 polypeptide), ability to form multimers, and ability to bind to a receptor or ligand for a DR4 polypeptide (e.g., TRAIL; Wiley et al., *Immunity* 3, 673-682 (1995)).

The functional activity of DR4 polypeptides, and fragments, variants derivatives, and analogs thereof, can be assayed by various methods.

For example, in one embodiment where one is assaying for the ability to bind or compete with full-length (complete) DR4 polypeptide for binding to anti-DR4 antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a DR4 ligand is identified (e.g., TRAIL), or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., *Microbiol. Rev.* 59:94-123 (1995). In another embodiment, physiological correlates of DR4 binding to its substrates (signal transduction) can be assayed.

In addition, assays described herein (see Examples 5 and 6), and those otherwise known in the art may routinely be applied to measure the ability of DR4 polypeptides and fragments, variants derivatives, and analogs thereof to elicit DR4 related biological activity (e.g., ability to bind TRAIL (see e.g., Example 6), ability to induce apoptosis in cells expressing the polypeptide (see e.g., Example 5) in vitro or in vivo). For example, biological activity can routinely be measured using the cell death assays performed essentially as previously described (Chinnaiyan et al., *Cell* 81:505-512 (1995); Boldin et al., *J. Biol. Chem.* 270:7795-8 (1995); Kischkel et al., *EMBO* 14:5579-5588 (1995); Chinnaiyan et al., *J. Biol. Chem.* 271:4961-4965 (1996)) and as set forth in Example 5 below. In one embodiment involving MCF7 cells, plasmids encoding full-length DR4 or a candidate death domain containing receptor are co-transfected with the pLantern reporter construct encoding green fluorescent protein. Nuclei of cells transfected with DR4 will exhibit apoptotic morphology as assessed by DAPI staining.

Other methods will be known to the skilled artisan and are within the scope of the invention.

Preferred nucleic acid fragments of the present invention include a nucleic acid molecule encoding a member selected from the group: a polypeptide comprising, or alternatively consisting of, the DR4 extracellular domain (amino acid residues from about 24 to about 238 in SEQ ID NO:2); a polypeptide comprising, or alternatively consisting of, the DR4 cysteine rich domain (amino acid residues from about 131 to about 229 in SEQ ID NO:2); a polypeptide comprising, or alternatively consisting of, the DR4 transmembrane domain (amino acid residues from about 239 to about 264 in SEQ ID NO:2); a fragment of the predicted mature DR4 polypeptide, wherein the fragment has a DR4 functional activity (e.g., antigenic activity or biological activity); a polypeptide comprising, or alternatively consisting of, the DR4 intracellular domain (amino acid residues from about 265 to about 468 in SEQ ID NO:2); a polypeptide comprising, or alternatively consisting of, the DR4 receptor extracellular and intracellular domains with all or part of the transmembrane domain deleted; a polypeptide comprising, or alternatively consisting of, DR4 receptor death domain (predicted to constitute amino acid residues from about 379 to about 422 in SEQ ID NO:2); a polypeptide comprising, or alternatively consisting of, one, two, three, four or more, epitope bearing portions of the DR4 receptor protein. In additional embodiments, the polynucleotide fragments of the invention encode a polypeptide comprising, or alternatively consisting of, any combination of 1, 2, 3, 4, 5, 6, 7, or all 8 of the above-encoded polypeptide embodiments. As above, with the leader sequence, the amino acid residues constituting the DR4 receptor extracellular, transmembrane and intracellular domains have been predicted by computer analysis. Thus, one of ordinary skill would appreciate that the amino acid residues constituting these domains may vary slightly (e.g., by about 1 to 15 residues) depending on the criteria used to define the domain. Polypeptides encoded by these nucleic acid molecules are also encompassed by the invention.

It is believed one or both of the extracellular cysteine rich motifs of the DR4 polypeptide disclosed in SEQ ID NO:2 is important for interactions between DR4 and its ligands (e.g., TRAIL). Accordingly, specific embodiments of the invention are directed to polynucleotides encoding polypeptides which comprise, or alternatively consist of, the amino acid sequence of one or both of amino acid residues 131 to 183, and/or 184 to 229 of SEQ ID NO:2. In a specific embodiment the polynucleotides encoding DR4 polypeptides of the invention comprise, or alternatively consist of both of the extracellular cysteine rich motifs disclosed in SEQ ID NO:2. Polypeptides encoded by these polynucleotides are also encompassed by the invention.

In additional embodiments, the polynucleotides of the invention encode functional attributes of DR4. Preferred embodiments of the invention in this regard include fragments that comprise, or alternatively consist of, one, two, three, four, or more of the following functional domains: alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of DR4.

Certain preferred regions in these regards are set out in FIG. 3, but may, as shown in Table I, be represented or identified by using tabular representations of the data presented in FIG. 3. The DNA*STAR computer algorithm used to generate FIG. 3 (set on the original default parameters) was used to present the data in FIG. 3 in a tabular format (See Table I). The tabular format of the data in FIG. 3 may be used to easily determine specific boundaries of a preferred region.

The above-mentioned preferred regions set out in FIG. 3 and in Table I include, but are not limited to, regions of the aforementioned types identified by analysis of the amino acid sequence set out in SEQ ID NO:2. As set out in FIG. 3 and in Table I, such preferred regions include Garnier-Robson alpha-regions, beta-regions, turn-regions, and coil-regions (columns I, III, V, and VII in Table I), Chou-Fasman alpha-regions, beta-regions, and turn-regions (columns II, IV, and VI in Table I), Kyte-Doolittle hydrophilic regions (column VIII in Table I), Hopp-Woods hydrophobic regions (column IX in Table I), Eisenberg alpha- and beta-amphipathic regions (columns X and XI in Table I), Karplus-Schulz flexible regions (column XII in Table I), Jameson-Wolf regions of high antigenic index (column XIII in Table I), and Emini surface-forming regions (column XIV in Table I). Among highly preferred polynucleotides in this regard are those that encode polypeptides comprising, or alternatively consisting of, regions of DR4 that combine several structural features, such as several (e.g., 1, 2, 3, or 4) of the same or different region features set out above.

The data representing the structural or functional attributes of DR4 set forth in FIG. 3 and/or Table I, as described above, was generated using the various modules and algorithms of the DNA*STAR set on default parameters. In a preferred embodiment, the data presented in columns VIII, XII, and XIII of Table I can be used to determine regions of DR4 which exhibit a high degree of potential for antigenicity. Regions of high antigenicity are determined from the data presented in columns VIII, XII, and/or XIII by choosing values which represent regions of the polypeptide which are likely to be exposed on the surface of the polypeptide in an environment in which antigen recognition may occur in the process of initiation of an immune response.

TABLE I

| Res | Pos. | I | II | III | IV | V | VI | VII | VIII | IX | X | XI | XII | XIII |
|-----|------|---|----|----|----|---|----|----|------|----|---|----|-----|------|
| Met | 1 | . | . | . | B | . | . | . | . | 0.12 | . | . | . | −0.10 | 0.90 |
| Ala | 2 | . | . | . | . | . | . | . | C | −0.08 | * | * | . | 0.25 | 1.08 |
| Pro | 3 | . | . | . | . | . | . | . | C | 0.42 | * | * | . | 0.10 | 0.86 |
| Pro | 4 | . | . | . | . | . | . | T | C | −0.04 | * | * | . | 1.05 | 1.69 |
| Pro | 5 | A | . | . | . | . | . | T | . | 0.31 | . | * | F | 1.00 | 1.24 |
| Ala | 6 | A | . | . | . | . | . | T | . | 0.10 | . | * | F | 1.00 | 1.10 |
| Arg | 7 | A | . | . | . | . | . | T | . | 0.34 | . | * | . | 0.10 | 0.58 |
| Val | 8 | . | . | . | B | B | . | . | . | −0.03 | . | * | . | −0.30 | 0.37 |
| His | 9 | . | . | . | B | B | . | . | . | −0.52 | . | * | . | −0.30 | 0.37 |
| Leu | 10 | . | . | . | B | B | . | . | . | −1.12 | . | * | . | −0.60 | 0.17 |
| Gly | 11 | . | . | . | B | B | . | . | . | −1.12 | . | * | . | −0.60 | 0.18 |
| Ala | 12 | . | . | . | B | B | . | . | . | −2.09 | . | * | . | −0.60 | 0.14 |
| Phe | 13 | . | . | . | B | B | . | . | . | −1.54 | . | * | . | −0.60 | 0.12 |
| Leu | 14 | . | . | . | B | B | . | . | . | −1.72 | . | . | . | −0.60 | 0.18 |
| Ala | 15 | . | . | . | B | B | . | . | . | −0.91 | . | . | . | −0.60 | 0.27 |
| Val | 16 | . | . | . | B | B | . | . | . | −0.78 | . | . | . | −0.60 | 0.51 |
| Thr | 17 | . | . | . | B | B | . | . | . | −0.53 | . | . | F | −0.45 | 0.95 |
| Pro | 18 | . | . | . | . | B | . | . | C | −0.13 | . | . | F | 0.05 | 0.93 |
| Asn | 19 | . | . | . | . | . | . | T | C | 0.09 | . | . | F | 0.60 | 1.69 |
| Pro | 20 | . | . | . | . | . | . | T | C | 0.09 | . | . | F | 0.60 | 1.18 |
| Gly | 21 | . | . | . | . | . | T | T | . | 0.64 | . | . | F | 0.65 | 0.77 |
| Ser | 22 | . | . | . | . | . | . | T | C | 0.61 | . | . | F | 0.45 | 0.64 |
| Ala | 23 | . | . | . | . | . | . | . | C | 0.51 | . | . | F | 0.25 | 0.41 |
| Ala | 24 | . | . | . | . | . | . | T | C | 0.51 | . | . | F | 0.45 | 0.60 |
| Ser | 25 | . | . | B | . | . | . | T | . | 0.13 | . | . | F | 0.85 | 0.78 |
| Gly | 26 | A | . | . | . | . | . | T | . | −0.11 | . | . | F | 0.85 | 0.78 |
| Thr | 27 | A | . | . | . | . | . | T | . | −0.40 | . | . | F | 0.85 | 0.78 |
| Glu | 28 | A | A | . | . | . | . | . | . | −0.40 | . | . | F | 0.45 | 0.58 |
| Ala | 29 | A | A | . | . | . | . | . | . | −0.12 | . | . | . | 0.30 | 0.60 |
| Ala | 30 | A | A | . | . | . | . | . | . | −0.03 | . | . | . | 0.30 | 0.60 |
| Ala | 31 | A | A | . | . | . | . | . | . | 0.01 | . | . | . | 0.30 | 0.53 |
| Ala | 32 | A | A | . | . | . | . | . | . | 0.37 | . | . | . | −0.30 | 0.71 |
| Thr | 33 | A | . | . | . | . | . | T | . | −0.49 | * | . | F | 1.00 | 1.40 |
| Pro | 34 | A | . | . | . | . | . | T | . | −0.19 | . | . | F | 1.00 | 1.03 |
| Ser | 35 | . | . | B | . | . | . | T | . | 0.06 | . | . | F | 0.40 | 1.07 |
| Lys | 36 | . | . | B | . | . | . | T | . | 0.34 | . | . | F | 0.25 | 0.73 |
| Val | 37 | . | . | B | B | . | . | . | . | 0.63 | . | . | F | −0.15 | 0.64 |
| Trp | 38 | . | . | B | B | . | . | . | . | 0.36 | . | . | F | −0.15 | 0.64 |
| Gly | 39 | . | . | B | B | . | . | . | . | 0.22 | * | * | F | −0.15 | 0.32 |
| Ser | 40 | . | . | . | . | . | . | . | C | 0.63 | * | * | F | −0.05 | 0.43 |
| Ser | 41 | . | . | . | . | . | . | T | C | −0.30 | * | * | F | 0.45 | 0.80 |
| Ala | 42 | . | . | . | . | . | . | T | C | 0.56 | * | * | F | 1.05 | 0.57 |

TABLE I-continued

| Res | Pos. | I | II | III | IV | V | VI | VII | VIII | IX | X | XI | XII | XIII |
|---|---|---|---|---|---|---|---|---|---|---|---|---|---|---|
| Gly | 43 | . | . | . | . | . | T | C | 0.63 | * | * | F | 1.35 | 0.73 |
| Arg | 44 | . | . | B | . | . | T | . | 1.09 | * | * | F | 1.49 | 0.84 |
| Ile | 45 | . | . | B | . | . | . | . | 1.04 | * | * | F | 1.78 | 1.63 |
| Glu | 46 | . | . | B | . | . | . | . | 1.00 | * | * | F | 2.12 | 1.63 |
| Pro | 47 | . | . | B | . | . | T | . | 1.24 | * | * | F | 2.51 | 0.83 |
| Arg | 48 | . | . | . | . | T | T | . | 1.70 | * | * | F | 3.40 | 1.17 |
| Gly | 49 | . | . | . | . | T | T | . | 1.24 | * | * | F | 3.06 | 1.32 |
| Gly | 50 | . | . | . | . | T | T | . | 1.54 | * | * | F | 2.57 | 0.84 |
| Gly | 51 | . | . | . | . | . | T | C | 0.73 | * | * | F | 2.03 | 0.44 |
| Arg | 52 | . | . | . | . | . | T | C | 0.73 | * | * | F | 1.39 | 0.36 |
| Gly | 53 | . | . | B | . | . | T | . | 0.31 | * | * | F | 0.85 | 0.57 |
| Ala | 54 | . | . | B | . | . | T | . | 0.36 | . | * | F | 0.85 | 0.83 |
| Leu | 55 | . | . | B | . | . | . | . | 0.10 | . | * | F | 0.65 | 0.57 |
| Pro | 56 | . | . | B | . | . | . | . | 0.10 | . | * | F | −0.25 | 0.57 |
| Thr | 57 | . | . | B | . | . | . | . | −0.01 | . | * | F | −0.25 | 0.55 |
| Ser | 58 | . | . | B | . | . | T | . | 0.30 | . | . | F | 0.10 | 1.16 |
| Met | 59 | . | . | B | . | . | T | . | 0.54 | . | . | F | 0.40 | 1.02 |
| Gly | 60 | . | . | B | . | . | T | . | 1.14 | . | . | F | 0.25 | 0.70 |
| Gln | 61 | . | . | . | . | T | T | . | 1.06 | . | . | F | 0.65 | 0.81 |
| His | 62 | . | . | . | . | . | . | C | 0.78 | . | * | F | 0.40 | 1.10 |
| Gly | 63 | . | . | . | . | . | T | C | 1.19 | . | * | F | 0.60 | 1.12 |
| Pro | 64 | . | . | . | . | . | T | C | 1.20 | . | * | F | 1.20 | 1.27 |
| Ser | 65 | . | . | . | . | . | T | C | 1.66 | . | * | F | 1.05 | 0.94 |
| Ala | 66 | . | . | B | . | . | T | . | 1.07 | . | * | F | 1.30 | 1.86 |
| Arg | 67 | . | . | B | . | . | . | . | 0.76 | * | * | . | 1.29 | 1.22 |
| Ala | 68 | . | . | B | . | . | . | . | 1.21 | * | * | . | 1.48 | 0.90 |
| Arg | 69 | . | . | B | . | . | T | . | 0.83 | . | * | . | 2.17 | 1.74 |
| Ala | 70 | . | . | B | . | . | T | . | 0.92 | . | * | F | 2.51 | 0.90 |
| Gly | 71 | . | . | . | . | T | T | . | 1.17 | . | * | F | 3.40 | 1.37 |
| Arg | 72 | . | . | . | . | . | T | C | 0.84 | . | * | F | 2.71 | 0.69 |
| Ala | 73 | . | . | . | . | . | T | C | 1.54 | * | . | F | 2.48 | 1.06 |
| Pro | 74 | . | . | . | . | . | T | C | 1.22 | * | . | F | 2.70 | 2.10 |
| Gly | 75 | . | . | . | . | . | T | C | 1.22 | * | . | F | 2.62 | 1.66 |
| Pro | 76 | . | . | . | . | . | T | C | 1.68 | * | * | F | 2.24 | 1.66 |
| Arg | 77 | . | . | . | . | . | . | C | 1.57 | * | . | F | 2.60 | 2.10 |
| Pro | 78 | . | A | B | . | . | . | . | 1.57 | * | . | F | 1.94 | 3.68 |
| Ala | 79 | . | A | B | . | . | . | . | 1.48 | * | . | F | 1.68 | 2.40 |
| Arg | 80 | . | A | B | . | . | . | . | 1.61 | * | * | F | 1.42 | 1.64 |
| Glu | 81 | . | A | B | . | . | . | . | 1.93 | * | * | F | 1.16 | 1.64 |
| Ala | 82 | A | A | . | . | . | . | . | 1.01 | * | * | F | 0.90 | 3.19 |
| Ser | 83 | A | . | . | . | . | T | . | 1.33 | * | * | F | 1.30 | 1.34 |
| Pro | 84 | A | . | . | . | . | T | . | 1.07 | * | * | F | 1.30 | 1.52 |
| Arg | 85 | A | . | . | . | . | T | . | 0.92 | * | * | F | 1.00 | 1.12 |
| Leu | 86 | A | . | . | . | . | T | . | 0.97 | . | * | . | 0.85 | 1.13 |
| Arg | 87 | A | . | . | B | . | . | . | 1.24 | . | * | . | 0.75 | 1.46 |
| Val | 88 | A | . | . | B | . | . | . | 0.84 | * | * | . | 0.75 | 1.08 |
| His | 89 | A | . | . | B | . | . | . | 1.10 | . | * | . | −0.15 | 1.13 |
| Lys | 90 | A | . | . | B | . | . | . | 0.29 | . | * | F | 0.90 | 1.16 |
| Thr | 91 | . | . | B | B | . | . | . | 0.24 | * | * | F | 0.00 | 1.35 |
| Phe | 92 | . | . | B | B | . | . | . | −0.72 | * | * | . | −0.30 | 0.74 |
| Lys | 93 | . | . | B | B | . | . | . | −0.72 | * | * | . | −0.30 | 0.27 |
| Phe | 94 | . | . | B | B | . | . | . | −1.03 | * | . | . | −0.60 | 0.14 |
| Val | 95 | . | . | B | B | . | . | . | −1.93 | * | . | . | −0.60 | 0.16 |
| Val | 96 | . | . | B | B | . | . | . | −2.43 | . | * | . | −0.60 | 0.06 |
| Val | 97 | . | . | B | B | . | . | . | −2.54 | . | * | . | −0.60 | 0.06 |
| Gly | 98 | . | . | B | B | . | . | . | −2.59 | . | * | . | −0.60 | 0.06 |
| Val | 99 | . | . | B | B | . | . | . | −2.74 | . | . | . | −0.60 | 0.15 |
| Leu | 100 | . | . | B | B | . | . | . | −2.74 | * | . | . | −0.60 | 0.15 |
| Leu | 101 | . | . | B | B | . | . | . | −2.10 | * | . | . | −0.60 | 0.11 |
| Gln | 102 | . | . | B | B | . | . | . | −1.54 | * | . | . | −0.60 | 0.23 |
| Val | 103 | . | . | B | B | . | . | . | −1.50 | . | . | . | −0.60 | 0.37 |
| Val | 104 | . | . | B | B | . | T | . | −1.23 | . | . | . | −0.20 | 0.61 |
| Pro | 105 | . | . | B | . | . | T | . | −1.01 | * | . | F | 0.25 | 0.35 |
| Ser | 106 | A | . | . | . | . | T | . | −0.51 | * | . | F | −0.05 | 0.48 |
| Ser | 107 | A | . | . | . | . | T | . | −1.40 | * | * | F | 0.25 | 0.94 |
| Ala | 108 | A | . | . | . | . | . | . | −0.50 | * | * | F | 0.05 | 0.43 |
| Ala | 109 | A | . | . | . | . | . | . | −0.46 | . | * | . | 0.50 | 0.63 |
| Thr | 110 | A | . | . | . | . | . | . | −0.28 | . | * | . | −0.10 | 0.39 |
| Ile | 111 | A | . | . | . | . | . | . | 0.02 | . | * | . | −0.10 | 0.53 |
| Lys | 112 | . | . | . | B | . | . | . | 0.32 | . | * | . | 0.50 | 0.87 |
| Leu | 113 | . | . | . | B | . | . | . | 0.61 | . | * | F | 1.05 | 1.04 |
| His | 114 | . | . | . | B | . | . | . | 0.31 | . | * | F | 1.30 | 1.99 |
| Asp | 115 | . | . | . | . | . | T | C | 0.28 | * | * | F | 1.80 | 0.70 |
| Gln | 116 | . | . | . | . | T | T | . | 0.86 | . | . | F | 1.65 | 0.84 |
| Ser | 117 | . | . | . | . | T | T | . | 0.81 | . | . | F | 2.50 | 0.89 |
| Ile | 118 | . | . | . | . | T | T | . | 1.62 | . | . | F | 2.25 | 0.92 |
| Gly | 119 | . | . | . | . | . | . | C | 1.37 | . | . | F | 1.00 | 0.92 |
| Thr | 120 | . | . | . | . | . | . | C | 1.37 | . | . | F | 0.45 | 0.72 |

TABLE I-continued

| Res | Pos. | I | II | III | IV | V | VI | VII | VIII | IX | X | XI | XII | XIII |
|---|---|---|---|---|---|---|---|---|---|---|---|---|---|---|
| Gln | 121 | . | . | B | . | . | . | C | 1.33 | . | . | F | 0.65 | 1.79 |
| Gln | 122 | . | . | B | . | . | . | . | 1.33 | . | . | F | 0.20 | 2.46 |
| Trp | 123 | . | . | B | . | . | . | . | 2.01 | . | . | . | 0.05 | 2.28 |
| Glu | 124 | . | . | . | . | . | . | C | 1.54 | . | . | . | 0.25 | 2.04 |
| His | 125 | . | . | . | . | . | . | C | 1.51 | . | . | . | 0.10 | 0.97 |
| Ser | 126 | . | . | . | . | . | T | C | 1.51 | . | . | F | 0.45 | 0.91 |
| Pro | 127 | . | . | . | . | T | T | . | 0.70 | . | . | F | 1.55 | 0.91 |
| Leu | 128 | . | . | . | . | T | T | . | 0.32 | . | . | F | 0.65 | 0.55 |
| Gly | 129 | . | . | . | . | T | T | . | 0.11 | . | . | F | 0.65 | 0.22 |
| Glu | 130 | . | . | . | . | . | T | . | −0.07 | . | . | F | 0.45 | 0.22 |
| Leu | 131 | . | . | B | . | . | . | . | −0.11 | * | . | . | 0.18 | 0.42 |
| Cys | 132 | . | . | B | . | . | . | . | −0.20 | * | . | F | 1.21 | 0.42 |
| Pro | 133 | . | . | B | . | . | T | . | 0.58 | * | * | F | 1.69 | 0.32 |
| Pro | 134 | . | . | . | . | T | T | . | 1.03 | . | * | F | 1.47 | 0.53 |
| Gly | 135 | . | . | . | . | T | T | . | 0.73 | . | * | F | 2.80 | 1.94 |
| Ser | 136 | . | . | . | . | . | T | C | 1.54 | * | . | F | 2.32 | 1.68 |
| His | 137 | . | . | . | . | . | . | C | 2.32 | * | . | F | 2.48 | 1.88 |
| Arg | 138 | . | . | B | . | . | . | . | 2.32 | * | . | F | 2.34 | 3.72 |
| Ser | 139 | . | . | B | . | . | . | . | 2.19 | * | . | F | 2.40 | 4.29 |
| Glu | 140 | . | . | . | . | . | T | . | 1.94 | * | . | F | 2.86 | 3.12 |
| Arg | 141 | . | . | . | . | T | T | . | 1.58 | * | . | F | 3.40 | 1.61 |
| Pro | 142 | . | . | . | . | T | T | . | 1.61 | . | * | F | 2.91 | 0.64 |
| Gly | 143 | . | . | . | . | T | T | . | 1.61 | . | * | F | 2.57 | 0.60 |
| Ala | 144 | . | . | . | . | T | T | . | 1.24 | . | * | . | 2.08 | 0.60 |
| Cys | 145 | . | . | . | . | T | . | . | 0.93 | . | * | . | 1.41 | 0.21 |
| Asn | 146 | . | . | B | . | . | . | . | 0.82 | . | * | . | 0.84 | 0.30 |
| Arg | 147 | . | . | B | . | . | . | . | 0.69 | * | . | . | 1.01 | 0.52 |
| Cys | 148 | . | . | B | . | . | T | . | 0.18 | * | . | F | 1.83 | 0.96 |
| Thr | 149 | . | . | B | . | . | T | . | 0.42 | * | . | F | 1.70 | 0.44 |
| Glu | 150 | . | . | B | . | . | T | . | 0.84 | * | . | F | 1.53 | 0.22 |
| Gly | 151 | . | . | B | . | . | T | . | 0.53 | * | . | F | 0.76 | 0.65 |
| Val | 152 | . | . | B | B | . | . | . | 0.42 | . | * | F | 0.19 | 0.65 |
| Gly | 153 | . | . | B | B | . | . | . | 0.50 | . | . | . | −0.13 | 0.61 |
| Tyr | 154 | . | . | B | B | . | . | . | 0.51 | . | . | . | −0.60 | 0.62 |
| Thr | 155 | . | . | B | B | . | . | . | 0.51 | . | . | F | −0.30 | 1.12 |
| Asn | 156 | . | . | . | B | . | . | C | 0.86 | . | . | F | 0.20 | 1.81 |
| Ala | 157 | . | . | . | . | T | T | . | 0.90 | . | . | F | 0.80 | 1.86 |
| Ser | 158 | . | . | . | . | T | T | . | 0.54 | . | . | F | 0.80 | 1.06 |
| Asn | 159 | . | . | . | . | T | T | . | 0.20 | . | . | F | 0.35 | 0.57 |
| Asn | 160 | . | . | . | . | T | T | . | −0.16 | * | . | F | 0.35 | 0.57 |
| Leu | 161 | . | A | B | . | . | . | . | −0.97 | * | . | . | −0.60 | 0.23 |
| Phe | 162 | . | A | B | . | . | . | . | −0.59 | . | . | . | −0.60 | 0.12 |
| Ala | 163 | . | A | B | . | . | . | . | −0.96 | . | . | . | −0.60 | 0.11 |
| Cys | 164 | . | A | B | . | . | . | . | −1.27 | * | . | . | −0.60 | 0.07 |
| Leu | 165 | . | . | B | . | . | T | . | −1.86 | . | . | . | −0.20 | 0.12 |
| Pro | 166 | . | . | B | . | . | T | . | −1.71 | * | . | . | −0.20 | 0.12 |
| Cys | 167 | . | . | . | . | T | T | . | −0.97 | * | . | . | 0.20 | 0.12 |
| Thr | 168 | A | . | . | . | . | T | . | −0.68 | . | . | . | 0.10 | 0.30 |
| Ala | 169 | A | . | . | . | . | . | . | −0.01 | . | . | . | 0.50 | 0.26 |
| Cys | 170 | A | . | . | . | . | T | . | 0.80 | . | . | . | 0.70 | 0.80 |
| Lys | 171 | A | . | . | . | . | T | . | 1.01 | . | . | F | 1.15 | 0.96 |
| Ser | 172 | A | . | . | . | . | T | . | 1.68 | . | * | F | 1.30 | 1.65 |
| Asp | 173 | A | . | . | . | . | T | . | 2.10 | . | * | F | 1.30 | 5.33 |
| Glu | 174 | A | A | . | . | . | . | . | 2.39 | . | * | F | 0.90 | 5.22 |
| Glu | 175 | A | A | . | . | . | . | . | 2.84 | . | * | F | 1.24 | 5.22 |
| Glu | 176 | A | A | . | . | . | . | . | 2.13 | . | * | F | 1.58 | 4.83 |
| Arg | 177 | . | A | . | . | T | . | . | 2.12 | . | . | F | 2.32 | 1.50 |
| Ser | 178 | . | . | . | . | . | T | C | 1.81 | . | . | F | 2.86 | 1.25 |
| Pro | 179 | . | . | . | . | T | T | . | 1.50 | * | . | F | 3.40 | 1.04 |
| Cys | 180 | . | . | . | . | T | T | . | 1.61 | * | . | F | 2.61 | 0.77 |
| Thr | 181 | . | . | . | . | T | T | . | 1.61 | * | . | F | 2.67 | 1.12 |
| Thr | 182 | . | . | . | . | T | . | . | 1.19 | * | * | F | 2.38 | 1.16 |
| Thr | 183 | . | . | . | . | T | T | . | 0.90 | . | . | F | 2.49 | 3.13 |
| Arg | 184 | . | . | . | . | T | T | . | 0.44 | . | . | F | 2.40 | 2.19 |
| Asn | 185 | . | . | . | . | T | T | . | 1.11 | . | . | F | 2.50 | 0.81 |
| Thr | 186 | . | . | . | . | T | T | . | 0.76 | * | . | F | 2.25 | 0.98 |
| Ala | 187 | . | . | . | . | T | . | . | 1.11 | * | . | . | 1.65 | 0.27 |
| Cys | 188 | . | . | . | . | T | . | . | 1.21 | * | . | . | 1.40 | 0.33 |
| Gln | 189 | . | . | B | . | . | . | . | 0.76 | * | . | . | 0.75 | 0.36 |
| Cys | 190 | . | . | B | . | . | . | . | 0.44 | . | . | . | 0.50 | 0.35 |
| Lys | 191 | . | . | B | . | . | T | . | 0.06 | . | * | F | 0.85 | 0.94 |
| Pro | 192 | . | . | . | . | T | T | . | 0.76 | . | . | F | 0.65 | 0.47 |
| Gly | 193 | . | . | . | . | T | T | . | 1.42 | . | * | F | 1.74 | 1.72 |
| Thr | 194 | . | . | B | . | . | T | . | 1.42 | . | * | F | 1.68 | 1.38 |
| Phe | 195 | . | . | B | . | . | T | . | 2.09 | . | * | F | 1.82 | 1.49 |
| Arg | 196 | . | . | . | . | T | . | . | 1.74 | . | * | F | 2.56 | 2.42 |
| Asn | 197 | . | . | . | . | T | T | . | 1.37 | . | * | F | 3.40 | 2.25 |
| Asp | 198 | . | . | . | . | T | T | . | 1.71 | . | * | F | 3.06 | 2.63 |

TABLE I-continued

| Res | Pos. | I | II | III | IV | V | VI | VII | VIII | IX | X | XI | XII | XIII |
|---|---|---|---|---|---|---|---|---|---|---|---|---|---|---|
| Asn | 199 | . | . | . | . | . | T | C | 1.42 | . | * | F | 2.52 | 2.32 |
| Ser | 200 | A | . | . | . | . | T | . | 1.46 | . | * | F | 1.98 | 1.43 |
| Ala | 201 | A | . | . | . | . | . | . | 1.46 | . | * | . | 1.14 | 0.46 |
| Glu | 202 | A | . | . | . | . | . | . | 1.50 | * | . | . | 0.80 | 0.56 |
| Met | 203 | A | . | . | . | . | . | . | 0.83 | * | . | . | 1.11 | 0.83 |
| Cys | 204 | A | . | . | . | . | T | . | 0.53 | * | . | . | 1.62 | 0.44 |
| Arg | 205 | . | . | . | . | . | T | T | 0.52 | * | . | . | 2.33 | 0.34 |
| Lys | 206 | . | . | . | . | . | T | T | 0.77 | * | . | F | 2.49 | 0.50 |
| Cys | 207 | . | . | . | . | . | T | T | 0.10 | * | . | F | 3.10 | 0.92 |
| Ser | 208 | . | . | . | . | . | T | . | 0.49 | * | * | F | 2.59 | 0.25 |
| Thr | 209 | . | . | . | . | . | T | . | 1.27 | * | * | F | 1.98 | 0.19 |
| Gly | 210 | . | . | . | . | . | T | . | 0.81 | * | . | F | 1.67 | 0.71 |
| Cys | 211 | . | . | B | . | . | T | . | 0.17 | * | * | F | 1.16 | 0.53 |
| Pro | 212 | . | . | . | . | . | T | T | −0.02 | * | * | F | 1.25 | 0.36 |
| Arg | 213 | . | . | . | . | . | T | T | 0.32 | * | * | F | 0.65 | 0.27 |
| Gly | 214 | . | . | B | . | . | T | . | −0.22 | * | * | . | 0.85 | 1.01 |
| Met | 215 | . | . | B | B | . | . | . | 0.17 | * | * | . | 0.30 | 0.48 |
| Val | 216 | . | . | B | B | . | . | . | 0.83 | * | * | . | 0.79 | 0.49 |
| Lys | 217 | . | . | B | B | . | . | . | 0.38 | * | * | . | 0.98 | 0.83 |
| Val | 218 | . | . | B | B | . | . | . | −0.04 | * | * | F | 1.32 | 0.45 |
| Lys | 219 | . | . | B | B | . | . | . | 0.09 | . | * | F | 1.51 | 0.88 |
| Asp | 220 | . | . | B | . | . | . | . | 0.40 | . | * | F | 1.90 | 0.68 |
| Cys | 221 | . | . | B | . | . | . | . | 0.96 | . | * | F | 0.81 | 0.96 |
| Thr | 222 | . | . | . | . | . | T | C | 0.91 | * | * | F | 1.62 | 0.65 |
| Pro | 223 | . | . | . | . | T | T | . | 0.88 | * | * | F | 1.63 | 0.65 |
| Trp | 224 | . | . | . | . | T | T | . | 0.83 | . | * | F | 0.54 | 0.84 |
| Ser | 225 | A | . | . | . | . | T | . | 0.17 | . | . | F | 1.00 | 1.01 |
| Asp | 226 | A | A | . | . | . | . | . | −0.02 | . | . | F | 0.45 | 0.35 |
| Ile | 227 | A | A | . | . | . | . | . | 0.26 | * | . | . | −0.30 | 0.25 |
| Glu | 228 | A | A | . | . | . | . | . | 0.51 | * | . | . | 0.30 | 0.25 |
| Cys | 229 | . | A | B | . | . | . | . | 0.80 | * | . | . | 0.60 | 0.30 |
| Val | 230 | A | A | . | . | . | . | . | 0.80 | * | * | . | 0.60 | 0.74 |
| His | 231 | A | A | . | . | . | . | . | 0.46 | * | * | . | 0.60 | 0.58 |
| Lys | 232 | A | A | . | . | . | . | . | 1.34 | * | . | F | 0.60 | 1.06 |
| Glu | 233 | . | A | . | . | T | . | . | 1.00 | * | . | F | 1.30 | 2.30 |
| Ser | 234 | . | . | . | . | T | T | . | 1.63 | * | . | F | 1.70 | 1.68 |
| Gly | 235 | . | . | . | . | T | T | . | 2.49 | * | . | F | 1.70 | 1.14 |
| Asn | 236 | . | . | . | . | T | T | . | 1.63 | * | . | F | 1.40 | 1.06 |
| Gly | 237 | . | . | . | . | . | T | C | 1.30 | * | . | F | 0.45 | 0.55 |
| His | 238 | . | . | . | B | . | . | C | 0.44 | . | . | . | −0.40 | 0.59 |
| Asn | 239 | . | . | . | B | . | . | C | −0.14 | . | . | . | −0.40 | 0.27 |
| Ile | 240 | . | . | B | B | . | . | . | −0.61 | . | . | . | −0.60 | 0.19 |
| Trp | 241 | . | . | B | B | . | . | . | −1.47 | . | . | . | −0.60 | 0.12 |
| Val | 242 | . | . | B | B | . | . | . | −1.98 | . | . | . | −0.60 | 0.05 |
| Ile | 243 | . | . | B | B | . | . | . | −2.26 | . | . | . | −0.60 | 0.06 |
| Leu | 244 | . | . | B | B | . | . | . | −3.07 | . | . | . | −0.60 | 0.08 |
| Val | 245 | . | . | B | B | . | . | . | −3.03 | . | . | . | −0.60 | 0.09 |
| Val | 246 | . | . | B | B | . | . | . | −3.60 | . | . | . | −0.60 | 0.09 |
| Thr | 247 | . | . | B | B | . | . | . | −2.96 | . | . | . | −0.60 | 0.08 |
| Leu | 248 | . | . | B | B | . | . | . | −2.88 | . | . | . | −0.60 | 0.17 |
| Val | 249 | . | . | B | B | . | . | . | −2.88 | . | * | . | −0.60 | 0.19 |
| Val | 250 | . | . | B | B | . | . | . | −2.83 | . | . | . | −0.60 | 0.11 |
| Pro | 251 | . | . | B | B | . | . | . | −2.83 | . | . | . | −0.60 | 0.11 |
| Leu | 252 | . | . | B | B | . | . | . | −3.11 | . | . | . | −0.60 | 0.11 |
| Leu | 253 | A | . | . | B | . | . | . | −3.16 | . | . | . | −0.60 | 0.15 |
| Leu | 254 | A | . | . | B | . | . | . | −3.11 | . | . | . | −0.60 | 0.07 |
| Val | 255 | A | . | . | B | . | . | . | −3.14 | . | . | . | −0.60 | 0.07 |
| Ala | 256 | A | . | . | B | . | . | . | −3.79 | . | . | . | −0.60 | 0.06 |
| Val | 257 | . | . | B | B | . | . | . | −3.64 | . | . | . | −0.60 | 0.05 |
| Leu | 258 | . | . | B | B | . | . | . | −3.50 | . | . | . | −0.60 | 0.04 |
| Ile | 259 | . | . | B | B | . | . | . | −3.36 | . | . | . | −0.60 | 0.02 |
| Val | 260 | . | . | B | B | . | . | . | −3.39 | . | . | . | −0.60 | 0.02 |
| Cys | 261 | . | . | B | B | . | . | . | −3.14 | . | . | . | −0.60 | 0.01 |
| Cys | 262 | . | . | B | B | . | . | . | −2.59 | . | . | . | −0.60 | 0.02 |
| Cys | 263 | . | . | B | B | . | . | . | −2.12 | . | . | . | −0.60 | 0.03 |
| Ile | 264 | . | . | B | B | . | . | . | −1.90 | . | . | . | −0.60 | 0.06 |
| Gly | 265 | . | . | . | . | T | T | . | −1.39 | . | . | F | 0.35 | 0.06 |
| Ser | 266 | . | . | . | . | T | T | . | −1.07 | . | . | F | 0.35 | 0.11 |
| Gly | 267 | . | . | . | . | T | T | . | −0.40 | . | . | F | 0.65 | 0.16 |
| Cys | 268 | . | . | . | . | T | T | . | 0.06 | . | . | F | 1.25 | 0.27 |
| Gly | 269 | . | . | . | . | . | T | . | 0.99 | . | * | F | 1.39 | 0.31 |
| Gly | 270 | . | . | . | . | . | T | . | 0.67 | . | . | F | 2.03 | 0.62 |
| Asp | 271 | . | . | . | . | . | T | C | 0.37 | . | . | F | 2.37 | 0.62 |
| Pro | 272 | . | . | . | . | T | T | . | 0.71 | * | * | F | 2.91 | 0.62 |
| Lys | 273 | . | . | . | . | T | T | . | 1.49 | * | * | F | 3.40 | 1.05 |
| Cys | 274 | . | . | B | . | . | T | . | 0.98 | * | * | . | 2.51 | 1.23 |
| Met | 275 | . | . | B | B | . | . | . | 0.66 | * | * | . | 1.62 | 0.59 |
| Asp | 276 | . | . | B | B | . | . | . | −0.04 | * | * | . | 1.28 | 0.16 |

TABLE I-continued

| Res | Pos. | I | II | III | IV | V | VI | VII | VIII | IX | X | XI | XII | XIII |
|---|---|---|---|---|---|---|---|---|---|---|---|---|---|---|
| Arg | 277 | . | . | B | B | . | . | . | −0.12 | . | * | . | 0.04 | 0.26 |
| Val | 278 | . | . | B | B | . | . | . | −0.06 | . | * | . | −0.60 | 0.27 |
| Cys | 279 | . | . | B | B | . | . | . | −0.20 | . | . | . | 0.30 | 0.32 |
| Phe | 280 | . | . | B | B | . | . | . | 0.06 | . | * | . | −0.60 | 0.13 |
| Trp | 281 | . | . | B | B | . | . | . | −0.76 | . | . | . | −0.60 | 0.18 |
| Arg | 282 | . | . | B | B | . | . | . | −1.68 | . | . | . | −0.60 | 0.28 |
| Leu | 283 | . | . | B | B | . | . | . | −0.71 | . | . | . | −0.60 | 0.26 |
| Gly | 284 | . | . | . | B | T | . | . | −0.39 | . | * | . | −0.20 | 0.49 |
| Leu | 285 | . | . | . | B | . | . | C | 0.10 | . | * | . | 0.50 | 0.25 |
| Leu | 286 | . | . | . | B | . | . | C | 0.04 | . | * | . | 0.20 | 0.46 |
| Arg | 287 | . | . | . | B | . | . | C | −0.66 | . | . | F | 0.65 | 0.46 |
| Gly | 288 | . | . | . | . | . | T | C | 0.16 | . | . | F | 1.35 | 0.57 |
| Pro | 289 | . | . | . | . | . | T | C | 0.50 | . | * | F | 2.70 | 1.19 |
| Gly | 290 | . | . | . | . | . | T | C | 1.31 | * | * | F | 3.00 | 1.01 |
| Ala | 291 | A | . | . | . | . | T | . | 1.53 | . | * | F | 2.50 | 1.65 |
| Glu | 292 | A | . | . | . | . | . | . | 1.39 | . | . | F | 2.00 | 1.08 |
| Asp | 293 | A | . | . | . | . | . | . | 1.73 | . | . | F | 1.70 | 1.48 |
| Asn | 294 | A | . | . | . | . | T | . | 1.94 | . | * | . | 1.45 | 2.36 |
| Ala | 295 | A | . | . | . | . | T | . | 1.40 | . | . | . | 1.15 | 2.36 |
| His | 296 | A | . | . | . | . | T | . | 1.18 | * | . | . | 1.00 | 0.99 |
| Asn | 297 | A | . | . | . | . | T | . | 0.88 | . | . | . | 0.10 | 0.51 |
| Glu | 298 | A | . | . | . | . | . | . | 0.88 | * | . | . | −0.10 | 0.67 |
| Ile | 299 | A | . | . | . | . | . | . | 0.29 | * | * | . | −0.10 | 0.80 |
| Leu | 300 | A | . | . | . | . | . | . | 0.88 | * | * | . | −0.10 | 0.50 |
| Ser | 301 | A | . | . | . | . | . | . | 0.61 | * | . | F | 0.65 | 0.48 |
| Asn | 302 | A | . | . | . | . | T | . | −0.20 | * | . | F | 0.25 | 0.92 |
| Ala | 303 | A | . | . | . | . | T | . | −0.50 | * | . | F | 0.25 | 0.92 |
| Asp | 304 | A | . | . | . | . | T | . | 0.08 | * | . | F | 0.85 | 0.92 |
| Ser | 305 | . | . | . | . | . | T | C | 0.19 | * | . | F | 1.05 | 0.83 |
| Leu | 306 | . | . | . | B | . | . | C | −0.37 | * | . | F | 0.05 | 0.71 |
| Ser | 307 | . | . | B | B | . | . | . | −0.67 | * | . | F | −0.15 | 0.31 |
| Thr | 308 | . | . | B | B | . | . | . | −0.08 | * | . | . | −0.60 | 0.31 |
| Phe | 309 | . | . | B | B | . | . | . | −0.08 | * | . | . | −0.30 | 0.66 |
| Val | 310 | A | . | . | B | . | . | . | 0.22 | . | . | F | −0.15 | 0.85 |
| Ser | 311 | A | A | . | . | . | . | . | 0.43 | . | . | F | 0.00 | 1.03 |
| Glu | 312 | A | A | . | . | . | . | . | 0.73 | . | . | F | 0.00 | 1.17 |
| Gln | 313 | A | A | . | . | . | . | . | 0.74 | . | . | F | 0.90 | 2.73 |
| Gln | 314 | A | A | . | . | . | . | . | 1.44 | . | . | F | 0.90 | 2.73 |
| Met | 315 | A | A | . | . | . | . | . | 2.30 | . | . | F | 0.90 | 2.73 |
| Glu | 316 | A | A | . | . | . | . | . | 2.39 | . | . | F | 0.90 | 2.73 |
| Ser | 317 | A | A | . | . | . | . | . | 1.80 | . | * | F | 0.90 | 2.44 |
| Gln | 318 | A | A | . | . | . | . | . | 1.80 | . | * | F | 0.90 | 2.49 |
| Glu | 319 | A | A | . | . | . | . | . | 0.99 | . | * | F | 0.90 | 2.40 |
| Pro | 320 | A | A | . | . | . | . | . | 1.28 | . | * | F | 0.90 | 1.48 |
| Ala | 321 | A | A | . | . | . | . | . | 0.93 | . | . | F | 0.60 | 1.23 |
| Asp | 322 | A | A | . | B | . | . | . | 0.38 | . | . | F | 0.45 | 0.70 |
| Leu | 323 | A | A | . | B | . | . | . | 0.07 | . | . | F | −0.15 | 0.34 |
| Thr | 324 | . | A | B | B | . | . | . | −0.79 | . | . | F | −0.15 | 0.48 |
| Gly | 325 | . | A | B | B | . | . | . | −0.58 | . | . | . | −0.30 | 0.21 |
| Val | 326 | . | . | B | B | . | . | . | −0.29 | . | . | . | −0.60 | 0.45 |
| Thr | 327 | . | . | B | B | . | . | . | −0.50 | . | . | . | −0.60 | 0.42 |
| Val | 328 | . | . | B | B | . | . | . | −0.03 | . | * | F | −0.17 | 0.65 |
| Gln | 329 | . | . | B | B | . | . | . | 0.28 | . | * | F | 0.11 | 0.87 |
| Ser | 330 | . | . | . | . | . | T | C | 0.03 | . | * | F | 2.04 | 1.05 |
| Pro | 331 | . | . | . | . | . | T | C | 0.89 | . | * | F | 2.32 | 1.42 |
| Gly | 332 | . | . | . | . | T | T | . | 0.53 | . | * | F | 2.80 | 1.42 |
| Glu | 333 | A | . | . | . | . | T | . | 0.58 | . | * | F | 1.97 | 0.57 |
| Ala | 334 | . | . | B | . | . | . | . | −0.23 | . | * | . | 0.74 | 0.30 |
| Gln | 335 | . | . | B | . | . | . | . | −0.28 | . | . | . | 0.46 | 0.25 |
| Cys | 336 | . | . | B | . | . | . | . | −0.28 | . | . | . | 0.18 | 0.14 |
| Leu | 337 | . | . | B | . | . | . | . | −0.52 | . | * | . | −0.40 | 0.22 |
| Leu | 338 | . | . | B | . | . | . | . | −0.52 | . | * | . | −0.40 | 0.13 |
| Gly | 339 | . | A | . | . | . | . | C | −0.52 | . | * | F | 0.05 | 0.42 |
| Pro | 340 | A | A | . | . | . | . | . | −0.52 | . | * | F | −0.15 | 0.51 |
| Ala | 341 | A | A | . | . | . | . | . | −0.20 | . | * | F | 0.60 | 1.07 |
| Glu | 342 | A | A | . | . | . | . | . | 0.31 | . | * | F | 0.90 | 1.07 |
| Ala | 343 | A | A | . | . | . | . | . | 1.12 | * | * | F | 0.75 | 0.93 |
| Glu | 344 | A | A | . | . | . | . | . | 1.58 | . | * | F | 0.90 | 1.60 |
| Gly | 345 | A | A | . | . | . | . | . | 1.90 | . | * | F | 0.90 | 1.80 |
| Ser | 346 | A | . | . | . | . | T | . | 2.60 | . | * | F | 1.30 | 3.50 |
| Gln | 347 | A | . | . | . | . | T | . | 1.79 | . | * | F | 1.30 | 3.96 |
| Arg | 348 | A | . | . | . | . | T | . | 1.57 | . | * | F | 1.30 | 3.30 |
| Arg | 349 | . | . | B | . | . | T | . | 0.71 | . | * | F | 1.30 | 2.03 |
| Arg | 350 | . | . | B | B | . | . | . | 0.84 | . | * | F | 0.75 | 0.87 |
| Leu | 351 | . | . | B | B | . | . | . | 0.56 | . | * | . | 0.60 | 0.69 |
| Leu | 352 | . | . | B | B | . | . | . | 0.56 | . | * | . | 0.30 | 0.35 |
| Val | 353 | . | . | B | B | . | . | . | 0.10 | * | * | . | −0.30 | 0.29 |
| Pro | 354 | . | . | B | . | . | T | . | −0.60 | * | . | . | −0.20 | 0.35 |

TABLE I-continued

| Res | Pos. | I | II | III | IV | V | VI | VII | VIII | IX | X | XI | XII | XIII |
|---|---|---|---|---|---|---|---|---|---|---|---|---|---|---|
| Ala | 355 | . | . | . | . | T | T | . | −0.71 | . | * | . | 0.50 | 0.43 |
| Asn | 356 | . | . | . | . | . | T | C | −0.11 | . | . | F | 1.65 | 0.96 |
| Gly | 357 | . | . | . | . | . | T | C | 0.39 | . | . | F | 1.95 | 0.96 |
| Ala | 358 | . | . | . | . | . | . | C | 1.24 | . | . | F | 2.20 | 1.37 |
| Asp | 359 | . | . | . | . | . | T | C | 1.14 | . | . | F | 3.00 | 1.48 |
| Pro | 360 | A | . | . | . | . | T | . | 0.92 | * | . | F | 2.50 | 2.16 |
| Thr | 361 | A | . | . | . | . | T | . | 0.32 | . | . | F | 1.90 | 1.76 |
| Glu | 362 | A | . | . | . | . | T | . | −0.14 | . | . | F | 1.60 | 1.04 |
| Thr | 363 | A | . | . | B | . | . | . | −0.26 | . | . | F | 0.15 | 0.56 |
| Leu | 364 | A | . | . | B | . | . | . | −0.96 | * | . | . | −0.60 | 0.33 |
| Met | 365 | A | . | . | B | . | . | . | −0.74 | * | . | . | −0.60 | 0.17 |
| Leu | 366 | A | . | . | B | . | . | . | −0.39 | * | . | . | −0.60 | 0.19 |
| Phe | 367 | A | . | . | B | . | . | . | −1.09 | * | . | . | −0.60 | 0.47 |
| Phe | 368 | A | . | . | B | . | . | . | −1.37 | * | . | . | −0.60 | 0.41 |
| Asp | 369 | A | . | . | B | . | . | . | −0.56 | * | . | . | −0.60 | 0.50 |
| Lys | 370 | A | A | . | . | . | . | . | −0.84 | * | . | . | −0.30 | 0.93 |
| Phe | 371 | A | A | . | B | . | . | . | −0.89 | * | . | . | −0.30 | 0.75 |
| Ala | 372 | A | A | . | B | . | . | . | −0.40 | * | . | . | −0.30 | 0.34 |
| Asn | 373 | . | A | B | B | . | . | . | −0.40 | * | . | . | −0.60 | 0.26 |
| Ile | 374 | . | A | B | B | . | . | . | −0.40 | * | . | . | −0.60 | 0.26 |
| Val | 375 | . | A | B | B | . | . | . | −0.74 | . | . | . | −0.60 | 0.43 |
| Pro | 376 | . | A | . | B | . | . | C | −0.33 | . | . | . | −0.10 | 0.36 |
| Phe | 377 | . | . | . | . | T | T | . | 0.26 | . | . | . | 0.20 | 0.54 |
| Asp | 378 | . | . | . | . | T | T | . | 0.26 | . | . | F | 0.80 | 1.21 |
| Ser | 379 | . | . | . | . | T | T | . | 0.33 | . | . | F | 1.40 | 1.35 |
| Trp | 380 | A | . | . | . | . | T | . | 0.59 | * | * | F | 0.40 | 1.29 |
| Asp | 381 | A | . | . | . | . | . | . | 0.91 | * | . | F | −0.15 | 0.76 |
| Gln | 382 | A | A | . | . | . | . | . | 1.61 | * | . | . | −0.15 | 1.11 |
| Leu | 383 | A | A | . | . | . | . | . | 0.80 | * | . | . | −0.15 | 1.84 |
| Met | 384 | A | A | . | . | . | . | . | 1.10 | * | . | . | 0.30 | 0.91 |
| Arg | 385 | A | A | . | . | . | . | . | 0.58 | * | . | . | 0.30 | 0.87 |
| Gln | 386 | A | A | . | . | . | . | . | 0.27 | * | . | . | −0.30 | 0.87 |
| Leu | 387 | A | A | . | . | . | . | . | 0.31 | * | . | . | 0.45 | 1.27 |
| Asp | 388 | A | A | . | . | . | . | . | 1.12 | * | . | . | 0.75 | 1.30 |
| Leu | 389 | A | A | . | . | . | . | . | 1.72 | * | . | F | 0.60 | 1.21 |
| Thr | 390 | A | . | . | . | . | T | . | 0.72 | * | . | F | 1.30 | 2.54 |
| Lys | 391 | A | . | . | . | . | T | . | 0.72 | . | * | F | 1.30 | 1.07 |
| Asn | 392 | A | . | . | . | . | T | . | 0.68 | * | * | F | 1.30 | 2.16 |
| Glu | 393 | A | . | . | . | . | T | . | −0.18 | * | . | F | 1.30 | 1.11 |
| Ile | 394 | . | . | B | B | . | . | . | 0.74 | * | . | F | 0.75 | 0.41 |
| Asp | 395 | . | . | B | B | . | . | . | 0.47 | * | * | . | 0.60 | 0.50 |
| Val | 396 | . | . | B | B | . | . | . | 0.08 | * | * | . | 0.60 | 0.29 |
| Val | 397 | . | . | B | B | . | . | . | −0.23 | . | . | . | 0.51 | 0.41 |
| Arg | 398 | . | . | B | . | . | T | . | −0.82 | * | . | . | 1.12 | 0.36 |
| Ala | 399 | . | . | B | . | . | T | . | −0.28 | . | . | . | 0.73 | 0.49 |
| Gly | 400 | . | . | . | . | T | T | . | −0.49 | * | . | F | 2.09 | 0.65 |
| Thr | 401 | . | . | . | . | . | T | C | 0.02 | * | * | F | 2.10 | 0.51 |
| Ala | 402 | . | . | . | . | . | . | C | 0.88 | * | * | F | 1.09 | 0.50 |
| Gly | 403 | . | . | . | . | . | T | C | 0.18 | * | * | F | 1.68 | 0.85 |
| Pro | 404 | . | . | . | . | . | T | C | −0.04 | . | . | F | 1.47 | 0.59 |
| Gly | 405 | . | . | . | . | . | T | C | 0.06 | . | . | F | 1.26 | 0.48 |
| Asp | 406 | A | . | . | . | . | T | . | −0.22 | . | . | F | 0.25 | 0.76 |
| Ala | 407 | A | A | . | . | . | . | . | −0.23 | . | . | . | −0.30 | 0.50 |
| Leu | 408 | A | A | . | . | . | . | . | −0.70 | . | . | . | −0.60 | 0.50 |
| Tyr | 409 | A | A | . | . | . | . | . | −1.09 | * | . | . | −0.60 | 0.25 |
| Ala | 410 | A | A | . | . | . | . | . | −0.70 | * | . | . | −0.60 | 0.24 |
| Met | 411 | A | A | . | . | . | . | . | −0.99 | * | . | . | −0.60 | 0.59 |
| Leu | 412 | A | A | . | . | . | . | . | −1.26 | * | . | . | −0.60 | 0.39 |
| Met | 413 | A | A | . | . | . | . | . | −0.44 | * | . | . | −0.60 | 0.29 |
| Lys | 414 | A | A | . | B | . | . | . | −0.16 | * | . | . | −0.60 | 0.47 |
| Trp | 415 | A | A | . | B | . | . | . | 0.12 | * | . | . | 0.15 | 1.14 |
| Val | 416 | A | A | . | B | . | . | . | 0.38 | * | * | . | 0.45 | 1.66 |
| Asn | 417 | A | . | . | . | . | T | . | 1.30 | * | . | F | 1.75 | 0.82 |
| Lys | 418 | A | . | . | . | . | T | . | 1.90 | * | . | F | 2.20 | 1.53 |
| Thr | 419 | . | . | . | . | . | T | C | 1.27 | * | . | F | 3.00 | 3.32 |
| Gly | 420 | . | . | . | . | . | T | C | 1.26 | * | . | F | 2.70 | 2.08 |
| Arg | 421 | . | . | . | . | T | . | . | 1.22 | * | . | F | 2.40 | 1.40 |
| Asn | 422 | . | . | . | . | . | T | C | 1.19 | * | . | F | 1.65 | 0.68 |
| Ala | 423 | . | . | B | . | . | T | . | 0.83 | . | . | . | 1.00 | 0.93 |
| Ser | 424 | . | . | B | . | . | T | . | 0.33 | . | . | . | 0.70 | 0.69 |
| Ile | 425 | . | . | B | . | . | T | . | −0.13 | . | * | . | −0.20 | 0.35 |
| His | 426 | . | A | B | . | . | . | . | −0.24 | . | * | . | −0.60 | 0.29 |
| Thr | 427 | . | A | B | . | . | . | . | −0.83 | * | * | . | −0.60 | 0.36 |
| Leu | 428 | A | A | . | . | . | . | . | −1.06 | * | * | . | −0.60 | 0.52 |
| Leu | 429 | A | A | . | . | . | . | . | −0.76 | * | * | . | −0.60 | 0.31 |
| Asp | 430 | A | A | . | . | . | . | . | 0.24 | * | * | . | −0.30 | 0.38 |
| Ala | 431 | A | A | . | . | . | . | . | −0.32 | * | * | . | 0.30 | 0.89 |
| Leu | 432 | A | A | . | . | . | . | . | −0.01 | * | * | . | 0.75 | 1.07 |

TABLE I-continued

| Res | Pos. | I | II | III | IV | V | VI | VII | VIII | IX | X | XI | XII | XIII |
|-----|------|---|----|----|----|---|----|----|------|----|----|----|----|------|
| Glu | 433 | A | A | . | . | . | . | . | 0.80 | * | * | . | 0.75 | 1.11 |
| Arg | 434 | A | A | . | . | . | . | . | 1.72 | * | * | F | 0.90 | 1.90 |
| Met | 435 | A | A | . | . | . | . | . | 1.69 | * | * | F | 0.90 | 4.52 |
| Glu | 436 | A | A | . | . | . | . | . | 1.69 | * | * | F | 0.90 | 3.55 |
| Glu | 437 | A | A | . | . | . | . | . | 2.54 | * | . | F | 0.90 | 1.83 |
| Arg | 438 | A | A | . | . | . | . | . | 2.54 | * | * | F | 0.90 | 3.70 |
| His | 439 | A | A | . | . | . | . | . | 2.48 | * | * | F | 0.90 | 3.70 |
| Ala | 440 | A | A | . | . | . | . | . | 2.19 | * | * | F | 0.90 | 4.28 |
| Lys | 441 | A | A | . | . | . | . | . | 2.19 | * | * | F | 0.90 | 1.53 |
| Glu | 442 | A | A | . | . | . | . | . | 2.19 | * | . | F | 0.90 | 1.95 |
| Lys | 443 | A | A | . | . | . | . | . | 1.27 | * | * | F | 0.90 | 3.22 |
| Ile | 444 | A | A | . | . | . | . | . | 0.49 | * | * | F | 0.90 | 1.33 |
| Gln | 445 | A | A | . | . | . | . | . | 0.22 | * | * | F | 0.75 | 0.63 |
| Asp | 446 | A | A | . | . | . | . | . | 0.18 | * | * | F | −0.15 | 0.23 |
| Leu | 447 | A | A | . | . | . | . | . | −0.12 | * | . | . | −0.30 | 0.56 |
| Leu | 448 | A | A | . | . | . | . | . | −0.51 | * | . | . | 0.55 | 0.43 |
| Val | 449 | A | A | . | . | . | . | . | 0.42 | * | . | F | 0.95 | 0.26 |
| Asp | 450 | A | . | . | . | . | T | . | −0.28 | * | . | F | 1.60 | 0.62 |
| Ser | 451 | . | . | . | . | T | T | . | −1.17 | * | . | F | 2.25 | 0.65 |
| Gly | 452 | . | . | . | . | T | T | . | −0.60 | * | . | F | 2.50 | 0.62 |
| Lys | 453 | . | . | B | . | . | T | . | −0.60 | . | . | F | 1.25 | 0.58 |
| Phe | 454 | . | A | B | . | . | . | . | 0.26 | . | . | . | 0.15 | 0.36 |
| Ile | 455 | . | A | B | . | . | . | . | 0.26 | . | . | . | 0.20 | 0.62 |
| Tyr | 456 | . | A | B | . | . | . | . | 0.21 | . | . | . | 0.55 | 0.52 |
| Leu | 457 | . | A | B | . | . | . | . | 0.24 | . | . | . | −0.03 | 0.59 |
| Glu | 458 | . | A | B | . | . | . | . | −0.14 | . | . | F | 0.54 | 1.22 |
| Asp | 459 | . | A | . | . | T | . | . | 0.26 | . | . | F | 1.66 | 0.77 |
| Gly | 460 | . | . | . | . | T | T | . | 0.56 | . | . | F | 2.78 | 1.26 |
| Thr | 461 | . | . | . | . | . | T | C | −0.06 | * | . | F | 2.70 | 0.73 |
| Gly | 462 | . | . | . | . | . | T | C | 0.46 | * | . | F | 2.13 | 0.33 |
| Ser | 463 | . | . | . | . | . | T | C | −0.36 | . | . | F | 1.26 | 0.44 |
| Ala | 464 | A | . | . | . | . | . | . | −0.36 | . | . | . | 0.14 | 0.25 |
| Val | 465 | . | . | B | . | . | . | . | −0.40 | . | . | . | 0.17 | 0.44 |
| Ser | 466 | . | . | B | . | . | . | . | −0.48 | . | . | . | −0.10 | 0.42 |
| Leu | 467 | . | . | B | . | . | . | . | −0.52 | . | . | . | −0.10 | 0.53 |
| Glu | 468 | A | . | . | . | . | . | . | −0.61 | . | . | . | 0.50 | 0.92 |

Preferred nucleic acid fragments of the invention encode a full-length DR4 polypeptide lacking the nucleotides encoding the amino-terminal methionine (nucleotides 19-21 in SEQ ID NO:1) as it is known that the methionine is cleaved naturally and such sequences maybe useful in genetically engineering DR4 expression vectors. Polypeptides encoded by such polynucleotides are also contemplated by the invention.

Among highly preferred fragments in this regard are those that comprise, or alternatively consist of, regions of DR4 that combine several structural features, such as several of the features set out above. Preferred nucleic acid fragments of the present invention further include nucleic acid molecules encoding a polypeptide comprising, or alternatively consisting of, one, two, three, four, five, or more epitope-bearing portions of the DR4 protein. In particular, such nucleic acid fragments of the present invention include nucleic acid molecules encoding: a polypeptide comprising, or alternatively consisting of, amino acid residues from about 35 to about 92 in SEQ ID NO:2; a polypeptide comprising, or alternatively consisting of, amino acid residues from about 114 to about 160 in SEQ ID NO:2; a polypeptide comprising, or alternatively consisting of, amino acid residues from about 169 to about 240 in SEQ ID NO:2; a polypeptide comprising, or alternatively consisting of, amino acid residues from about 267 to about 298 in SEQ ID NO:2; a polypeptide comprising, or alternatively consisting of, amino acid residues from about 330 to about 364 in SEQ ID NO:2; a polypeptide comprising, or alternatively consisting of, amino acid residues from about 391 to about 404 in SEQ ID NO:2; and a polypeptide comprising, or alternatively consisting of, amino acid residues from about 418 to about 465 in SEQ ID NO:2. In this context "about" includes the particularly recited size, larger or smaller by several (5, 4, 3, 2, or 1) amino acid residues, at either terminus or at both termini. The inventors have determined that the above polypeptide fragments are antigenic regions of the DR4 protein. Methods for determining other such epitope-bearing portions of the DR4 protein are described in detail below. Polypeptides encoded by these nucleic acids are also encompassed by the invention.

In specific embodiments, the polynucleotides of the invention are less than 100000 kb, 50000 kb, 10000 kb, 1000 kb, 500 kb, 400 kb, 350 kb, 300 kb, 250 kb, 200 kb, 175 kb, 150 kb, 125 kb, 100 kb, 75 kb, 50 kb, 40 kb, 30 kb, 25 kb, 20 kb, 15 kb, 10 kb, 7.5 kb, or 5 kb in length.

In further embodiments, polynucleotides of the invention comprise, or alternatively consist of, at least 15, at least 30, at least 50, at least 100, or at least 250, at least 500, or at least 1000 contiguous nucleotides of DR4 coding sequence, but consist of less than or equal to 1000 kb, 500 kb, 250 kb, 200 kb, 150 kb, 100 kb, 75 kb, 50 kb, 30 kb, 25 kb, 20 kb, 15 kb, 10 kb, or 5 kb of genomic DNA that flanks the 5' or 3' coding nucleotide set forth in SEQ ID NO: 1. In further embodiments, polynucleotides of the invention comprise, or alternatively consist of, at least 15, at least 30, at least 50, at least 100, or at least 250, at least 500, or at least 1000 contiguous nucleotides of DR4 coding sequence, but do not comprise all or a portion of any DR4 intron. In another embodiment, the nucleic acid comprising, or alternatively consisting of, DR4 coding sequence does not contain coding sequences of a genomic flanking gene (i.e., 5' or 3' to the DR4 gene in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

In addition, the invention provides nucleic acid molecules having nucleotide sequences related to extensive portions of SEQ ID NO:1 as follows: HTOIY07R (SEQ ID NO:6) and HTXEY80R (SEQ ID NO:7) both shown in FIG. 4.

Further, the invention includes a polynucleotide comprising, or alternatively consisting of, any portion of at least about 30 nucleotides, preferably at least about 50 nucleotides, of SEQ ID NO:1 from residue 365 to 1,422. In this context "about" includes the particularly recited size, larger or smaller by several (5, 4, 3, 2, or 1) nucleotides, at either terminus or at both termini.

In another embodiment, the invention provides an isolated nucleic acid molecule comprising, or alternatively consisting of, a polynucleotide which hybridizes under stringent hybridization conditions to a portion of the polynucleotide in a nucleic acid molecule of the invention described above, for instance, the sequence complementary to the coding and/or noncoding (i.e., transcribed, untranslated) sequence depicted in SEQ ID NO:1, the cDNA contained in ATCC Deposit No. 97853, and the sequence encoding a DR4 domain or a polynucleotide fragment as described herein. By "stringent hybridization conditions" is intended overnight incubation at 42° C. in a solution comprising, or alternatively consisting of: 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C. Polypeptides encoded by these nucleic acids are also encompassed by the invention.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70 nt of the reference polynucleotide. In this context "about" includes the particularly recited size, larger or smaller by several (5, 4, 3, 2, or 1) nucleotides, at either terminus or at both termini. By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in SEQ ID NO:1. These have uses, which include, but are not limited to, as diagnostic probes and primers as discussed above and in more detail below.

Of course, a polynucleotide which hybridizes only to a poly A sequence (such as the 3 terminal poly(A) tract of the DR4 cDNA shown in SEQ ID NO:1), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA).

As indicated, nucleic acid molecules of the present invention which encode the DR4 polypeptide may include, but are not limited to the coding sequence for the mature polypeptide, by itself; the coding sequence for the mature polypeptide and additional sequences, such as those encoding a leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al., *Proc. Natl. Acad. Sci. USA* 86:821-824 (1989), for instance, hexa-histidine provides for convenient purification of the fusion protein. The HA tag corresponds to an epitope derived of influenza hemagglutinin protein, which has been described by Wilson et al., *Cell* 37:767 (1984), for instance.

The present invention further relates to variants of the nucleic acid molecules of the present invention, which encode for fragments, analogs or derivatives of the DR4 polypeptide. Variants may occur naturally, such as an allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions which may involve one or more nucleotides. The variants may be altered in coding or non-coding regions or both. Alterations in the coding regions may produce conservative or non-conservative amino acid substitutions, deletions or additions. Especially preferred among these are silent substitutions, additions and deletions, which do not alter the properties and functional activities of the DR4 receptor or portions thereof. Also especially preferred in this regard are conservative substitutions.

Further embodiments of the invention include isolated nucleic acid molecules that are at least 80% identical, and more preferably at least 85%, 90%, 92%, 95%, 96%, 97%, 98% or 99% identical, to (a) a nucleotide sequence encoding the full-length DR4 polypeptide having the complete amino acid sequence in SEQ ID NO:2, including the predicted leader sequence; (b) nucleotide sequence encoding the full-length DR4 polypeptide having the complete amino acid sequence in SEQ ID NO:2, including the predicted leader sequence but lacking the amino terminal methionine; (c) a nucleotide sequence encoding the mature DR4 polypeptide (full-length polypeptide with the leader removed) having the amino acid sequence at positions about 24 to about 468 in SEQ ID NO:2; (d) a nucleotide sequence encoding the full-length DR4 polypeptide having the complete amino acid sequence including the leader encoded by the cDNA contained in ATCC Deposit No. 97853; (e) a nucleotide sequence encoding the full-length DR4 polypeptide having the complete amino acid sequence including the leader but lacking the amino terminal methionine encoded by the cDNA contained in ATCC Deposit No. 97853; (f) a nucleotide sequence encoding the mature DR4 polypeptide having the amino acid sequence encoded by the cDNA contained in ATCC Deposit No. 97853; (g) a nucleotide sequence that encodes the DR4 extracellular domain having the amino acid sequence at positions about 24 to about 238 in SEQ ID NO:2, or the DR4 extracellular domain encoded by the cDNA contained in ATCC Deposit No. 97853; (h) a nucleotide sequence that encodes the DR4 transmembrane domain having the amino acid sequence at positions about 239 to about 264 in SEQ ID NO:2, or the DR4 transmembrane domain encoded by the cDNA contained in ATCC Deposit No. 97853; (i) a nucleotide sequence that encodes the DR4 intracellular domain having the amino acid sequence at positions about 265 to about 468 in SEQ ID NO:2, or the DR4 intracellular domain encoded by the cDNA contained in ATCC Deposit No. 97853; (j) a nucleotide sequence that encodes the DR4 death domain having the amino acid sequence at positions about 379 to about 422 in SEQ ID NO:2, or the DR4 death domain encoded by the cDNA contained in ATCC Deposit No. 97853; (k) a nucleotide sequence that encodes the DR4 cysteine rich domain having the amino acid sequence at positions about 131 to about 229 in SEQ ID NO:2, or the DR4 cysteine rich domain encoded by the cDNA contained in ATCC Deposit No. 97853; (l) a nucleotide sequence that encodes the DR4 receptor extracellular and intracellular domains with all or part of the transmembrane domain deleted; (m) a nucleotide sequence that encodes a fragment of the polypeptide of (c) having DR4 functional activity (e.g., antigenic or biological activity); or (n) a nucleotide sequence complementary to any of the nucleotide sequences in (a), (b), (c), (d), (e), (f), (g), (h), (i), (j), (k), (l), or (m) above. In this context "about" includes the particularly recited size, larger or smaller by several (5, 4, 3, 2, or 1) amino acid residues, at either terminus or at both termini. Polypeptides encoded by these nucleic acids are also encompassed by the invention.

By a polynucleotide having a nucleotide sequence at least, for example, 95% "identical" to a reference nucleotide sequence encoding a DR4 polypeptide is intended that the nucleotide sequence of the polynucleotide is identical to the reference sequence except that the polynucleotide sequence may include up to five mismatches per each 100 nucleotides of the reference nucleotide sequence encoding the DR4 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mismatches of the reference sequence may occur at the 5' or 3' terminal positions of the reference nucleotide sequence or anywhere between those terminal positions, interspersed either individually among nucleotides in the reference sequence or in one or more contiguous groups within the reference sequence. The reference (query) sequence may be the entire DR4 nucleotide sequence shown in SEQ ID NO:1 or any fragment (e.g., a polynucleotide encoding the amino acid sequence of a DR4 N- and/or C-terminal deletion described herein) as described herein.

As a practical matter, whether any particular nucleic acid molecule is at least 80%, 85%, 90%, 92%, 95%, 96%, 97%, 98% or 99% identical to, for instance, the nucleotide sequence shown in SEQ ID NO:1 or to the nucleotide sequences of the deposited cDNA can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2:482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237-245 (1990)). Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

The present application is directed to nucleic acid molecules at least 80%, 85%, 90%, 92%, 95%, 96%, 97%, 98% or 99% identical to the nucleic acid sequence shown in SEQ ID NO:1 or to the nucleic acid sequence of the deposited cDNAs, irrespective of whether they encode a polypeptide having DR4 functional activity. This is because even where a particular nucleic acid molecule does not encode a polypeptide having DR4 functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having DR4 functional activity include, inter alia, (1) isolating the DR4 gene or allelic variants thereof in a cDNA library; (2) in situ hybridization (e.g., "FISH") to metaphase chromosomal spreads to provide precise chromosomal location of the DR4 gene, as described in Verma et al., *Human Chromosomes: A*

*Manual of Basic Techniques*, Pergamon Press, New York (1988); and (3) Northern Blot analysis for detecting DR4 mRNA expression in specific tissues.

Preferred, however, are nucleic acid molecules having sequences at least 80%, 85%, 90%, 92%, 95%, 96%, 97%, 98% or 99% identical to the nucleic acid sequence shown in SEQ ID NO:1 or to the nucleic acid sequence of the deposited cDNAs which do, in fact, encode a polypeptide having DR4 protein functional activity. By "a polypeptide having DR4 protein functional activity" is intended polypeptides exhibiting activity similar, but not necessarily identical, to an activity of the DR4 protein of the invention (either the full-length protein (i.e. complete) or, preferably, the mature protein), as measured in a particular functional and/or biological assay. For example, DR4 polypeptide functional activity can be measured by the ability of a polypeptide sequence described herein to form multimers (e.g., homodimers and homotrimers) with complete DR4, and to bind a DR4 ligand (e.g., TRAIL). These functional assays can be routinely performed using techniques described herein and otherwise known in the art.

For example, DR4 protein functional activity (e.g., biological activity) can routinely be measured using the cell death assays performed essentially as previously described (A. M. Chinnaiyan, et al., *Cell* 81, 505-12 (1995); M. P. Boldin, et al., *J Biol Chem* 270, 7795-8 (1995); F. C. Kischkel, et al., *EMBO* 14, 5579-5588 (1995); A. M. Chinnaiyan, et al., *J Biol Chem* 271, 4961-4965 (1996)) or as set forth in Example 5, below. In MCF7 cells, plasmids encoding full-length DR4 or a candidate death domain containing receptors are co-transfected with the pLantern reporter construct encoding green fluorescent protein. Nuclei of cells transfected with DR4 will exhibit apoptotic morphology as assessed by DAPI staining. Similar to TNFR-1 and Fas/APO-1 (M. Muzio, et al., *Cell* 85, 817-827 (1996); M. P. Boldin, et al., *Cell* 85, 803-815 (1996); M. Tewari, et al., *J Biol Chem* 270, 3255-60 (1995)), DR4-induced apoptosis is blocked by the inhibitors of ICE-like proteases, CrmA and z-VAD-fmk.

Of course, due to the degeneracy of the genetic code, one of ordinary skill in the art will immediately recognize that a large number of the nucleic acid molecules having a sequence at least 80%, 85%, 90%, 92%, 95%, 96%, 97%, 98% or 99% identical to, for example, the nucleic acid sequence of the deposited cDNA or the nucleic acid sequence shown in SEQ ID NO:1 will encode "a polypeptide having DR4 protein functional activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having DR4 protein functional activity. This is because the skilled artisan is fully aware of amino acid substitutions that are either less likely or not likely to significantly effect protein function (e.g., replacing one aliphatic amino acid with a second aliphatic amino acid), as further described below.

For example, guidance concerning how to make phenotypically silent amino acid substitutions is provided in Bowie, J. U. et al., "Deciphering the Message in Protein Sequences: Tolerance to Amino Acid Substitutions," *Science* 247:1306-1310 (1990), wherein the authors indicate that proteins are surprisingly tolerant of amino acid substitutions.

Polynucleotide Assays

This invention is also related to the use of the DR4 polynucleotides to detect complementary polynucleotides such as, for example, as a diagnostic reagent. Detection of a mutated form of DR4 associated with a dysfunction will provide a diagnostic tool that can add or define a diagnosis of a disease or susceptibility to a disease which results from under-expression over-expression or altered expression of DR4 or a soluble form thereof, such as, for example, tumors or autoimmune disease.

Individuals carrying mutations in the DR4 gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR prior to analysis. (Saiki et al., *Nature* 324:163-166 (1986)). RNA or cDNA may also be used in the same ways. As an example, PCR primers complementary to the nucleic acid encoding DR4 can be used to identify and analyze DR4 expression and mutations. For example, deletions and insertions can be detected by a change in size of the amplified product in comparison to the normal genotype. Point mutations can be identified by hybridizing amplified DNA to radiolabeled DR4RNA or alternatively, radiolabeled DR4 antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science* 230:1242 (1985)).

Sequence changes at specific locations also may be revealed by nuclease protection assays, such as RNase and S1 protection or the chemical cleavage method (e.g., Cotton et al., *Proc. Natl. Acad. Sci. USA* 85: 4397-4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In addition to more conventional gel-electrophoresis and DNA sequencing, mutations also can be detected by in situ analysis.

Vectors and Host Cells

The present invention also relates to vectors which include DNA molecules of the present invention, host cells which are genetically engineered with vectors of the invention and the production of polypeptides of the invention by recombinant techniques.

Host cells can be genetically engineered to incorporate nucleic acid molecules and express polypeptides of the present invention. The polynucleotides may be introduced alone or with other polynucleotides. Such other polynucleotides may be introduced independently, co-introduced or introduced joined to the polynucleotides of the invention.

In accordance with this aspect of the invention the vector may be, for example, a plasmid vector, a single or double-stranded phage vector, a single or double-stranded RNA or DNA viral vector. Such vectors may be introduced into cells as polynucleotides, preferably DNA, by well-known techniques for introducing DNA and RNA into cells. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

A great variety of expression vectors can be used to express a polypeptide of the invention. Such vectors include chromosomal, episomal and virus-derived vectors e.g., vectors derived from bacterial plasmids, from bacteriophage, from yeast episomes, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The DNA sequence in the expression vector is operatively linked to appropriate expression control sequence(s)), including, for instance, a promoter to direct mRNA transcription. Representatives of such promoters include the phage lambda PL promoter, the *E. coli* lac, trp and tac promoters, the SV40 early and late promoters and promoters of retroviral LTRs, to name just a few of the well-known promoters. In general, expression constructs will contain sites for transcription, initiation and termination, and, in the transcribed region, a ribosome binding site for translation. The coding portion of the mature transcripts expressed by the constructs will include a translation initiating AUG at the beginning and a termination codon (UAA, UGA or UAG) appropriately positioned at the end of the polypeptide to be translated.

In addition, the constructs may contain control regions that regulate as well as engender expression. Generally, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing *E. coli* and other bacteria.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Hosts for of a great variety of expression constructs are well known, and those of skill will be enabled by the present disclosure readily to select a host for expressing a polypeptides in accordance with this aspect of the present invention.

Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors available to those of skill in the art.

Selection of appropriate vectors and promoters for expression in a host cell is a well-known procedure and the requisite techniques for expression vector construction, introduction of the vector into the host and expression in the host are routine skills in the art.

The present invention also relates to host cells containing the above-described vector constructs described herein, and additionally encompasses host cells containing nucleotide sequences of the invention that are operably associated with one or more heterologous control regions (e.g., promoter and/or enhancer) using techniques known of in the art. The host cell can be a higher eukaryotic cell, such as a mammalian cell (e.g., a human derived cell), or a lower eukaryotic cell, such as a yeast cell, or the host cell can be a prokaryotic cell, such as a bacterial cell. The host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., phosphorylation, cleavage) of proteins. Appropriate cell lines can be chosen to ensure the desired modifications and processing of the foreign protein expressed.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods in Molecular Biology* (1986).

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., DR4 coding sequence), and/or to include genetic material (e.g., heterologous polynucleotide sequences) that is operably associated with DR4 polynucleotides of the invention, and which activates, alters, and/or amplifies endogenous DR4 polynucleotides. For example, techniques known in the art may be used to operably associate heterologous control regions (e.g., promoter and/or enhancer) and endogenous DR4 polynucleotide sequences via homologous recombination (see, e.g., U.S. Pat. No. 5,641,670, issued Jun. 24, 1997; International Publication Number WO 96/29411, published Sep. 26, 1996; International Publication Number WO 94/12650, published Aug. 4, 1994; Koller et al., Proc. Natl. Acad. Sci. USA 86:8932-8935 (1989); and Zijlstra et al., Nature 342:435-438 (1989), the disclosures of each of which are incorporated by reference in their entireties).

The polypeptide may be expressed in a modified form, such as a fusion protein, and may include not only secretion signals but also additional heterologous functional regions. Such a fusion protein can be made by ligating polynucleotides of the invention and the desired nucleic acid sequence encoding the desired amino acid sequence to each other, by methods known in the art, in the proper reading frame, and expressing the fusion protein product by methods known in the art. Alternatively, such a fusion protein can be made by protein synthetic techniques, e.g., by use of a peptide synthesizer. Thus, for instance, a region of additional amino acids, particularly charged amino acids, may be added to the N-terminus of the polypeptide to improve stability and persistence in the host cell, during purification or during subsequent handling and storage. Also, region also may be added to the polypeptide to facilitate purification. Such regions may be removed prior to final preparation of the polypeptide. For example, in one embodiment, polynucleotides encoding DR4 polypeptides of the invention may be fused to the pelB pectate lyase signal sequence to increase the efficiency to expression and purification of such polypeptides in Gram-negative bacteria. See, U.S. Pat. Nos. 5,576,195 and 5,846,818, the contents of which are herein incorporated by reference in their entireties.

The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5-receptor has been fused with Fc portions for the purpose of high-throughput screening assays to identify antagonists of hIL-5. See, D. Bennett et al., *Journal of Molecular Recognition*, Vol. 8:52-58 (1995) and K. Johanson et al., *The Journal of Biological Chemistry*, Vol. 270, No. 16:9459-9471 (1995).

As mentioned, DR4 polypeptides may be modified by either natural processes, such as posttranslational processing, or by chemical modification techniques which are well known in the art. It will be appreciated that the same type of modification may be present in the same or varying degrees at several sites in a given DR4 polypeptide. Also, a given DR4 polypeptide may contain many types of modifications. DR4 polypeptides may be branched, for example, as a result of ubiquitination, and they may be cyclic, with or without branching. Cyclic, branched, and branched cyclic DR4 polypeptides may result from posttranslational natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W.H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992).)

The DR4 can be recovered and purified from chemical synthesis and recombinant cell cultures by standard methods which include, but are not limited to, ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. Most preferably, high performance liquid chromatography ("HPLC") is employed for purification.

DR4 polynucleotides and polypeptides may be used in accordance with the present invention for a variety of applications, particularly those that make use of the chemical and biological properties of DR4. Among these are applications in the treatment and prevention of tumors, parasitic infections, bacterial infections, viral infections, restenosis, and graft vs. host disease; to induce resistance to parasites, bacteria and viruses; to induce proliferation of T-cells, endothelial cells and certain hematopoietic cells; to regulate anti-viral responses; and to treat and prevent certain autoimmune diseases after stimulation of DR4 by an agonist. Additional applications relate to diagnosis, treatment, and prevention of disorders of cells, tissues and organisms. These aspects of the invention are discussed further below.

DR4Proteins and Fragments

The invention further provides for DR4 proteins containing polypeptide sequences encoded by the polynucleotides of the invention.

The DR4 proteins of the invention may be in monomers or multimers (i.e., dimers, trimers, tetramers, and higher multimers). Accordingly, the present invention relates to monomers and multimers of the DR4 proteins of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only DR4 proteins of the invention (including DR4 fragments, variants, and fusion proteins, as described herein). These homomers may contain DR4 proteins having identical or different polypeptide sequences. In a specific embodiment, a homomer of the invention is a multimer containing only DR4 proteins having an identical polypeptide sequence. In another specific embodiment, a homomer of the invention is a multimer containing DR4 proteins having different polypeptide sequences. In specific embodiments, the multimer of the invention is a homodimer (e.g., containing DR4 proteins having identical or different polypeptide sequences) or a homotrimer (e.g., containing DR4 proteins having identical or different polypeptide sequences). In additional embodiments, the homomeric multimer of the invention is at least a homodimer, at least a homotrimer, or at least a homotetramer.

As used herein, the term heteromer refers to a multimer containing heterologous proteins (i.e., proteins containing only polypeptide sequences that do not correspond to a polypeptide sequences encoded by the DR4 gene) in addition to the DR4 proteins of the invention. In a specific embodiment, the multimer of the invention is a heterodimer, a heterotrimer, or a heterotetramer. In additional embodiments, the homomeric multimer of the invention is at least a homodimer, at least a homotrimer, or at least a homotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when proteins of the invention contact one another in solution. In another embodiment, heteromultimers of the invention, such as, for example, heterotrimers or heterotetramers, are formed when proteins of the invention contact antibodies to the polypeptides of the invention (including antibodies to the heterologous polypeptide sequence in a fusion protein of the invention) in solution. In other embodiments, multimers of the invention are formed by covalent associations with and/or between the DR4 proteins of the invention. Such covalent associations may involve one or more amino acid residues contained in the polypeptide sequence of the protein (e.g., the polypeptide sequence recited in SEQ ID NO: 2 or the polypeptide encoded by the deposited cDNA). In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a DR4 fusion protein. In one example, covalent associations are between the heterologous sequence contained in a fusion protein of the invention (see, e.g., U.S. Pat. No. 5,478,925). In a specific example, the covalent associations are between the heterologous sequence contained in a DR4-Fc fusion protein of the invention (as described herein). In another specific example, covalent associations of fusion proteins of the invention are between heterologous polypeptide sequences from another TNF family ligand/receptor member that is capable of forming covalently associated multimers, such as for example, oseteoprotegerin (see, e.g., International Publication No. WO 98/49305, the contents of which are herein incorporated by reference in its entirety).

The multimers of the invention may be generated using chemical techniques known in the art. For example, proteins desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the polypeptide sequence of the proteins desired to be contained in the multimer (see, e.g., U.S. Pat. No. 5,478,925, which is herein incorporated by reference in its entirety). Further, proteins of the invention may be routinely modified by the addition of cysteine or biotin to the C-terminus or N-terminus of the polypeptide sequence of the protein and techniques known in the art may be applied to generate multimers containing one or more of these modified proteins (see, e.g., U.S. Pat. No. 5,478,925, which is herein incorporated by reference in its entirety). Additionally, techniques known in the art may be applied to generate liposomes containing the protein components desired to be contained in the multimer of the invention (see, e.g., U.S. Pat. No. 5,478,925, which is herein incorporated by reference in its entirety).

Alternatively, multimers of the invention may be generated using genetic engineering techniques known in the art.

In one embodiment, proteins contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain and which can be incorporated by membrane reconstitution techniques into liposomes (see, e.g., U.S. Pat. No. 5,478,925, which is herein incorporated by reference in its entirety).

The polypeptides of the present invention are preferably provided in an isolated form, and preferably are substantially purified. Accordingly, in one embodiment, the invention further provides an isolated DR4 polypeptide having the amino acid sequence encoded by the deposited cDNA, or the amino acid sequence shown in SEQ ID NO:2 or a peptide or polypeptide portion (i.e., fragment) comprising a portion of the above polypeptides.

Polypeptide fragments of the present invention include polypeptides comprising, or alternatively consisting of, an amino acid sequence contained in SEQ ID NO:2, encoded by the cDNA contained in the deposited plasmid, or encoded by nucleic acids which hybridize (e.g., under stringent hybridization conditions) to the nucleotide sequence contained in the deposited plasmid, or shown in SEQ ID NO:1 or the complementary strand thereto. Protein fragments may be "free-standing," or comprised within a larger polypeptide of which the fragment forms a part or region, most preferably as a single continuous region. Representative examples of polypeptide fragments of the invention, include, for example, fragments that comprise, or alternatively consisting of, from about amino acid residues: 1 to 23, 24 to 43, 44 to 63, 64 to 83, 84 to 103, 104 to 123, 124 to 143, 144 to 163, 164 to 183, 184 to 203, 204 to 223, 224 to 238, 239 to 264, 265 to 284, 285 to 304, 305 to 324, 325 to 345, 346 to 366, 367 to 387, 388 to 418, 419 to 439, and/or 440 to the end of the coding region of SEQ ID NO:2. Additional representative examples of polypeptide fragments of the invention, include, for example, fragments that comprise, or alternatively consisting of, from about amino acid residues: 1-60, 11-70, 21-80, 31-90, 41-100, 51-110, 61-120, 71-130, 81-140, 91-150, 101-160, 111-170, 121-180, 131-190, 141-200, 151-210, 161-220, 171-230, 181-240, 191-250, 201-260, 211-270, 221-280, 231-290, 241-300, 251-310, 261-320, 271-330, 281-340, 291-350, 301-360, 311-370, 321-380, 331-390, 341-400, 351-410, 361-420, 371-430, 381-440, 391-450, and/or 401-468 of SEQ ID NO:2, as well as isolated polynucleotides which encode these polypeptides. In this context "about" includes the particularly recited value, larger or smaller by several (5, 4, 3, 2, or 1) amino acids, at either extreme or at both extremes. Moreover, polypeptide fragments can be at least about 10, 20, 30, 40, 50, 60, 70, 80, 90, 100, 110, 120, 130, 140, 150, 175 or 200 amino acids in length. Polynucleotides encoding these polypeptides are also encompassed by the invention.

Preferred polypeptide fragments of the present invention include a member selected from the group: a polypeptide comprising, or alternatively consisting of, the DR4 receptor extracellular domain (predicted to constitute amino acid residues from about 24 to about 238 in SEQ ID NO:2); a polypeptide comprising, or alternatively consisting of, the DR4 cysteine rich domain (predicted to constitute amino acid residues from about 131 to about 229 in SEQ ID NO:2); a polypeptide comprising, or alternatively consisting of, the DR4 receptor transmembrane domain (predicted to constitute amino acid residues from about 239 to about 264 in SEQ ID NO:2); a polypeptide comprising, or alternatively consisting of, a fragment of the predicted mature DR4 polypeptide, wherein the fragment has a DR4 functional activity (e.g., antigenic activity or biological activity); a polypeptide comprising, or alternatively consisting of, the DR4 receptor intracellular domain (predicted to constitute amino acid residues from about 265 to about 468 in SEQ ID NO:2); a polypeptide comprising, or alternatively consisting of, the DR4 receptor extracellular and intracellular domains with all or part of the transmembrane domain deleted; a polypeptide comprising, or alternatively consisting of, the DR4 receptor death domain (predicted to constitute amino acid residues from about 379 to about 422 in SEQ ID NO:2); and a polypeptide comprising, or alternatively consisting of, one, two, three, four or more, epitope bearing portions of the DR4 receptor protein. In additional embodiments, the polypeptide fragments of the invention comprise, or alternatively consist of, any combination of 1, 2, 3, 4, 5, 6, 7, or all 8 of the above members. As above, with the leader sequence, the amino acid residues constituting the DR4 receptor extracellular, transmembrane and intracellular domains have been predicted by computer analysis. Thus, as one of ordinary skill would appreciate, the amino acid residues constituting these domains may vary slightly (e.g., by about 1 to about 15 amino acid residues) depending on the criteria used to define each domain. Polynucleotides encoding these polypeptides are also encompassed by the invention.

As discussed above, it is believed that one or both of the extracellular cysteine rich motifs of DR4 is important for interactions between DR4 and its ligands (e.g., TRAIL). Accordingly, in preferred embodiments, polypeptide fragments of the invention comprise, or alternatively consist of, amino acid residues 131 to 183, and/or 184 to 229 of SEQ ID NO:2. In a specific embodiment the polypeptides of the invention comprise, or alternatively consist of, both of the extracellular cysteine rich motifs disclosed in SEQ ID NO:2. Polynucleotides encoding these polypeptide fragments are also encompassed by the invention.

Among the especially preferred polypeptide fragments of the invention are fragments comprising, or alternatively consisting of, structural or functional attributes of DR4. Such fragments include amino acid residues that comprise, or alternatively consisting of, one, two, three, four or more of the following functional domains: alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) DR4. Certain preferred regions are those set out in FIG. 3 and Table I and include, but are not limited to, regions of the aforementioned types identified by analysis of the amino acid sequence depicted in SEQ ID NO:2, such preferred regions include; Garnier-Robson predicted alpha-regions, beta-regions, turn-regions, and coil-regions; Chou-Fasman predicted alpha-regions, beta-regions, and turn-regions; Kyte-Doolittle predicted hydrophilic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

The present invention encompasses polypeptides comprising, or alternatively consisting of, an epitope of the polypeptide having an amino acid sequence of SEQ ID NO:2, or an epitope of the polypeptide sequence encoded by a polynucleotide sequence contained in the cDNA assigned ATCC Accession No. 97853, encoded by a polynucleotide that hybridizes to the complement of the sequence of SEQ ID NO:1, or contained in the cDNA assigned ATCC Accession No. 97853 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., *Proc. Natl. Acad. Sci. USA* 81:3998-4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments that function as epitopes may be produced by any conventional means. (See, e.g., Houghten, *Proc. Natl. Acad. Sci. USA* 82:5131-5135 (1985), further described in U.S. Pat. No. 4,631,211).

Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767-778 (1984) at 777.

In the present invention, antigenic epitopes preferably contain a sequence of at least 4, at least 5, at least 6, at least 7, more preferably at least 8, at least 9, at least 10, at least 15, at least 20, at least 25, and, most preferably, between about 15 to about 30 amino acids contained within the amino acid sequence of a polypeptide of the invention. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Antigenic epitopes are useful, for example, to raise antibodies, including monoclonal antibodies, that specifically bind the epitope. Antigenic epitopes can be used as the target molecules in immunoassays. (See, for instance, Wilson et al., *Cell* 37:767-778 (1984); Sutcliffe et al., *Science* 219:660-666 (1983)). Polynucleotides encoding these polypeptides are also encompassed by the invention.

Similarly, immunogenic epitopes can be used, for example, to induce antibodies according to methods well known in the art. (See, for instance, Sutcliffe et al., supra; Wilson et al., supra; Chow et al., *Proc. Natl. Acad. Sci. USA* 82:910-914; and Bittle et al., *J. Gen. Virol.* 66:2347-2354 (1985). A preferred immunogenic epitope includes the secreted protein. The polypeptides comprising one or more immunogenic epitopes may be presented for eliciting an antibody response together with a carrier protein, such as an albumin, to an animal system (such as, for example, rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., *J. Gen. Virol.,* 66:2347-2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as, for example, rabbits, rats, and mice are immunized with either free or carrier-coupled peptides, for instance, by intraperitoneal and/or intradermal injection of emulsions containing about 100 micrograms of peptide or carrier protein and Freund's adjuvant or any other adjuvant known for stimulating an immune response. Several booster injections may be needed, for instance, at intervals of about two weeks, to provide a useful titer of anti-peptide antibody that can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. *Science* 219:660-666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Non-limiting examples of antigenic polypeptides or peptides that can be used to generate DR4-specific antibodies include: a polypeptide comprising, or alternatively consisting of, amino acid residues from about 35 to about 92 in SEQ ID NO:2; a polypeptide comprising, or alternatively consisting of, amino acid residues from about 114 to about 160 in SEQ ID NO:2; a polypeptide comprising, or alternatively consisting of, amino acid residues from about 169 to about 240 in SEQ ID NO:2; a polypeptide comprising, or alternatively consisting of, amino acid residues from about 267 to about 298 in SEQ ID NO:2; a polypeptide comprising, or alternatively consisting of, amino acid residues from about 330 to about 364 in SEQ ID NO:2; a polypeptide comprising, or alternatively consisting of, amino acid residues from about 391 to about 404 in SEQ ID NO:2; and a polypeptide comprising, or alternatively consisting of, amino acid residues from about 418 to about 465 in SEQ ID NO:2. In this context "about" includes the particularly recited range, larger or smaller by several (5, 4, 3, 2, or 1) amino acid residues, at either terminus or at both termini. As indicated above, the inventors have determined that the above polypeptide fragments are antigenic regions of the DR4 protein. Polynucleotides encoding these polypeptides are also encompassed by the invention.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., *Nature,* 331:84-86 (1988). IgG Fusion proteins that have a disulfide-linked dimeric structure due to the IgG portion disulfide bonds have also been found to be more efficient in binding and neutralizing other molecules than monomeric polypeptides or fragments thereof alone.

See, e.g., Fountoulakis et al., *J. Biochem.*, 270:3958-3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix-binding domain for the fusion protein. Extracts from cells infected with the recombinant vaccinia virus are loaded onto $Ni^{2+}$ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811, 238; 5,830,721; 5,834,252; and 5,837,458, and Patten et al., Curr. Opinion Biotechnol. 8:724-33 (1997); Harayama, Trends Biotechnol. 16(2):76-82 (1998); Hansson et al., J. Mol. Biol. 287:265-76 (1999); and Lorenzo and Blasco, Biotechniques 24(2):308-13 (1998) (each of these patents and publications are hereby incorporated by reference in its entirety). In one embodiment, alteration of polynucleotides corresponding to SEQ ID NO:1 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide coding a polypeptide of the invention may be recombined with one or more components, motifs, sections, parts, domains, fragments, etc. of one or more heterologous molecules.

As one of skill in the art will appreciate, DR4 polypeptides of the present invention and the epitope-bearing fragments thereof described herein (e.g., corresponding to a portion of the extracellular domain such as, for example, amino acid residues 1 to 240 of SEQ ID NO:2) can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84-86 (1988)). Fusion proteins that have a disulfide-linked dimeric structure due to the IgG part can also be more efficient in binding and neutralizing other molecules than the monomeric DR4 protein or protein fragment alone (Fountoulakis et al., *J Biochem* 270:3958-3964 (1995)).

The epitope-bearing peptides and polypeptides of the invention may be produced by any conventional means. Houghten, R. A., "General method for the rapid solid-phase synthesis of large numbers of peptides: specificity of antigenantibody interaction at the level of individual amino acids," *Proc. Natl. Acad. Sci. USA* 82:5131-5135 (1985). This "Simultaneous Multiple Peptide Synthesis (SMPS)" process is further described in U.S. Pat. No. 4,631,211 to Houghten et al. (1986).

To improve or alter the characteristics of DR4 polypeptides, protein engineering may be employed. Recombinant DNA technology known to those skilled in the art can be used to create novel mutant proteins or "muteins" including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron et al., *J. Biol. Chem.*, 268:2984-2988 (1993) reported modified KGF proteins that had heparin binding activity even if 3, 8, or 27 amino-terminal amino acid residues were missing. In the present case, since the protein of the invention is a member of the death domain containing receptor (DDCR) polypeptide family, deletions of N-terminal amino acids up to the cysteine residue at position 132 in SEQ ID NO:2 may retain some biological activity such as the ability to induce apoptosis. Polypeptides having further N-terminal deletions including the cysteine residue at position 132 (C-132) in SEQ ID NO:2 would not be expected to retain such biological activities because this residue is conserved among family members, see FIG. 2, and may be required for forming a disulfide bridge to provide structural stability which is needed for receptor binding.

However, even if deletion of one or more amino acids from the N-terminus of a protein results in modification or loss of one or more biological functions of the protein, other functional activities (e.g., biological activities, ability to multimerize, ability to bind DR4 ligand (e.g., TRAIL)) may still be retained. For example, the ability of shortened DR4 muteins to induce and/or bind to antibodies which recognize the complete or mature forms of the DR4 polypeptides of the invention (preferably antibodies that bind specifically to DR4) generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that an DR4 mutein with a large number of deleted N-terminal amino acid residues may retain some biological or immunogenic activities. In fact, peptides composed of as few as six DR4 amino acid residues may often evoke an immune response.

Accordingly, the present invention further provides polypeptides having one or more residues deleted from the amino terminus of the DR4 amino acid sequence shown in SEQ ID NO:2, up to the serine residue at position number 463 and polynucleotides encoding such polypeptides. In particular, the present invention provides polypeptides comprising, or alternatively consisting of, the amino acid sequence of residues n¹-468 of SEQ ID NO:2, where n¹ is an integer from 2 to 463 corresponding to the position of the amino acid residue in SEQ ID NO:2.

More in particular, the invention provides polynucleotides encoding polypeptides comprising, or alternatively consisting of, the amino acid sequence of residues of A-2 to E-468; P-3 to E-468; P4 to E-468; P-5 to E-468; A-6 to E-468; R-7 to E-468; V-8 to E-468; H-9 to E-468; L-10 to E-468; G-11 to E-468; A-12 to E-468; F-13 to E-468; L-14 to E-468; A-15 to E-468; V-16 to E-468; T-17 to E-468; P-18 to E-468; N-19 to E-468; P-20 to E-468; G-21 to E-468; S-22 to E-468; A-23 to E-468; A-24 to E-468; S-25 to E-468; G-26 to E-468; T-27 to E-468; E-28 to E-468; A-29 to E-468; A-30 to E-468; A-31 to E-468; A-32 to E-468; T-33 to E-468; P-34 to E-468; S-35 to E-468; K-36 to E-468; V-37 to E-468; W-38 to E-468; G-39 to E-468; S40 to E-468; S-41 to E-468; A-42 to E-468; G-43 to E-468; R-44 to E-468; I-45 to E-468; E-46 to E-468; P47 to E-468; R-48 to E-468; G-49 to E-468; G-50 to E-468; G-51 to E-468; R-52 to E-468; G-53 to E-468; A-54 to E-468; L-55 to E-468; P-56 to E-468; T-57 to E-468; S-58 to E-468; M-59 to E-468; G-60 to E-468; Q-61 to E-468; H-62 to E-468; G-63 to E-468; P-64 to E-468; S-65 to E-468; A-66 to E-468; R-67 to E-468; A-68 to E-468; R-69 to E-468; A-70 to E-468; G-71 to E-468; R-72 to E-468; A-73 to E-468; P-74 to E-468; G-75 to E-468; P-76 to E-468; R-77 to E-468; P-78 to E-468; A-79 to E-468; R-80 to E-468; E-81 to E-468; A-82 to E-468; S-83 to E-468; P-84 to E-468; R-85 to E-468; L-86 to E-468; R-87 to E-468; V-88 to E-468; H-89 to E-468; K-90 to E-468; T-91 to E-468; F-92 to E-468; K-93 to E-468; F-94 to E-468; V-95 to E-468; V-96 to E-468; V-97 to E-468; G-98 to E-468; V-99 to E-468; L-100 to E-468; L-101 to E-468; Q-102 to E-468; V-103 to E-468; V-104 to E-468; P-105 to E-468; S-106 to E-468; S-107 to E-468; A-108 to E-468; A-109 to E-468; T-110 to E-468; I-111 to E-468; K-112 to E-468; L-113 to E-468; H-114 to E-468; D-115 to E-468; Q-116 to E-468; S-117 to E-468; I-118 to E-468; G-119 to E-468; T-120 to E-468; Q-121 to E-468; Q-122 to F-468; W-123 to E-468; E-124 to F-468; H-125 to F-468; S-126 to E-468; P-127 to E-468; L-128 to E-468; G-129 to E-468; E-130 to E-468; L-131 to E-468; C-132 to E-468; P-133 to E-468; P-134 to E-468; G-135 to E-468; S-136 to E-468; H-137 to E-468; R-138 to E-468; S-139 to E-468; E-140 to E-468; R-141 to E-468; P-142 to E-468; G-143 to E-468; A-144 to E-468; C-145 to E-468; N-146 to E-468; R-147 to E-468; C-148 to E-468; T-149 to E-468; E-150 to E-468; G-151 to E-468; V-152 to E-468; G-153 to E-468; Y-154 to E-468; T-155 to E-468; N-156 to E-468; A-157 to E-468; S-158 to E-468; N-159 to E-468; N-160 to E-468; L-161 to E-468; F-162 to E-468; A-163 to E-468; C-164 to E-468; L-165 to E-468; P-166 to E-468; C-167 to E-468; T-168 to E-468; A-169 to E-468; C-170 to E-468; K-171 to E-468S; S-172 to E-468; D-173 to E-468; E-174 to E-468; E-175 to E-468; E-176 to E-468; R-177 to E-468; S-178 to E-468; P-179 to E-468; C-180 to E-468; T-181 to E-468; T-182 to E-468; T-183 to E-468; R-184 to E-468; N-185 to E-468; T-186 to E-468; A-187 to E-468; C-188 to E-468; Q-189 to E-468; C-190 to E-468; K-191 to E-468; P-192 to E-468; G-193 to E-468; T-194 to E-468; F-195 to E-468; R-196 to E-468; N-197 to E-468; D-198 to E-468; N-199 to E-468; S-200 to E-468; A-201 to E-468; E-202 to E-468; M-203 to E-468; C-204 to E-468; R-205 to E-468; K-206 to E-468; C-207 to E-468; S-208 to E-468; T-209 to E-468; G-210 to E-468; C-211 to E-468; P-212 to E-468; R-213 to E-468; G-214 to E-468; M-215 to E-468; V-216 to E-468; K-217 to E-468; V-218 to E-468; K-219 to E-468; D-220 to E-468; C-221 to E-468; T-222 to E-468; P-223 to E-468; W-224 to E-468; S-225 to E-468; D-226 to E-468; I-227 to E-468; E-228 to E-468; C-229 to E-468; V-230 to E-468; H-231 to E-468; K-232 to E-468; E-233 to E-468; S-234 to E-468; G-235 to E-468; N-236 to E-468; G-237 to E-468; H-238 to E-468; N-239 to E-468; I-240 to E-468; W-241 to E-468; V-242 to E-468; I-243 to E-468; L-244 to E-468; V-245 to E-468; V-246 to E-468; T-247 to E-468; L-248 to E-468; V-249 to E-468; V-250 to E-468; P-251 to E-468; L-252 to E-468; L-253 to E-468; L-254 to E-468; V-255 to E-468; A-256 to E-468; V-257 to E-468; L-258 to E-468; I-259 to E-468; V-260 to E-468; C-261 to E-468; C-262 to E-468; C-263 to E-468; I-264 to E-468; G-265 to E-468; S-266 to E-468; G-267 to E-468; C-268 to E-468; G-269 to E-468; G-270 to E-468; D-271 to E-468; P-272 to E-468; K-273 to E-468; C-274 to E-468; M-275 to E-468; D-276 to E-468; R-277 to E-468; V-278 to E-468; C-279 to E-468; F-280 to E-468; W-281 to E-468; R-282 to E-468; L-283 to E-468; G-284 to E-468; L-285 to E-468; L-286 to E-468; R-287 to E-468; G-288 to E-468; P-289 to E-468; G-290 to E-468; A-291 to E-468; E-292 to E-468; D-293 to E-468; N-294 to E-468; A-295 to E-468; H-296 to E-468; N-297 to E-468; E-298 to E-468; I-299 to E-468; L-300 to E-468; S-301 to E-468; N-302 to E-468; A-303 to E-468; D-304 to E-468; S-305 to E-468; L-306 to E-468; S-307 to E-468; T-308 to E-468; F-309 to E-468; V-310 to E-468; S-311 to E-468; E-312 to E-468; Q-313 to E-468; Q-314 to E-468; M-315 to E-468; E-316 to E-468; S-317 to E-468; Q-318 to E-468; E-319 to E-468; P-320 to E-468; A-321 to E-468; D-322 to E-468; L-323 to E-468; T-324 to E-468; G-325 to E-468; V-326 to E-468; T-327 to E-468; V-328 to E-468; E-329 to E-468; S-330 to E-468; P-331 to E-468; G-332 to E-468; E-333 to E-468; A-334 to E-468; Q-335 to E-468; C-336 to E-468; L-337 to E-468; L-338 to E-468; G-339 to E-468; P-340 to E-468; A-341 to E-468; E-342 to E-468; A-343 to E-468; E-344 to E-468; G-345 to E-468; S-346 to E-468; Q-347 to E-468; R-348 to E-468; R-349 to E-468; R-350 to E-468; L-351 to E-468; L-352 to E-468; V-353 to E-468; P-354 to E-468; A-355 to E-468; N-356 to E-468; G-357 to E-468; A-358 to E-468; D-359 to E-468; P-360 to E-468; T-361 to E-468; E-362 to E-468; T-363 to E-468; L-364 to E-468; M-365 to E-468; L-366 to E-468; F-367 to E-468; F-368 to E-468; D-369 to E-468; K-370 to E-468; F-371 to E-468; A-372 to E-468; N-373 to E-468; I-374 to E-468; V-375 to E-468; P-376 to E-468; F-377 to E-468; D-378 to E-468; S-379 to E-468; W-380 to E-468; D-381 to E-468; Q-382 to E-468; L-383 to E-468; M-384 to E-468; R-385 to E-468; Q-386 to E-468; L-387 to E-468; D-388 to E-468; L-389 to E-468; T-390 to E-468; K-391 to E-468; N-392 to E-468; E-393 to E-468; I-394 to E-468; D-395 to E-468; V-396 to E-468; V-397 to E-468; R-398 to E-468; A-399 to E-468; G-400 to E-468; T-401 to E-468; A-402 to E-468; G-403 to E-468; P404 to E-468; G-405 to E-468; D-406 to E-468; A-407 to E-468; L-408 to E-468; Y-409 to E-468; A-410 to E-468; M-411 to E-468; L-412 to E-468; M-413 to E-468; K-414 to E-468; W-415 to E-468; V-416 to E-468; N-417 to E-468; K-418 to E-468; T-419 to E-468; G-420 to E-468; R-421 to E-468; N-422 to E-468; A-423 to E-468; S424 to E-468; I-425 to E-468; H-426 to E-468; T-427 to E-468; L-428 to E-468; L-429 to E-468; D-430 to E-468; A-431 to E-468; L-432 to E-468; E-433 to E-468; R-434 to E-468; M-435 to E-468; E-436 to E-468; E-437 to E-468; R-438 to E-468; H-439 to E-468; A-440 to E-468; K-441 to E-468; E-442 to E-468; K-443 to E-468; I-444 to E-468; Q-445 to E-468; D-446 to E-468; L-447 to E-468; L-448 to E-468; V-449 to E-468; D-450 to E-468; S451 to E-468; G-452 to E-468; K-453 to E-468; F-454 to E-468; I-455 to E-468; Y-456 to E-468; L-457 to E-468; E-458 to E-468; D-459 to E-468;

G-460 to E-468; T-461 to E-468; G-462 to E-468; and S-463 to E-468 of the DR4 sequence shown in SEQ ID NO:2.

The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The invention is further directed to nucleic acid molecules comprising, or alternatively consisting of, polynucleotide sequences which encode polypeptides that are at least 80%, 85%, 90%, 92%, 95%, 96%, 97%, 98%, or 99% identical to the polypeptides described above. The present invention also encompasses the above polynucleotide sequences fused to a heterologous polynucleotide sequence. Polypeptides encoded by these polynucleotides are also encompassed by the invention.

In another embodiment, N-terminal deletions of the DR4 polypeptide can be described by the general formula $n^2$ to 238 where $n^2$ is a number from 2 to 238 corresponding to the amino acid sequence identified in SEQ ID NO:2. In specific embodiments, N-terminal deletions of the DR4 receptors of the invention provides polynucleotides encoding polypeptides comprising, or alternatively consisting of, the amino acid sequence of residues: A-2 to H-238; P-3 to H-238; P4 to H-238; P-5 to H-238; A-6 to H-238; R-7 to H-238; V-8 to H-238; H-9 to H-238; L-10 to H-238; G-11 to H-238; A-12 to H-238; F-13 to H-238; L-14 to H-238; A-15 to H-238; V-16 to H-238; T-17 to H-238; P-18 to H-238; N-19 to H-238; P-20 to H-238; G-21 to H-238; S-22 to H-238; A-23 to H-238; A-24 to H-238; S-25 to H-238; G-26 to H-238; T-27 to H-238; E-28 to H-238; A-29 to H-238; A-30 to H-238; A-31 to H-238; A-32 to H-238; T-33 to H-238; P-34 to H-238; S-35 to H-238; K-36 to H-238; V-37 to H-238; W-38 to H-238; G-39 to H-238; S-40 to H-238; S41 to H-238; A-42 to H-238; G-43 to H-238; R-44 to H-238; 1-45 to H-238; E-46 to H-238; P-47 to H-238; R-48 to H-238; G-49 to H-238; G-50 to H-238; G-51 to H-238; R-52 to H-238; G-53 to H-238; A-54 to H-238; L-55 to H-238; P-56 to H-238; T-57 to H-238; S-58 to H-238; M-59 to H-238; G-60 to H-238; Q-61 to H-238; H-62 to H-238; G-63 to H-238; P-64 to H-238; S-65 to H-238; A-66 to H-238; R-67 to H-238; A-68 to H-238; R-69 to H-238; A-70 to H-238; G-71 to H-238; R-72 to H-238; A-73 to H-238; P-74 to H-238; G-75 to H-238; P-76 to H-238; R-77 to H-238; P-78 to H-238; A-79 to H-238; R-80 to H-238; E-81 to H-238; A-82 to H-238; S-83 to H-238; P-84 to H-238; R-85 to H-238; L-86 to H-238; R-87 to H-238; V-88 to H-238; H-89 to H-238; K-90 to H-238; T-91 to H-238; F-92 to H-238; K-93 to H-238; F-94 to H-238; V-95 to H-238; V-96 to H-238; V-97 to H-238; G-98 to H-238; V-99 to H-238; L-100 to H-238; L-101 to H-238; Q-102 to H-238; V-103 to H-238; V-104 to H-238; P-105 to H-238; S-106 to H-238; S-107 to H-238; A-108 to H-238; A-109 to H-238; T-110 to H-238; 1-111 to H-238; K-112 to H-238; L-113 to H-238; H-114 to H-238; D-115 to H-238; Q-116 to H-238; S-117 to H-238; 1-118 to H-238; G-119 to H-238; T-120 to H-238; Q-121 to H-238; Q-122 to H-238; W-123 to H-238; E-124 to H-238; H-125 to H-238; S-126 to H-238; P-127 to H-238; L-128 to H-238; G-129 to H-238; E-130 to H-238; L-131 to H-238; C-132 to H-238; P-133 to H-238; P-134 to H-238; G-135 to H-238; S-136 to H-238; H-137 to H-238; R-138 to H-238; S-139 to H-238; E-140 to H-238; R-141 to H-238; P-142 to H-238; G-143 to H-238; A-144 to H-238; C-145 to H-238; N-146 to H-238; R-147 to H-238; C-148 to H-238; T-149 to H-238; E-150 to H-238; G-151 to H-238; V-152 to H-238; G-153 to H-238; Y-154 to H-238; T-155 to H-238; N-156 to H-238; A-157 to H-238; S-158 to H-238; N-159 to H-238; N-160 to H-238; L-161 to H-238; F-162 to H-238; A-163 to H-238; C-164 to H-238; L-165 to H-238; P-166 to H-238; C-167 to H-238; T-168 to H-238; A-169 to H-238; C-170 to H-238; K-171 to H-238; S-172 to H-238; D-173 to H-238; E-174 to H-238; E-175 to H-238; E-176 to H-238; R-177 to H-238; S-178 to H-238; P-179 to H-238; C-180 to H-238; T-181 to H-238; T-182 to H-238; T-183 to H-238; R-184 to H-238; N-185 to H-238; T-186 to H-238; A-187 to H-238; C-188 to H-238; Q-189 to H-238; C-190 to H-238; K-191 to H-238; P-192 to H-238; G-193 to H-238; T-194 to H-238; F-195 to H-238; R-196 to H-238; N-197 to H-238; D-198 to H-238; N-199 to H-238; S-200 to H-238; A-201 to H-238; E-202 to H-238; M-203 to H-238; C-204 to H-238; R-205 to H-238; K-206 to H-238; C-207 to H-238; S-208 to H-238; T-209 to H-238; G-210 to H-238; C-211 to H-238; P-212 to H-238; R-213 to H-238; G-214 to H-238; M-215 to H-238; V-216 to H-238; K-217 to H-238; V-218 to H-238; K-219 to H-238; D-220 to H-238; C-221 to H-238; T-222 to H-238; P-223 to H-238; W-224 to H-238; S-225 to H-238; D-226 to H-238; 1-227 to H-238; E-228 to H-238; C-229 to H-238; V-230 to H-238; H-231 to H-238; K-232 to H-238; and E-233 to H-238 of the DR4 extracellular domain sequence shown in SEQ ID NO:2.

The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The invention is further directed to nucleic acid molecules comprising, or alternatively consisting of, polynucleotide sequences which encode polypeptides that are at least 80%, 85%, 90%, 92%, 95%, 96%, 97%, 98%, or 99% identical to the polypeptides described above. The present invention also encompasses the above polynucleotide sequences fused to a heterologous polynucleotide sequence. Polypeptides encoded by these polynucleotides are also encompassed by the invention.

Similarly, many examples of functional C-terminal deletion muteins are known. For instance, interferon gamma shows up to ten times higher activities by deleting 8-10 amino acid residues from the carboxy terminus of the protein (Döbeli et al., *J. Biotechnology* 7:199-216 (1988). In the present case, since the protein of the invention is a member of the DDCR polypeptide family, deletions of C-terminal amino acids up to the cysteine at position 221 (C-221) of SEQ ID NO:2 may retain some biological activity such as receptor binding. Polypeptides having further C-terminal deletions including C-221 of SEQ ID NO:2 would not be expected to retain such biological activities because this residue is conserved among DDCR family members and is required for forming a disulfide bridge to provide structural stability which is needed for receptor-ligand binding.

As mentioned above, even if deletion of one or more amino acids from the C-terminus of a protein results in modification of loss of one or more biological functions of the protein, other functional activities (e.g., biological activities, ability to multimerize, ability to bind DR4 ligand (e.g., TRAIL)) may still be retained. For example the ability of the shortened DR4 mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a DR4 mutein with a large number of deleted C-terminal amino acid residues may retain some biological or immunogenic activities. In fact, peptides composed of as few as six DR4 amino acid residues may often evoke an immune response.

Accordingly, the present invention further provides polypeptides having one or more residues deleted from the carboxy terminus of the amino acid sequence of the DR4 polypeptide shown in SEQ ID NO:2, up to the alanine residue at position number 30, and polynucleotides encoding such polypeptides. In particular, the present invention provides polypeptides comprising, or alternatively consisting of, the amino acid sequence of residues 24-$m^1$ of SEQ ID NO:2, where $m^1$ is an integer from 30 to 467 corresponding to the position of the amino acid residue in SEQ ID NO:2.

More in particular, the invention provides polynucleotides encoding polypeptides comprising, or alternatively consisting of, the amino acid sequence of residues A-24 to L-467; A-24 to S-466; A-24 to V-465; A-24 to A-464; A-24 to S-463; A-24 to G-462; A-24 to T-461; A-24 to G-460; A-24 to D-459; A-24 to E-458; A-24 to L-457; A-24 to Y-456; A-24 to I-455; A-24 to F-454; A-24 to K-453; A-24 to G-452; A-24 to S-451; A-24 to D-450; A-24 to V-449; A-24 to L-448; A-24 to L-447; A-24 to D-446; A-24 to Q-445; A-24 to I-444; A-24 to K-443; A-24 to E-442; A-24 to K-441; A-24 to A-440; A-24 to H-439; A-24 to R-438; A-24 to E-437; A-24 to E-436; A-24 to M-435; A-24 to R-434; A-24 to E-433; A-24 to L-432; A-24 to A-431; A-24 to D-430; A-24 to L-429; A-24 to L-428; A-24 to T-427; A-24 to H-426; A-24 to I-425; A-24 to S-424; A-24 to A-423; A-24 to N-422; A-24 to R-421; A-24 to G-420; A-24 to T-419; A-24 to K-418; A-24 to N-417; A-24 to V-416; A-24 to W-415; A-24 to K-414; A-24 to M-413; A-24 to L-412; A-24 to M-411; A-24 to A-410; A-24 to Y-409; A-24 to L-408; A-24 to A-407; A-24 to D-406; A-24 to G-405; A-24 to P-404; A-24 to G-403; A-24 to A-402; A-24 to T-401; A-24 to G-400; A-24 to A-399; A-24 to R-398; A-24 to V-397; A-24 to V-396; A-24 to D-395; A-24 to I-394; A-24 to E-393; A-24 to N-392; A-24 to K-391; A-24 to T-390; A-24 to L-389; A-24 to D-388; A-24 to L-387; A-24 to Q-386; A-24 to R-385; A-24 to M-384; A-24 to L-383; A-24 to Q-382; A-24 to D-381; A-24 to W-380; A-24 to S-379; A-24 to D-378; A-24 to F-377; A-24 to P-376; A-24 to V-375; A-24 to I-374; A-24 to N-373; A-24 to A-372; A-24 to F-371; A-24 to K-370; A-24 to D-369; A-24 to F-368; A-24 to F-367; A-24 to L-366; A-24 to M-365; A-24 to L-364; A-24 to T-363; A-24 to E-362; A-24 to T-361; A-24 to P-360; A-24 to D-359; A-24 to A-358; A-24 to G-357; A-24 to N-356; A-24 to A-355; A-24 to P-354; A-24 to V-353; A-24 to L-352; A-24 to L-351; A-24 to R-350; A-24 to R-349; A-24 to R-348; A-24 to Q-347; A-24 to S-346; A-24 to G-345; A-24 to E-344; A-24 to A-343; A-24 to E-342; A-24 to A-341; A-24 to P-340; A-24 to G-339; A-24 to L-338; A-24 to L-337; A-24 to C-336; A-24 to Q-335; A-24 to A-334; A-24 to E-333; A-24 to G-332; A-24 to P-331; A-24 to S-330; A-24 to Q-329; A-24 to V-328; A-24 to T-327; A-24 to V-326; A-24 to G-325; A-24 to T-324; A-24 to L-323; A-24 to D-322; A-24 to A-321; A-24 to P-320; A-24 to E-319; A-24 to Q-318; A-24 to S-317; A-24 to E-316; A-24 to M-315; A-24 to Q-314; A-24 to Q-313; A-24 to E-312; A-24 to S-311; A-24 to V-310; A-24 to F-309; A-24 to T-308; A-24 to S-307; A-24 to L-306; A-24 to S-305; A-24 to D-304; A-24 to A-303; A-24 to N-302; A-24 to S-301; A-24 to L-300; A-24 to I-299; A-24 to E-298; A-24 to N-297; A-24 to H-296; A-24 to A-295; A-24 to N-294; A-24 to D-293; A-24 to E-292; A-24 to A-291; A-24 to G-290; A-24 to P-289; A-24 to G-288; A-24 to R-287; A-24 to L-286; A-24 to L-285; A-24 to G-284; A-24 to L-283; A-24 to R-282; A-24 to W-281; A-24 to F-280; A-24 to C-279; A-24 to V-278; A-24 to R-277; A-24 to D-276; A-24 to M-275; A-24 to C-274; A-24 to K-273; A-24 to P-272; A-24 to D-271; A-24 to G-270; A-24 to G-269; A-24 to C-268; A-24 to G-267; A-24 to S-266; A-24 to G-265; A-24 to I-264; A-24 to C-263; A-24 to C-262; A-24 to C-261; A-24 to V-260; A-24 to I-259; A-24 to L-258; A-24 to V-257; A-24 to A-256; A-24 to V-255; A-24 to L-254; A-24 to L-253; A-24 to L-252; A-24 to P-251; A-24 to V-250; A-24 to V-249; A-24 to L-248; A-24 to T-247; A-24 to V-246; A-24 to V-245; A-24 to L-244; A-24 to I-243; A-24 to V-242; A-24 to W-241; A-24 to I-240; A-24 to N-239; A-24 to H-238; A-24 to G-237; A-24 to N-236; A-24 to G-235; A-24 to S-234; A-24 to E-233; A-24 to K-232; A-24 to H-231; A-24 to V-230; A-24 to C-229; A-24 to E-228; A-24 to I-227; A-24 to D-226; A-24 to S-225; A-24 to W-224; A-24 to P-223; A-24 to T-222; A-24 to C-221; A-24 to D-220; A-24 to K-219; A-24 to V-218; A-24 to K-217; A-24 to V-216; A-24 to M-215; A-24 to G-214; A-24 to R-213; A-24 to P-212; A-24 to C-211; A-24 to G-210; A-24 to T-209; A-24 to S-208; A-24 to C-207; A-24 to K-206; A-24 to R-205; A-24 to C-204; A-24 to M-203; A-24 to E-202; A-24 to A-201; A-24 to S-200; A-24 to N-199; A-24 to D-198; A-24 to N-197; A-24 to R-196; A-24 to F-195; A-24 to T-194; A-24 to G-193; A-24 to P-192; A-24 to K-191; A-24 to C-190; A-24 to Q-189; A-24 to C-188; A-24 to A-187; A-24 to T-186; A-24 to N-185; A-24 to R-184; A-24 to T-183; A-24 to T-182; A-24 to T-181; A-24 to C-180; A-24 to P-179; A-24 to S-178; A-24 to R-177; A-24 to E-176; A-24 to E-175; A-24 to E-174; A-24 to D-173; A-24 to S-172; A-24 to K-171; A-24 to C-170; A-24 to A-169; A-24 to T-168; A-24 to C-167; A-24 to P-166; A-24 to L-165; A-24 to C-164; A-24 to A-163; A-24 to N-162; A-24 to L-161; A-24 to N-160; A-24 to N-159; A-24 to S-158; A-24 to A-157; A-24 to N-156; A-24 to T-155; A-24 to Y-154; A-24 to G-153; A-24 to V-152; A-24 to G-151; A-24 to E-150; A-24 to T-149; A-24 to C-148; A-24 to R-147; A-24 to N-146; A-24 to C-145; A-24 to A-144; A-24 to G-143; A-24 to P-142; A-24 to R-141; A-24 to E-140; A-24 to S-139; A-24 to R-138; A-24 to H-137; A-24 to S-136; A-24 to G-135; A-24 to P-134; A-24 to P-133; A-24 to C-132; A-24 to L-131; A-24 to E-130; A-24 to G-129; A-24 to L-128; A-24 to P-127; A-24 to S-126; A-24 to H-125; A-24 to E-124; A-24 to W-123; A-24 to Q-122; A-24 to Q-121; A-24 to T-120; A-24 to G-119; A-24 to I-118; A-24 to S-117; A-24 to Q-116; A-24 to D-115; A-24 to H-114; A-24 to L-113; A-24 to K-112; A-24 to I-111; A-24 to T-110; A-24 to A-109; A-24 to A-108; A-24 to S-107; A-24 to S-106; A-24 to P-105; A-24 to V-104; A-24 to V-103; A-24 to Q-102; A-24 to L-101; A-24 to L-100; A-24 to V-99; A-24 to G-98; A-24 to V-97; A-24 to V-96; A-24 to V-95; A-24 to F-94; A-24 to K-93; A-24 to F-92; A-24 to T-91; A-24 to K-90; A-24 to H-89; A-24 to V-88; A-24 to R-87; A-24 to L-86; A-24 to R-85; A-24 to P-84; A-24 to S-83; A-24 to A-82; A-24 to E-81; A-24 to R-80; A-24 to A-79; A-24 to P-78; A-24 to R-77; A-24 to P-76; A-24 to G-75; A-24 to P-74; A-24 to A-73; A-24 to R-72; A-24 to G-71; A-24 to A-70; A-24 to R-69; A-24 to A-68; A-24 to R-67; A-24 to A-66; A-24 to S-65; A-24 to P-64; A-24 to G-63; A-24 to H-62; A-24 to Q-61; A-24 to G-60; A-24 to M-59; A-24 to S-58; A-24 to T-57; A-24 to P-56; A-24 to L-55; A-24 to A-54; A-24 to G-53; A-24 to R-52; A-24 to G-51; A-24 to G-50; A-24 to G-49; A-24 to R-48; A-24 to P-47; A-24 to E-46; A-24 to 145; A-24 to R-44; A-24 to G-43; A-24 to A-42; A-24 to S-41; A-24 to S-40; A-24 to G-39; A-24 to W-38; A-24 to V-37; A-24 to K-36; A-24 to S-35; A-24 to P-34; A-24 to T-33; A-24 to A-32; A-24 to A-31; and A-24 to A-30 of the DR4 sequence shown in SEQ ID NO:2.

The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The invention is further directed to nucleic acid molecules comprising, or alternatively consisting of, polynucleotide sequences which encode polypeptides that are at least 80%, 85%, 90%, 92%, 95%, 96%, 97%, 98%, or 99% identical to the polypeptides described above. The present invention also encompasses the above polynucleotide sequences fused to a heterologous polynucleotide sequence. Polypeptides encoded by these polynucleotides are also encompassed by the invention.

In another embodiment, C-terminal deletions of the DR4 polypeptide can be described by the general formula 24-m$^2$ where m$^2$ is a number from 30 to 238 corresponding to the amino acid sequence identified in SEQ ID NO:2. In specific embodiments, the invention provides polynucleotides encoding polypeptides comprising, or alternatively consisting of, the amino acid sequence of residues: A-24 to G-237; A-24 to N-236; A-24 to G-235; A-24 to S-234; A-24 to E-233; A-24 to K-232; A-24 to H-231; A-24 to V-230; A-24 to C-229; A-24 to E-228; A-24 to I-227; A-24 to D-226; A-24 to S-225; A-24 to W-224; A-24 to P-223; A-24 to T-222; A-24 to C-221; A-24 to D-220; A-24 to K-219; A-24 to V-218; A-24 to K-217; A-24 to V-216; A-24 to M-215; A-24 to G-214; A-24 to R-213; A-24 to P-212; A-24 to C-211; A-24 to G-210; A-24 to T-209; A-24 to S-208; A-24 to C-207; A-24 to K-206; A-24 to R-205; A-24 to C-204; A-24 to M-203; A-24 to E-202; A-24 to A-201; A-24 to S-200; A-24 to N-199; A-24 to D-198; A-24 to N-197; A-24 to R-196; A-24 to F-195; A-24 to T-194; A-24 to G-193; A-24 to P-192; A-24 to K-191; A-24 to C-190; A-24 to Q-189; A-24 to C-188; A-24 to A-187; A-24 to T-186; A-24 to N-185; A-24 to R-184; A-24 to T-183; A-24 to T-182; A-24 to T-181; A-24 to C-180; A-24 to P-179; A-24 to S-178; A-24 to R-177; A-24 to E-176; A-24 to E-175; A-24 to E-174; A-24 to D-173; A-24 to S-172; A-24 to K-171; A-24 to C-170; A-24 to A-169; A-24 to T-168; A-24 to C-167; A-24 to P-166; A-24 to L-165; A-24 to C-164; A-24 to A-163; A-24 to F-162; A-24 to L-161; A-24 to N-160; A-24 to N-159; A-24 to S-158; A-24 to A-157; A-24 to N-156; A-24 to T-155; A-24 to Y-154; A-24 to G-153; A-24 to V-152; A-24 to G-151; A-24 to E-150; A-24 to T-149; A-24 to C-148; A-24 to R-147; A-24 to N-146; A-24 to C-145; A-24 to A-144; A-24 to G-143; A-24 to P-142; A-24 to R-141; A-24 to E-140; A-24 to S-139; A-24 to R-138; A-24 to H-137; A-24 to S-136; A-24 to G-135; A-24 to P-134; A-24 to P-133; A-24 to C-132; A-24 to L-131; A-24 to E-130; A-24 to G-129; A-24 to L-128; A-24 to P-127; A-24 to S-126; A-24 to H-125; A-24 to E-124; A-24 to W-123; A-24 to Q-122; A-24 to Q-121; A-24 to T-120; A-24 to G-119; A-24 to I-118; A-24 to S-117; A-24 to Q-116; A-24 to D-115; A-24 to H-114; A-24 to L-113; A-24 to K-112; A-24 to I-111; A-24 to T-110; A-24 to A-109; A-24 to A-108; A-24 to S-107; A-24 to S-106; A-24 to P-105; A-24 to V-104; A-24 to V-103; A-24 to Q-102; A-24 to L-101; A-24 to L-100; A-24 to V-99; A-24 to G-98; A-24 to V-97; A-24 to V-96; A-24 to V-95; A-24 to F-94; A-24 to K-93; A-24 to F-92; A-24 to T-91; A-24 to K-90; A-24 to H-89; A-24 to V-88; A-24 to R-87; A-24 to L-86; A-24 to R-85; A-24 to P-84; A-24 to S-83; A-24 to A-82; A-24 to E-81; A-24 to R-80; A-24 to A-79; A-24 to P-78; A-24 to R-77; A-24 to P-76; A-24 to G-75; A-24 to P-74; A-24 to A-73; A-24 to R-72; A-24 to G-71; A-24 to A-70; A-24 to R-69; A-24 to A-68; A-24 to R-67; A-24 to A-66; A-24 to S-65; A-24 to P-64; A-24 to G-63; A-24 to H-62; A-24 to Q-61; A-24 to G-60; A-24 to M-59; A-24 to S-58; A-24 to T-57; A-24 to P-56; A-24 to L-55; A-24 to A-54; A-24 to G-53; A-24 to R-52; A-24 to G-51; A-24 to G-50; A-24 to G-49; A-24 to R-48; A-24 to P-47; A-24 to E-46; A-24 to I45; A-24 to R-44; A-24 to G-43; A-24 to A-42; A-24 to S-41; A-24 to S40; A-24 to G-39; A-24 to W-38; A-24 to V-37; A-24 to K-36; A-24 to S-35; A-24 to P-34; A-24 to T-33; A-24 to A-32; A-24 to A-31; and A-24 to A-30 of the DR4 extracellular domain sequence shown in SEQ ID NO:2.

The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The invention is further directed to nucleic acid molecules comprising, or alternatively consisting of, polynucleotide sequences which encode polypeptides that are at least 80%, 85%, 90%, 92%, 95%, 96%, 97%, 98%, or 99% identical to the polypeptides described above. The present invention also encompasses the above polynucleotide sequences fused to a heterologous polynucleotide sequence. Polypeptides encoded by these polynucleotides are also encompassed by the invention.

The present invention further provides polypeptides having one or more residues from the carboxy terminus of the amino acid sequence of the DR4 shown in SEQ ID NO:2, up to C-221 of SEQ ID NO:2, and polynucleotides encoding such polypeptides. In particular, the present invention provides polypeptides having the amino acid sequence of residues 1-m$^2$ of the amino acid sequence in SEQ ID NO:2, where m$^2$ is any integer in the range of 221-468 and residue C-221 is the position of the first residue from the C-terminus of the complete DR4 polypeptide (shown in SEQ ID NO:2) believed to be required for receptor binding activity of the DR4 protein. Polynucleotides encoding these polypeptides also are provided.

The invention also provides polypeptides having one or more amino acids deleted from both the amino and the carboxyl termini of an DR4 polypeptide, which may be described generally as having residues n$^1$-m$^1$ and/or n$^2$-m$^2$ of SEQ ID NO:2, where n$^1$, n$^2$, m$^1$, and m$^2$ are integers as described above.

Also included are a nucleotide sequence encoding a polypeptide consisting of a portion of the complete DR4 amino acid sequence encoded by the cDNA contained in ATCC Deposit No. 97853, where this portion excludes from 1 to about 108 amino acids from the amino terminus of the complete amino acid sequence encoded by the cDNA contained in ATCC Deposit No. 97853, or from 1 to about 247 amino acids from the carboxy terminus, or any combination of the above amino terminal and carboxy terminal deletions, of the complete amino acid sequence encoded by the cDNA contained in ATCC Deposit No. 97853. Polynucleotides encoding all of the above deletion mutant polypeptide forms also are provided.

Preferred amongst the N- and C-terminal deletion mutants are those comprising only a portion of the extracellular domain; i.e., within residues 24-238, since any portion therein is expected to be soluble.

It will be recognized in the art that some amino acid sequence of DR4 can be varied without significant effect of the structure or function of the protein. If such differences in sequence are contemplated, it should be remembered that there will be critical areas on the protein which determine activity. Such areas will usually comprise residues which make up the ligand binding site or the death domain, or which form tertiary structures which affect these domains.

Thus, the invention further includes variations of the DR4 protein which show substantial DR4 protein activity or which include regions of DR4 such as the protein fragments discussed below. Such mutants include deletions, insertions, inversions, repeats, and type substitutions. As indicated above, guidance concerning which amino acid changes are likely to be phenotypically silent can be found in Bowie, J. U. et al., *Science* 247:1306-1310 (1990).

Thus, the fragment, derivative, or analog of the polypeptide of SEQ ID NO:2, or that encoded by the deposited cDNA, may be (i) one in which at least one or more of the amino acid residues are substituted with a conserved or non-conserved amino acid residue (preferably a conserved amino acid residue(s), and more preferably at least one but less than ten conserved amino acid residues) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein. Polynucleotides encoding these fragments, derivatives or analogs are also encompassed by the invention.

Of particular interest are substitutions of charged amino acids with another charged amino acid and with neutral or negatively charged amino acids. The latter results in proteins with reduced positive charge to improve the characteristics of the DR4 protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331-340 (1967); Robbins et al., *Diabetes* 36:838-845 (1987); Cleland et al. *Crit. Rev. Therapeutic Drug Carrier Systems* 10:307-377 (1993)).

The replacement of amino acids can also change the selectivity of binding to cell surface receptors. Ostade et al., *Nature* 361:266-268 (1993) describes certain mutations resulting in selective binding of TNF-alpha to only one of the two known types of TNF receptors. Thus, the DR4 receptor of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table II).

TABLE II

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

In specific embodiments, the number of substitutions, additions or deletions in the amino acid sequence of SEQ ID NO:2 and/or any of the polypeptide fragments described herein (e.g., the extracellular domain or intracellular domain) is 75, 70, 60, 50, 40, 35, 30, 25, 20, 15, 10, 9, 8, 7, 6, 5, 4, 3, 2, 1 or 30-20, 20-15, 20-10, 15-10, 10-1, 5-10, 1-5, 1-3 or 1-2.

Amino acids in the DR4 protein of the present invention that are essential for function can be identified by methods known in the art, such as site-directed mutagenesis or alanine-scanning mutagenesis (Cunningham and Wells, *Science* 244: 1081-1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)).

Additionally, protein engineering may be employed to improve or alter the characteristics of DR4 polypeptides. Recombinant DNA technology known to those skilled in the art can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

Non-naturally occurring variants may be produced using art-known mutagenesis techniques, which include, but are not limited to oligonucleotide mediated mutagenesis, alanine scanning, PCR mutagenesis, site directed mutagenesis (see e.g., Carter et al., *Nucl. Acids Res.* 13:4331 (1986); and Zoller et al., *Nucl. Acids Res.* 10:6487 (1982)), cassette mutagenesis (see e.g., Wells et al., *Gene* 34:315 (1985)), restriction selection mutagenesis (see e.g., Wells et al., *Philos. Trans. R. Soc. London SerA* 317:415 (1986)).

Thus, the invention also encompasses DR4 derivatives and analogs that have one or more amino acid residues deleted, added, or substituted to generate DR4 polypeptides that are better suited for expression, scale up, etc., in the host cells chosen. For example, cysteine residues can be deleted or substituted with another amino acid residue in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions on any one or more of the glycosylation recognitions sequences in the DR4 polypeptides of the invention, and/or an amino acid deletion at the second position of any one or more such recognition sequences will prevent glycosylation of the DR4 at the modified tripeptide sequence (see, e.g., Miyajimo et al., *EMBO J.* 5(6):1193-1197).

The polypeptides of the present invention also include a polypeptide comprising, or alternatively consisting of, the polypeptide encoded by the deposited cDNA (the deposit having ATCC Accession No. 97853) including the leader; a polypeptide comprising, or alternatively consisting of, the mature polypeptide encoded by the deposited the cDNA minus the leader (i.e., the mature protein); a polypeptide comprising, or alternatively consisting of, the polypeptide of SEQ ID NO:2 including the leader; a polypeptide comprising, or alternatively consisting of, the polypeptide of SEQ ID NO:2 minus the amino terminal methionine; a polypeptide comprising, or alternatively consisting of, the polypeptide of SEQ ID NO:2 minus the leader; a polypeptide comprising, or alternatively consisting of, the DR4 extracellular domain; a polypeptide comprising, or alternatively consisting of, the DR4 cysteine rich domain; a polypeptide comprising, or alternatively consisting of, the DR4 transmembrane domain; a polypeptide comprising, or alternatively consisting of, the DR4 intracellular domain; a polypeptide comprising, or alternatively consisting of, the DR4 death domain; a polypeptide comprising, or alternatively consisting of, soluble polypeptides comprising all or part of the extracellular and intracellular domains but lacking the transmembrane domain; as well as polypeptides which are at least 80% identical, more preferably at least 90% or 95% identical, still more preferably at least 96%, 97%, 98% or 99% identical to the polypeptides described above (e.g., the polypeptide encoded by the deposited cDNA, the polypeptide of SEQ ID NO:2, and portions of such polypeptides with at least 30 amino acids and more preferably at least 50 amino acids. Polynucleotides encoding these polypeptides are also encompassed by the invention.

By a polypeptide having an amino acid sequence at least, for example, 95% "identical" to a reference amino acid sequence of a DR4 polypeptide is intended that the amino acid sequence of the polypeptide is identical to the reference sequence except that the polypeptide sequence may include up to five amino acid alterations per each 100 amino acids of the reference amino acid of the DR4 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 92%, 95%, 96%, 97%, 98% or 99% identical to, for instance, the amino acid sequence shown in SEQ ID NO:2 or to the amino acid sequence encoded by the deposited cDNA can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237-245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The present application is also directed to proteins containing polypeptides at least 80%, 85%, 90%, 92%, 95%, 96%, 97%, 98% or 99% identical to the DR4 polypeptide sequence set forth herein as $n^1$-$m^1$, and/or $n^2$-$m^2$. In preferred embodiments, the application is directed to proteins containing polypeptides at least 80%, 85%, 90%, 92%, 95%, 96%, 97%, 98% or 99% identical to polypeptides having the amino acid sequence of the specific DR4 N- and C-terminal deletions recited herein. Polynucleotides encoding these polypeptides are also encompassed by the invention.

In certain preferred embodiments, DR4 proteins of the invention comprise fusion proteins as described above wherein the DR4 polypeptides are those described as $n^1$-$m^1$, and/or $n^2$-$m^2$ herein. In preferred embodiments, the application is directed to nucleic acid molecules at least 80%, 85%, 90%, 92%, 95%, 96%, 97%, 98% or 99% identical to the nucleic acid sequences encoding polypeptides having the amino acid sequence of the specific N- and C-terminal deletions recited herein. Polynucleotides encoding these polypeptides are also encompassed by the invention.

The present inventors have discovered that the DR4 polypeptide is a 468 residue protein exhibiting three main structural domains. First, the ligand binding domain (extracellular domain) was identified within residues from about 24 to about 238 in SEQ ID NO:2. Second, the transmembrane domain was identified within residues from about 239 to about 264 in SEQ ID NO:2. Third, the intracellular domain was identified within residues from about 265 to about 468 in SEQ ID NO:2. Importantly, the intracellular domain includes a death domain at residues from about 379 to about 422 in SEQ ID NO:2. Further preferred fragments of the polypeptide shown in SEQ ID NO:2 include the mature protein from residues about 24 to about 468 and soluble polypeptides comprising all or part of the extracellular and intracellular domains but lacking the transmembrane domain. In this context "about" includes the particularly recited range, larger or smaller by several (5, 4, 3, 2, or 1) amino acid residues, at either terminus or at both termini.

In another aspect, the invention provides a peptide or polypeptide comprising an epitope-bearing portion of a polypeptide described herein. The epitope of this polypeptide portion is an immunogenic or antigenic epitope of a polypeptide of the invention. The number of immunogenic epitopes of a protein generally is less than the number of antigenic epitopes. See, for instance, Geysen et al., *Proc. Natl. Acad. Sci. USA* 81:3998-4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. *Science* 219:660-666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Non-limiting examples of antigenic polypeptides or peptides that can be used to generate DR4-specific antibodies include: a polypeptide comprising, or alternatively consisting of, amino acid residues from about 35 to about 92 in SEQ ID NO:2; a polypeptide comprising, or alternatively consisting of, amino acid residues from about 114 to about 160 in SEQ ID NO:2; a polypeptide comprising, or alternatively consisting of, amino acid residues from about 169 to about 240 in SEQ ID NO:2; a polypeptide comprising, or alternatively consisting of, amino acid residues from about 267 to about 298 in SEQ ID NO:2; a polypeptide comprising, or alternatively consisting of, amino acid residues from about 330 to about 364 in SEQ ID NO:2; a polypeptide comprising, or alternatively consisting of, amino acid residues from about 391 to about 404 in SEQ ID NO:2; and a polypeptide comprising, or alternatively consisting of, amino acid residues from about 418 to about 465 in SEQ ID NO:2. In this context "about" includes the particularly recited range, larger or smaller by several (5, 4, 3, 2, or 1) amino acids, at either terminus or at both termini. As indicated above, the inventors have determined that the above polypeptide fragments are antigenic regions of the DR4 protein. Polynucleotides encoding these polypeptides are also encompassed by the invention.

The epitope-bearing peptides and polypeptides of the invention may be produced by any conventional means. Houghten, R. A., "General method for the rapid solid-phase synthesis of large numbers of peptides: specificity of antigen-antibody interaction at the level of individual amino acids," *Proc. Natl. Acad. Sci. USA* 82:5131-5135 (1985). This "Simultaneous Multiple Peptide Synthesis (SMPS)" process is further described in U.S. Pat. No. 4,631,211 to Houghten et al. (1986). As one of skill in the art will appreciate, DR4 polypeptides of the present invention and the epitope-bearing fragments thereof described herein (e.g., corresponding to a portion of the extracellular domain such as, for example, amino acid residues 1 to 240 of SEQ ID NO:2) can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84-86 (1988)). Fusion proteins that have a disulfide-linked dimeric structure due to the IgG part can also be more efficient in binding and neutralizing other molecules than the monomeric DR4 protein or protein fragment alone (Fountoulakis et al., *J Biochem* 270: 3958-3964 (1995)).

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

In addition, proteins of the invention can be chemically synthesized using techniques known in the art (e.g., see Creighton, 1983, Proteins: Structures and Molecular Principles, W.H. Freeman & Co., N.Y., and Hunkapiller, M. et al., *Nature* 310:105-111 (1984)). For example, a peptide corresponding to a fragment of the DR4 polypeptides of the invention can be synthesized by use of a peptide synthesizer. Furthermore, if desired, nonclassical amino acids or chemical amino acid analogs can be introduced as a substitution or addition into the DR4 polypeptide sequence. Non-classical amino acids include, but are not limited to, to the D-isomers of the common amino acids, 2,4-diaminobutyric acid, alpha-amino isobutyric acid, 4-aminobutyric acid, Abu, 2-amino butyric acid, alpha-Abu, alpha-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, alpha-alanine, fluoro-amino acids, designer amino acids such as alpha-methyl amino acids, Ca-methyl amino acids, Na-methyl amino acids, and amino acid analogs in general. Furthermore, the amino acid can be D (dextrorotary) or L (levorotary).

Non-naturally occurring variants may be produced using art-known mutagenesis techniques, which include, but are not limited to oligonucleotide mediated mutagenesis, alanine scanning, PCR mutagenesis, site directed mutagenesis (see, e.g., Carter et al., *Nucl. Acids Res.* 13:4331 (1986); and Zoller et al., *Nucl. Acids Res.* 10:6487 (1982)), cassette mutagenesis (see, e.g., Wells et al., *Gene* 34:315 (1985)), restriction selection mutagenesis (see, e.g., Wells et al., *Philos. Trans. R. Soc. London SerA* 317:415 (1986)).

The invention additionally, encompasses DR4 polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of DR4 which may provide additional advantages such as increased solubility, stability and circulating time of the polypeptide, or decreased immunogenicity (see U.S. Pat. No. 4,179,337). The chemical moieties for derivation may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59-72 (1996); Vorobjev et al., *Nucleosides Nucleotides* 18:2745-2750 (1999); and Caliceti et al., *Bioconjug. Chem.* 10:638-646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., *Exp. Hematol.* 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues, glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249-304 (1992); Francis et al., *Intern. J of Hematol.* 68:1-18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., *Crit. Rev. Thera. Drug Carrier Sys.* 9:249-304 (1992).

As mentioned, DR4 polypeptides may be modified by either natural processes, such as posttranslational processing, or by chemical modification techniques, which are well known in the art. It will be appreciated that the same type of modification may be present in the same or varying degrees at several sites in a given DR4 polypeptide. Also, a given DR4 polypeptide may contain many types of modifications. DR4 polypeptides may be branched, for example, as a result of ubiquitination, and they may be cyclic, with or without branching. Cyclic, branched, and branched cyclic DR4 polypeptides may result from natural posttranslational processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W.H. Freeman and Company, New York (1993); POSTRRANSLATIONAL COVALENT MODIFICATION OF PROTEINS, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992)).

The DR4 polypeptides can be recovered and purified from chemical synthesis and recombinant cell cultures by standard methods which include, but are not limited to, ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. Most preferably, high performance liquid chromatography ("HPLC") is employed for purification. Well-known techniques for refolding protein may be employed to regenerate active conformation when the polypeptide is denatured during isolation and/or purification.

DR4 polynucleotides and polypeptides may be used in accordance with the present invention for a variety of applications, particularly those that make use of the chemical and biological properties of DR4. Among these are applications in the treatment and/or prevention of tumors, parasitic infections, bacterial infections, viral infections, restenosis, and graft vs. host disease; to induce resistance to parasites, bacteria and viruses; to induce proliferation of T-cells, endothelial cells and certain hematopoietic cells; to regulate anti-viral responses; and to treat and/or prevent certain autoimmune diseases after stimulation of DR5 by an agonist. Additional applications relate to diagnosis, treatment, and/or prevention of disorders of cells, tissues and organisms. These aspects of the invention are discussed further below.

The present invention encompasses polypeptides comprising, or alternatively consisting of, an epitope of the polypeptide having an amino acid sequence of SEQ ID NO:2, or an epitope of the polypeptide sequence encoded by a polynucleotide sequence contained in the cDNA deposited as ATCC Deposit No. 97853 or encoded by a polynucleotide that hybridizes to the complement of the sequence of SEQ ID NO:1 or contained in the cDNA deposited as ATCC Deposit No. 97853 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

In another aspect, the invention provides a peptide or polypeptide comprising an epitope-bearing portion of a polypeptide described herein. The epitope of this polypeptide portion is an immunogenic or antigenic epitope of a polypeptide of the invention. The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998-4002 (1983).

Fragments that function as epitopes may be produced by any conventional means. (See, e.g., Houghten, *Proc. Natl. Acad. Sci. USA* 82:5131-5135 (1985), further described in U.S. Pat. No. 4,631,211).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A., "Antibodies That React With Predetermined Sites on Proteins," *Science* 219:660-666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Non-limiting examples of antigenic polypeptides or peptides that can be used to generate DR4-specific antibodies include: a polypeptide comprising, or alternatively consisting of, amino acid residues from about 35 to about 92 in FIG. 1 (about 35 to about 92 in SEQ ID NO:2); a polypeptide comprising, or alternatively consisting of, amino acid residues from about 114 to about 160 in FIG. 1 (about 114 to about 160 in SEQ ID NO:2); a polypeptide comprising, or alternatively consisting of, amino acid residues from about 169 to about 240 in FIG. 1 (about 169 to about 240 in SEQ ID NO:2); a polypeptide comprising, or alternatively consisting of, amino acid residues from about 267 to about 298 in FIG. 1 (about 267 to about 298 in SEQ ID NO:2); a polypeptide comprising, or alternatively consisting of, amino acid residues from about 330 to about 364 in FIG. 1 (about 330 to about 364 in SEQ ID NO:2); a polypeptide comprising, or alternatively consisting of, amino acid residues from about 391 to about 404 in FIG. 1 (about 391 to about 404 in SEQ ID NO:2); and a polypeptide comprising, or alternatively consisting of, amino acid residues from about 418 to about 465 in FIG. 1 (about 418 to about 465 in SEQ ID NO:2). As indicated above, the inventors have determined that the above polypeptide fragments are antigenic regions of the DR4 protein.

The epitope-bearing peptides and polypeptides of the invention may be produced by any conventional means. Houghten, R. A., "General Method for the Rapid Solid-Phase Synthesis of Large Numbers of Peptides: Specificity of Antigen-Antibody Interaction at the Level of Individual Amino Acids," Proc. Natl. Acad. Sci. USA 82:5131-5135 (1985). This "Simultaneous Multiple Peptide Synthesis (SMPS)" process is further described in U.S. Pat. No. 4,631,211 to Houghten et al. (1986). As one of skill in the art will appreciate, DR4 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., Nature 331:84-86 (1988)). Fusion proteins that have a disulfide-linked dimeric structure due to the IgG part can also be more efficient in binding and neutralizing other molecules than the monomeric DR5 protein or protein fragment alone (Fountoulakis et al., J. Biochem. 270:3958-3964 (1995)).

Antibodies

The present invention further relates to antibodies and T-cell antigen receptors (TCR) which immunospecifically bind a polypeptide, preferably an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a $V_L$ or $V_H$ domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine, donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt et al., J. Immunol. 147:60-69 (1991); U.S. Pat. Nos. 4,474, 893; 4,714,681; 4,925,648; 5,573,920; 5,601,819; Kostelny et al., J. Immunol. 148:1547-1553 (1992).

Antibodies of the present invention may be described or specified in terms of the epitope(s) or portion(s) of a polypeptide of the present invention that they recognize or specifically bind. The epitope(s) or polypeptide portion(s) may be specified as described herein, e.g., by N-terminal and C-terminal positions, by size in contiguous amino acid residues, or listed in the Tables and Figures. Antibodies that specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies that bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10^{-2}$M, $10^{-2}$M, $5\times10^{-3}$M, $10^{-3}$M, $5\times10^{-4}$M, $10^{-4}$M, $5\times10^{-5}$M, $10^{-5}$M, $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{15}$M, and $10^{-15}$M.

Antibodies that bind DR4 receptor polypeptides may bind them as isolated polypeptides or in their naturally occurring state. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the DR4 polypeptide is substantially purified by the one-step method described in Smith and Johnson, Gene 67:31-40 (1988). Thus, antibodies of the present invention may bind recombinantly produced DR4 receptor polypeptides.

In a specific embodiment, antibodies of the present invention bind a full-length DR4 receptor expressed on the surface of a cell comprising a polynucleotide encoding amino acids 1 to 468 of SEQ ID NO:2 operably associated with a regulatory sequence that controls gene expression. In another specific embodiment, antibodies of the present invention bind a full-length DR4 receptor expressed on the surface of a cell comprising a polynucleotide encoding the amino acid sequence encoded by the cDNA contained in ATCC Deposit No. 97853, operably associated with a regulatory sequence that controls gene expression.

In preferred embodiments, antibodies of the present invention bind the mature DR4 receptor expressed on the surface of a cell comprising a polynucleotide encoding amino acids about 24 to about 468 of SEQ ID NO:2 operably associated with a regulatory sequence that controls gene expression. In other preferred embodiments, antibodies of the present invention bind mature DR4 receptor expressed on the surface of a cell comprising a polynucleotide encoding the amino acid sequence of the mature polypeptide encoded by the cDNA contained in ATCC Deposit No. 97853, operably associated with a regulatory sequence that controls gene expression.

In preferred embodiments, antibodies of the present invention bind the extracellular domain of a DR4 receptor expressed on the surface of a cell comprising a polynucleotide encoding amino acids about 24 to about 238 of SEQ ID NO:2 operably associated with a regulatory sequence that controls gene expression. In other preferred embodiments, antibodies of the present invention bind the extracellular domain of a DR4 receptor expressed on the surface of a cell comprising a polynucleotide encoding the amino acid sequence of the extracellular domain of the polypeptide encoded by the cDNA contained in ATCC Deposit No. 97853, operably associated with a regulatory sequence that controls gene expression.

The present invention also provides antibodies that bind DR5 polypeptides that act as either DR4 agonists or DR4 antagonists. In specific embodiments, the antibodies of the invention stimulate apoptosis of DR4 expressing cells. In other specific embodiments, the antibodies of the invention inhibit TRAIL binding to DR4. In other specific embodiments, the antibodies of the invention upregulate DR4 expression.

The present invention also provides antibodies that inhibit apoptosis of DR4 expressing cells. In other specific embodiments, the antibodies of the invention downregulate DR4 expression.

In further embodiments, the antibodies of the invention have a dissociation constant ($K_D$) of $10^{-7}$ M or less. In preferred embodiments, the antibodies of the invention have a dissociation constant ($K_D$) of $10^{-9}$ M or less.

The present invention further provides antibodies that stimulate apoptosis of DR4 expressing cells better than an equal concentration of TRAIL polypeptide stimulates apoptosis of DR4 expressing cells.

The present invention further provides antibodies that stimulate apoptosis of DR4 expressing cells equally well in the presence or absence of antibody cross-linking reagents; and/or stimulate apoptosis with equal or greater potency as an equal concentration of TRAIL in the absence of a cross-linking antibody or other cross-linking agent.

In further embodiments, antibodies of the invention have an off rate ($k_{off}$) of $10^{-3}$/sec or less. In preferred embodiments, antibodies of the invention have an off rate ($k_{off}$) of $10^{-4}$/sec or less. In other preferred embodiments, antibodies of the invention have an off rate ($k_{off}$) of $10^{-5}$/sec or less.

The present invention further encompasses methods and compositions for killing of cells expressing DR4 on their surface, comprising, or alternatively consisting of, contacting anti-DR4 antibodies of the invention with such cells expressing DR4 on their surface.

In specific embodiments, the present invention encompasses methods and compositions for inducing apoptosis in cells expressing DR4 on their surface, comprising, or alternatively consisting of, contacting anti-DR4 antibodies of the invention with such cells expressing DR4 on their surface.

In further specific embodiments, the present invention encompasses methods and compositions for inducing apoptosis in cells expressing a polypeptide comprising amino acids about 52 to about 184 of SEQ ID NO:2 on their surface, comprising, or alternatively consisting of, contacting anti-DR4 antibodies of the invention with such cells expressing said polypeptide on their surface.

In further specific embodiments, the present invention encompasses methods and compositions for inducing apoptosis in cells expressing a polypeptide comprising the extracellular domain of the polypeptide encoded by the cDNA clone contained in ATCC Deposit No. 97920 on their surface, comprising, or alternatively consisting of, contacting anti-DR4 antibodies of the invention with such cells expressing said polypeptide on their surface.

The present invention further encompasses methods and compositions for killing of cells expressing DR4 on their surface, comprising, or alternatively consisting of, administering to an animal, anti-DR4 antibodies of the invention in an amount effective to kill such DR4 expressing cells.

In specific embodiments, the present invention encompasses methods and compositions for inducing apoptosis in cells expressing DR4 on their surface, comprising, or alternatively consisting of, administering to an animal, anti-DR4 antibodies of the invention in an amount effective to induce apoptosis in such DR4 expressing cells.

In further specific embodiments, the present invention encompasses methods and compositions for inducing apoptosis in cells expressing a polypeptide comprising amino acids about 52 to about 184 of SEQ ID NO:2 on their surface, comprising, or alternatively consisting of, administering to an animal, anti-DR4 antibodies of the invention in an amount effective to induce apoptosis in such cells expressing said polypeptide on their surface.

In further specific embodiments, the present invention encompasses methods and compositions for inducing apoptosis in cells expressing a polypeptide comprising the extracellular domain of the polypeptide encoded by the cDNA clone contained in ATCC Deposit No. 97920 on their surface, comprising, or alternatively consisting of, administering to an animal, anti-DR4 antibodies of the invention in an amount effective to induce apoptosis in such cells expressing said polypeptide on their surface.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 90%, at least 80%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand or receptor activity by at least 90%, at least 80%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation. The antibodies may be specified as agonists, antagonists or inverse agonists for biological activities comprising the specific biological activities of the peptides of the invention disclosed herein. Thus, the invention further relates to antibodies which act as agonists or antagonists of the polypeptides of the present invention. The above antibody agonists can be made using methods known in the art. See, e.g., PCT publication WO 96/40281; U.S. Pat. No. 5,811,097; Deng et al., *Blood* 92(6):1981-1988 (1998); Chen et al., *Cancer Res.* 58(16):3668-3678 (1998); Harrop et al., *J. Immunol.* 161(4):1786-1794 (1998); Zhu et al., *Cancer Res.* 58(15): 3209-3214 (1998); Yoon et al., *J. Immunol.* 160(7):3170-3179 (1998); Prat et al., *J. Cell. Sci.* 111(Pt2):237-247 (1998); Pitard et al., *J. Immunol. Methods* 205(2):177-190 (1997); Liautard et al., *Cytokine* 9(4):233-241 (1997); Carlson et al., *J. Biol. Chem.* 272(17):11295-11301 (1997); Taryman et al., *Neuron* 14(4):755-762 (1995); Muller et al., *Structure* 6(9): 1153-1167 (1998); Bartunek et al., *Cytokine* 8(1):14-20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Example 29, below, as well as Harlow et al., Antibodies: A Laboratory Manual, (Cold Spring Harbor Laboratory Press, 2nd ed. 1988) (incorporated by reference herein in its entirety).

Furthermore, antibodies of the present invention may be used to cause death of cells which express polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen of interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. Monoclonal antibodies can be prepared using a wide variety of techniques known in the art including the use of hybridoma and recombinant and phage display technology.

Methods for producing and screening for specific antibodies using hybridoma technology are routine and well-known in the art and are discussed in detail in Example 21. Briefly, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187:9-18 (1997); Burton et al., *Advances in Immunology* 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., *BioTechniques* 12(6):864-869 (1992); and Sawai et al., *AJRI* 34:26-34 (1995); and Better et al., *Science* 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., PNAS 90:7995-7999 (1993); and Skerra et al., *Science* 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, *Science* 229:1202 (1985); Oi et al., *BioTechniques* 4:214 (1986); Gillies et al., (1989) *J. Immunol. Methods* 125:191-202; U.S. Pat. Nos. 5,807,715; 4,816,567; and 4,816397, which are incorporated herein by reference in their entireties. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., *PNAS* 91:969-973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and Gen-Pharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/technology* 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, *FASEB J* 7(5):437-444 (1989) and Nissinoff, *J. Immunol.* 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Antibodies of the invention may also include multimeric forms of antibodies. For example, antibodies of the invention may take the form of antibody dimers, trimers, or higher-order multimers of monomeric immunoglobulin molecules. Dimers of whole immunoglobulin molecules or of $F(ab')_2$ fragments are tetravalent, whereas dimers of Fab fragments or scFv molecules are bivalent. Individual monomers within an antibody multimer may be identical or different, i.e., they may be heteromeric or homomeric antibody multimers. For example, individual antibodies within a multimer may have the same or different binding specificities.

Multimerization of antibodies may be accomplished through natural aggregation of antibodies or through chemical or recombinant linking techniques known in the art. For example, some percentage of purified antibody preparations (e.g., purified IgG1 molecules) spontaneously form protein aggregates containing antibody homodimers, and other higher-order antibody multimers. Alternatively, antibody homodimers may be formed through chemical linkage techniques known in the art. For example, heterobifunctional crosslinking agents including, but not limited to, SMCC [succinimidyl 4-(maleimidomethyl)cyclohexane-1-carboxylate] and SATA [N-succinimidyl S-acetylthio-acetate] (available, for example, from Pierce Biotechnology, Inc. (Rockford, Ill.)) can be used to form antibody multimers. An exemplary protocol for the formation of antibody homodimers is given in Ghetie et al., *Proceedings of the National Academy of Sciences USA* (1997) 94:7509-7514, which is hereby incorporated by reference in its entirety. Antibody homodimers can be converted to Fab'2 homodimers through digestion with pepsin. Alternatively, antibodies can be made to multimerize through recombinant DNA techniques. IgM and IgA naturally form antibody multimers through the interaction with the J chain polypeptide. Non-IgA or non-IgM molecules, such as IgG molecules, can be engineered to contain the J chain interaction domain of IgA or IgM, thereby conferring the ability to form higher order multimers on the non-IgA or non-IgM molecules. (see, for example, Chintalacharuvu et al., (2001) *Clinical Immunology* 101:21-31. and Frigerio et al., (2000) *Plant Physiology* 123:1483-94., both of which are hereby incorporated by reference in their entireties.) ScFv dimers can also be formed through recombinant techniques known in the art; an example of the construction of scFv dimers is given in Goel et al., (2000) *Cancer Research* 60:6964-6971, which is hereby incorporated by reference in its entirety. Antibody multimers may be purified using any suitable method known in the art, including, but not limited to, size exclusion chromatography.

A. Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., *BioTechniques* 17:242 (1994)), which, briefly, involves the synthesis of overlapping oligonucleotides containing portions of the sequence encoding the antibody, annealing and ligation of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., *J. Mol. Biol.* 278:457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., 1984, *Proc. Natl. Acad. Sci.* 81:851-855; Neuberger et al., 1984, *Nature* 312: 604-608; Takeda et al., 1985, *Nature* 314:452-454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine monoclonal antibody and a human immunoglobulin constant region, e.g., humanized antibodies.

Alternatively, techniques described for the production of single chain antibodies (U.S. Pat. No. 4,694,778; Bird, 1988, *Science* 242:423-42; Huston et al., 1988, *Proc. Natl. Acad. Sci. USA* 85:5879-5883; and Ward et al., 1989, Nature 334: 544-554) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., 1988, *Science* 242:1038-1041).

B. Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, e.g., a heavy or light chain of an antibody of the invention, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, *Gene* 45:101; Cockett et al., 1990, *Bio/Technology* 8:2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., 1983, *EMBO J.* 2:1791), in which the antibody coding sequence may be ligated individually into the vector in frame with the lac Z coding region so that a fusion protein is produced; pIN vectors (Inouye & Inouye, 1985, *Nucleic Acids Res.* 13:3101-3109; Van Heeke & Schuster, 1989, *J. Biol. Chem.* 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, 1984, *Proc. Natl. Acad. Sci. USA* 81:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, *Methods in Enzymol.* 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., 1977, *Cell* 11:223), hypoxanthine-guanine phosphoribosyltransferase (Szybalska & Szybalski, 192, *Proc. Natl. Acad. Sci. USA* 48:202), and adenine phosphoribosyltransferase (Lowy et al., 1980, *Cell* 22:817) genes can be employed in tk-, hgprt- or aprt-cells, respectively. Also, antimetabolite resistance can be used as the basis of selection for the following genes: dhfr, which confers resistance to methotrexate (Wigler et al., 1980, *Natl. Acad. Sci. USA* 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260: 926-932; and Morgan and Anderson, 1993, Ann. Rev. Biochem. 62:191-217; May, 1993, TIB TECH 11(5):155-215); and hygro, which confers resistance to hygromycin (Santerre et al., 1984, Gene 30:147). Methods commonly known in the art of recombinant DNA technology which can be used are described in Ausubel et al. (eds.), 1993, *Current Protocols in Molecular Biology*, John Wiley & Sons, NY; Kriegler, 1990, *Gene Transfer and Expression, A Laboratory Manual*, Stockton Press, NY; and in Chapters 12 and 13, Dracopoli et al. (eds), 1994, Current Protocols in Human Genetics, John Wiley & Sons, NY.; Colberre-Garapin et al., 1981, *J. Mol. Biol.* 150:1, which are incorporated by reference herein in their entireties.

The expression levels of an antibody molecule can be increased by vector amplification (for a review, see Bebbington and Hentschel, *The use of vectors based on gene amplification for the expression of cloned genes in mammalian cells in DNA cloning*, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, *Mol. Cell. Biol.* 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, *Nature* 322:52; Kohler, 1980, *Proc. Natl. Acad. Sci. USA* 77:2197). The coding sequences for the heavy and light chains may comprise cDNA or genomic DNA.

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins.

C. Antibody Conjugates

The present invention encompasses antibodies recombinantly fused or chemically conjugated (including both covalently and non-covalently conjugations) to a polypeptide (or portion thereof, preferably at least 10, 20 or 50 amino acids of the polypeptide) of the present invention to generate fusion proteins. Also encompassed are antibodies of the invention recombinantly fused or chemically conjugated (including both covalently and non-covalently conjugations) to a polypeptide (or portion thereof, preferably at least 10, 20 or 50 amino acids of the polypeptide) to generate fusion proteins. The fusion does not necessarily need to be direct, but may occur through linker sequences. The antibodies may be specific for antigens other than polypeptides (or portion thereof, preferably at least 10, 20 or 50 amino acids of the polypeptide) of the present invention. Furthermore, the antibodies may be specific for polypeptides (or portion thereof, preferably at least 10, 20 or 50 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Alternatively, antibodies of the present invention may be used to target conjugated polypeptides and/or compounds to particular cell types, either in vitro or in vivo, by fusing or conjugating the antibodies of the present invention to the polypeptides and/or compounds to be targeted.

Antibodies fused or conjugated to the polypeptides of the present invention may also be used in in vitro immunoassays and purification methods using methods known in the art. Also, antibodies of the present invention fused or conjugated to polypeptides and/or compounds may be used in in vitro immunoassays and purification methods using methods known in the art. See e.g., Harbor et al., supra, and PCT publication WO 93/21232; EP 439,095; Naramura et al., *Immunol. Lett.* 39:91-99 (1994); U.S. Pat. No. 5,474,981; Gillies et al., *PNAS* 89:1428-1432 (1992); Fell et al., *J. Immunol.* 146:2446-2452 (1991), which are incorporated by reference in their entireties.

The present invention further includes compositions comprising the polypeptides, including antibodies, of the present invention fused or conjugated to antibody domains other than the variable regions. Furthermore, the present invention includes compositions comprising the antibodies of the present invention fused or conjugated to heterologous antibody domains other than variable regions. For example, the polypeptides including antibodies of the present invention may be fused or conjugated to a heterologous antibody Fc region, or portion thereof.

The antibody portion fused to a polypeptide and/or antibody of the present invention may comprise the constant region, hinge region, CH1 domain, CH2 domain, and CH3 domain or any combination of whole domains or portions thereof. The polypeptides, including antibodies, may also be fused or conjugated to the above antibody portions to form multimers. For example, Fc portions fused to the polypeptides, including antibodies, of the present invention can form dimers through disulfide bonding between the Fc portions. Higher multimeric forms can be made by fusing the polypeptides, including antibodies of the present invention, to portions of IgA and IgM. Methods for fusing or conjugating the polypeptides, including antibodies, of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341 (1992) (said references incorporated by reference in their entireties).

As discussed, supra, the polypeptides, including antibodies, of the present invention may be fused or conjugated to the above antibody portions to increase the in vivo half life of the polypeptides or for use in immunoassays using methods known in the art. Further, the polypeptides, including antibodies, of the present invention may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84-86 (1988).

The polypeptides, including antibodies, of the present invention fused or conjugated to an antibody having disulfide-linked dimeric structures (due to the IgG) may also be more efficient in binding and neutralizing, agonizing and/or antagonizing other molecules, than the monomeric secreted antibody, protein, antibody fragment or protein fragment alone. (Fountoulakis et al., J. Biochem. 270:3958-3964 (1995)). In many cases, the heterologous Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5 receptor, have been fused with Fc portions for the purpose of high-throughput screening assays to identify antagonists of hIL-5. (See, D. Bennett et al., *J Molecular Recognition* 8:52-58 (1995); K. Johanson et al., *J. Biol. Chem.* 270:9459-9471 (1995).

The present invention further includes compositions comprising the antibodies of the present invention fused or conjugated to human serum albumin to increase the in vivo half-life of the antibodies or for use in immunoassays using methods known in the art. Further, the antibodies of the present invention may be fused or conjugated to human serum albumin to facilitate purification. In many cases, the human serum albumin part in a fusion protein is beneficial in therapy and diagnosis, and thus can result in, for example, improved pharmacokinetic properties. See e.g., U.S. Pat. No. 5,876,969, EP Patent 0413622, and U.S. Pat. No. 5,766,883, herein incorporated by reference in their entirety.

Moreover, the antibodies or fragments thereof of the present invention can be fused to marker sequences, such as a peptide to facilitates their purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., *Cell* 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment and/or prevention regimens. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, 3-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and acquorin; and examples of suitable radioactive material include $^{125}$I, $^{131}$I, $^{111}$In or $^{99}$Tc.

Further, an antibody or fragment thereof may be conjugated to a therapeutic moiety such as a cytotoxin, e.g., a cytostatic or cytocidal agent, a therapeutic agent or a radioactive metal ion. A cytotoxin or cytotoxic agent includes any agent that is detrimental to cells. Examples include paclitaxol, cytochalasin B, gramnicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in *Monoclonal Antibodies And Cancer Therapy*, Reisfeld et al. (eds.), pp. 243-56 (Alan R. Liss, Inc. 1985); Hellstrom et al., "Antibodies For Drug Delivery", in *Controlled Drug Delivery* (2nd Ed.), Robinson et al. (eds.), pp. 623-53 (Marcel Dekker, Inc. 1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), pp. 303-16 (Academic Press 1985), and Thorpe et al., "The Preparation And Cytotoxic Properties Of Antibody-Toxin Conjugates", *Immunol. Rev.* 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Additionally, antibodies of the invention may be modified by post-translational modifications encompassed including, for example, N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of procaryotic host cell expression.

Also provided by the invention are chemically modified antibody derivatives, which may provide additional advantages such as increased solubility, stability and circulating time of the antibody, or decreased immunogenicity (see, U.S. Pat. No. 4,179,337). The chemical moieties for derivation may be selected from water soluble polymers such as polyethylene glycol, ethylene glycol/propylene glycol copolymers, carboxymethylcellulose, dextran, polyvinyl alcohol and the like. The antibodies may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59-72 (1996); Vorobjev et al., *Nucleosides Nucleotides* 18:2745-2750 (1999); and Caliceti et al., *Bioconjug. Chem.* 10:638-646 (1999), the disclosures of each of which are incorporated herein by reference.

The polyethylene glycol molecules (or other chemical moieties) should be attached to the antibody with consideration of effects on binding specificity and agonistic and/or antagonistic properties of the antibody.

As described supra, there are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride) and polyethylene glycol may be attached to antibodies via linkage to any of a number of amino acid residues. Furthermore, one may specifically desire antibodies chemically modified at the N-terminus.

Polyethylene glycol may be attached to the antibody either directly or by an intervening linker. Linkerless systems for attaching polyethylene glycol to proteins are described in Delgado et al., *Crit. Rev. Thera. Drug Carrier Sys.* 9:249-304 (1992); Francis et al., *Intern. J of Hematol.* 68:1-18 (1998); U.S. Pat. No. 4,002,531; U.S. Pat. No. 5,349,052; WO 95/06058; and WO 98/32466, the disclosures of each of which are incorporated herein by reference.

As described supra, polyethylene glycol can also be attached to antibodies using a number of different intervening linkers. See e.g., U.S. Pat. No. 5,612,460, the entire disclosure of which is incorporated herein by reference.

The number of polyethylene glycol moieties attached to each antibody of the invention (i.e., the degree of substitution) may also vary. For example, the pegylated antibodies of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5,4-6, 5-7, 6-8, 7-9, 8-10, 9-11, 10-12, 11-13, 12-14, 13-15, 14-16, 15-17, 16-18, 17-19, or 18-20 polyethylene glycol moieties per antibody molecule. Methods for determining the degree of substitution are discussed, for example, in Delgado et al., *Crit. Rev. Thera. Drug Carrier Sys.* 9:249-304 (1992).

As described supra, antibodies may be modified by natural processes, such as posttranslational processing, or by chemical modification techniques, which are well known in the art. It will be appreciated that the same type of modification may be present in the same or varying degrees at several sites in a given antibody. Also, a given antibody may contain many types of modifications.

Modifications may include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W.H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992)).

D. Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP40 or Triton X-100, 1% sodium deoxycholate, 0.1% SDS, 0.15 M NaCl, 0.01 M sodium phosphate at pH 7.2, 1% Trayslol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al., eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^{3}H$ or $^{125}I$) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest is conjugated to a labeled compound (e.g., $^{3}H$ or $^{125}I$) in the presence of increasing amounts of an unlabeled second antibody.

E. Antibody Based Therapies

The present invention is further directed to antibody-based therapies which involve administering antibodies of the invention to an animal, preferably a mammal, and most preferably a human, patient for treating and/or preventing one or more of the disorders or conditions described herein. Therapeutic compounds of the invention include, but are not limited to, antibodies of the invention (including fragments, analogs and derivatives thereof as described herein) and nucleic acids encoding antibodies of the invention (including fragments, analogs and derivatives thereof as described herein).

While not intending to be bound to theory, DR4 receptors are believed to induce programmed cell death by a process which involves the association/cross-linking of death domains between different receptor molecules. Further, DR4 ligands (e.g., TRAIL) which induce DR4 mediated programmed cell death are believed to function by causing the association/cross-linking of DR4 death domains. Thus, agents (e.g., antibodies) which prevent association/cross-linking of DR4 death domains will prevent DR4 mediated programmed cell death, and agents (e.g., antibodies) which facilitate the association/cross-linking of DR4 death domains will induce DR4 mediated programmed cell death.

As noted above, DR4 receptors have been shown to bind TRAIL. DR4 receptors are also known to be present in a number of tissues and on the surfaces of a number of cell types. These tissues and cell types include amniotic cells, heart, liver cancer cells, kidney, leukocytes, activated T-cells, K562 cells (an erythroleukemia cell line) plus PMA, W138 cells (a human lung fibroblast cell line), Th2 cells (lymphocytes), human tonsils, and CD34 depleted buffy coat cells of cord blood. Further, as explained in more detail below, TRAIL has been shown to induce apoptosis and to inhibit the growth of tumor cells in vivo. Additionally, TRAIL activities are believed to be modulated, at least in part, through interaction with DR4 and DR5 receptors.

TRAIL is a member of the TNF family of cytokines which has been shown to induce apoptotic cell death in a number of tumor cell lines and appears to mediate its apoptosis inducing effects through interaction with DR4 and DR5 receptors. These death domain containing receptors are believed to form membrane-bound self-activating signaling complexes which initiate apoptosis through cleavage of caspases.

In addition to DR4 and DR5 receptors, TRAIL also binds to several receptors proposed to be "decoy" receptors, DcR2 (a receptor with a truncated death domain), DcR1 (a GP1-anchored receptor), and OPG (a secreted protein which binds to another member of the TNF family, RANKL).

Further, recent studies have shown that the rank-order of affinities of TRAIL for the recombinant soluble forms of its receptors is strongly temperature dependent. In particular, at 37° C., DR5 has the highest affinity for TRAIL and OPG having the lowest affinity.

The DR4 and DR5 receptor genes, as well as genes encoding two decoy receptors, have been shown to be located on human chromosome 8p21-22. Further, this region of the human genome is frequently disrupted in head and neck cancers.

It has recently been found that the FaDu nasopharyngeal cancer cell line contains an abnormal chromosome 8p21-22 region. (Ozoren et al., *Int. J. Oncol.* 16:917-925 (2000).) In particular, a homozygous deletion involving DR4, but not DR5, has been found in these cells. (Ozoren et al., *Int. J. Oncol.* 16:917-925 (2000).) The homozygous loss within the DR4 receptor gene in these FaDu cells encompasses the DR4 receptor death domain. This disruption of the DR4 receptor death domain is associated with resistance to TRAIL-mediated cytotoxicity. Further, re-introduction of a wild-type DR4 receptor gene has been shown to both lead to apoptosis and restoration of TRAIL sensitivity of FaDu cells. (Ozoren et al., *Int. J. Oncol.* 16:917-925 (2000).) These data indicate that the DR4 receptor gene may be inactivated in human cancers and DR4 receptor gene disruption may contribute to resistance to TRAIL therapy. It is expected that similar results would be found in cells having analogous deletions in the DR5 gene.

It has also been shown that overexpression of the cytoplasmic domain of the DR4 receptor in human breast, lung, and colon cancer cell lines leads to p53-independent apoptotic cell death which involves the cleavage of caspases. (Xu et al., *Biochem. Biophys. Res. Commun.* 269:179-190 (2000).) Further, DR4 cytoplasmic domain overexpression has also been shown to result in cleavage of both poly(ADP-ribose) polymerase (PARP) and a DNA fragmentation factor (i.e., ICAD-DFF45). (Xu et al., Biochem. Biophys. Res. Commun. 269:179-190 (2000).) In addition, despite similar levels of DR4 cytoplasmic domain protein as compared to cancer cells tested, normal lung fibroblasts have been shown to be resistant to DR4 cytoplasmic domain overexpression and show no evidence of caspase-cleavage. (Xu et al., *Biochem. Biophys. Res. Commun.* 269:179-190 (2000).) Again, similar results are expected with cells that overexpress the cytoplasmic domain of DR5. Thus, the cytoplasmic domains of the DR4 and DR5 receptors are useful as agents for inducing apoptosis, for example, in cancer cells.

Further, overexpression of the cyclin-dependent kinase inhibitor p21(WAF1/CIP1), as well as the N-terminal 91 amino acids of this protein, has cell cycle-inhibitory activity and inhibits DR4 cytoplasmic domain-dependent caspase cleavage. Thus, DR4 receptors are also involved in the regulation of cell cycle progression. As above, similar results are expected with the DR5 receptor. Thus, the DR4 and DR5 receptors, as well as agonists and antagonists of these receptors, are useful for regulating cell cycle progression.

Antibodies which bind to DR4 receptors are useful for treating and/or preventing diseases and conditions associated with increased or decreased DR4-induced apoptotic cells death. Further, these antibodies vary in the effect they have on DR4 receptors. These effects differ based on the specific portions of the DR4 receptor to which the antibodies bind, the three-dimensional conformation of the antibody molecules themselves, and/or the manner in which they interact with the DR4 receptor. Thus, antibodies which bind to the extracellular domain of a DR4 receptor can either stimulate or inhibit DR4 activities (e.g., the induction of apoptosis). Antibodies which stimulate DR4 receptor activities (e.g., by facilitating the association between DR4 receptor death domains) are DR4 agonists, and antibodies which inhibit DR4 receptor activities (e.g., by blocking the binding of TRAIL and/or preventing the association between DR4 receptor death domains) are DR4 antagonists.

Antibodies of the invention which function as agonists and antagonists of DR4 receptors include antigen-binding antibody fragments such as Fab and F(ab')$_2$ fragments, Fd, single-chain Fvs (scFv), disulfide-linked Fvs (sdFv) and fragments comprising either a $V_L$ or $V_H$ domain, as well as polyclonal, monoclonal and humanized antibodies. Divalent antibodies are preferred as agonists. Each of these antigen-binding antibody fragments and antibodies are described in more detail elsewhere herein.

In view of the above, antibodies of the invention, as well as other agonists, are useful for stimulating DR4 death domain activity to promote apoptosis in cells which express DR4 receptors (e.g., cancer cells). Antibodies of this type are useful for prevention and/or treating diseases and conditions associated with increased cell survival and/or insensitivity to apoptosis-inducing agents (e.g., TRAIL), such as solid tissue cancers (e.g., skin cancer, head and neck tumors, breast tumors, endothelioma, lung cancer, osteoblastoma, osteoclastoma, and Kaposi's sarcoma) and leukemias.

Antagonists of the invention (e.g., anti-DR4 antibodies) function by preventing DR4 mediated apoptosis and are useful for preventing and/or treating diseases associated with increased apoptotic cell death. Examples of such diseases include diabetes mellitus, AIDS, neurodegenerative disorders, myelodysplastic syndromes, ischemic injury, toxin-induced liver disease, septic shock, cachexia and anorexia.

As noted above, DR4 receptors are present on the surfaces of T-cells. Thus, agonists of the invention (e.g., anti-DR4 receptor antibodies) are also useful for inhibiting T-cell mediated immune responses, as well as preventing and/or treating diseases and conditions associated with increased T-cell proliferation. Diseases and conditions associated with T-cell mediated immune responses and increased T-cell proliferation include graft-v-host responses and diseases, osteoarthritis, psoriasis, septicemia, inflammatory bowel disease, inflammation in general, autoimmune diseases, and T-cell leukemias.

When an agonist of the invention is administered to an individual for the treatment and/or prevention of a disease or condition associated with increased T-cell populations or increased cell proliferation (e.g., cancer), the antagonist may be co-administered with another agent which induces apoptosis (e.g., TRAIL) or otherwise inhibits cell proliferation (e.g., an anti-cancer drug). Combination therapies of this nature, as well as other combination therapies, are discussed below in more detail.

Further, antagonists of the invention (e.g., anti-DR4 receptor antibodies) are also useful for enhancing T-cell mediated immune responses, as well as preventing and/or treating diseases and conditions associated with decreased T-cell proliferation. Antibodies of the invention which block the binding of DR4 receptor ligands to DR4 receptors or interfere with DR4 receptor conformational changes associated with membrane signal transduction can inhibit DR4 mediated T-cell apoptosis. The inhibition of DR4-mediated apoptosis can, for examples, either result in an increase in the expansion rate of in vivo T-cell populations or prevent a decrease in the size of such populations. Thus, antagonists of the invention can be used to prevent and/or treat diseases or conditions associated with decreased or decreases in T-cell populations. Examples of such diseases and conditions included acquired immune deficiency syndrome (AIDS) and related afflictions (e.g., AIDS related complexes), T-cell immunodeficiencies, radiation sickness, and T-cell depletion due to radiation and/or chemotherapy.

When an antagonist of the invention is administered to an individual for the treatment and/or prevention of a disease or condition associated with decreased T-cell populations, the antagonist may be co-administered with an agent which activates and/or induces lymphocyte proliferation (e.g., a cytokine). Combination therapies of this nature, as well as other combination therapies, are discussed below in more detail.

Similarly, agonists and antagonists of the invention (e.g., anti-DR5 receptor antibodies) are also useful when administered alone or in combination with another therapeutic agent for either inhibiting or enhancing B-cell mediated immune responses, as well as preventing and/or treating diseases and conditions associated with increased or decreased B-cell proliferation.

Anti-DR4 antibodies are thus useful for treating and/or preventing malignancies, premalignant conditions, abnormalities, diseases and/or conditions involving tissues and cell types which express DR4 receptors. Further, malignancies, premalignant conditions, abnormalities, diseases and/or conditions which can be treated and/or prevented by the induction of programmed cell death in cells which express DR4 receptors can be treated and/or prevented using DR4 receptor agonists of the invention. Similarly, malignancies, premalignant conditions, abnormalities, diseases and/or conditions which can be treated and/or prevented by inhibiting programmed cell death in cells which express DR4 receptors can be treated and/or prevented using DR4 receptor antagonists of the invention.

A number of additional malignancies, premaligant conditions, abnormalities, diseases and/or conditions which can be treated using the agonists and antagonists of the invention are set out elsewhere herein, for example, in the section below entitled "Therapeutics".

The antibodies of the present invention may be used therapeutically in a number of ways. For example, antibodies which bind polynucleotides or polypeptides of the present invention can be administered to an individual (e.g., a human) either locally or systemically. Further, these antibodies can be administered alone, in combination with another therapeutic agent, or associated with or bound to a toxin.

The present invention provides antibodies, which may be administered in combination with one or more therapeutic agents and/or procedures in the treatment, prevention, amelioration and/or cure of cancers. In preferred embodiments, agonistic antibodies of the invention may be administered in combination with one or more therapeutic agents and/or procedures in the treatment, prevention, amelioration and/or cure of cancers and premalignant conditions.

In a specific embodiment, antibodies or antibody compositions of the invention are administered in combination with $DAB_{389}EGF$, a diphtheria toxin fused to Epidermal Growth Factor. $DAB_{389}EGF$ is described in Shaw et al., (1991) *The Journal of Biological Chemistry*, 266:21118-24, which is hereby incorporated by reference in its entirety. In a specific embodiment, antibodies or antibody compositions of the invention are administered in combination with $DAB_{389}EGF$ for the treatment of cancer, such as brain cancers and epithelial cancers. In a specific embodiment, antibodies or antibody compositions of the invention are administered in combination with $DAB_{389}EGF$ for the treatment of astrocytomas. In a specific embodiment, antibodies or antibody compositions of the invention are administered in combination with $DAB_{389}EGF$ for the treatment of glioblastyoma multiforme (GBM).

Therapeutic agents, useful in the treatment, prevention, amelioration and/or cure of cancers and premalignant conditions, with which antibodies of the present invention may be administered, include, for example, biological agents (e.g., inhibitors of signaling pathways, inhibitors of gene transcription, inhibitors of multi-drug resistance (MDR) mechanisms, inhibitors of angiogenesis, inhibitors of matrix metalloproteinases, hormones and hormone antagonists, and compounds of unknown mechanism), chemotherapeutic agents (e.g., alkylating agents, antimetabolites, farnesyl transferase inhibitors, mitotic spindle inhibitors (plant-derived alkaloids), nucleotide analogs, platinum analogs, and topoisomerase inhibitors), corticosteroids, gene therapies, immunotherapeutic agents (e.g., monoclonal antibodies, cytokines and vaccines), phototherapy, radiosensitizing agents, treatment support agents (e.g., anti-emetic agents, analgesic agents and hematopoietic agents), and other miscellaneous drug types. Therapeutic procedures, useful in the treatment, prevention, amelioration and/or cure of cancers and premalignant conditions, with which agonistic antibodies of the present invention may be administered, include, for example, but are not limited to, surgical procedures and radiation therapies.

In preferred embodiments, agonistic antibodies of the invention are administered in combination with one or more of the above-described therapeutic agents in the treatment, prevention, amelioration and/or cure of cancers and premalignant conditions.

In specific embodiments, antibodies of the present invention may be administered in combination with one or more therapeutic agents useful in the treatment, prevention, amelioration and/or cure of cancers and premalignant conditions including, but not limited to, 81C6 (Anti-tenascin monoclonal antibody), 2-chlorodeoxyadenosine, A007 (4-4'-dihydroxybenzophenone-2, 4-dinitrophenylhydrazone), Abarelixg (Abarelix-Depot-Mg, PPI-149, R-3827); Abiraterone acetates (CB-7598, CB-7630), ABT-627 (ET-1 inhibitor), ABX-EGF (anti-EGFr MAb), Acetyldinaline (CI-994, GOE-5549, GOR-5549, PD-130636), AG-2034 (AG-2024, AG-2032, GARFT [glycinamide ribonucleoside transformylase] inhibitor), Alanosine, Aldesleukin (IL-2, Proleukin®), Alemtuzumab® (Campath®), Alitretinoin (Panretin®, LGN-1057), Allopurinol (Aloprim®D, Zyloprim®), Altretamine (Hexylen®, hexamethylmelamine, Hexastat®), Amifostine (Ethyol®), Aminocamnptothecin (9-AC, 9-Aminocamptothecin, NSC 603071), Aminoglutethimide (Cytadren®), Aminolevulinic acid (Levulan®, Kerastick®), Aminopterin, Amsacrine, Anastrozole (Arimidex®), Angiostatin, Annamycin (AR-522, annamycin LF, Aronex®), Anti-idiotype therapy (BsAb), Anti-CD 19/CD3 MAb (anti-CD 19/CD3 scFv, anti-NHL MAb), APC-8015 (Provenge®, Dendritic cell therapy), Aplidine (Aplidin®, Aplidina®), Arabinosylguanine (Ara-G, GW506U78, Nelzarabine®, Compound 506U78), Arsenic trioxide (Trisenox®, ATO, Atrivex®), Avorelin® (Meterelin®, MF-6001, EP-23904), B43-Genistein (anti-CD19 Ab/genistein conjugate), B43-PAP (anti-CD19 Ab/pokeweed antiviral protein conjugate), B7 antibody conjugates, BAY 43-9006 (Raf kinase inhibitor), BBR 3464, Betathine (Beta-LT), Bevacizumab® (Anti-VEGF monoclonal antibody, rhuMAb-VEGF), Bexarotene (Targreting, LGD1069), BIBH-1 (Anti-FAP MAb), BIBX-1382, Biclutamide (Casodex®), Biricodar dicitrate (Incel®, Incel MDR Inhibitor), Bleomycin (Blenoxane®), BLP-25 (MUC-1 peptide), BLyS antagonists, BMS-214662 (BMS-192331, BMS-193269, BMS-206635), BNP-1350 (BNPI-1100, Karenitecins), Boronated Protoporphyrin Compound (PDIT, Photodynarnic Immunotherapy), Bryostatin-1

(Bryostatin®g, BMY-45618, NSC-339555), Budesonide (Rhinocort®), Busulfan (Busulfex®, Myleran®), C225 (IMC-225, EGFR inhibitor, Anti-EGFr MAb, Cetuximab®), C242-DM1 (huC242-DM1), Cabergoline (Dostinex®), Capecitabine (Xeloda®, Doxifluridine®, oral 5-FU), Carbendazin® (FB-642), Carboplatin (Paraplatin®, CBDCA), Carboxyamidotriazole (NSC 609974, CAI, L-651582), Cannustine (DTI-015, BCNU, BiCNU, Gliadel Wafer®), CC49-zeta gene therapy, CEA-cide® (Labetuzumab®, Anti-CEA monoclonal antibody, hMN-14), CeaVac® (MAb 3H1), Celecoxib (Celebrex®), CEP-701 (KT-5555), Cereport® (Lobradimil®, RMP-7), Chlorambucil (Leukeran®), CHML (Cytotropic Heterogeneous Molecular Lipids), Cholecaliferol, CI-1033 (Pan-erbB RTK inhibitor), Cilengitide (EMD-121974, integrin alphavbeta3 antagonist), Cisplatin (Platinol®, CDDP), Cisplatin-epinephrine gel (IntraDose®, FocaCist®), Cisplatin-liposomal (SPI-077), 9-cis retinoic acid (9-cRA), Cladribine (2-CdA, Leustatin®), Clofarabine (chloro-fluoro-araA), Clonadine hydrochloride (Duraclon®), CMB-401 (Anti-PEM MAb/calicheamycin), CMT-3 (COL-3, Metastat®), Cordycepin, Cotara® (chTNT-1/B, [$^{131}$I]-chTNT-1/B), CN-706, CP-358774 (Tarceva®, OSI-774, EGFR inhibitor), CP-609754, CP IL-4-toxin (IL-4 fusion toxin), CS-682, CT-2584 (Apra®, CT-2583, CT-2586, CT-3536), CTP-37 (Avicine®, hCG blocking vaccine), Cyclophosphamide (Cytoxan®, Neosar®, CTX), Cytarabine (Cytosar-US, ara-C, cytosine arabinoside, DepoCyte), D-limonene, DAB389-EGF (EGF fusion toxin), Dacarbazine (DTIC), Daclizumab® (Zenapax®), Dactinomycin (Cosmegen®), Daunomycin (Daunorubicin®, Cerubidine®), Daunorubicin (DaunoXome®, Daunorubicin®, Cerubidine®), DeaVac® (CEA anti-idiotype vaccine), Decitabine (5-aza-2'-deoxyytidine), Declopramide (Oxi-104), Denileukin diftitox (Ontak®), Depsipeptide (FR901228, FK228), Dexamethasone (Decadron®), Dexrazoxane (Zinecard®), Diethylnorspennine (DENSPM), Diethylstilbestrol (DES), Dihydro-5-azacytidine, Docetaxel (Taxotere®, Taxane®), Dolasetron mesylate (Anzemet®), Dolastatin-10 (DOLA-10, NSC-376128), Doxorubicin (Adriamycin®, Doxil®, Rubex®), DPPE, DX-8951f (DX-8951), Edatrexate, EGF-P64k Vaccine, Elliott's B Solution®, EMD-121974, Endostatin, Eniluracil (776c85), EO9 (EO1, EO4, EO68, EO70, EO72), Epirubicin (Ellence®, EPI, 4' epi-doxorubicin), Epratuzumab® (Lymphocide®, humanized anti-CD22, HAT), Erythropoietin (EPO®, Epogen®), Procrit®), Estramustine (Emcyt®), Etanidazole (Radinyl®), Etoposide phosphate (Etopophos®), Etoposide (VP-16, Vepesid®), Exemestane (Aromasin®, Nikidess®), Exetecan mesylate (DX-8951, DX-8951f), Exisulind (SAAND, Aptosyn®, cGMP-PDE2 and 5 inhibitor), F19 (Anti-FAP monoclonal antibody, iodinated anti-FAP MAb), Fadrozole (Afema®, Fadrozole hydrochloride, Arensin®), Fenretinideg (4HPR), Fentanyl citrate (Actiq®), Filgrastim (Neupogen®, G-CSF), FK-317 (FR-157471, FR-70496), Flavopiridol (HMR-1275), Fly3/flk2 ligand (Mobista®), Fluasterone, Fludarabine (Fludara®, FAMP), Fludeoxyglucose (F-18®), Fluorouracil (5-FU, Adrucil®, Fluoroplex®, Efudex®), Flutamide (Eulexin®), FMdC (KW-2331, MDL-101731), Formestane (Lentaron®), Fotemustine (Muphoran®, Mustophoran®), FUDR (Floxuridine®), Fulvestrant (Faslodex®), G3139 (Genasense®, GentaAnticode®, Bcl-2 antisense), Gadolinium texaphyrin (Motexafin gadolinium, Gd-Tex®, Xcytrin®), Galarubicin hydrochloride (DA-125), GBC-590, Gastrimmune® (Anti-gastrin-17 immunogen, anti-g17), Gemcitabine (Gemto®, Gemzar®), Gentuzumab-ozogamicin (Mylotarg®), GL331, Globo H hexasaccharide (Globo H-KLH®), Glufosfamide®& (O-D-glucosyl-isofosfamide mustard, D19575, INN), Goserelin acetate (Zoladex®)), Granisetrori (Kytril™)), GVAX (GM-CSF gene therapy), Her-2/Neu vaccine, Herceptin® (Trastuzumab®, Anti-HER-2 monoclonal antibody, Anti-EGFR-2 MAb), HSPPC-96 (HSP cancer vaccine, gp96 heat shock protein-peptide complex), HulDiO (anti-HLA-DR MAb, SMART ID10), HumaLYM (anti-CD20 MAb), Hydrocortisone, Hydroxyurea (Hydrea®), Hypericing (VIMRxyn®), 1-131 Lipidiol®, Ibritumomab® tiuxetan (Zevalin®), Idarubicin (Idamycin®, DMDR, IDA), Ifosfamide (IFEX®), Imatinib mesylate (STI-571, Imatinib®, Glivece, Gleevec®, Ab1 tyrosine kinase inhibitor), INGN-101 (p53 gene therapy/retrovirus), INGN-201 (p53 gene therapy/adenovirus), Interferon alpha (Alfaferone®, Alpha-IF®), Interferon alpha 2a (Intron A®), Interferon gamma (Gamma-interferon, Gamma 1000, Gamma-IF), Interleukin-2 (ProleiukinR®), Intoplicine (RP 60475), Irinotecan (Camptosar®, CPT-11, Topotecin®, CaptoCPT-1), Irofulven (MGI-114, Ivofulvan, Acylfulvene analogue), ISIS-2053 (PKC-alpha antisense), ISIS-2503 (Ras antisense), ISIS-3521 (PKC-alpha antisense), ISIS-5132 (K-ras/raf antisense), Isotretinoin (13-CRA, 13-cis retinoic acid, Accutane®), Ketoconazole (Nizoral®), KRN-8602 (MX, MY-5, NSC-619003, MX-2), L-778123 (Ras inhibitors), L-asparaginase (Elspar®, Crastinin®, Asparaginase Medac®, Kidrolase®), Leflunomide (SU-101, SU-0200), Letrozole (Femara®), Leucovorin (Leucovorin®, Wellcovorin®), Leuprolide acetate (Viadur®, Lupron®, Leuprogel®, Eligard®), Leuvectin® (cytofectin+IL-2 gene, IL-2 gene therapy), Levamisole (Ergamisol®), Liarozole (Liazal, Liazol, R-75251, R-85246, Ro-85264), Lmb-2 immunotoxin (anti-CD25 recombinant immuno toxin, anti-Tac(Fv)-PE38), Lometrexol (T-64, T-904064), Lomustine (CCNU®, CeeNU®), LY-335979, Lym-1 (131-I LYM-1), Lymphoma vaccine (Genitope), Mannan-MUC1 vaccine, Marimastat® (BB-2516, TA-2516, MMP inhibitor), MDX447 (MDX-220, BAB-447, EMD-82633, H447, anti-EGFr/FcGammaR1r), Mechlorethamine (Nitrogen Mustard, $HN_2$, Mustargen®), Megestrol acetate (Megace®, Pallace®), Melphalan (L-PAM, Alkeran®, Phenylalanine mustard), Mercaptopurine (6-mercaptopurine, 6-MP), Mesna (Mesnex®), Methotrexate® (MTX, Mexate®, Folex®), Methoxsalen (Uvadex®), 2-Methoxyestradiol (2-ME, 2-ME2), Methylprednisolone (Solumedrol®), Methyltestosterone (Android-10®, Testred®, Virilon®), MGV, Mitomycin C (Mitomycin®, Mutamycin®, Mito Extra®), Mitoxantrone (Novantrone®, DHAD), Mitumomab® (BEC-2, EMD-60205), Mivobulin isethionate (CI-980), MN-14 (Anti-CEA immunoradiotherapy, $^{131}$I-MN-14, $^{188}$Re-MN-14), Motexafin Lutetium (Lutrin®, Optrin®, Lu-Tex®, lutetium texaphyrin, Lucyn®, Antrin®), MPV-2213ad (Finrozole®), MS-209, Muc-1 vaccine, NaPro Paclitaxel, Nelarabine (Compound 506, U78), Neovastat® (AE-941, MMP inhibitor), Neugene compounds (Oncomyc-NG, Resten-NG, myc antisense), Nilutamide (Nilandron®), NovoMAb-G2 scFv (NovoMAb-G2 IgM), NPI-0052 (proteasome inhibitor), O6-benzylguanine (BG, Procept®), Octreotide acetate (Sandostatin LAR® Depot), Odansetron (Zofran®), Onconase (Ranpirnase®), OncoVAX-CL, OncoVAX-CL Jenner (GA-733-2 vaccine), OncoVAX-P (OncoVAX-PrPSA), Onyx-015 (p53 gene therapy), Oprelvekin (Neumageo), Orzel (Tegafur+Uracil+Leucovorin), Oxaliplatin (Eloxatine®, Eloxatin®), Pacis® (BCG, live), Paclitaxel (Paxene®, Taxol®), Paclitaxel-DHA (Taxoprexin®), Pamidronate (Aredia®), PC SPES, Pegademase (Adagen®, Pegademase bovine), Pegaspargase®V (Oncospar®), Peldesine (BCX-34, PNP inhibitor), Pemetrexed disodium (Alimta®, MTA, multitargeted antifolate, LY 231514), Pentostatin (Nipent®, 2-deoxycoformycin), Perfosfamide (4-hydroperoxycyclophosphamide, 4-HC), Perillyl alcohol (perilla alcohol, perillic alcohol, perillol, NSC-641066), Phenylbutyrate, Pirarubicin (THP), Pivaloyloxymethyl butyrate (AN-9, Pivanex®), Porfimer sodium (Photofrin®), Prednisone, Prinomastat® (AG-3340, MMP inhibitor), Procarbazine (Matulane®), PROSTVAC, Providence Portland Medical Center Breast Cancer Vaccine, PS-341 (LDP-341, 26S proteasome inhibitor), PSMA MAb (Prostate Specific Membrane Antigen monoclonal antibody), Pyrazoloacridine (NSC-366140, PD-115934), Quinine, R115777 (Zarnestra®), Raloxifene hydrochloride (Evista®, Keoxifene hydrochloride), Raltitrexed (Tomudex®, ZD-1694), Rebeccamycin, Retinoic acid, R-flurbiprofen (Flurizan®, E-7869, MPC-7869), RFS-2000 (9-nitrocamptothecan, 9-NC, Rubitecan®), Rituximab® (Rituxan®, anti-$CD_{20}$ MAb), RSR-13 (GSJ-61), Satraplatin (BMS-182751, JM-216), SCH 6636, SCH-66336, Sizofilan® (SPG, Sizofuran®, Schizophyllan®, Sonifilan®), SKI-2053R(NSC-D644591), Sobuzoxane (MST-16, Perazolin®), Squalamine (MSI-1256F), SR-49059 (vasopressin receptor inhibitor, Vla), Streptozocin (Zanosar®), SU5416 (Semaxanib®, VEGF inhibitor), SU6668 (PDGF-TK inhibitor), T-67 (T-138067, T-607), Talc (Sclerosol®), Tamoxifen (Nolvadex®), Taurolidine (Taurolin®), Temozolamide (Temodar®, NSC 362856), Teniposide (VM-26, Vumon®), TER-286, Testosterone (Andro®, Androderm®, Testoderm TTS®, Testoderm®, Depo-Testosterone®, Androgel®, depoAndro®), Tf-CRM107 (Transferrin-CRM-107), Thalidomide and thalidomide analogs, including but not limited to, lenalidomide (CC-5013, REVLIMID®) and CC-4047 (ACTIMID™), Theratope, Thioguanine (6-thioguanine, 6-TG), Thiotepa (triethylenethiophosphaoramide, Thioplex®), Thymosin alpha I (Zadaxin®, Thymalfasin®), Tiazofurin (Thiazole®), Tirapazamine (SR-259075, SR-4233, Tirazone®, Win-59075), TNP-470 (AGM-1470, Fumagillin), Tocladesine (8-Cl-cAMP), Topotecan (Hycamtin®, SK&F-104864, NSC-609699, Evotopin®), Toremifene (Estrimex®, Fareston®), Tositumomab® (Bexxar®), Tretinoin (Retin-A®, Atragen®, ATRA, Vesanoid®), TriAb® (anti-idiotype antibody immune stimulator), Trilostane (Modrefen®), Triptorelin pamoate (Treistar Depot®, Decapeptyl®), Trimetrexate (Neutrexin®), Troxacitabine (BCH-204, BCH-4556, Troxatyl®), TS-1, UCN-01 (7-hydroxystaurosporine), Valrubicin (Valstar®), Vaispodar (PSC 833), Vapreotide® (BMY-41606), Vaxid (B-cell lymphoma DNA vaccine), Vinblastine (Velban®, VLB), Vincristine (Oncovin®, Onco TCS®, VCR, Leurocristine®), Vindesine (Eldisine®, Fildesin®), Vinorelbine (Navelbine®), Vitaxin® (LM-609, integrin alphavbeta3 antagonistic MAb), WF10 (macrophage regulator), WHI-P131, WT1 Vaccine, XR-5000 (DACA), XR-9576 (XR-9351, P-glycoprotein/MDR inhibitor), ZD-9331, ZD-1839 (IRESSA®), and Zoledronate (Zometa®).

In one embodiment, antibodies of the present invention may be administered in combination with a taxane. In another embodiment, antibodies of the present invention may be administered in combination with a taxane for the treatment of cancers and premalignant conditions that are resistant to individual chemotherapies. In a specific embodiment, antibodies of the present invention may be administered in combination with Docetaxel (Taxotere®). In a specific embodiment, antibodies of the present invention may be administered in combination with Docetaxel (Taxotere®) for the treatment of cancers and premalignant conditions that are resistant to individual chemotherapies.

In one embodiment, agonistic antibodies of the present invention may be administered in combination with a taxane. In another embodiment, agonistic antibodies of the present invention may be administered in combination with a taxane for the treatment of cancers and premalignant conditions that are resistant to individual chemotherapies. In a specific embodiment, agonistic antibodies of the present invention may be administered in combination with Docetaxel (Taxotere®). In a specific embodiment, agonistic antibodies of the present invention may be administered in combination with Docetaxel (Taxotere®) for the treatment of cancers and premalignant conditions that are resistant to individual chemotherapies In one embodiment, antibodies of the present invention may be administered in combination with a platinum-based chemotherapeutic. In another embodiment, antibodies of the present invention may be administered in combination with a platinum-based chemotherapeutic for the treatment of cancers and premalignant conditions that are resistant to individual chemotherapies. In another specific embodiment, antibodies of the invention may be administered in combination with Carboplatin (Paraplatin®, CBDCA). In another specific embodiment, antibodies of the present invention may be administered in combination with Carboplatin (Paraplatin®, CBDCA) for the treatment of cancers that are resistant to individual chemotherapies.

In one embodiment, agonistic antibodies of the present invention may be administered in combination with a platinum-based chemotherapeutic. In another embodiment, agonistic antibodies of the present invention may be administered in combination with a platinum-based chemotherapeutic for the treatment of cancers and premalignant conditions that are resistant to individual chemotherapies. In another specific embodiment, agonistic antibodies of the invention may be administered in combination with Carboplatin (Paraplatin®, CBDCA). In another specific embodiment, agonistic antibodies of the present invention may be administered in combination with Carboplatin (Paraplatin®, CBDCA) for the treatment of cancers that are resistant to individual chemotherapies.

In one embodiment, antibodies of the present invention may be administered in combination with a topoisomerase inhibitor. In another embodiment, antibodies of the present invention may be administered in combination with a topoisomerase inhibitor for the treatment of cancers and premalignant conditions that are resistant to individual chemotherapies. In a specific embodiment, antibodies of the present invention may be administered in combination with Irinotecan (Camptosar®, CPT-11, Topotecin®, CaptoCPT-1). In a specific embodiment, antibodies of the present invention may be administered in combination with Irinotecan (Camptosar®, CPT-11, Topotecin®, CaptoCPT-1) for the treatment of cancers that are resistant to individual chemotherapies.

In one embodiment, agonistic antibodies of the present invention may be administered in combination with a topoisomerase inhibitor. In another embodiment, agonistic antibodies of the present invention may be administered in combination with a topoisomerase inhibitor for the treatment of cancers and premalignant conditions that are resistant to individual chemotherapies. In a specific embodiment, agonistic antibodies of the present invention may be administered in combination with Irinotecan (Camptosar®, CPT-11, Topotecin®, CaptoCPT-1). In a specific embodiment, agonistic antibodies of the present invention may be administered in combination with Irinotecan (Camptosar®, CPT-11, Topotecin®, CaptoCPT-1) for the treatment of cancers and premalignant conditions that are resistant to individual chemotherapies.

In one embodiment, antibodies of the present invention may be administered in combination with a fluoropyrimidine. In another embodiment, antibodies of the present invention may be administered in combination with a fluoropyrimidine for the treatment of cancers and premalignant conditions that are resistant to individual chemotherapies. In another specific embodiment, antibodies of the invention may be administered in combination with Fluorouracil (5-FU, Adrucil®). In another specific embodiment, antibodies of the present invention may be administered in combination with Fluorouracil (5-FU, Adrucil®) for the treatment of cancers and premalignant conditions that are resistant to individual chemotherapies.

In one embodiment, agonistic antibodies of the present invention may be administered in combination with a fluoropyrimidine. In another embodiment, agonistic antibodies of the present invention may be administered in combination with a fluoropyrimidine for the treatment of cancers and premalignant conditions that are resistant to individual chemotherapies. In another specific embodiment, agonistic antibodies of the invention may be administered in combination with Fluorouracil (5-FU, Adrucil®). In another specific embodiment, agonistic antibodies of the present invention may be administered in combination with Fluorouracil (5-FU, Adrucil®) for the treatment of cancers and premalignant conditions that are resistant to individual chemotherapies.

In one embodiment, the antibody compositions of the invention are administered in combination with apoptosis inducing polypeptides. In a specific embodiment, antibodies of the invention are administered in combination with Smac (second mitochondria-derived activator of caspases) proteins, also known as DIABLO (direct IAP (inhibitor of apoptosis) binding protein with low pI) (GenBank Accession No.: NP_063940 which is hereby incorporated by reference in its entirety). Smac is a 239 amino acid protein. The N-terminal 55 amino acids serve as a mitochondrial targeting sequence which is cleaved after import to the mitochondria. Apoptosis inducing polypeptides may be delivered using techniques known in the art. For example, one way to deliver Smac protein would be through the delivery of a nucleic acid encoding either the full length or mature form of Smac (amino acids 56-239 of GenBank Accession No.: NP_063940, a cytosolic form that bypasses mitochondrial processing). Alternatively, antibody compositions of the invention may be administered in combination with cell permeable, synthetic Smac peptides which are capable of inhibiting IAP proteins (e.g., those containing amino acid residues 56-62 of GenBank Accession No.: NP 063940; AVPIAQK as described in Chai et al., (2000) Nature 406:855-862 and Fulda et al., (2002) Nature Medicine 8:808-815, both of which are hereby incorporated by reference in their entireties. Alternatively, an antibody composition of the invention may be administered in combination with a small molecule IAP inhibitor compound. In specific embodiments, the IAP inhibitor compound mimics the activity of SMAC by binding to one or more IAPs and blocking IAP-mediated caspase inhibition. The IAP inhibitor may be a monomer, a dimer, a trimer, or a higher-order multimer. In specific embodiments the small molecule IAP inhibitor binds to and inhibits the activity of X-linked inhibitor of apoptosis (XIAP). In further embodiments, an antibody composition of the invention is administered with one, two, three, or more of the IAP inhibitors described in Li et al. Science. 2004305(5689):1471-4 (2004) (e.g., "Compound 3"); Schimmer et al., Cancer Cell. 5(1):25-35 (2004) (e.g., compounds 1396-12 and 1396-34); and Zobel et al., ACS Chem. Biol. 1(8):525-33 (2006); which are hereby incorporated by reference in their entirety. Exemplary IAP inhibitors that may be administered in combination with an antibody compound of the invention also include one, two, three, or more of the IAP inhibitors described in U.S. Patent Publication Nos. 20070003535; 20060264379; 20060194741; 20060167066; 20060128632; 20060084611; 20060025347; 20060014700; 20050261203; 20050197403; 20040077542; 20030143579; 20020177557; and International Publication Nos. WO 05/094818; WO 05/097791; WO 06/014361; WO 2006/069063; WO 2006/091972; WO 2006/113376; WO 05/092326; WO 05/069894; and WO 05/069888; each of which are hereby incorporated by reference in their entirety.

In one embodiment, an antibody composition of the invention is administered in combination with a histone deacetylase inhibitor (e.g., trichostatin A, trapoxins, depsipeptide (e.g., FK-288 and FR901228), MS-275, and the triterpenoid 2-cyano-3,12-dioxooleana-1,9-dien-28-oic acid (CDDO) or other molecules related to CDDO, valproic acid, suberoylanilide hydroxamic acid (SAHA), pyroxamide, trapoxin, (depsipeptide), and N-acetyl dinaline (CI-994). In additional embodiments an antibody composition of the invention is administered in combination with one, two, three, or more histone deacytelase inhibitors selected from APHA Compound 8 (3-(1-Methyl-4-phenylacetyl-1H-2-pyrrolyl)-N-hydroxy-2-propenamide); Apicidin (Cyclo[(2S)-2-amino-8-oxodecanoyl-1-methoxy-L-tryptophyl-L-isoleucyl-(2R)-2-piperidinexcarbonyl]); Sodium Butyrate (Butyric Acid Sodium salt); (−)-Depudecin (4,5:8,9-Dianhydro-1,2,6,7,11-pentadeoxy-D-threo-D-ido-undeca-1,6-dienitol); Scriptaid (6-(1,3-Dioxo-1H,3H-benzo[de]isoquinolin-2-yl)-hexanoic acid hydroxyamide); Sirtinol (2-[(2-Hydroxynaphthalen-1-ylmethylene)amino]-N-(1-phenethyl)benzamide); Trichostatin A ([R-(E,E)]-7-[4-(Dimethylamino)phenyl]-N-hydroxy-4,6-dimethyl-7-oxo-2,4-heptadienamide); and histone deacetylase inhibitors described in US Patent Publication Nos. 20050131018; 20050124679; 20050222414; 20050119250; 20050171103; 20070004806; 20060235012; 20050026907; 20050148613; 20060052599; 20030216345; 20060235231; 20070015809; 20040224991; 20060264415; 20020103192; 20060047123; 20030134865; 20060030543; 20050107384; 20060058553; 20070010669; 20050176686; 20060030554; 20050165016; 20060122234; 20050171347; 20050113373; 20040077698; and 20040087652; and International Publication No. WO 05/025619; each of which are hereby incorporated by reference in their entirety.

In one embodiment, an antibody composition of the invention is administered in combination with a nitric oxide donor (e.g., sodium nitroprusside, GEA 3175 (1,2,3,4-oxatriazolium, 3-(3-chloro-2-methylphenyl)-5-[[(methylphenyl)sulphonyl]amino]), isosorbide dinitrate, and nitroglycerin).

In one embodiment, an antibody composition of the invention is administered in combination with curcumin (diferuloylmethane).

In one embodiment an antibody composition of the invention is administered in combination with resveratrol (3,5,4'-trihydroxystilbene).

In another embodiment, an antibody composition of the invention is administered in combination with a protein kinase inhibitor. In particular embodiments, the protein kinase inhibitor is a multi-target kinase inhibitor, including but not limited to Zactima™ (ZD6474), AMG706, MP-412, sorafenib, dasatinib, CEP-701 (lestaurtinib), XL647, XL999, lapatinib, MLN518 (CT53518), PKC412, ST1571, AMN107, AEE788, OSI-930, OSI-817, sunitinib (SUI 1248), and AG-013736.

In another embodiment, an antibody composition of the invention is administered in combination with a Heat Shock Protein (HSP) Inhibitor. In a specific embodiment the HSP inhibitor is an HSP90 inhibitor, such as geldanamycin; geldanamycin analogs (e.g. 17-allylamino-17-demethoxygeldanamycin (17AAG) and 17-aminogeldanamycin (17-AG)); and radicicol.

In another embodiment, an antibody composition of the invention is administered in combination with a peroxisome proliferator-activated receptor-gamma (PPAR-gamma) antagonist, such as, but not limited to, GW9662 and T0070907.

In another embodiment, an antibody composition of the invention is administered in combination with a AKT/mTOR signaling pathway inhibitor, such as, but not limited to, rapamycin, temsirolimus (CCI-779), AP23573, everolimus (RAD001) and MKC-1.

In another embodiment, an antibody composition of the invention is administered in combination with a BCL-2 inhibitor, such as, but not limited to, HA14-1, GX15-070, and ABT-263.

In preferred embodiments, agonistic antibodies of the invention are administered in combination with one or more of the above-described therapeutic agents in the treatment, prevention, amelioration and/or cure of cancers and premalignant conditions.

In further specific embodiments, antibodies of the present invention may be administered in combination with one or more combinations of therapeutic agents useful in the treatment, prevention, amelioration and/or cure of cancers and premalignant conditions including, but not limited to, 9-aminocamptothecin+G-CSF, Adriamycing+Blenoxane+Vinblastine+Dacarbazine (ABVD), BCNU (Carmustine)+Etoposide+Ara-C (Cytarabine)+Melphalen (BEAM), Bevacizumab®+Leucovorin, Bleomycin+Etoposide+Platinolg (Cisplatin) (BEP), Bleomycin+Etoposide+Adriamycin+Cyclophosphamide+Vincristine+Procarbazine+Prednisone (BEACOPP), Bryostatin+Vincristine, Busulfan+Melphalan, Carboplatin+Cereport®, Carboplatin+Cyclophosphamide, Carboplatin+Paclitaxel, Carboplatin+Etoposide+Bleomycin (CEB), Carboplatin+Etoposide+Thiotepa, Cisplatin+Cyclophosphamide, Cisplatin+Docetaxel, Cisplatin+Doxorubicin, Cisplatin+Etoposide, Cisplatin+Gemcitabine, Cisplatin+Interferon alpha, Cisplatin+Irinotecan, Cisplatin+Paclitaxel, Cisplatin+Teniposide, Cisplatin+Vinblastine, Cisplatin+Vindesine, Cisplatin+Vinorelbine, Cisplatin+Cytarabine+Ifosfamide, Cisplatin+Ifosfamide+Vinblastine, Cisplatin+Vinblastine+Mitomycin C, Cisplatin+Vincristine+Fluorouracil, Cisplatin+Vincristine+Lomustine, Cisplatin+Vinorelbine+Gemcitabine, Cisplatin+Carmustine+Dacarbazine+Tamoxifen, Cisplatin+Cyclophosphamide+Etoposide+Vincristine, Cisplatin (Platinol®)+Oncovin®+Doxorubicin (Adriamycin®)+Etoposide (CODE), Cisplatin+Cytarabine+Ifosfamide+Etoposide+Methotrexate, Cyclophosphamide+Adriamycin® (Doxorubicin), Cyclophosphamide+Melphalan, Cyclophosphamide+SCH 6636, Cyclophosphamide+Adriamycing+Cisplatin (Platinol®) (CAP), Cyclophosphamide+Adriamycin®+Vincristine (CAV), Cyclophosphamide+Doxorubicin+Teniposide+Prednisone, Cyclophosphamide+Doxorubicin+Teniposide+Prednisone+Interferon alpha, Cyclophosphamide+Epirubicin+Cisplatin (Platinol®) (CEP), Cyclophosphamide+Epirubicin+Fluorouracil, Cyclophosphamide+Methotrexate+Fluroruracil (CMF), Cyclophosphamide+Methotrexate+Vincristine (CMV), Cyclophosphamide+Adriamycing+Methotrexate+Fluorouracil (CAMF), Cyclophosphamide+Adriamycin®+Methotrexate+Procarbazine (CAMP), Cyclophosphamide+Adriamycin®+Vincristine+Etoposide (CAV-E), Cyclophosphamide+Adriamycing+Vincristine+Prednisone (CHOP), Cyclophosphamide+Novantrone® (Mitoxantrone)+Vincristine (Oncovorin)+Prednisone (CNOP), Cyclophosphamide+Adriamycin®+Vincristine+Prednisone+Rituximab (CHOP+Rituximab), Cyclophosphamide+Adriamycin®+Vincristine+Teniposide (CAV-T), Cyclophosphamide+Adriamycin®+Vincristine alternating with Platinol®+Etoposide (CAV/PE), Cyclophosphamide+BCNU (Carmustine)+VP-16 (Etoposide) (CBV), Cyclophosphamide+Vincristine+Prednisone (CVP), Cyclophosphamide+Oncovin®+Methotrexate+Fluorouracil (COMF), Cytarabine+Methotrexate, Cytarabine+Bleomycin+Vincristine+Methotrexate (CytaBOM), Dactinomycin+Vincristine, Dexamethasone+Cytarabine+Cisplatin (DHAP), Dexamethasone+Ifosfamide+Cisplatin+Etoposide (DICE), Docetaxel+Gemcitabine, Docetaxel+Vinorelbine, Doxorubicin+Vinblastine+Mechlorethamine+Vincristine+Bleomycin+Etoposide+Prednisone (Stanford V), Epirubicin+Gemcitabine, Estramustine+Docetaxel, Estramustine+Navelbine, Estramustine+Paclitaxel, Estramustine+Vinblastine, Etoposide (Vepesid®)+Ifosfamide+Cisplatin (Platinol®) (VIP), Etoposide+Vinblastine+Adriamycin (EVA), Etoposide (Vepesid®)+Ifosfamide+Cisplatin+Epirubicin (VIC-E), Etoposide+Methylprednisone+Cytarabine+Cisplatin (ESHAP), Etoposide+Prednisone+Ifosfamide+Cisplatin (EPIC), Fludarabine+Mitoxantrone+Dexamethasone (FMD), Fludarabine+Dexamethasone+Cytarabine (ara-C)+Cisplatin (Platinol®) (FluDAP), Fluorouracil+Bevacizumab®, Fluorouracil+CeaVac®, Fluorouracil+Leucovorin, Fluorouracil+Levamisole, Fluorouracil+Oxaliplatin, Fluorouracil+Raltitrexed, Fluorouracil+SCH 6636, Fluorouracil+Trimetrexate, Fluorouracil+Leucovorin+Bevacizumab®, Fluorouracil+Leucovorin+Oxaliplatin, Fluorouracil+Leucovorin+Trimetrexate, Fluorouracil+Oncovin®+Mitomycin C (FOMi), Hydrazine+Adriamycin®+Methotrexate (HAM), Ifosfamide+Docetaxel, Ifosfamide+Etoposide, Ifosfamide+Gemcitabine, Ifosfamide+Paclitaxel, Ifosfamide+Vinorelbine, Ifosfamide+Carboplatin+Etoposide (ICE), Ifosfamide+Cisplatin+Doxorubicin, Irinotecan+C225 (Cetuximab®), Irinotecan+Docetaxel, Irinotecan+Etoposide, Irinotecan+Fluorouracil, Irinotecan+Gemcitabine, Mechlorethamine+Oncovin® (Vincristine)+Procarbazine (MOP), Mechlorethamine+Oncovin® (Vincristine)+Procarbazine+Prednisone (MOPP), Mesna+Ifosfamide+Idarubicin+Etoposide (MIZE), Methotrexate+Interferon alpha, Methotrexate+Vinblastine, Methotrexate+Cisplatin, Methotrexate with leucovorin rescue+Bleomycin+Adriamycin+Cyclophosphamide+Oncovorin+Dexamethasone (m-BACOD), Mitomycin C+Ifosfamide+Cisplatin (Platinol®) (MIP), Mitomycin C+Vinblastine+Paraplatin® (MVP), Mitoxantrone+Hydrocortisone, Mitoxantrone+Prednisone, Oncovin®+SCH 6636, Oxaliplatin+Leucovorin, Paclitaxel+Doxorubicin, Paclitaxel+SCH 6636, Paraplatin®+Docetaxel, Paraplatin®+Etoposide, Paraplatin®+Gemcitabine, Paraplatin®+Interferon alpha, Paraplatin®+Irinotecan, Paraplatin®+Paclitaxel, Paraplatin®+Vinblastine, Carboplatin (Paraplatin®)+Vincristine, Paraplatin®+Vindesine, Paraplatin®+Vinorelbine, Pemetrexed disodium+Gemcitabine, Platinolg (Cisplatin)+Vinblastine+Bleomycin (PVB), Prednisone+Methotrexate+Adriamycin+Cyclophosphamide+Etoposide (ProMACE), Procarbazine+Lomustine, Procarbazine+Lomustine+Vincristine, Procarbazine+Lomustine+Vincristine+Thioguanine, Procarbazine+Oncovin®+CCNU®+Cyclophosphamide (POCC), Quinine+Doxorubicin, Quinine+Mitoxantrone+Cytarabine, Thiotepa+Etoposide, Thiotepa+Busulfan+Cyclophosphamide, Thiotepa+Busulfan+Melphalan, Thiotepa+

Etoposide+Carmustine, Thiotepa+Etoposide+Carboplatin, Topotecan+Paclitaxel, Trimetrexate+Leucovorin, Vinblastine+Doxorubicin+Thiotepa, Vinblastine+Bleomycin+Etoposide+Carboplatin, Vincristine+Lomustine+Prednisone, Vincristine (Oncovin®)+Adriamycin®+Dexamethasone (VAD), Vincristine (Oncovin®)+Adriamycin®+Procarbazine (VAP), Vincristine+Dactinomycin+Cyclophosphamide, and Vinorelbine+Gemcitabine.

In one embodiment, antibodies of the present invention may be administered in combination with a taxane and a platinum-based chemotherapeutic. In another embodiment, antibodies of the present invention may be administered in combination with a taxane and a platinum-based chemotherapeutic for the treatment of cancers and premalignant conditions that are resistant to individual chemotherapies. In a specific embodiment, antibodies of the present invention may be administered in combination with Docetaxel (Taxotere®) and Carboplatin (Paraplatin®, CBDCA). In another specific embodiment, antibodies of the present invention may be administered in combination with Docetaxel (Taxotere®) and Carboplatin (Paraplatin®, CBDCA) for the treatment of cancers and premalignant conditions that are resistant to individual chemotherapies.

In one embodiment, agonistic antibodies of the present invention may be administered in combination with a taxane and a platinum-based chemotherapeutic. In another embodiment, agonistic antibodies of the present invention may be administered in combination with a taxane and a platinum-based chemotherapeutic for the treatment of cancers and premalignant conditions that are resistant to individual chemotherapies. In a specific embodiment, agonistic antibodies of the present invention may be administered in combination with Docetaxel (Taxotere®) and Carboplatin (Paraplatin®, CBDCA). In another specific embodiment, agonistic antibodies of the present invention may be administered in combination with Docetaxel (Taxotere®) and Carboplatin (Paraplatin®, CBDCA) for the treatment of cancers and premalignant conditions that are resistant to individual chemotherapies.

In one embodiment, antibodies of the present invention may be administered in combination with a topoisomerase inhibitor and a fluoropyrimidine. In another embodiment, antibodies of the present invention may be administered in combination with a topoisomerase inhibitor and a fluoropyrimidine for the treatment of cancers and premalignant conditions that are resistant to individual chemotherapies. In a specific embodiment, antibodies of the present invention may be administered in combination with Irinotecan (Camptosar®, CPT-11, Topotecin®, CaptoCPT-1) and Fluorouracil (5-FU, Adrucil®). In another specific embodiment, antibodies of the present invention may be administered in combination with Irinotecan (Camptosar®, CPT-11, Topotecin®, CaptoCPT-1) and Fluorouracil (5-FU, Adrucil®) for the treatment of cancers and premalignant conditions that are resistant to individual chemotherapies.

In one embodiment, agonistic antibodies of the present invention may be administered in combination with: a topoisomerase inhibitor and a fluoropyrimidine. In another embodiment, agonistic antibodies of the present invention may be administered in combination with a topoisomerase inhibitor and a fluoropyrimidine for the treatment of cancers and premalignant conditions that are resistant to individual chemotherapies. In a specific embodiment, agonistic antibodies of the present invention may be administered in combination with Irinotecan (Camptosar®, CPT-11, Topotecin®, CaptoCPT-1) and Fluorouracil (5-FU, Adrucil®). In another specific embodiment, agonistic antibodies of the present invention may be administered in combination with Irinotecan (Camptosar®, CPT-11, Topotecin®, CaptoCPT-1) and Fluorouracil (5-FU, Adrucil®) for the treatment of cancers and premalignant conditions that are resistant to individual chemotherapies.

In preferred embodiments, agonistic antibodies of the invention are administered in combination with one or more of the above-described combinations of therapeutic agents in the treatment, prevention, amelioration and/or cure of cancers and premalignant conditions.

Antibodies of the present invention may be administered in combination with one or more therapeutic agents described above to treat, prevent, ameliorate and/or cure cancers and premalignant conditions of any tissue known to express DR4 receptor. In preferred embodiments, agonistic antibodies of the present invention are administered in combination with one or more therapeutic agents described above to treat, prevent, ameliorate and/or cure cancers and premalignant conditions of any tissue known to express DR4 receptor.

Tissues known to express DR4 receptor include, but are not limited to, heart, placenta, liver, pancreas, spleen, thymus, prostate, testis, ovary, stomach, small intestine, colon, kidney, bone marrow, skin, blood, tonsil and palate.

In specific embodiments antibodies of the present invention may be administered in combination with one or more therapeutic agents, as described above, in the treatment, prevention, amelioration and/or cure of solid tissue cancers and premalignant conditions (e.g., skin cancer, prostate cancer, pancreatic cancer, hepatic cancer, lung cancer, ovarian cancer, colorectal cancer, head and neck tumors, breast tumors, endothelioma, osteoblastoma, osteoclastoma, Ewing's sarcoma, and Kaposi's sarcoma), as well as hematological cancers (e.g., leukemia, acute lymphocytic leukemia, chronic lymphocytic leukemia, non-Hodgkin's lymphoma, multiple myeloma).

In preferred embodiments, agonistic antibodies of the invention are administered in combination with one or more therapeutic agents, as described above, in the treatment, prevention, amelioration and/or cure of solid tissue cancers and premalignant conditions (e.g., skin cancer, prostate cancer, pancreatic cancer, hepatic cancer, lung cancer, ovarian cancer, colorectal cancer, head and neck tumors, breast tumors, endothelioma, osteoblastoma, osteoclastoma, Ewing's sarcoma, and Kaposi's sarcoma), as well as hematological cancers (e.g., leukemia, acute lymphocytic leukemia, chronic lymphocytic leukemia, non-Hodgkin's lymphoma, multiple myeloma).

In specific embodiments antibodies of the present invention are used to treat, ameliorate and/or prevent skin cancers and premalignant conditions including basal cell carcinoma, squamous cell carcinoma and malignant melanoma. Antibodies of the present invention may be used in combination with one or more surgical and/or radiological procedures and/or therapeutic agents to treat, ameliorate and/or prevent skin cancers and premalignant conditions.

In preferred embodiments agonistic antibodies of the present invention are used to treat, ameliorate and/or prevent skin cancers and premalignant conditions including basal cell carcinoma, squamous cell carcinoma and malignant melanoma. Agonistic antibodies of the present invention may be used in combination with one or more surgical and/or radiological procedures and/or therapeutic agents to treat, ameliorate and/or prevent skin cancers and premalignant conditions.

Antibodies of the present invention may be administered in combination with one or more therapeutic agents useful in the treatment of skin cancers and premalignant conditions including, but not limited to, Bleomycin (Blenoxane®), Carmustine (DTI-015, BCNU, BiCNU, Gliadel Wafer®), Cisplatin (Platinol®, CDDP), Dacarbazine (DTIC), Interferon alpha 2b (Intron A®), Interleukin-2 (ProleiukinR®), Tamoxifen (Nolvadex®), Temozolamide (Temodar®, NSC 362856), Vinblastine (Velban®, VLB), Vincristine (Oncovin®, Onco TCS®, VCR, Leurocristine®), and Vindesine (Eldisine®, Fildesin®). Combinations of therapeutic agents useful in the treatment of skin cancers include, but are not limited to, Cisplatin+Carmustine+Dacarbazine+Tamoxifen.

In preferred embodiments, agonistic antibodies of the invention are administered in combination with one or more of the above-described therapeutic agents in the treatment, amelioration and/or prevention of skin cancers and premalignant conditions.

In further particular embodiments, antibodies of the present invention are used to treat, ameliorate and/or prevent head and neck cancers including brain cancers, and premalignant conditions. Antibodies of the present invention may be used in combination with one or more surgical and/or radiological procedures and/or therapeutic agents to treat, ameliorate and/or prevent head and neck cancers including brain cancers, and premalignant conditions. Brain cancers which may be treated using antibodies of the present invention include, but are not limited to, gliomas such as astrocytomas and oligodendromas, non-glial tumors such as neuronal, meningeal, ependymal and choroid plexus cell tumors, and metastatic brain tumors such as those originating as breast, lung, prostate and skin cancers.

In further preferred embodiments, agonistic antibodies of the present invention are used to treat, ameliorate and/or prevent head and neck cancers including brain cancers, and premalignant conditions. Agonistic antibodies of the present invention may be used in combination with one or more surgical and/or radiological procedures and/or therapeutic agents to treat, ameliorate and/or prevent head and neck cancers including brain cancers, and premalignant conditions. Brain cancers which may be treated using agonistic antibodies of the present invention include, but are not limited to, gliomas such as astrocytomas and oligodendromas, non-glial tumors such as neuronal, meningeal, ependymal and choroid plexus cell tumors, and metastatic brain tumors such as those originating as breast, lung, prostate and skin cancers.

In one preferred embodiment, agonistic antibodies of the invention are used to treat brain tumors. In a further preferred embodiment, agonistic antibodies of the invention are used to treat glioblastoma multiforme.

Antibodies of the present invention may be administered in combination with one or more radiological procedures useful in the treatment of brain cancers including, but not limited to, external beam radiation therapy, stereotactic radiation therapy, conformal radiation therapy, intensity-modulated radiation therapy (IMRT), and radiosurgery.

In preferred embodiments, agonistic antibodies of the invention are administered in combination with one or more radiological procedures useful in the treatment of brain cancers including, but not limited to, external beam radiation therapy, stereotactic radiation therapy, conformal radiation therapy, intensity-modulated radiation therapy (IMRT), and radiosurgery.

Antibodies of the present invention may be administered in combination with one or more therapeutic agents useful in the treatment of brain cancers including, but not limited to, Bleomycin (Blenoxane®), Busulfan (Busulfex®, Myleran®), Carboplatin (Paraplatin®, CBDCA), Carmustine (DTI-015, BCNU, BiCNU, Gliadel Wafer®), Cisplatin (Platinol®, CDDP), Cisplatin-epinephrine gel (IntraDose®, FocaCist®), Cyclophosphamide (Cytoxan®, CTX), Cytarabine (Cytosar-U®, ara-C, cytosine arabinoside, DepoCyt®), Dacarbazine (DTIC®), Dactinomycin (Cosmegen®), Daunorubicin (Daunomycin, DaunoXome®, Daunorubicin®, Cerubidine®), Docetaxel (Taxotere®, Taxane®), Dexamethasone (Decadron®), Etoposide phosphate (Etopophos®), Etoposide (VP-16, Vepesid®), Fluorouracil (5-FU, Adrucil®), Hydroxyurea (Hydrea®), Ifosfamide (IFEX®), Lomustine (CCNU®, CeeNU®), Melphalan (L-PAM, Alkeran®, Phenylalanine mustard), Mercaptopurine (6-mercaptopurine, 6-MP), Methchlorethamine (Nitrogen Mustard, $HN_2$, Mustargen®), Methotrexate® (MTX, Mexate®, Folex®), Paclitaxel (Paxene®), Taxol®), Paclitaxel-DHA (Taxoprexin®), Procarbazine (Matulane®)), Temozolamide (Temodar®, NSC 362856), Teniposide (VM-26, Vumon®), Thioguanine (6-thioguanine, 6-TG), Thiotepa (triethylenethiophosphaoramide), Topotecan (Hycamtin®, SK&F-104864, NSC-609699, Evotopin®), and Vincristine (Oncovin®, Onco TCS®, VCR, Leurocristine®).

In preferred embodiments, agonistic antibodies of the invention are administered in combination with one or more of the above-described therapeutic agents in the treatment, amelioration and/or prevention of brain cancers and premalignant conditions.

Further examples of therapeutic agents useful in the treatment of brain cancers which may be administered in combination with antibodies of the present invention include, but are not limited to, 81C6 (Anti-tenascin monoclonal antibody), BIBX-1382, Cereport® (Lobradimil®, RMP-7), Cilengitide® (EMD-121974, integrin alphavbeta3 antagonist), CMT-3 (Metastat®), Cotara®) (chTNT-1/B, [$^{131}$I]-chTNT-1/B), CP IL-4-toxin (IL-4 fusion toxin), Fenretinideg (4HPR), Fotemustine (Muphoran®, Mustophoran®), Gemcitabine (Gemto®, Gemzar®), Hypericin® (VIMRxyn®), Imatinib mesylate (STI-571, Imatinib®, Glivec®, Gleevec®, Ab1 tyrosine kinase inhibitor), Irinotecan (Camptosar®, CPT-11, Topotecin®, CaptoCPT-1), Leflunomide (SU-101, SU-0200), Mivobulin isethionate (CI-980), O6-benzylguanine (BG, Procept®), Prinomastat® (AG-3340, MMP inhibitor), R115777 (Zamestra®), SU6668 (PDGF-TK inhibitor), T-67 (T-138067, T-607), Tamoxifen (Nolvadex®), Tf-CRM107 (Transferrin-CRM-107), Thalidomide and thalidomide analogs, including but not limited to, lenalidomide (CC-5013, REVLIMID®) and CC-4047 (ACTIMID™), Tiazofurin (Thiazole®), Vapreotide® (BMY-41606), Vinorelbine (Navelbine®), and XR-5000 (DACA).

In preferred embodiments, agonistic antibodies of the invention are administered in combination with one or more of the above-described therapeutic agents in the treatment, amelioration and/or prevention of brain cancers and premalignant conditions.

Preferred combinations of therapeutic agents useful in the treatment of brain cancers which may be administered in combination with antibodies of the present invention include, but are not limited to, Busulfan+Melphalan, Carboplatin+Cereport®, Carboplatin+Etoposide, Carboplatin+Etoposide+Thiotepa, Cisplatin+Etoposide, Cisplatin+Cytarabine+Ifosfamide, Cisplatin+Vincristine+Lomustine, Cisplatin+Cyclophosphamide+Etoposide+Vincristine, Cisplatin+Cytarabine+Ifosfamide+Etoposide+Methotrexate, Cyclophosphamide+Melphalan, Cytarabine+Methotrexate, Dactinomycin+Vincristine, Mechlorethamine+Oncovin® (Vincristine)+Procarbazine (MOP), Mechlorethamine+Oncovin® (Vincristine)+Procarbazine+Prednisone (MOPP), Carboplatin (Paraplatin®)+Etoposide, Carboplatin (Paraplatin®)+Vincristine, Procarbazine+Lomustine, Procarbazine+Lomustine+Vincristine, Procarbazine+Lomustine+Vincristine+Thioguanine, Thiotepa+Etoposide, Thiotepa+

Etoposide+Carmustine, Thiotepa+Etoposide+Carboplatin, Vinblastine+Bleomycin+Etoposide+Carboplatin, and Vincristine+Lomustine+Prednisone.

In preferred embodiments, agonistic antibodies of the invention are administered in combination with one or more of the above-described combinations of therapeutic agents in the treatment, amelioration and/or prevention of brain cancers and premalignant conditions.

In further particular embodiments, antibodies of the present invention are used to treat, ameliorate and/or prevent breast cancer and premalignant conditions. Antibodies of the present invention may be used in combination with one or more surgical and/or radiological procedures and/or therapeutic agents to treat, ameliorate and/or prevent breast cancer and premalignant conditions. Breast cancers which may be treated using antibodies of the present invention include, but are not limited to, ductal carcinoma, stage I, stage II, stage III and stage IV breast cancers as well as invasive breast cancer and metastatic breast cancer.

In preferred embodiments, agonistic antibodies of the present invention are used to treat, ameliorate and/or prevent breast cancer and premalignant conditions. Agonistic antibodies of the present invention may be used in combination with one or more surgical and/or radiological procedures and/or therapeutic agents to treat, ameliorate and/or prevent breast cancer and premalignant conditions. Breast cancers which may be treated using agonistic antibodies of the present invention include, but are not limited to, ductal carcinoma, stage I, stage II, stage III and stage IV breast cancers as well as invasive breast cancer and metastatic breast cancer.

In one preferred embodiment, agonistic antibodies of the invention are used to treat metastatic breast cancer.

Antibodies of the present invention may be administered in combination with one or more surgical and/or radiological procedures useful in the treatment of breast cancer and premalignant conditions.

In preferred embodiments, agonistic antibodies of the present invention may be administered in combination with one or more surgical and/or radiological procedures useful in the treatment of breast cancer and premalignant conditions.

Antibodies of the present invention may be administered in combination with one or more therapeutic agents useful in the treatment of breast cancer and premalignant conditions including, but not limited to, Amifostine (Ethyol®), Aminoglutethimide (Cytadren®), Anastrozole (Arimidex®), Bleomycin (Blenoxane®), Capecitabine (Xeloda®, Doxifluridine®, oral 5-FU), Cisplatin (Platinol®, CDDP), Cisplatin-epinephrine gel (IntraDose®, FocaCist®), Cyclophosphamide (Cytoxan®, Neosar®, CTX), Docetaxel (Taxotere®, Taxane®), Doxorubicin (Adriamycin®, Doxil®, Rubex®), Epirubicin (Ellence®, EPI, 4' epi-doxorubicin), Exemestane (Aromasin®, Nikidess®), Fadrozole (Afema®, Fadrozole hydrochloride, Arensin®), Fluorouracil (5-FU, Adrucil®, Fluoroplex®, Efudex®), Herceptin® (Trastuzumab®, Anti-HER-2 monoclonal antibody, Anti-EGFR-2 MAb), Ifosfamide (IFEX®), Letrozole (Femara®), Leucovorin (Leucovorin®, Wellcovorin®), Mechlorethamine (Nitrogen Mustard, $HN_2$, Mustargen®), Megestrol acetate (Megace®, Pallace®), Melphalan (L-PAM, Alkeran®, Phenylalanine mustard), Methotrexate® (MTX, Mexate®, Folex®), Methyltestosterone (Android-108, Testred®, Virilon®), Mitomycin C (Mitomycin®, Mutamycin®, Mito Extra®), Orzel® (Tegafur+Uracil+Leucovorin), Paclitaxel (Paxene®, Taxol®), Sobuzoxane (MST-16, Perazolin®), Tamoxifen (Nolvadex®), Testosterone (Andro®, Androderm®, Testoderm TTS®, Testoderm®, Depo-Testosterone®, Androgel®, depoAndro®), Vinblastine (Velban®, VLB), Vincristine (Oncovin®, Onco TCS®, VCR, Leurocristine®), and Vinorelbine (Navelbine®).

In preferred embodiments, agonistic antibodies of the invention are administered in combination with one or more of the above-described therapeutic agents in the treatment, amelioration and/or prevention of breast cancers and premalignant conditions.

Further examples of therapeutic agents useful in the treatment of breast cancer and premalignant conditions which may be administered in combination with antibodies of the present invention include, but are not limited to, Aldesleukin (IL-2, Proleukin®), Altretamine (Hexylen®, hexamethylmelamine, Hexastat®), Angiostatin, Annamycin (AR-522, annamycin LF, Aronex®), Biricodar dicitrate (Incel®, Incel MDR Inhibitor), Boronated Protoporphyrin Compound (PDIT, Photodynamic Immunotherapy), Bryostatin-1 (Bryostatin, BMY-45618, NSC-339555), Busulfan (Busulfex®, Myleran®), Carmustine (DTI-015, BCNU, BiCNU, Gliadel Wafer®), D-limonene, Dacarbazine (DTIC), Daunorubicin (Daunomycin, DaunoXome®, Daunorubicin®, Cerubidine®), Dolastatin-10 (DOLA-10, NSC-376128), DPPE, DX-8951f (DX-8951), EMD-121974, Endostatin, EO9 (EO1, EO4, EO68, EO70, EO72), Etoposide phosphate (Etopophos®), Etoposide (VP-16, Vepesid®V), Fluasterone, Fludarabine (Fludara®, FAMP), Flutamide (Eulexin®), Formestane (Lentaron®), Fulvestrant (Faslodex®), Galarubicin hydrochloride (DA-125), Gemcitabine (Gemto®, Gemzar®), Her-2/Neu vaccine, Hydroxyurea (Hydrea®), Idarubicin (Idamycin®, DMDR, IDA), Interferon alpha 2a (Intron A®), Interferon gamma (Gamma-interferon, Gamma 100®, Gamma-IF), Irinotecan (Camptosar®, CPT-11, Topotecin®, CaptoCPT-1), Ketoconazole (Nizoral®), KRN-8602 (MX, MY-5, NSC-619003, MX-2), L-asparaginase (Elspar®), Leuprolide acetate (Viadur®, Lupron®), Lomustine (CCNU®, CeeNU®), LY-335979, Mannan-MUC1 vaccine, 2-Methoxyestradiol (2-ME, 2-ME2), Mitoxantrone (Novantrone®, DHAD), Motexafin Lutetium (Lutrin®, Optrin®, Lu-Tex®, lutetium texaphyrin, Lucyn®, Antrin®), MPV-2213ad (Finrozole®), MS-209, Muc-1 vaccine, NaPro Paclitaxel, Perillyl alcohol (perilla alcohol, perillic alcohol, perillol, NSC-641066), Pirarubicin (THP), Procarbazine (Matulane®), Providence Portland Medical Center Breast Cancer Vaccine, Pyrazoloacridine (NSC-366140, PD-115934), Raloxifene hydrochloride (Evista®, Keoxifene hydrochloride), Raltitrexed (Tomudex®, ZD-1694), Rebeccamycin, Streptozocin (Zanosar®), Temozolamide (Temodar®, NSC 362856), Theratope, Thiotepa (triethylenethiophosphaoramide, Thioplex®), Topotecan (Hycamtin®, SK&F-104864, NSC-609699, Evotopin®), Toremifene (Estrimex®, Fareston®), Trilostane (Modrefen®), and XR-9576 (XR-9351, P-glycoprotein/MDR inhibitor).

In preferred embodiments, agonistic antibodies of the invention are administered in combination with one or more of the above-described therapeutic agents in the treatment, amelioration and/or prevention of breast cancers and premalignant conditions.

Preferred combinations of therapeutic agents useful in the treatment of breast cancer which may be administered in combination with antibodies of the present invention include, but are not limited to, Cyclophosphamide+Adriamycin® (Doxorubicin), Cyclophosphamide+Epirubicin+Fluorouracil, Cyclophosphamide+Methotrexate+Fluorouracil (CMF), Paclitaxel+Doxorubicin, and Vinblastine+Doxorubicin+Thiotepa.

In preferred embodiments, agonistic antibodies of the invention are administered in combination with one or more of the above-described therapeutic agent combinations in the treatment, amelioration and/or prevention of breast cancers and premalignant conditions.

In further particular embodiments, antibodies of the present invention are used to treat, ameliorate and/or prevent lung cancer and premalignant conditions. Antibodies of the present invention may be used in combination with one or more surgical and/or radiological procedures and/or therapeutic agents to treat, ameliorate and/or prevent lung cancer and premalignant conditions. Lung cancer which may be treated using antibodies of the present invention includes, but is not limited to, non-small cell lung cancer (NSCLC) including early stage NSCLC (i.e., Stage IA/IB and Stage IIA/IIB), Stage IIIA NSCLC, Stage IIA (unresectable)/IIIB NSCLC and Stage IV NSCLC, small cell lung cancer (SCLC) including limited stage SCLC and extensive stage SCLC as well as Malignant Pleural Mesothelioma.

In preferred embodiments, agonistic antibodies of the present invention are used to treat, ameliorate and/or prevent lung cancer and premalignant conditions. Agonistic antibodies of the present invention may be used in combination with one or more surgical and/or radiological procedures and/or therapeutic agents to treat, ameliorate and/or prevent lung cancer and premalignant conditions. Lung cancer which may be treated using agonistic antibodies of the present invention includes, but is not limited to, non-small cell lung cancer (NSCLC) including early stage NSCLC (i.e., Stage IA/IB and Stage IIA/IIB), Stage IIIA NSCLC, Stage IIA (unresectable)/IIIB NSCLC and Stage IV NSCLC, small cell lung cancer (SCLC) including limited stage SCLC and extensive stage SCLC as well as Malignant Pleural Mesothelioma.

In one preferred embodiment, agonistic antibodies of the invention are used to treat non-small cell lung cancers.

Antibodies of the present invention may be administered in combination with one or more therapeutic agents useful in the treatment of lung cancer and premalignant conditions including, but not limited to, BAY 43-9006 (Raf kinase inhibitor), Carboplatin (Paraplatin®, CBDCA), Chlorambucil (Leukeran®), Cisplatin (Platinol®, CDDP), Cisplatin-epinephrine gel (IntraDose®, FocaCist®), Cyclophosphamide (Cytoxan®, Neosar®, CTX), Docetaxel (Taxotere®, Taxane®), Doxorubicin (Adriamycin®, Doxil®, Rubex®), Edatrexate, Epirubicin (Ellence®, EPI, 4' epi-doxorubicin), Etoposide phosphate (Etopophos®), Etoposide (VP-16, Vepesid®), Gemcitabine (Gemto®, Gemzar®), Herceptin® (Trastuzumab®, Anti-HER-2 monoclonal antibody, Anti-EGFR-2 MAb), Ifosfamide (IFEX®), Irinotecan (Camptosar®, CPT-11, Topotecin®, CaptoCPT-1), Lomustine (CCNU®, CeeNU®), Mechlorethamine (Nitrogen Mustard, $HN_2$, Mustargen®), Melphalan (L-PAM, Alkeran®, Phenylalanine mustard), Methotrexate® (MTX, Mexate®, Folex®), Mitomycin C (Mitomycin®, Mutarnycin®, Mito Extra®), Paclitaxel (Paxene®, Taxol®), Paclitaxel-DHA (Taxoprexin®), Porfimer sodium (Photofrin®), Procarbazine (Matulane®), SKI-2053R(NSC-D644591), Teniposide (VM-26, Vumon®), Topotecan (Hycamtin®, SK&F-104864, NSC-609699, Evotopin®V), Vinblastine (Velban®, VLB), Vincristine (Oncovin®, Onco TCS®, VCR, Leurocristine®), Vindesine (Eldisine®, Fildesin®), and Vinorelbine (Navelbine®).

In preferred embodiments, agonistic antibodies of the invention are administered in combination with one or more of the above-described therapeutic agents in the treatment, amelioration and/or prevention of lung cancers and premalignant conditions.

Further examples of therapeutic agents useful in the treatment of lung cancer and premalignant conditions which may be administered in combination with antibodies of the present invention include, but are not limited to, ABX-EGF (anti-EGFr MAb), Acetyldinaline (CI-994), AG-2034 (AG-2024, AG-2032, GARFT [glycinamide ribonucleoside transformylase] inhibitor), Alanosine, Aminocamptothecin (9-AC, 9-Aminocamptothecin, NSC 603071), Angiostatin, Aplidine (Aplidin®, Aplidina®), BBR 3464, Bexarotene (Targretin®, LGD1069), BIBH-1 (Anti-FAP MAb), BIBX-1382, BLP-25 (MUC-1 peptide), Bryostatin-1 (Bryostatin®, BMY-45618, NSC-339555), Budesonide (Rhinocort®), C225 (IMC-225, EGFR inhibitor, Anti-EGFr MAb, Cetuximab®), Capecitabine (Xeloda®, Doxifluridine®, oral 5-FU), Carboxyamidotriazole (NSC 609974, CAI, L-651582), CEA-cide® (Labetuzumab®, Anti-CEA monoclonal antibody, hMN-14), Cereport® (Lobradimil®, RMP-7), CI-1033 (Pan-erbB RTK inhibitor), Cilengitide® (EMD-121974, integrin alphavbeta3 antagonist), 9-cis retinoic acid (9-cRA), Cisplatin-liposomal (SPI-077), CMB-401 (Anti-PEM MAb/calicheamycin), CMT-3 (Metastat®), CP-358774 (Tarceva®, OS1-774, EGFR inhibitor), CT-2584 (Apra®), DAB389-EGF (EGF fusion toxin), DeaVac® (CEA anti-idiotype vaccine), Decitabine (5-aza-2'-deoxyytidine), Diethylnorspermine (DENSPM), Dihydro-5-azacytidine, EGF-P64k Vaccine, Endostatin, Etanidazole (Radinyl®), Exetecan mesylate (DX-8951, DX-8951f), Exisulind (SAAND, Aptosyn®, cGMP-PDE2 and 5 inhibitor), FK-317 (FR-157471, FR-70496), Flavopiridol (HMR-1275), Fotemustine (Muphoran®, Mustophoran®), G3139 (Genasense®, GentaAnticode®, Bcl-2 antisense), Gadolinium texaphyrin (Motexafin gadolinium, Gd-Tex®, Xcytrin®), GBC-590, GL331, Galarubicin hydrochloride (DA-125), Glufosfamide®S(O-D-glucosyl-isofosfamide mustard, D19575, INN), GVAX (GM-CSF gene therapy), INGN-101 (p53 gene therapy/retrovirus), INGN-201 (p53 gene therapy/adenovirus), Irofulven (MGI-114), ISIS-2053, ISIS-3521 (PKC-alpha antisense), ISIS-5132 (K-ras/raf antisense), Isotretinoin (13-CRA, 13-cis retinoic acid, Accutane®), Lometrexol (T-64, T-904064), Marimastat® (BB-2516, TA-2516, MMP inhibitor), MDX-447 (BAB-447, EMD-82633, H-447, anti-EGFr/FcGammaR1r), MGV, Mitumomab® (BEC-2, EMD-60205), Mivobulin isethionate (CI-980), Neovastat® (AE-941, MMP inhibitor), NPI-0052 (proteasome inhibitor), Onconase (Ranpimase®), Onyx-015 (p53 gene therapy), Pemetrexed disodium (Alimta®, MTA, multitargeted antifolate, LY 231514), Pivaloyloxymethyl butyrate (AN-9, Pivanex®), Prinomastat®) (AG-3340, MMP inhibitor), PS-341 (LDP-341, 26S proteasome inhibitor), Pyrazoloacridine (NSC-366140, PD-115934), R115777 (Zarnestra®), Raltitrexed (Tomudex®, ZD-1694), R-flurbiprofen (Flurizan®, E-7869, MPC-7869), RFS-2000 (9-nitrocamptothecan, 9-NC, Rubitecan®), RSR-13 (GSJ-61), Satraplatin (BMS-182751, JM-216), SCH-66336, Sizofilan® (SPG, Sizofuran®, Schizophyllan®, Sonifilan®), Squalamine (MSI-1256F), SR-49059 (vasopressin receptor inhibitor, V1a), SU5416 (Semaxanib®, VEGF inhibitor), Taurolidine (Taurolin®), Temozolamide (Temodar®, NSC 362856), Thalidomide and thalidomide analogs, including but not limited to, lenalidomide (CC-5013, REVLIMID®) and CC-4047 (AC-TIMID™) Thymosin alpha I (Zadaxin®, Thymalfasin®), Tirapazamine (SR-259075, SR-4233, Tirazone®, Win-59075), TNP-470 (AGM-1470), TriAb® (anti-idiotype antibody immune stimulator), Tretinoin (Retin-A®, Atragen®, ATRA, Vesanoid®), Troxacitabine (BCH-204, BCH-4556, Troxatyl®), Vitaxin® (LM-609, integrin alphavbeta3 antagonistic MAb), XR-9576 (P-glycoprotein/MDR inhibitor), and ZD-1839 (IRESSA®).

In preferred embodiments, agonistic antibodies of the invention are administered in combination with one or more of the above-described therapeutic agents in the treatment, amelioration and/or prevention of lung cancers and premalignant conditions.

In one embodiment, antibodies of the present invention may be administered in combination with a taxane. In another embodiment, antibodies of the present invention may be administered in combination with a taxane for the treatment of lung cancers, such as non-small cell lung cancer, that are resistant to individual chemotherapies. In a specific embodiment, antibodies of the present invention may be administered in combination with Docetaxel (Taxotere®). In a specific embodiment, antibodies of the present invention may be administered in combination with Docetaxel (Taxotere®) for the treatment of lung cancers, such as non-small cell lung cancer, that are resistant to individual chemotherapies.

In one embodiment, agonistic antibodies of the present invention may be administered in combination with a taxane. In another embodiment, agonistic antibodies of the present invention may be administered in combination with a taxane for the treatment of lung cancers, such as non-small cell lung cancer, that are resistant to individual chemotherapies. In a specific embodiment, agonistic antibodies of the present invention may be administered in combination with Docetaxel (Taxotere®). In a specific embodiment, agonistic antibodies of the present invention may be administered in combination with Docetaxel (Taxotere®) for the treatment of lung cancers, such as non-small cell lung cancer, that are resistant to individual chemotherapies.

In one embodiment, antibodies of the present invention may be administered in combination with a platinum-based chemotherapeutic. In another embodiment, antibodies of the present invention may be administered in combination with a platinum-based chemotherapeutic for the treatment of lung cancers, such as non-small cell lung cancer, that are resistant to individual chemotherapies. In another specific embodiment, antibodies of the invention may be administered in combination with Carboplatin (Paraplatin®, CBDCA). In another specific embodiment, antibodies of the present invention may be administered in combination with Carboplatin (Paraplatin®, CBDCA) for the treatment of lung cancers, such as non-small cell lung cancer, that are resistant to individual chemotherapies.

In one embodiment, agonistic antibodies of the present invention may be administered in combination with a platinum-based chemotherapeutic. In another embodiment, agonistic antibodies of the present invention may be administered in combination with a platinum-based chemotherapeutic for the treatment of lung cancers, such as non-small cell lung cancer, that are resistant to individual chemotherapies. In another specific embodiment, agonistic antibodies of the invention may be administered in combination with Carboplatin (Paraplatin®, CBDCA). In another specific embodiment, agonistic antibodies of the present invention may be administered in combination with Carboplatin (Paraplatin®, CBDCA) for the treatment of lung cancers, such as non-small cell lung cancer, that are resistant to individual chemotherapies.

Preferred combinations of therapeutic agents useful in the treatment of lung cancer and premalignant conditions which may be administered in combination with antibodies of the present invention include, but are not limited to, Cisplatin+Docetaxel, Cisplatin+Etoposide, Cisplatin+Gemcitabine, Cisplatin+Interferon alpha, Cisplatin+Irinotecan, Cisplatin+Paclitaxel, Cisplatin+Teniposide, Cisplatin+Vinblastine, Cisplatin+Vindesine, Cisplatin+Vinorelbine, Cisplatin+Vinblastine+Mitomycin C, Cisplatin+Vinorelbine+Gemcitabine, Cisplatin (Platinol®)+Oncovin®+Doxorubicin (Adriamycin®)+Etoposide (CODE), Cyclophosphamide+Adriamycin®+Cisplatin (Platinol®) (CAP), Cyclophosphamide+Adriamycin®+Vincristine (CAV), Cyclophosphamide+Epirubicin+Cisplatin (Platinol®) (CEP), Cyclophosphamide+Methotrexate+Vincristine (CMV), Cyclophosphamide+Adriamycin®, Methotrexate+Fluorouracil (CAMF), Cyclophosphamide+Adriamycin®, Methotrexate+Procarbazine (CAMP), Cyclophosphamide+Adriamycin®, Vincristine+Etoposide (CAV-E), Cyclophosphamide+Adriamycin®, Vincristine+Teniposide (CAV-T), Cyclophosphamide+Oncovin®, Methotrexate+Fluorouracil (COMF), Cyclophosphamide+Adriamycin®+Vincristine, alternating with Cisplatin+Etoposide (CAV/PE), Docetaxel+Gemcitabine, Docetaxel+Vinorelbine, Etoposide (Vepesid®)+Ifosfamide+Cisplatin (Platinol®) (VIP), Etoposide (Vepesid®)+Ifosfamide, Cisplatin+Epirubicin (VIC-E), Fluorouracil+Oncovin®+Mitomycin C (FOMi), Hydrazine+Adriamycin®+Methotrexate (HAM), Ifosfamide+Docetaxel, Ifosfamide+Etoposide, Ifosfamide+Gemcitabine, Ifosfamide+Paclitaxel, Ifosfamide+Vinorelbine, Ifosfamide+Carboplatin+Etoposide (ICE), Irinotecan+Docetaxel, Irinotecan+Etoposide, Irinotecan+Gemcitabine, Methotrexate+Cisplatin, Methotrexate+Interferon alpha, Methotrexate+Vinblastine, Mitomycin C+Ifosfamide+Cisplatin (Platinol®) (MIP), Mitomycin C+Vinblastine+Paraplatin® (MVP), Paraplatin®+Docetaxel, Paraplatin®+Etoposide, Paraplatin®+Gemcitabine, Paraplatin®+Interferon alpha, Paraplatin®+Irinotecan, Paraplatin®+Paclitaxel, Paraplatin®+Vinblastine, Paraplatin®+Vindesine, Paraplatin®+Vinorelbine, Procarbazine+Oncovin®+CCNU® (Lomustine)+Cyclophosphamide (POCC), Vincristine (Oncovin®)+Adriamycin®+Procarbazine (VAP), and Vinorelbine+Gemcitabine.

In preferred embodiments, agonistic antibodies of the invention are administered in combination with one or more of the above-described therapeutic agent combinations in the treatment, amelioration and/or prevention of lung cancers and premalignant conditions.

In one embodiment, antibodies of the present invention may be administered in combination with a taxane and a platinum-based chemotherapeutic. In another embodiment, antibodies of the present invention may be administered in combination with a taxane and a platinum-based chemotherapeutic for the treatment of lung cancers, such as non-small cell lung cancer, that are resistant to individual chemotherapies. In a specific embodiment, antibodies of the present invention may be administered in combination with Docetaxel (Taxotere®) and Carboplatin (Paraplatin®, CBDCA). In another specific embodiment, antibodies of the present invention may be administered in combination with Docetaxel (Taxotere®) and tin (Paraplatin®, CBDCA) for the treatment of lung cancers, such as non-small cell lung cancer, that are resistant to chemotherapies.

In one embodiment, agonistic antibodies of the present invention may be administered in combination with a taxane and a platinum-based chemotherapeutic. In another embodiment, agonistic antibodies of the present invention may be administered in combination with a taxane and a platinum-based chemotherapeutic for the treatment of lung cancers, such as non-small cell lung cancer, that are resistant to individual chemotherapies. In a specific embodiment, agonistic antibodies of the present invention may be administered in combination with Docetaxel (Taxotere®) and Carboplatin (Paraplatin®, CBDCA). In another specific embodiment, agonistic antibodies of the present invention may be administered in combination with Docetaxel (Texatere®) and Carboplatin (Paraplatin®, CBDCA) for the treatment of lung cancers, such as non-small cell lung cancer, that are resistant to individual chemotherapies.

In further particular embodiments, antibodies of the present invention are used to treat, ameliorate and/or prevent colorectal cancer and premalignant conditions. Antibodies of the present invention may be used in combination with one or more surgical and/or radiological procedures and/or therapeutic agents to treat, ameliorate and/or prevent colorectal cancer and premalignant conditions. Colorectal cancers which may be treated using antibodies of the present invention include, but are not limited to, colon cancer (e.g., early stage colon cancer (stage I and II), lymph node positive colon cancer (stage 111), metastatic colon cancer (stage IV)) and rectal cancer.

In preferred embodiments, agonistic antibodies of the present invention are used to treat, ameliorate and/or prevent colorectal cancer and premalignant conditions. Agonistic antibodies of the present invention may be used in combination with one or more surgical and/or radiological procedures and/or therapeutic agents to treat, ameliorate and/or prevent colorectal cancer and premalignant conditions. Colorectal cancers which may be treated using agonistic antibodies of the present invention include, but are not limited to, colon cancer (e.g., early stage colon cancer (stage I and II), lymph node positive colon cancer (stage III), metastic colon cancer (stage 1V)) and rectal cancer.

In one preferred embodiment, agonistic antibodies of the invention are used to treat colon cancer.

Antibodies of the present invention may be administered in combination with one or more therapeutic agents useful in the treatment of colorectal cancer and premalignant conditions including, but not limited to, Capecitabine (Xeloda®, Doxifluridine®, oral 5-FU), Fluorouracil (5-FU, Adrucil®, Fluoroplex®, Efudex®), Irinotecan (Camptosar®, CPT-11, Topotecin®, CaptoCPT-1), Leucovorin (Leucovorin®, Wellcovorin®), and Levamisole (Ergamisol®).

In one embodiment, antibodies of the present invention may be administered in combination with a topoisomerase inhibitor. In another embodiment, antibodies of the present invention may be administered in combination with a topoisomerase inhibitor for the treatment of colon cancer that is resistant to individual chemotherapies. In a specific embodiment, antibodies of the present invention may be administered in combination with Irinotecan (Camptosar®, CPT-11, Topotecin®, CaptoCPT-1). In a specific embodiment, antibodies of the present invention may be administered in combination with Irinotecan (Camptosar®, CPT-11, Topotecin®, CaptoCPT-1) for the treatment of colon cancer that is resistant to individual chemotherapies.

In one embodiment, agonistic antibodies of the present invention may be administered in combination with a topoisomerase inhibitor. In another embodiment, agonistic antibodies of the present invention may be administered in combination with a topoisomerase inhibitor for the treatment of colon cancer that is resistant to individual chemotherapies. In a specific embodiment, agonistic antibodies of the present invention may be administered in combination with Irinotecan (Camptosar®, CPT-11, Topotecin®, CaptoCPT-1). In a specific embodiment, agonistic antibodies of the present invention may be administered in combination with Irinotecan (Camptosar®, CPT-11, Topotecin®, CaptoCPT-1) for the treatment of colon cancer that is resistant to individual chemotherapies.

In one embodiment, antibodies of the present invention may be administered in combination with a fluoropyrimidine.

In another embodiment, antibodies of the present invention may be administered in combination with a fluoropyrimidine for the treatment of colon cancer that is resistant to individual chemotherapies. In another specific embodiment, antibodies of the invention may be administered in combination with Fluorouracil (5-FU, Adrucil®). In another specific embodiment, antibodies of the present invention may be administered in combination with Fluorouracil (5-FU, Adrucil®) for the treatment of colon cancer that is resistant to individual chemotherapies.

In one embodiment, agonistic antibodies of the present invention may be administered in combination with a fluoropyrimidine. In another embodiment, agonistic antibodies of the present invention may be administered in combination with a fluoropyrimidine for the treatment of colon cancer that is resistant to individual chemotherapies. In another specific embodiment, agonistic antibodies of the invention may be administered in combination with Fluorouracil (5-FU, Adrucil®). In another specific embodiment, agonistic antibodies of the present invention may be administered in combination with Fluorouracil (5-FU, Adrucil®) for the treatment of colon cancer that is resistant to individual chemotherapies.

In preferred embodiments, agonistic antibodies of the invention are administered in combination with one or more of the above-described therapeutic agents in the treatment, amelioration and/or prevention of colorectal cancers and premalignant conditions.

Preferred combinations of therapeutic agents useful in the treatment of colorectal cancer and premalignant conditions which may be administered in combination with antibodies of the present invention include, but are not limited to, Fluorouracil+Leucovorin, and Fluorouracil+Levamisole.

In one embodiment, antibodies of the present invention may be administered in combination with a topoisomerase inhibitor and a fluoropyrimidine. In another embodiment, antibodies of the present invention may be administered in combination with a topoisomerase inhibitor and a fluoropyrimidine for the treatment of colon cancer, that are resistant to individual chemotherapies. In a specific embodiment, antibodies of the present invention may be administered in combination with Irinotecan (Camptosar®, CPT-11, Topotecin®, CaptoCPT-1) and Fluorouracil (5-FU, Adrucil®). In another specific embodiment, antibodies of the present invention may be administered in combination with Irinotecan (Camptosar®, CPT-11, Topotecin®, CaptoCPT-1) and Fluorouracil (5-FU, Adrucil®) for the treatment of colon cancer that is resistant to individual chemotherapies.

In one embodiment, agonistic antibodies of the present invention may be administered in combination with a topoisomerase inhibitor and a fluoropyrimidine. In another embodiment, agonistic antibodies of the present invention may be administered in combination with a topoisomerase inhibitor and a fluoropyrimidine for the treatment of colon cancer, that are resistant to individual chemotherapies. In a specific embodiment, agonistic antibodies of the present invention may be administered in combination with Irinotecan (Camptosar®, CPT-11, Topotecin®, CaptoCPT-1) and Fluorouracil (5-FU, Adrucil®). In another specific embodiment, agonistic antibodies of the present invention may be administered in combination with Irinotecan (Camptosar®, CPT-11, Topotecin®, CaptoCPT-1) and Fluorouracil (5-FU, Adrucil®) for the treatment of colon cancer, that are resistant to individual chemotherapies.

In preferred embodiments, agonistic antibodies of the invention are administered in combination with one or more of the above-described therapeutic agent combinations in the treatment, amelioration and/or prevention of colorectal cancers and premalignant conditions.

Further examples of therapeutic agents useful in the treatment of colorectal cancer which may be administered in combination with antibodies of the present invention include, but are not limited to, Aminocamptothecin (9-AC, 9-Aminocamptothecin, NSC 603071), Aplidine (Aplidin®, Aplidina®), Bevacizumab® (Anti-VEGF monoclonal antibody, rhuMAb-VEGF), C225 (IMC-225, EGFR inhibitor, Anti-EGFr MAb, Cetuximab®), C242-DM1 (huC242-DM1), CC49-zeta gene therapy, CEA-cide® (Labetuzumab®, Anti-CEA monoclonal antibody, hMN-14), CeaVac® (MAb 3H1), CP-609754, CTP-37 (Avicine®, hCG blocking vaccine), Declopramide (Oxi-104), Eniluracil (776c85), F19 (Anti-FAP monoclonal antibody, iodinated anti-FAP MAb), FMdC (KW-2331, MDL-101731), FUDR (Floxuridine®), Gemcitabine (Gemto®, Gemzar®), Herceptin® (Trastuzumab®, Anti-HER-2 monoclonal antibody, Anti-EGFR-2 MAb), Intoplicine (RP 60475), L-778123 (Ras inhibitors), Leuvectin® (cytofectin+IL-2 gene, IL-2 gene therapy), MN-14 (Anti-CEA immunoradiotherapy, 131I-MN-14, $^{188}$Re-MN-14), OncoVAX-CL, OncoVAX-CL-Jenner (GA-733-2 vaccine) Orzel® (Tegafur+Uracil+Leucovorin), Oxaliplatin (Eloxatine®, Eloxatin®), Paclitaxel-DHA (Taxoprexin®), Pemetrexed disodium (Alimta®, MTA, multitargeted antifolate, LY 231514), R115777 (Zamestra®), Raltitrexed (Tomudex®, ZD-1694), SCH 66336, SU5416 (Semaxanib®, VEGF inhibitor), Tocladesine (8-Cl-cAMP), Trimetrexate (Neutrexin®), TS-1, and ZD-9331.

In preferred embodiments, agonistic antibodies of the invention are administered in combination with one or more of the above-described therapeutic agents in the treatment, amelioration and/or prevention of colorectal cancers and premalignant conditions.

Further exemplary combinations of therapeutic agents useful in the treatment of colorectal cancer and premalignant conditions which may be administered in combination with antibodies of the present invention include, but are not limited to, Aminocamptothecin+G-CSF, Bevacizumab®+Fluorouracil, Bevacizumab®+Leucovorin, Bevacizumab®+Fluorouracil+Leucovorin, Cyclophosphamide+SCH 6636, Fluorouracil+CeaVac®, Fluorouracil+Oxaliplatin, Fluorouracil+Raltitrexed, Fluorouracil+SCH 6636, Fluorouracil+Trimetrexate, Fluorouracil+Leucovorin+Oxaliplatin, Fluorouracil+Leucovorin+Trimetrexate, Irinotecan+C225 (Cetuximab®), Oncovin®+SCH 6636, Oxaliplatin+Leucovorin, Paclitaxel+SCH 6636, Pemetrexed disodium+Gemcitabine, and Trimetrexate+Leucovorin.

In preferred embodiments, agonistic antibodies of the invention are administered in combination with one or more of the above-described therapeutic agent combinations in the treatment, amelioration and/or prevention of colorectal cancers and premalignant conditions.

In further particular embodiments, antibodies of the present invention are used to treat, ameliorate and/or prevent prostrate cancer and premalignant conditions. Antibodies of the present invention may be used in combination with one or more surgical and/or radiological procedures and/or therapeutic agents to treat, ameliorate and/or prevent prostate cancer. Prostate cancer which may be treated using antibodies of the present invention includes, but is not limited to, benign prostatic hyperplasia, malignant prostate cancer (e.g., stage I, stage II, stage III or stage IV) and metastatic prostate cancer.

In preferred embodiments, agonistic antibodies of the present invention are used to treat, ameliorate and/or prevent prostate cancer and premalignant conditions. Agonistic antibodies of the present invention may be used in combination with one or more surgical and/or radiological procedures and/or therapeutic agents to treat, ameliorate and/or prevent prostate cancer and premalignant conditions. Prostate cancer which may be treated using agonistic antibodies of the present invention includes, but is not limited to, benign prostatic hyperplasia, malignant prostate cancer (e.g., stage I, stage II, stage III or stage IV) and metastatic prostate cancer.

In one preferred embodiment, agonistic antibodies of the invention are used to treat malignant prostate cancer. In a further preferred embodiment, agonistic antibodies of the invention are used to treat metastatic prostate cancer.

Antibodies of the present invention may be administered in combination with one or more surgical, radiological and/or hormonal procedures useful in the treatment of prostate cancer and premalignant conditions including, but not limited to, prostatectomy (e.g., radical retropubic prostatectomy), external beam radiation therapy, brachytherapy, orchiectomy and hormone treatment (e.g., LHRH agonists, androgen receptor inhibitors).

In preferred embodiments, agonistic antibodies of the present invention may be administered in combination with one or more surgical, radiological and/or hormonal procedures useful in the treatment of prostate cancer including, but not limited to, prostatectomy (e.g., radical retropubic prostatectomy), external beam radiation therapy, brachytherapy, orchiectomy and hormone treatment (e.g., LHRH agonists, androgen receptor inhibitors).

Antibodies of the present invention may be administered in combination with one or more therapeutic agents useful in the treatment of prostate cancer including, but not limited to, Aminoglutethimide (Cytadren®), Biclutamide (Casodex®), Cyclophosphamide (Cytoxan®, Neosar®, CTX), Diethylstilbestrol (DES), Doxorubicin (Adriamycin®, Doxil®, Rubex®), Flutamide (Eulexin®), Hydrocortisone, Ketoconazole (Nizoral®), Leuprolide acetate (Viadur®, Lupron®, Leuprogel®, Eligard®), Mitoxantrone (Novantrone®, DHAD), Nilutamide (Nilandron®), Paclitaxel (Paxene®, Taxol®), Paclitaxel-DHA (Taxoprexin®), PC SPES, Prednisone, Triptorelin pamoate (Trelstar Depot®, Decapeptyl®), and Vinblastine (Velban®, VLB).

In preferred embodiments, agonistic antibodies of the invention are administered in combination with one or more of the above-described therapeutic agents in the treatment, amelioration and/or prevention of prostate cancers and premalignant conditions.

Further examples of therapeutic agents useful in the treatment of prostate cancer which may be administered in combination with antibodies of the present invention include, but are not limited to, Abarelix® (Abarelix-Depot-M®, PPI-149, R-3827); Abiraterone Acetate® (CB-7598, CB-7630), ABT-627 (ET-1 inhibitor), APC-8015 (Provenge®, Dendritic cell therapy), Avorelin® (Meterelin®, MF-6001, EP-23904), CEP-701 (KT-5555), CN-706, CT-2584 (Apra®, CT-2583, CT-2586, CT-3536), GBC-590, Globo H hexasaccharide (Globo H-KLH®), Interferon alpha 2a (Intron A®), Liarozole (Liazal, Liazol, R-75251, R-85246, Ro-85264), MDX-447 (MDX-220, BAB-447, EMD-82633, H-447, anti-EGFr/FcGammaR1r), NPI-0052 (proteasome inhibitor), OncoVAX-P (OncoVAX-PrPSA), PROSTVAC, PS-341 (LDP-341, 26S proteasome inhibitor), PSMA MAb (Prostate Specific Membrane Antigen monoclonal antibody), and R-flurbiprofen (Flurizan®, E-7869, MPC-7869).

In preferred embodiments, agonistic antibodies of the invention are administered in combination with one or more of the above-described therapeutic agents in the treatment, amelioration and/or prevention of prostate cancers and premalignant conditions.

Preferred combinations of therapeutic agents useful in the treatment of prostate cancer which may be administered in combination with antibodies of the present invention include, but are not limited to, Docetaxel+Estramustine, Mitoxantrone+Hydrocortisone, Mitoxantrone+Prednisone, Navelbine+Estramustine, Paclitaxel+Estramustine, and Vinblastine+Estramustine.

In preferred embodiments, agonistic antibodies of the invention are administered in combination with one or more of the above-described therapeutic agent combinations in the treatment, amelioration and/or prevention of prostate cancers and premalignant conditions.

In further particular embodiments, antibodies of the present invention are used to treat, ameliorate and/or prevent pancreatic cancer and premalignant conditions. Antibodies of the present invention may be used in combination with one or more surgical and/or radiological procedures and/or therapeutic agents to treat, ameliorate and/or prevent pancreatic cancer and premalignant conditions. Pancreatic cancers which may be treated using antibodies of the present invention include, but are not limited to, adenocarcinoma, endocrine (islet cell) tumors, tumors confined to the pancreas, locally advanced pancreatic cancer and metastatic pancreatic cancer.

In preferred embodiments, agonistic antibodies of the present invention are used to treat, ameliorate and/or prevent pancreatic cancer and premalignant conditions. Agonistic antibodies of the present invention may be used in combination with one or more surgical and/or radiological procedures and/or therapeutic agents to treat, ameliorate and/or prevent pancreatic cancer and premalignant conditions. Pancreatic cancers which may be treated using agonistic antibodies of the present invention include, but are not limited to, adenocarcinoma, endocrine (islet cell) tumors, tumors confined to the pancreas, locally advanced pancreatic cancer and metastatic pancreatic cancer.

In one preferred embodiment, agonistic antibodies of the invention are used to treat locally advanced pancreatic cancer. In a further preferred embodiment, agonistic antibodies of the invention are used to treat metastatic pancreatic cancer.

Antibodies of the present invention may be administered in combination with one or more surgical and/or radiological procedures useful in the treatment of pancreatic cancer including, but not limited to, pancreaticoduodenumectomy (Whipple resection).

In preferred embodiments, agonistic antibodies of the present invention may be administered in combination with one or more surgical and/or radiological procedures useful in the treatment of pancreatic cancer including, but not limited to, pancreaticoduodenumectomy (Whipple resection).

Antibodies of the present invention may be administered in combination with one or more therapeutic agents useful in the treatment of pancreatic cancer including, but not limited to, Capecitabine (Xeloda®, Doxifluridine®, oral 5-FU), Cisplatin (Platinol®, CDDP), Fluorouracil (5-FU, Adrucil®, Fluoroplex®, Efudex®), Gemcitabine (Gemto®, Gemzar®), and Irinotecan (Camptosar®, CPT-11, Topotecin®, CaptoCPT-1).

In preferred embodiments, agonistic antibodies of the invention are administered in combination with one or more of the above-described therapeutic agents in the treatment, amelioration and/or prevention of pancreatic cancers and premalignant conditions.

Preferred combinations of therapeutic agents useful in the treatment of pancreatic cancer which may be administered in combination with antibodies of the present invention include, but are not limited to, Cisplatin+Gemcitabine, CP-358774+Gemcitabine, Docetaxel+Gemcitabine, Irinotecan+Fluorouracil, Irinotecan+Gemcitabine, and Paclitaxel+Gemcitabine.

In preferred embodiments, agonistic antibodies of the invention are administered in combination with one or more of the above-described therapeutic agent combinations in the treatment, amelioration and/or prevention of pancreatic cancers and premalignant conditions.

Further examples of therapeutic agents useful in the treatment of pancreatic cancer which may be administered in combination with antibodies of the present invention include, but are not limited to, ABX-EGF (anti-EGFr MAb), Acetyldinaline (CI-994, GOE-5549, GOR-5549, PD-130636), BMS-214662 (BMS-192331, BMS-193269, BMS-206635), BNP-1350 (BNPI-1100, Karenitecins), C225 (IMC-225, EGFR inhibitor, Anti-EGFr MAb, Cetuximab®), C242-DM1 (huC242-DM1, SB-408075), Carbendazin® (FB-642), Cannustine (DTI-015, BCNU, BiCNU, Gliadel Wafer®), CMT-3 (COL-3, Metastat®), CP-358774 (Tarceva®, OSI-774, EGFR inhibitor), Docetaxel (Taxotere®, Taxane®), Exetecan mesylate (DX-8951, DX-8951f), Flavopiridol (HMR-1275), Gastrimmune® (Anti-gastrin-17 immunogen, anti-g17), GBC-590, Herceptin® (Trastuzumab®, Anti-HER-2 monoclonal antibody, Anti-EGFR-2 MAb), HSPPC-96 (HSP cancer vaccine, gp96 heat shock protein-peptide complex), Irofulven (MGI-114), ISIS-2503 (Ras antisense), Onyx-015 (p53 gene therapy), Paclitaxel (Paxene®, Taxol®), Pemetrexed disodium (Alimta®, MTA, multitargeted antifolate, LY 231514), Perillyl alcohol (perilla alcohol, perillic alcohol, perillol, NSC-641066), RFS-2000 (9-nitrocamptothecan, 9-NC, Rubitecan®), and Rituximab® (Rituxan®, anti-CD20 MAb).

In preferred embodiments, agonistic antibodies of the invention are administered in combination with one or more of the above-described therapeutic agents in the treatment, amelioration and/or prevention of pancreatic cancers and premalignant conditions.

In further particular embodiments, antibodies of the present invention are used to treat, ameliorate and/or prevent hepatic cancer and premalignant conditions. Antibodies of the present invention may be used in combination with one or more surgical and/or radiological procedures and/or therapeutic agents to treat, ameliorate and/or prevent hepatic cancer and premalignant conditions. Hepatic cancers which may be treated using antibodies of the present invention include, but are not limited to, hepatocellular carcinoma, malignant hepatoma, cholangiocarcinoma, mixed hepatocellular cholangiocarcinoma or hepatoblastoma.

In preferred embodiments, agonistic antibodies of the present invention are used to treat, ameliorate and/or prevent hepatic cancer and premalignant conditions. Agonistic antibodies of the present invention may be used in combination with one or more surgical and/or radiological procedures and/or therapeutic agents to treat, ameliorate and/or prevent hepatic cancer and premalignant conditions. Hepatic cancers which may be treated using agonistic antibodies of the present invention include, but are not limited to, hepatocellular carcinoma, malignant hepatoma, cholangiocarcinoma, mixed hepatocellular cholangiocarcinoma or hepatoblastoma.

In one preferred embodiment, agonistic antibodies of the invention are used to treat hepatoblastoma. In one further preferred embodiment, agonistic antibodies of the invention are used to treat hepatocellular carcinoma.

Antibodies of the present invention may be administered in combination with one or more surgical and/or radiological procedures useful in the treatment of hepatic cancers including, but not limited to, partial hepatectomy, liver transplant, radiofrequency ablation, laser therapy, microwave therapy, cryosurgery, percutaneous ethanol injection, hepatic arterial infusion, hepatic artery ligation, chemoembolization and external beam radiation therapy.

In preferred embodiments, agonistic antibodies of the present invention may be administered in combination with one or more surgical and/or radiological procedures useful in the treatment of hepatic cancers and premalignant conditions including, but not limited to, partial hepatectomy, liver transplant, radiofrequency ablation, laser therapy, microwave therapy, cryosurgery, percutaneous ethanol injection, hepatic arterial infusion, hepatic artery ligation, chemoembolization and external beam radiation therapy.

Antibodies of the present invention may be administered in combination with one or more therapeutic agents useful in the treatment of hepatic cancer and premalignant conditions including, but not limited to, Aldesleukin (IL-2, Proleukin®), Cisplatin (Platinol®, CDDP), Doxorubicin (Adriamycin®, Doxil®, Rubex®), Etoposide phosphate (Etopophos®), Etoposide (VP-16, Vepesid®), Fluorouracil (5-FU, Adrucil®, Fluoroplex®, Efudex®), 1-131 Lipidiol®, Ifosfamide (IFEX®), Megestrol acetate (Megace®, Pallace®), Pravastatin sodium (Pravachol®), and Vincristine (Oncovin®, Onco TCS®, VCR, Leurocristine®).

In preferred embodiments, agonistic antibodies of the invention are administered in combination with one or more of the above-described therapeutic agents in the treatment, amelioration and/or prevention of hepatic cancers and premalignant conditions.

Preferred combinations of therapeutic agents useful in the treatment of hepatic cancer and premalignant conditions which may be administered in combination with antibodies of the present invention include, but are not limited to, Cisplatin+Doxorubicin, Cisplatin+Etoposide, Cisplatin+Vincristine+Fluorouracil, and Ifosfamide+Cisplatin+Doxorubicin.

In preferred embodiments, agonistic antibodies of the invention are administered in combination with one or more of the above-described therapeutic agent combinations in the treatment, amelioration and/or prevention of hepatic cancers and premalignant conditions.

In further particular embodiments, antibodies of the present invention are used to treat, ameliorate and/or prevent ovarian cancer. Antibodies of the present invention may be used in combination with one or more surgical and/or radiological procedures and/or therapeutic agents to treat, ameliorate and/or prevent ovarian cancer. Ovarian cancers which may be treated using antibodies of the present invention include, but are not limited to, epithelial carcinoma, germ cell tumors and stromal tumors.

In preferred embodiments, agonistic antibodies of the present invention are used to treat, ameliorate and/or prevent ovarian cancer and premalignant conditions. Agonistic antibodies of the present invention may be used in combination with one or more surgical and/or radiological procedures and/or therapeutic agents to treat, ameliorate and/or prevent ovarian cancer and premalignant conditions. Ovarian cancers which may be treated using agonistic antibodies of the present invention include, but are not limited to, epithelial carcinoma, germ cell tumors and stromal tumors.

In one preferred embodiment, agonistic antibodies of the invention are used to treat germ cell tumors and premalignant conditions. In one further preferred embodiment, agonistic antibodies of the invention are used to treat epithelial carcinoma.

Antibodies of the present invention may be administered in combination with one or more surgical and/or radiological procedures useful in the treatment of ovarian cancer and premalignant conditions including, but not limited to, hysterectomy, oophorectomy, hysterectomy with bilateral salpingo-oophorectomy, omentectomy, tumor debulking, external beam radiation therapy and intraperitoneal radiation therapy.

In preferred embodiments, agonistic antibodies of the present invention may be administered in combination with one or more surgical and/or radiological procedures useful in the treatment of ovarian cancer and premalignant conditions including, but not limited to, hysterectomy, oophorectomy, hysterectomy with bilateral salpingo-oophorectomy, omentectomy, tumor debulking, external beam radiation therapy and intraperitoneal radiation therapy.

Antibodies of the present invention may be administered in combination with one or more therapeutic agents useful in the treatment of ovarian cancer and premalignant conditions including, but not limited to, Altretamine (Hexylen®, hexamethylmelamine, Hexastat®), Bleomycin (Blenoxane®), Carboplatin (Paraplatin®, CBDCA), Cisplatin (Platinol®, CDDP), Cyclophosphamide (Cytoxan®, Neosar®, CTX), Dactinomycin (Cosmegen®), Doxorubicin (Adriamycin®, Doxil®, Rubex®), Etoposide phosphate (Etopophos®), Etoposide (VP-16, Vepesid®), Fluorouracil (5-FU, Adrucil®, Fluoroplex®, Efudex®), Gemcitabine (Gemto®, Gemzar®), Ifosfamide (IFEX®), Irinotecan (Camptosar®, CPT-11, Topotecin®, CaptoCPT-1), Leucovorin (Leucovorin®, Welicovorin®), Melphalan (L-PAM, Alkeran®, Phenylalanine mustard), Paclitaxel (Paxene®, Taxol®), Tamoxifen (Nolvadex®), Vinblastine (Velban®, VLB) and Vincristine (Oncovin®, Onco TCS®, VCR, Leurocristine®).

In preferred embodiments, agonistic antibodies of the invention are administered in combination with one or more of the above-described therapeutic agents in the treatment, amelioration and/or prevention of ovcarian cancers and premalignant conditions.

Preferred combinations of therapeutic agents useful in the treatment of ovarian cancer and premalignant conditions which may be administered in combination with antibodies of the present invention include, but are not limited to, Bleomycin+Etoposide+Platinol® (Cisplatin) (BEP), Carboplatin+Cyclophosphamide, Carboplatin+Paclitaxel, Carboplatin+Etoposide+Bleomycin (CEB), Cisplatin+Cyclophosphamide, Cisplatin+Etoposide, Cisplatin+Paclitaxel, Cisplatin+Ifosfamide+Vinblastine, Fluorouracil+Leucovorin, Platinolg (Cisplatin)+Vinblastine+Bleomycin (PVB), and Vincristine+Dactinomycin+Cyclophosphamide.

In preferred embodiments, agonistic antibodies of the invention are administered in combination with one or more of the above-described therapeutic agent combinations in the treatment, amelioration and/or prevention of ovarian cancers and premalignant conditions.

In further particular embodiments, antibodies of the present invention are used to treat, ameliorate and/or prevent Ewing's sarcoma. Antibodies of the present invention may be used in combination with one or more surgical and/or radiological procedures and/or therapeutic agents to treat, ameliorate and/or prevent Ewing's sarcoma. Ewing's sarcoma family tumors which may be treated using antibodies of the present invention include, but are not limited to, Ewing's tumor of bone (ETB), extraosseus Ewing's (EOE), primitive neuroectodermal tumors (PNET or peripheral neuroepithelioma) and Askin's tumor.

In preferred embodiments, agonistic antibodies of the present invention are used to treat, ameliorate and/or prevent Ewing's sarcoma. Agonistic antibodies of the present invention may be used in combination with one or more surgical and/or radiological procedures and/or therapeutic agents to treat, ameliorate and/or prevent Ewing's sarcoma. Ewing's sarcoma family tumors which may be treated using agonistic antibodies of the present invention include, but are not limited to, Ewing's tumor of bone (ETB), extraosseus Ewing's (EOE), primitive neuroectodermal tumors (PNET or peripheral neuroepithelioma) and Askin's tumor.

In one preferred embodiment, agonistic antibodies of the invention are used to treat Ewing's tumor of bone. In one further referred embodiment, agonistic antibodies of the invention are used to treat peripheral neuroepithelioma.

Antibodies of the present invention may be administered in combination with one or more surgical and/or radiological procedures useful in the treatment of Ewing's sarcoma family tumors.

In preferred embodiments, agonistic antibodies of the invention are administered in combination with one or more surgical and/or radiological procedures useful in the treatment of Ewing's sarcoma family tumors.

Antibodies of the present invention may be administered in combination with one or more therapeutic agents useful in the treatment of Ewing's sarcoma family tumors including, but not limited to, Cyclophosphamide (Cytoxan®, Neosar®, CTX), Doxorubicin (Adriamycin®, Doxil®, Rubex®), Etoposide phosphate (Etopophos®), Etoposide (VP-16, Vepesid®), Filgrastim (Neupogen®, G-CSF), Ifosfamide (IFEX®), Topotecan (Hycamtin®, SK&F-104864, NSC-609699, Evotopin®), and Vincristine (Oncovin®, Onco TCS®, VCR, Leurocristine®).

In preferred embodiments, agonistic antibodies of the invention are administered in combination with one or more of the above-described therapeutic agents in the treatment, amelioration and/or prevention of Ewing's sarcoma family tumors.

Preferred combinations of therapeutic agents useful in the treatment of Ewing's sarcoma family tumors which may be administered in combination with antibodies of the present invention include, but are not limited to, Cyclophosphamide+Topotecan, Cyclophosphamide+Doxorubicin+Vincristine, Cyclophosphamide+Doxorubicin+Vincristine, alternating with Ifosfamide+Etoposide andcyclophosphamide+Doxorubicin+Vincristine, alternating with Filgrastim+Ifosfamide+Etoposide.

In preferred embodiments, agonistic antibodies of the invention are administered in combination with one or more of the above-described therapeutic agent combinations in the treatment, amelioration and/or prevention of Ewing's sarcoma family tumors.

In further particular embodiments, antibodies of the present invention are used to treat, ameliorate and/or prevent hematological cancers and premalignant conditions. Antibodies of the present invention may be used in combination with one or more surgical and/or radiological procedures and/or therapeutic agents to treat, ameliorate and/or prevent hematological cancers and premalignant conditions. Hematological cancers which may be treated using antibodies of the present invention include, but are not limited to, non-Hodgkin's lymphoma (e.g., small lymphocytic lymphoma, follicular center cell lymphoma, lymphoplasmacytoid lymphoma, marginal zone lymphoma, mantle cell lymphoma, immunoblastic lymphoma, burkitt's lymphoma, lymphoblastic lymphoma, peripheral T-cell lymphoma, anaplastic large cell lymphoma and intestinal T-cell lymphoma), leukemia, acute lymphocytic leukemia, chronic lymphocytic leukemia and plasma cell neoplasms including multiple myeloma.

In preferred embodiments, agonistic antibodies of the present invention are used to treat, ameliorate and/or prevent hematological cancers and premalignant conditions. Agonistic antibodies of the present invention may be used in combination with one or more surgical and/or radiological procedures and/or therapeutic agents to treat, ameliorate and/or prevent hematological cancers and premalignant conditions. Hematological cancers which may be treated using agonistic antibodies of the present invention include, but are not limited to, non-Hodgkin's lymphoma (e.g., small lymphocytic lymphoma, follicular center cell lymphoma, lymphoplasmacytoid lymphoma, marginal zone lymphoma, mantle cell lymphoma, immunoblastic lymphoma, burkitt's lymphoma, lymphoblastic lymphoma, peripheral T-cell lymphoma, anaplastic large cell lymphoma and intestinal T-cell lymphoma), leukemia, acute lymphocytic leukemia, chronic lymphocytic leukemia and plasma cell neoplasms including multiple myeloma.

In one preferred embodiment, agonistic antibodies of the invention are used to treat plasma cell neoplasms. In a specific embodiment, that plasma cell neoplasm is multiple myeloma.

In another preferred embodiment, agonistic antibodies of the invention are used to treat non-Hodgkin's lymphoma.

In another preferred embodiment, agonistic antibodies of the invention are used to treat leukemia. In a specific embodiment, that leukemia is acute lymphocytic leukemia. In another specific embodiment, that leukemia is chronic lymphocytic leukemia.

Antibodies of the present invention may be administered in combination with one or more surgical and/or radiological procedures useful in the treatment of hematological cancer and premalignant conditions including, but not limited to, bone marrow transplantation, external beam radiation and total body irradiation.

In preferred embodiments, agonistic antibodies of the invention are administered in combination with one or more surgical and/or radiological procedures useful in the treatment of hematological cancer and premalignant conditions including, but not limited to, bone marrow transplantation, external beam radiation and total body irradiation.

In one preferred embodiment, agonistic antibodies of the present invention may be administered in combination with one or more surgical and/or radiological procedures useful in the treatment of multiple myeloma including, but not limited to, allogeneic bone marrow transplantation and peripheral stem cell support.

In another preferred embodiment, agonistic antibodies of the present invention may be administered in combination with one or more surgical and/or radiological procedures useful in the treatment of non-Hodgkin's lymphoma including, but not limited to, allogeneic bone marrow transplantation and peripheral stem cell support.

In further specific embodiments, agonistic antibodies of the present invention may be administered in combination with one or more surgical and/or radiological procedures useful in the treatment of leukemia including, but not limited to, allogeneic bone marrow transplantation and peripheral stem cell support. In one specific preferred embodiment, agonistic antibodies of the invention are used to treat acute lymphocytic leukemia (ALL). In another specific preferred embodiment, agonistic antibodies of the invention are used to treat chronic lymphocytic leukemia (CLL).

Antibodies of the present invention may be administered in combination with one or more therapeutic agents useful in the treatment of multiple myeloma including, but not limited to, Alkylating agents, Anthracyclines, Carmustine (DTI-015, BCNU, BiCNU, Gliadel Wafer®), Cyclophosphamide (Cytoxan®, Neosar®, CTX), Dexamethasone (Decadron®), Doxorubicin (Adriamycin®, Doxil®, Rubex®), Melphalan (L-PAM, Alkeran®, Phenylalanine mustard), Prednisone, Thalidomide and thalidomide analogs, including but not limited to, lenalidomide (CC-5013, REVLIMID®) and CC-4047 (ACTIMID™), and Vincristine (Oncovorin®, Onco TCS®, VCR, Leurocristine®).

In preferred embodiments, agonistic antibodies of the invention are administered in combination with one or more of the above-described therapeutic agents in the treatment, amelioration and/or prevention of multiple myeloma.

Preferred combinations of therapeutic agents useful in the treatment of multiple myeloma which may be administered in combination with antibodies of the present invention include, but are not limited to, Cyclophosphamide+Prednisone, Melphalan+Prednisone (MP), Vincristine+Adriamycin®+Dexamethasone (VAD), Vincristine+Carmustine+Melphalan+Cyclophosphamide+Prednisone (VBMCP; the M2 protocol), and Vincristine+Melphalan+Cyclophosphamide+Prednisone alternating with Vincristine+Carmustine+Doxorubicin+Prednisone (VMCP/VBAP).

In preferred embodiments, agonistic antibodies of the invention are administered in combination with one or more of the above-described therapeutic agent combinations in the treatment, amelioration and/or prevention of multiple myeloma.

Antibodies of the present invention may be administered in combination with one or more therapeutic agents useful in the treatment of non-Hodgkin's lymphoma including, but not limited to, 2-chlorodeoxyadenosine, Amifostine (Ethyol®, Ethiofos®, WR-272), Bexarotene (Targretin®, Targretin Gel®, Targretin Oral®, LGD1069), Bleomycin (Blenoxane®), Busulfan (Busulfex®, Myleran®), Carboplatin (Paraplatin®, CBDCA), Carmustine (DTI-015, BCNU, BiCNU, Gliadel Wafer®), Chloranbucil (Leukeran®), Cisplatin (Platinol®, CDDP), Cladribine (2-CdA, Leustatin®), Cyclophosphamide (Cytoxan®, Neosar®, CTX), Cytarabine (Cytosar-U®, ara-C, cytosine arabinoside, DepoCyt®), Dacarbazine (DTIC), Daunorubicin (Daunomycin, DaunoXome®, Daunorubicin®, Cerubidine®), Denileukin diftitox (Ontak®), Dexamethasone (Decadron®), Dolasetron mesylate (Anzemet®), Doxorubicin (Adriamycin®, Doxil®, Rubex®), Erythropoietin (EPO®, Epogen®, Procrit®), Etoposide phosphate (Etopophos®), Etoposide (VP-16, Vepesid®), Fludarabine (Fludara®, FAMP), Granisetron (Kytril®), Hydrocortisone, Idarubicin (Idamycin®, DMDR, IDA), Ifosfamide (IFEX®), Interferon alpha (Alfaferone®, Alpha-IF®), Interferon alpha 2a (Intron A®), Mechlorethamine (Nitrogen Mustard, $HN_2$, Mustargen®), Melphalan (L-PAM, Alkeran®, Phenylalanine mustard), Methotrexate® (MTX, Mexate®, Folex®), Methylprednisolone (Solumedrol®), Mitoxantrone (Novantrone®, DHAD), Ondansetron (Zofran®), Pentostatin (Nipent®, 2-deoxycoformycin), Perfosfamide (4-hydroperoxycyclophosphamide, 4-HC), Prednisone, Procarbazine (Matulane®), Rituximab® (Rituxan®, anti-CD20 MAb), Thiotepa (triethylenethiophosphaoramide, Thioplex®), Topotecan (Hycamtin®, SK&F-104864, NSC-609699, Evotopin®), Vinblastine (Velban®, VLB), Vincristine (Oncovin®, Onco TCS®, VCR, Leurocristine®) and Vindesine (Eldisine®, Fildesin®)).

In preferred embodiments, agonistic antibodies of the invention are administered in combination with one or more of the above-described therapeutic agents in the treatment, amelioration and/or prevention of non-Hodgkin's lymphoma.

Preferred combinations of therapeutic agents useful in the treatment of non-Hodgkin's lymphoma which may be administered in combination with antibodies of the present invention include, but are not limited to, Adriamycin®+Blenoxane+Vinblastine+Dacarbazine (ABVD), Anti-idiotype therapy (BsAb)+Interferon alpha, Anti-idiotype therapy (BsAb)+Chlorambucil, Anti-idiotype therapy (BsAb)+Interleukin-2, BCNU (Carmustine)+Etoposide+Ara-C (Cytarabine)+Melphalen (BEAM), Bleomycin+Etoposide+Adriamycin+Cyclophosphamide+Vincristine+Procarbazine+Prednisone (BEACOPP), Bryostatin+Vincristine, Cyclophosphamide+BCNU (Carmustine)+VP-16 (Etoposide) (CBV), Cyclophosphamide+Vincristine+Prednisone (CVP), Cyclophosphamide+Adriamycin® (Hydroxyldaunomycin)+Vincristine (Oncovorin)+Prednisone (CHOP), Cyclophosphamide+Novantrone® (Mitoxantrone)+Vincristine (Oncovorin)+Prednisone (CNOP), Cyclophosphamide+Doxorubicin+Teniposide+Prednisone, Cyclophosphamide+Adriamycin® (Hydroxyldaunomycin)+Vincristine (Oncovorin)+Prednisone+Rituximab (CHOP+Rituximab), Cyclophosphamide+Doxorubicin+Teniposide+Prednisone+Interferon alpha, Cytarabine+Bleomycin+Vincristine+Methotrexate (CytaBOM), Dexamethasone+Cytarabine+Cisplatin (DHAP), Dexamethasone+Ifosfamide+Cisplatin+Etoposide (DICE), Doxorubicin+Vinblastine+Mechlorethamine+Vincristine+Bleomycin+Etoposide+Prednisone (Stanford V), Etoposide+Vinblastine+Adriamycin (EVA), Etoposide+Methylprednisone+Cytarabine+Cisplatin (ESHAP), Etoposide+Prednisone+Ifosfamide+Cisplatin (EPIC), Fludarabine, Mitoxantrone+Dexamethasone (FMD), Fludarabine, Dexamethasone, Cytarabine (ara-C), +Cisplatin (Platinol®) (FluDAP), Ifosfamide+Cisplatin+Etoposide (ICE), Mechlorethamine+Oncovin® (Vincristine)+Procarbazine+Prednisone (MOPP), Mesna+Ifosfamide+Idarubicin+Etoposide (MIZE), Methotrexate with leucovorin rescue+Bleomycin+Adriamycin+Cyclophosphamide+Oncovorin+Dexamethasone (m-BACOD), Prednisone+Methotrexate+Adriamycin+Cyclophosphamide+Etoposide (ProMACE), Thiotepa+Busulfan+Cyclophosphamide, Thiotepa+Busulfan+Melphalan, Topotecan+Paclitaxel, and Vincristine (Oncovin®)+Adriamycin®+Dexamethasone (VAD).

In preferred embodiments, agonistic antibodies of the invention are administered in combination with one or more of the above-described therapeutic agent combinations in the treatment, amelioration and/or prevention of non-Hodgkin's lymphoma.

Further examples of therapeutic agents useful in the treatment of non-Hodgkin's lymphoma which may be administered in combination with antibodies of the present invention include, but are not limited to, A007 (4-4'-dihydroxybenzophenone-2,4-dinitrophenylhydrazone), AG-2034 (AG-2024, AG-2032, GARFT [glycinamide ribonucleoside transformylase] inhibitor), Aldesleukin (IL-2, Proleukin®), Alemtuzumab (Campath®), Alitretinoin (Panretin®, LGN-1057), Altretamine (Hexylen®, hexamethylmelamine, Hexastat®), Aminocamptothecin (9-AC, 9-Aminocamptothecin, NSC 603071), Anti-CD19/CD3 MAb (anti-CD19/CD3 scFv, anti-NHL MAb), Anti-idiotype therapy (BsAb), Arabinosylguanine (Ara-G, GW506U78), Arsenic trioxide (Trisenox®, ATO), B43-Genistein (anti-CD19 Ab/genistein conjugate), B7 antibody conjugates, Betathine (Beta-LT), BLyS antagonists, Bryostatin-1 (Bryostatin®, BMY-45618, NSC-339555), CHML (Cytotropic Heterogeneous Molecular Lipids), Clofarabine (chloro-fluoro-araA), Daclizumab (Zenapax®), Depsipeptide (FR901228, FK228), Dolastatin-10 (DOLA-10, NSC-376128), Epirubicin (Ellence®, EPI, 4' epidoxorubicin), Epratuzumab (Lymphocide®, humanized anti-CD22, HAT), Fly3/flk2 ligand (Mobista®), G3139 (Genasense®, GentaAnticode®, Bcl-2 antisense), HuID10 (anti-HLA-DR MAb, SMART ID10), HumaLYM (anti-CD20 MAb), Ibritumomab tiuxetan (Zevalin®), Interferon gamma (Gamma-interferon, Gamma 1000, Gamma-IF), Irinotecan (Camptosar®, CPT-11, Topotecin®, CaptoCPT-1), ISIS-2053, ISIS-3521 (PKC-alpha antisense), Lmb-2 immunotoxin (anti-CD25 recombinant immuno toxin, anti-Tac(Fv)-PE38), Leuvectin® (cytofectin+IL-2 gene, IL-2 gene therapy), Lym-1 (131-I LYM-I), Lymphoma vaccine (Genitope), Nelarabine (Compound 506, U78), Neugene compounds (Oncomyc-NG®, Resten-NG®, myc antisense), NovoMAb-G2 scFv (NovoMAb-G2 IgM), 06-benzylguanine (BG, Procept®), Oxaliplatin (Eloxatine®, Eloxatin®), Paclitaxel (Paxene®, Taxol®), Paclitaxel-DHA (Taxoprexin®), Peldesine (BCX-34, PNP inhibitor), Rebeccamycin and Rebeccamycin analogues, SCH-66336, Sobuzoxane (MST-16, Perazolin®), SU5416 (Semaxanib®, VEGF inhibitor), TER-286, Thalidomide and thalidomide analogs, including but not limited to, lenalidomide (CC-5013, REVLIMID®) and CC-4047 (ACTIMID™), TNP-470 (AGM-1470), Tositumomab (Bexxar®), Valspodar (PSC 833), Vaxid (B-cell lymphoma DNA vaccine), Vinorelbine (Navelbine®), WF10 (macrophage regulator) and XR-9576 (XR-9351, P-glycoprotein/MDR inhibitor).

In preferred embodiments, agonistic antibodies of the invention are administered in combination with one or more of the above-described therapeutic agents in the treatment, amelioration and/or prevention of non-Hodgkin's lymphoma.

Antibodies of the present invention may be administered in combination with one or more therapeutic agents useful in the treatment of acute lymphocytic leukemia including, but not limited to, Amsacrine, Carboplatin (Paraplatin®, CBDCA), Carmustine (DTI-015, BCNU, BiCNU, Gliadel Wafer®), Cholecaliferol, Cyclophosphamide (Cytoxan®, Neosar®, CTX), Cytarabine (Cytosar-U®, ara-C, cytosine arabinoside, DepoCyt®), Daunorubicin (Daunomycin, DaunoXome®, Daunorubicin®, Cerubidine®), Dexamethasone (Decadron®), Doxorubicin (Adriamycin®, Doxil®, Rubex®), Etoposide (VP-16, Vepesid®), Filgrastam® (Neupogen®, G-CSF, Leukine®), Fludarabine (Fludara®, FAMP), Idarubicin (Idamycin®, DMDR, IDA), Ifosfamide (IFEX®), Imatinib mesylate (STI-571, Imatinib®, Glivec®, Gleevec®, Ab1 tyrosine kinase inhibitor), Interferon gamma (Gamma-interferon, Gamma 1000, Gamma-IF), L-asparaginase (Elspar®, Crastinin®, Asparaginase Medac®, Kidrolase®), Mercaptopurine (6-mercaptopurine, 6-MP), Methotrexate® (MTX, Mexate®, Folex®), Mitoxantrone (Novantrone®, DHAD), Pegaspargase® (Oncospar®), Prednisone, Retinoic acid, Teniposide (VM-26, Vumon®), Thioguanine (6-thioguanine, 6-TG), Topotecan (Hycamtin®, SK&F-104864, NSC-609699, Evotopin®), Tretinoin (Retin-A®, Atragen®, ATRA, Vesanoid®) and Vincristine (Oncovorin®, Onco TCS®, VCR, Leurocristine®).

In preferred embodiments, agonistic antibodies of the invention are administered in combination with one or more of the above-described therapeutic agents in the treatment, amelioration and/or prevention of acute lymphocytic leukemia.

Further examples of therapeutic agents useful in the treatment of acute lymphocytic leukemia which may be administered in combination with antibodies of the present invention include, but are not limited to, Aminocamptothecin (9-AC, 9-Aminocamptothecin, NSC 603071), Aminopterin, Annamycin (AR-522, annamycin LF, Aronex®), Arabinosylguanine (Ara-G, GW506U78, Nelzarabine®), Arsenic trioxide (Trisenox®, ATO, Atrivex®V), B43-Genistein (anti-CD19 Ab/genistein conjugate), B43-PAP (anti-CD19 Ab/pokeweed antiviral protein conjugate), Cordycepin, CS-682, Decitabine (5-aza-2'-deoxyytidine), Dolastatin-10 (DOLA-10, NSC-376128), G3139 (Genasense®, GentaAnticode®, Bcl-2 antisense), Irofulven (MGI-114, Ivofulvan, Acylfulvene analogue), MS-209, Phenylbutyrate, Quinine, TNP-470 (AGM-1470, Fumagillin), Trimetrexate (Neutrexin®), Troxacitabine (BCH-204, BCH-4556, Troxatyl®), UCN-01 (7-hydroxystaurosporine), WHI-P131 and WT1 Vaccine.

In preferred embodiments, agonistic antibodies of the invention are administered in combination with one or more of the above-described therapeutic agents in the treatment, amelioration and/or prevention of acute lymphocytic leukemia.

Preferred combinations of therapeutic agents useful in the treatment of acute lymphocytic leukemia which may be administered in combination with antibodies of the present invention include, but are not limited to, Carboplatin+Mitoxantrone, Carmustine+Cyclophosphamide+Etoposide, Cytarabine+Daunorubicin, Cytarabine+Doxorubicin, Cytarabine+Idarubicin, Cytarabine+Interferon gamma, Cytarabine+L-asparaginase, Cytarabine+Mitoxantrone, Cytarabine+Fludarabine and Mitoxantrone, Etoposide+Cytarabine, Etoposide+Ifosfamide, Etoposide+Mitoxantrone, Ifosfamide+Etoposide+Mitoxantrone, Ifosfamide+Teniposide, Methotrexate+Mercaptopurine, Methotrexate+Mercaptopurine+Vincristine+Prednisone, Phenylbutyrate+Cytarabine, Phenylbutyrate+Etoposide, Phenylbutyrate+Topotecan, Phenylbutyrate+Tretinoin, Quinine+Doxorubicin, Quinine+Mitoxantrone+Cytarabine, Thioguanine+Cytarabine+Amsacrine, Thioguanine+Etoposide+Idarubicin, Thioguanine+Retinoic acid+Cholecaliferol, Vincristine+Prednisone, Vincristine+Prednisone and L-asparaginase, Vincristine+Dexamethasone/Prednisone+Asparaginase+Daunorubicin/Doxorubicin, Vincristine+Dexamethasone/Prednisone+Asparaginase+Daunorubicin/Doxorubicin+Filgrastim, Vincristine+Dexamethasone/Prednisone+Asparaginase+Daunorubicin/Doxorubicin+Cyclophosphamide+Methotrexate, and Vincristine+Dexamethasone/Prednisone+Asparaginase+Daunorubicin/Doxorubicin+Cyclophosphamide+Methotrexate+Filgrastim.

In preferred embodiments, agonistic antibodies of the invention are administered in combination with one or more of the above-described therapeutic agent combinations in the treatment, amelioration and/or prevention of acute lymphocytic leukemia.

Antibodies of the present invention may be administered in combination with one or more therapeutic agents useful in the treatment of chronic lymphocytic leukemia including, but not limited to, Chlorambucil (Leukeran®), Cladribine (2-CdA, Leustatin®), Cyclophosphamide (Cytoxan®, Neosar®, CTX), Cytarabine (Cytosar-U®, ara-C, cytosine arabinoside, DepoCyt®, cytarabine ocfosfate, ara-CMP), Doxorubicin (Adriamycin®, Doxil®, Rubex®), Fludarabine (Fludara®, FAMP), Pentostatin (Nipent®, 2-deoxycoformycin), Prednisone and Vincristine (Oncovorin®, Onco TCS®, VCR, Leurocristine®).

In preferred embodiments, agonistic antibodies of the invention are administered in combination with one or more of the above-described therapeutic agents in the treatment, amelioration and/or prevention of chronic lymphocytic leukemia.

Further examples of therapeutic agents useful in the treatment of chronic lymphocytic leukemia which may be administered in combination with antibodies of the present invention include, but are not limited to, Alemtuzumab (Campath®), Aminocamptothecin (9-AC, 9-Aminocamptothecin, NSC 603071), Aminopterin, Annamycin (AR-522, annamycin LF, Aronex®), Arabinosylguanine (Ara-G, GW506U78, Nelzarabine®, Compound 506U78), Arsenic trioxide (Trisenox®, ATO, Atrivex®), Bryostatin-1 (Bryostatin®, BMY-45618, NSC-339555), CS-682, Dolastatin-10 (DOLA-10, NSC-376128), Filgrastim (Neupogen®, G-CSF, Leukine), Flavopiridol (NSC-649890, HMR-1275), G3139 (Genasense®, GentaAnticode®, Bcl-2 antisense), Irofulven (MGI-114, Ivofulvan, Acylfulvene analogue), MS-209, Phenylbutyrate, Rituximab® (Rituxan®, anti-CD20 MAb), Thalidomide and thalidomide analogs, including but not limited to, lenalidomide (CC-5013, REVLIMID®) and CC-4047 (ACTIMID™), Theophylline, TNP-470 (AGM-1470, Fumagillin), UCN-01 (7-hydroxystaurosporine) and WHI-P131.

In preferred embodiments, agonistic antibodies of the invention are administered in combination with one or more of the above-described therapeutic agents in the treatment, amelioration and/or prevention of chronic lymphocytic leukemia.

Preferred combinations of therapeutic agents useful in the treatment of chronic lymphocytic leukemia which may be administered in combination with antibodies of the present invention include, but are not limited to, Fludarabine+Prednisone, and Cyclophosphamide+Doxorubicin+Vincristine+Prednisone (CHOP).

In preferred embodiments, agonistic antibodies of the invention are administered in combination with one or more of the above-described therapeutic agent combinations in the treatment, amelioration and/or prevention of chronic lymphocytic leukemia.

Anti-DR4 antibodies may be utilized in combination with other monoclonal or chimeric antibodies, or with lymphokines, tumor necrosis factors or TNF-related molecules (e.g., TNF-α, TNF-β, TNF-γ, TNF-γ-β, TNF-γ-β, and TRAIL), or hematopoietic growth factors (e.g., IL-2, IL-3 and IL-7). For example, agonistic anti-DR4 antibodies may be administered in conjunction with TRAIL when one seeks to induce DR4 mediated cell death in cells which express DR4 receptors of the invention. Combination therapies of this nature, as well as other combination therapies, are discussed below in more detail.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5 \times 10^{-6}$M, $10^{-6}$M, $5 \times 10^{-7}$M, $10^{-7}$M, $5 \times 10^{-8}$M, $10^{-8}$M, $5 \times 10^{-9}$M, $10^{-9}$M, $5 \times 10^{-10}$M, $10^{-11}$M, $5 \times 10^{-11}$M, $10^{-11}$M, $5 \times 10^{-12}$M, $10^{-12}$M, $5 \times 10^{-13}$M, $10^{-13}$M, $5 \times 10^{-14}$M, $10^{-14}$M, $5 \times 10^{-15}$M, and $10^{-15}$M.

Polypeptide Assays

The present invention also relates to diagnostic assays such as quantitative and diagnostic assays for detecting levels of DR4 protein, or the soluble form thereof, in cells and tissues, including determination of normal and abnormal levels. Thus, for instance, a diagnostic assay in accordance with the invention for detecting over-expression of DR4, or soluble form thereof, compared to normal control tissue samples may be used to detect the presence of tumors, for example. Assay techniques that can be used to determine levels of a protein, such as a DR4 protein of the present invention, or a soluble form thereof, in a sample derived from a host are well-known to those of skill in the art. Such assay methods include radioimmunoassays, competitive-binding assays, Western Blot analysis and ELISA assays.

Assaying DR4 protein levels in a biological sample can occur using any art-known method. By "biological sample" is intended any biological sample obtained from an individual, cell line, tissue culture, or other source containing DR4 receptor protein or mRNA. Preferred for assaying DR4 protein levels in a biological sample are antibody-based techniques. For example, DR4 protein expression in tissues can be studied with classical immunohistological methods. (Jalkanen, M., et al., *J. Cell. Biol.* 101:976-985 (1985); Jalkanen, M., et al., *J. Cell. Biol.* 105:3087-3096 (1987)). Other antibody-based methods useful for detecting DR4 protein gene expression include immunoassays, such as the enzyme linked immunosorbent assay (ELISA) and the radioimmunoassay (RIA).

Suitable labels are known in the art and include enzyme labels, such as glucose oxidase, radioisotopes, such as iodine ($^{125}$I, $^{121}$I), carbon ($^{14}$C), sulphur ($^{35}$S), tritium ($^{3}$H), indium ($^{112}$In), and technetium ($^{99m}$Tc), and fluorescent labels, such as fluorescein and rhodamine, and biotin.

Transgenics and "Knock-Outs"

The proteins of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., nucleic acids of the invention) into animals to produce the founder lines of transgenic animals. Such techniques include, but are not limited to, pronuclear microinjection (Paterson et al., Appl. Microbiol. Biotechnol. 40:691-698 (1994); Carver et al., Biotechnology (NY) 11:1263-1270 (1993); Wright et al., Biotechnology (NY) 9:830-834 (1991); and Hoppe et al., U.S. Pat. No. 4,873,191 (1989)); retrovirus mediated gene transfer into germ lines (Van der Putten et al., Proc. Natl. Acad. Sci., USA 82:6148-6152 (1985)), blastocysts or embryos; gene targeting in embryonic stem cells (Thompson et al., Cell 56:313-321 (1989)); electroporation of cells or embryos (Lo, Mol. Cell. Biol. 3:1803-1814 (1983)); introduction of the polynucleotides of the invention using a gene gun (see, e.g., Ulmer et al., Science 259:1745 (1993); introducing nucleic acid constructs into embryonic pluripotent stem cells and transferring the stem cells back into the blastocyst; and sperm-mediated gene transfer (Lavitrano et al., Cell 57:717-723 (1989); etc. For a review of such techniques, see Gordon, "Transgenic Animals," *Intl. Rev. Cytol.* 115:171-229 (1989), which is incorporated by reference herein in its entirety. Further, the contents of each of the documents recited in this paragraph is herein incorporated by reference in its entirety. See also, U.S. Pat. No. 5,464,764 (Capecchi et al., Positive-Negative Selection Methods and Vectors); U.S. Pat. No. 5,631,153 (Capecchi et al., Cells and Non-Human Organisms Containing Predetermined Genomic Modifications and Positive-Negative Selection Methods and Vectors for Making Same); U.S. Pat. No. 4,736,866 (Leder et al., Transgenic Non-Human Animals); and U.S. Pat. No. 4,873,191 (Wagner et al., Genetic Transformation of Zygotes); each of which is hereby incorporated by reference in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campbell et al., Nature 380:64-66 (1996); Wilmut et al., *Nature* 385:810-813 (1997)), each of which is herein incorporated by reference in its entirety).

The present invention provides for transgenic animals that carry the transgene in all their cells, as well as animals which carry the transgene in some, but not all their cells, i.e., mosaic animals or chimeric animals. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (*Proc. Natl. Acad. Sci. USA* 89:6232-6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (*Science* 265:103-106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic and "knock-out" animals of the invention have uses which include, but are not limited to, animal model systems useful in elaborating the biological function of DR4 polypeptides, studying conditions and/or disorders associated with aberrant DR4 expression, and in screening for compounds effective in ameliorating such conditions and/or disorders.

In further embodiments of the invention, cells that are genetically engineered to express the proteins of the invention, or alternatively, that are genetically engineered not to express the proteins of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells, etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally. Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959, each of which is incorporated by reference herein in its entirety).

When the cells to be administered are non-autologous or non-MHC compatible cells, they can be administered using well-known techniques which prevent the development of a host immune response against the introduced cells. For example, the cells may be introduced in an encapsulated form that, while allowing for an exchange of components with the immediate extracellular environment, does not allow the introduced cells to be recognized by the host immune system.

Therapeutics

The Tumor Necrosis Factor (TNF) family ligands are known to be among the most pleiotropic cytokines, inducing a large number of cellular responses, including cytotoxicity, anti-viral activity, immunoregulatory activities, and the transcriptional regulation of several genes (Goeddel, D. V. et al., "Tumor Necrosis Factors: Gene Structure and Biological Activities," *Symp. Quant. Biol.* 51:597-609 (1986), Cold Spring Harbor; Beutler, B., and Cerami, A., *Annu. Rev. Biochem.* 57:505-518 (1988); Old, L. J., *Sci. Am.* 258:59-75 (1988); Fiers, W., *FEBS Lett.* 285:199-224 (1991)). The TNF-family ligands induce such various cellular responses by binding to TNF-family receptors, including the DR4 receptors of the present invention.

DR4 polynucleotides and polypeptides of the invention may be used in developing treatments and/or prevention methods for any disorder mediated (directly or indirectly) by defective, or insufficient amounts of DR4. DR4 polypeptides may be administered to a patient (e.g., mammal, preferably human) afflicted with such a disorder. Alternatively, a gene therapy approach may be applied to treat and/or prevent such disorders. Disclosure herein of DR4 nucleotide sequences permits the detection of defective DR4 genes, and the replacement thereof with normal DR4-encoding genes. Defective genes may be detected in in vitro diagnostic assays, and by comparison of the DR4 nucleotide sequence disclosed herein with that of a DR4 gene derived from a patient suspected of harboring a defect in this gene. Defective genes may be replaced with normal DR4-encoding genes using techniques known to one skilled in the art.

In another embodiment, the polypeptides of the present invention are used as a research tool for studying the biological effects that result from inhibiting TRAIL/DR4 interactions on different cell types. DR4 polypeptides also may be employed in in vitro assays for detecting TRAIL or DR4 or the interactions thereof.

In another embodiment, a purified DR4 polypeptide or DR4 antagonist of the invention is used to inhibit binding of TRAIL to endogenous cell surface TRAIL receptors. Certain ligands of the TNF family (of which TRAIL is a member) have been reported to bind to more than one distinct cell surface receptor protein. TRAIL likewise is believed to bind multiple cell surface proteins. By binding TRAIL, soluble DR4 polypeptides and/or DR4 antagonists of the present invention may be employed to inhibit the binding of TRAIL not only to cell surface DR4, but also to TRAIL receptor proteins that are distinct from DR4. Thus, in another embodiment, a DR4 polypeptide and/or antagonist is used to inhibit a biological activity of TRAIL, in in vitro or in vivo procedures. By inhibiting binding of TRAIL to cell surface receptors, a DR4 polypeptide and antagonist also inhibits biological effects that result from the binding of TRAIL to endogenous receptors. Various forms of DR4 polypeptides may be employed, including, for example, the above-described DR4 fragments, derivatives, and variants that are capable of binding TRAIL. In a preferred embodiment, a soluble DR4 is employed to inhibit a biological activity of TRAIL, e.g., to inhibit TRAIL-mediated apoptosis of cells susceptible to such apoptosis.

In a further embodiment, DR4 compositions (e.g., DR4 polynucleotides, polypeptides, agonists and/or antagonists) of the invention are administered to a mammal (e.g., a human) to treat and/or prevent a TRAIL-mediated disorder. Such TRAIL-mediated disorders include conditions caused (directly or indirectly) or exacerbated by TRAIL.

Cells which express the DR4 polypeptide and are believed to have a potent cellular response to DR4 ligands include amniotic cells, heart, liver cancer, kidney, peripheral blood leukocytes, activated T-cells, tissue corresponding to Th2 cells, human tonsils, and CD34 depleted buffy coat (cord blood). By "a cellular response to a TNF-family ligand" is intended any genotypic, phenotypic, and/or morphologic change to a cell, cell line, tissue, tissue culture or patient that is induced by a TNF-family ligand. As indicated, such cellular responses include not only normal physiological responses to TNF-family ligands, but also diseases associated with increased apoptosis or the inhibition of apoptosis. Apoptosis-programmed cell death-is a physiological mechanism involved in the deletion of peripheral T lymphocytes of the immune system, and its dysregulation can lead to a number of different pathogenic processes (Ameisen, J. C., AIDS 8:1197-1213 (1994); Krammer, P. H. et al., Curr. Opin. Immunol. 6:279-289 (1994)).

Diseases associated with increased cell survival, or the inhibition of apoptosis, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostrate cancer, Kaposi's sarcoma and ovarian cancer); autoimmune disorders (such as multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis rheumatoid arthritis) and viral infections (such as herpes viruses, pox viruses and adenoviruses), information graft v. host disease, acute graft rejection, and chronic graft rejection. In preferred embodiments, DR4 polynucleotides, polypeptides, and/or antagonists of the invention are used to inhibit growth, progression, and/or metastasis of cancers, in particular those listed above or in the paragraph that follows.

Additional diseases or conditions associated with increased cell survival include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Additional diseases or conditions associated with increased cell survival include, but are not limited to, premalignant conditions. Such conditions are known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W.B. Saunders Co., Philadelphia, pp. 68-79.)

Hyperplasia is a form of controlled cell proliferation, involving an increase in cell number in a tissue or organ, without significant alteration in structure or function. Hyperplastic disorders which can be diagnosed, prognosed, prevented, and/or treated with compositions of the invention (including polynucleotides, polypeptides, agonists or antagonists) include, but are not limited to, angiofollicular mediastinal lymph node hyperplasia, angiolymphoid hyperplasia with eosinophilia, atypical melanocytic hyperplasia, basal cell hyperplasia, benign giant lymph node hyperplasia, cementum hyperplasia, congenital adrenal hyperplasia, congenital sebaceous hyperplasia, cystic hyperplasia, cystic hyperplasia of the breast, denture hyperplasia, ductal hyperplasia, endometrial hyperplasia, fibromuscular hyperplasia, focal epithelial hyperplasia, gingival hyperplasia, inflammatory fibrous hyperplasia, inflammatory papillary hyperplasia, intravascular papillary endothelial hyperplasia, nodular hyperplasia of prostate, nodular regenerative hyperplasia, pseudoepitheliomatous hyperplasia, senile sebaceous hyperplasia, and verrucous hyperplasia.

Metaplasia is a form of controlled cell growth in which one type of adult or fully differentiated cell substitutes for another type of adult cell. Metaplastic disorders which can be diagnosed, prognosed, prevented, and/or treated with compositions of the invention (including polynucleotides, polypeptides, agonists or antagonists) include, but are not limited to, agnogenic myeloid metaplasia, apocrine metaplasia, atypical metaplasia, autoparenchymatous metaplasia, connective tissue metaplasia, epithelial metaplasia, intestinal metaplasia, metaplastic anemia, metaplastic ossification, metaplastic polyps, myeloid metaplasia, primary myeloid metaplasia, secondary myeloid metaplasia, squamous metaplasia, squamous metaplasia of amnion, and symptomatic myeloid metaplasia.

Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation. Dysplastic disorders which can be diagnosed, prognosed, prevented, and/or treated with compositions of the invention (including polynucleotides, polypeptides, agonists or antagonists) include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders include, but are not limited to, benign dysproliferative disorders (e.g., benign tumors, fibrocystic conditions, tissue hypertrophy, intestinal polyps, colon polyps, and esophageal dysplasia), leukoplakia, keratoses, Bowen's disease, Farmer's Skin, solar cheilitis, and solar keratosis.

Polynucleotides and/or polypeptides of the invention and/or agonists and/or antagonists thereof may be administered in combination with one or more therapeutic agents and/or procedures in the treatment, prevention, amelioration and/or cure of cancers and premalignant conditions.

In preferred embodiments, agonists and/or antagonists of the invention may be administered in combination with one or more therapeutic agents and/or procedures in the treatment, prevention, amelioration and/or cure of cancers and premalignant conditions.

Therapeutic agents, useful in the treatment, prevention, amelioration and/or cure of cancers and premalignant conditions, with which polynucleotides and/or polypeptides of the invention and/or agonists and/or antagonists thereof may be administered, include, for example, biological agents (e.g., inhibitors of signaling pathways, inhibitors of gene transcription, inhibitors of multi-drug resistance (MDR) mechanisms, inhibitors of angiogenesis, inhibitors of matrix metalloproteinases, hormones and hormone antagonists, and compounds of unknown mechanism), chemotherapeutic agents (e.g., alkylating agents, antimetabolites, farnesyl transferase inhibitors, mitotic spindle inhibitors (plant-derived alkaloids), nucleotide analogs, platinum analogs, and topoisomerase inhibitors), corticosteroids, gene therapies, immunotherapeutic agents (e.g., monoclonal antibodies, cytokines and vaccines), phototherapy, radiosensitizing agents, treatment support agents (e.g., anti-emetic agents, analgesic agents and hematopoietic agents), and other miscellaneous drug types. Therapeutic procedures, useful in the treatment, prevention, amelioration and/or cure of cancers and premalignant conditions, with which polynucleotides and/or polypeptides of the invention and/or agonists and/or antagonists thereof may be administered, include, for example, but are not limited to, surgical procedures and radiation therapies.

In preferred embodiments, agonists and/or antagonists of the invention are administered in combination with one or more of the above-described therapeutic agents and/or therapeutic procedures in the treatment, prevention, amelioration and/or cure of cancers and premalignant conditions.

In specific embodiments, polynucleotides and/or polypeptides of the invention and/or agonists and/or antagonists thereof may be administered in combination with one or more therapeutic agents useful in the treatment, prevention, amelioration and/or cure of cancers and premalignant conditions, including, but not limited to, 81C6 (Anti-tenascin monoclonal antibody), 2-chlorodeoxyadenosine, A007 (4-4'-dihydroxybenzophenone-2,4-dinitrophenylhydrazone), Abarelix ((Abarelix-Depot-Me, PPI-149, R-3827); Abiraterone Acetate® (CB-7598, CB-7630), ABT-627 (ET-1 inhibitor), ABX-EGF (anti-EGFr MAb), Acetyldinaline (CI-994, GOE-5549, GOR-5549, PD-130636), AG-2034 (AG-2024, AG-2032, GARFT [glycinamide ribonucleoside transformylase] inhibitor), Alanosine, Aldesleukin (IL-2, Proleukin®), Alemtuzumab® (Campath®), Alitretinoin (Panretin®, LGN-1057), Allopurinol (Aloprim®, Zyloprim®), Altretamine (Hexylen®, hexamethylmelamine, Hexastat®), Amifostine (Ethyol®), Aminocamptothecin (9-AC, 9-Aminocamptothecin, NSC 603071), Aminoglutethimide (Cytadren®), Aminolevulinic acid (Levulan®, Kerastick®), Aminopterin, Amsacrine, Anastrozole (Arimidex®), Angiostatin, Annamycin (AR-522, annamycin LF, Aronex®), Anti-idiotype therapy (BsAb), Anti-CD19/CD3 MAb (anti-CD19/CD3 scFv, anti-NHL MAb), APC-8015 (Provenge®, Dendritic cell therapy), Aplidine (Aplidin®, Aplidina®), Arabinosylguanine (Ara-G, GW506U78, Nelzarabine®, Compound 506U78), Arsenic trioxide (Trisenox®, ATO, Atrivex®), Avorelin® (Meterelin®, MF-6001, EP-23904), B43-Genistein (anti-CD19 Ab/genistein conjugate), B43-PAP (anti-CD19 Ab/pokeweed antiviral protein conjugate), B7 antibody conjugates, BAY 43-9006 (Raf kinase inhibitor), BBR 3464, Betathine (Beta-LT), Bevacizumab® (Anti-VEGF monoclonal antibody, rhuMAb-VEGF), Bexarotene (Targretin®, LGD1069), BIBH-1 (Anti-FAP MAb), BIBX-1382, Biclutamide (Casodex®), Biricodar dicitrate (Incel®, Incel MDR Inhibitor), Bleomycin (Blenoxane®), BLP-25 (MUC-1 peptide), BLyS antagonists, BMS-214662 (BMS-192331, BMS-193269, BMS-206635), BNP-1350 (BNPI-1100, Karenitecins), Boronated Protoporphyrin Compound (PDIT, Photodynamic Immunotherapy), Bryostatin-1 (Bryostatin®, BMY-45618, NSC-339555), Budesonide (Rhinocort®), Busulfan (Busulfex®, Myleran®), C225 (IMC-225, EGFR inhibitor, Anti-EGFr MAb, Cetuximab®), C242-DM1 (buC242-DM1), Cabergoline (Dostinex®), Capecitabine (Xeloda®, Doxifluridine®, oral 5-FU), Carbendazin® (FB-642), Carboplatin (Paraplatin®, CBDCA), Carboxyamidotriazole (NSC 609974, CAI, L-651582), Carmustine (DTI-015, BCNU, BiCNU, Gliadel Wafer®), CC49-zeta gene therapy, CEA-cide® (Labetuzumab®, Anti-CEA monoclonal antibody, hMN-14), CeaVac® (MAb 3H1), Celecoxib (Celebrex®), CEP-701 (KT-5555), Cereport® (Lobradimil®, RMP-7), Chlorambucil (Leukeran®), CHML (Cytotropic Heterogeneous Molecular Lipids), Cholecaliferol, CI-1033 (Pan-erbB RTK inhibitor), Cilengitide (EMD-121974, integrin alphavbeta3 antagonist), Cisplatin (Platinol®, CDDP), Cisplatin-epinephrine gel (IntraDose®, FocaCist®), Cisplatin-liposomal (SPI-077), 9-cis retinoic acid (9-cRA), Cladribine (2-CdA, Leustatin®), Clofarabine (chloro-fluoro-araA), Clonadine hydrochloride (Duraclon®), CMB-401 (Anti-PEM MAb/calicheamycin), CMT-3 (COL-3, Metastat®), Cordycepin, Cotara® (chTNT-1/B, [$^{131}$I]-chTNT-1/B), CN-706, CP-358774 (Tarceva®, OSI-774, EGFR inhibitor), CP-609754, CP IL-4-toxin (IL-4 fusion toxin), CS-682, CT-2584 (Apra®, CT-2583, CT-2586, CT-3536), CTP-37 (Avicine®, hCG blocking vaccine), Cyclophosphamide (Cytoxan®, Neosar®, CTX), Cytarabine (Cytosar-U®, ara-C, cytosine arabinoside, DepoCyt®), D-limonene, DAB389-EGF (EGF fusion toxin), Dacarbazine (DTIC), Daclizumab® (Zenapax®), Dactinomycin (Cosmegen®), Daunomycin (Daunorubicin®, Cerubidine®), Daunorubicin (DaunoXome®, Daunorubicin®, Cerubidine®V), DeaVac® (CEA anti-idiotype vaccine), Decitabine (5-aza-2'-deoxyytidine), Declopramide (Oxi-104), Denileukin diftitox (Ontak®), Depsipeptide (FR901228, FK228), Dexamethasone (Decadron®), Dexrazoxane (Zinecard®), Diethylnorspermine (DENSPM), Diethylstilbestrol (DES), Dihydro-5-azacytidine, Docetaxel (Taxotere®, Taxane®), Dolasetron mesylate (Anzemet®), Dolastatin-10 (DOLA-10, NSC-376128), Doxorubicin (Adriamycin®, Doxil®, Rubex®), DPPE, DX-8951f (DX-8951), Edatrexate, EGF-P64k Vaccine, Elliott's B Solution®, EMD-121974, Endostatin, Eniluracil (776c85), EO9 (EO1, EO4, EO68, EO70, EO72), Epirubicin (Ellence®, EPI, 4' epi-doxorubicin), Epratuzumab® (Lymphocide®, humanized anti-CD22, HAT), Erythropoietin (EPO®, Epogen®, Procrit®), Estramustine (Emcyt®), Etanidazole (Radinyl®), Etoposide phosphate (Etopophos®), Etoposide (VP-16, Vepesid®), Exemestane (Aromasin®, Nikidess®), Exetecan mesylate (DX-8951, DX-8951f, Exisulind (SAAND, Aptosyn®, cGMP-PDE2 and 5 inhibitor), F19 (Anti-FAP monoclonal antibody, iodinated anti-FAP MAb), Fadrozole (Afema®, Fadrozole hydrochloride, Arensin®), Fenretinide® (4HPR), Fentanyl citrate (Actiq®), Filgrastim (Neupogen®, G-CSF), FK-317 (FR-157471, FR-70496), Flavopiridol (HMR-1275), Fly3/flk2 ligand (Mobista®), Fluasterone, Fludarabine (Fludara®, FAMP), Fludeoxyglucose (F-18®), Fluorouracil (5-FU, Adrucil®, Fluoroplex®, Efudex®), Flutamide (Eulexin®), FMdC (KW-2331, MDL-101731), Formestane (Lentaron®), Fotemustine (Muphoran®, Mustophoran®), FUDR (Floxuridine®), Fulvestrant (Faslodex®), G3139 (Genasense®, GentaAnticode®, Bcl-2 antisense), Gadolinium texaphyrin (Motexafin gadolinium, Gd-Tex®, Xcytrin®), Galarubicin hydrochloride (DA-125), GBC-590, Gastrimmune® (Anti-gastrin-17 immunogen, anti-g17), Gemcitabine (Gemto®, Gemzar®), Gentuzumab-ozogamicin (Mylotarg®), GL331, Globo H hexasaccharide (Globo H-KLH®), Glufosfamide® (β-D-glucosyl-isofosfamide mustard, D19575, INN), Goserelin acetate (Zoladex®), Granisetron (Kytril®), GVAX (GM-CSF gene therapy), Her-2/Neu vaccine, Herceptin® (Trastuzumab®, Anti-HER-2 monoclonal antibody, Anti-EGFR-2 MAb), HSPPC-96 (HSP cancer vaccine, gp96 heat shock protein-peptide complex), Hu1D10 (anti-HLA-DR MAb, SMART 1D10), HumaLYM (anti-CD20 MAb), Hydrocortisone, Hydroxyurea (Hydrea®), Hypericin® (VIMRxyn®), I-131 Lipidiol®, Ibritumomab® tiuxetan (Zevalin®), Idarubicin (Idamycin®, DMDR, IDA), Ifosfamide (IFEX®), Imatinib mesylate (STI-571, Imatinib®, Glivec®, Gleevec®, Ab1 tyrosine kinase inhibitor), INGN-101 (p53 gene therapy/retrovirus), INGN-201 (p53 gene therapy/adenovirus), Interferon alpha (Alfaferone®, Alpha-IF®), Interferon alpha 2a (Intron A®), Interferon gamma (Gamma-interferon, Gamma 100®, Gamma-IF), Interleukin-2 (ProleiukinR®), Intoplicine (RP 60475), Irinotecan (Camptosar®, CPT-11, Topotecin®V, CaptoCPT-1), Irofulven (MGI-114, Ivofulvan, Acylfulvene analogue), ISIS-2053 (PKC-alpha antisense), ISIS-2503 (Ras antisense), ISIS-3521 (PKC-alpha antisense), ISIS-5132 (K-ras/raf antisense), Isotretinoin (13-CRA, 13-cis retinoic acid, Accutane®), Ketoconazole (Nizoral®), KRN-8602 (MX, MY-5, NSC-619003, MX-2), L-778123 (Ras inhibitors), L-asparaginase (Elspar®, Crastinin®, Asparaginase Medac®, Kidrolase®), Leflunomide (SU-101, SU-0200), Letrozole (Femara®), Leucovorin (Leucovorin®, Welicovorin®), Leuprolide acetate (Viadur®, Lupron®, Leuprogel®, Eligard®), Leuvectin® (cytofectin+IL-2 gene, IL-2 gene therapy), Levamisole (Ergamisol®), Liarozole (Liazal, Liazol, R-75251, R-85246, Ro-85264), Lmb-2 immunotoxin (anti-CD25 recombinant immuno toxin, anti-Tac(Fv)-PE38), Lometrexol (T-64, T-904064), Lomustine (CCNU®, CeeNU®), LY-335979, Lym-1 (131-I LYM-1), Lymphoma vaccine (Genitope), Mannan-MUC1 vaccine, Marimastat® (BB-2516, TA-2516, MMP inhibitor), MDX-447 (MDX-220, BAB-447, EMD-82633, H-447, anti-EGFr/FcGammaR1r), Mechlorethamine (Nitrogen Mustard, HN$_2$, Mustargen®), Megestrol acetate (Megace®, Pallace®), Melphalan (L-PAM, Alkeran®, Phenylalanine mustard), Mercaptopurine (6-mercaptopurine, 6-MP), Mesna (Mesnex®), Methotrexate® (MTX, Mexate®, Folex®), Methoxsalen (Uvadex®), 2-Methoxyestradiol (2-ME, 2-ME2), Methylprednisolone (Solumedrol®), Methyltestosterone (Android-10®, Testred®, Virilon®), MGV, Mitomycin C (Mitomycin®, Mutamycin®, Mito Extra®), Mitoxantrone (Novantrone®, DHAD), Mitumomab® (BEC-2, EMD-60205), Mivobulin isethionate (CI-980), MN-14 (Anti-CEA immunoradiotherapy, $^{131}$I-MN-14, $^{188}$Re-MN-14), Motexafin Lutetium (Lutrin®, Optrin®, Lu-Tex®, lutetium texaphyrin, Lucyn®, Antrin®), MPV-2213ad (Finrozole®), MS-209, Muc-1 vaccine, NaPro Paclitaxel, Nelarabine (Compound 506, U78), Neovastat® (AE-941, MMP inhibitor), Neugene compounds (Oncomyc-NG, Resten-NG, myc antisense), Nilutamide (Nilandron®), NovoMAb-G2 scFv (NovoMAb-G2 IgM), NPI-0052 (proteasome inhibitor), 06-benzylguanine (BG, Procept®), Octreotide acetate (Sandostatin LAR® Depot), Odansetron (Zofran®R), Onconase (Ranpimase®), OncoVAX-CL, OncoVAX-CL Jenner (GA-733-2 vaccine), OncoVAX-P (OncoVAX-PrPSA), Onyx-015 (p53 gene therapy), Oprelvekin (Neumage®), Orzel (Tegafur+Uracil+Leucovorin), Oxaliplatin (Eloxatine®, Eloxatin®), Pacis® (BCG, live), Paclitaxel (Paxene®, Taxol®), Paclitaxel-DHA (Taxoprexin®), Pamidronate (Aredia®), PC SPES, Pegademase (Adagen®, Pegademase bovine), Pegaspargase® (Oncospar®), Peldesine (BCX-34, PNP inhibitor), Pemetrexed disodium (Alimta®, MTA, multitargeted antifolate, LY 231514), Pentostatin (Nipent®, 2-deoxycoformycin), Perfosfamide (4-hydroperoxycyclophosphamide, 4-HC), Perillyl alcohol (perilla alcohol, perillic alcohol, perillol, NSC-641066), Phenylbutyrate, Pirarubicin (THP), Pivaloyloxymethyl butyrate (AN-9, Pivanex®), Porfimer sodium (Photofrin®), Prednisone, Prinomastat® (AG-3340, MMP inhibitor), Procarbazine (Matulane®), PROSTVAC, Providence Portland Medical Center Breast Cancer Vaccine, PS-341 (LDP-341, 26S proteasome inhibitor), PSMA MAb (Prostate Specific Membrane Antigen monoclonal antibody), Pyrazoloacridine (NSC-366140, PD-115934), Quinine, R115777 (Zarnestra®), Raloxifene hydrochloride (Evista®, Keoxifene hydrochloride), Raltitrexed (Tomudex®, ZD-1694), Rebeccamycin, Retinoic acid, R-flurbiprofen (Flurizan®, E-7869, MPC-7869), RFS-2000 (9-nitrocamptothecan, 9-NC, Rubitecan®), Rituximab® (Rituxan®, anti-CD20 MAb), RSR-13 (GSJ-61), Satraplatin (BMS-182751, JM-216), SCH 6636, SCH-66336, Sizofilan® (SPG, Sizofuran®, Schizophyllan®, Sonifilan®), SKI-2053R(NSC-D644591), Sobuzoxane (MST-16, Perazolin®), Squalamine (MSI-1256F), SR-49059 (vasopressin receptor inhibitor, Vla), Streptozocin (Zanosar®), SU5416 (Semaxanib®, VEGF inhibitor), SU6668 (PDGF-TK inhibitor), T-67 (T-138067, T-607), Talc (Sclerosol®), Tamoxifen (Nolvadex®), Taurolidine (Taurolin®), Temozolamide (Temodar®, NSC 362856), Teniposide (VM-26, Vumon®), TER-286, Testosterone (Andro®, Androderm®, Testoderm TTS®, Testoderm®, Depo-Testosterone®, Androgel®, depoAndro®), Tf-CRM107 (Transferrin-CRM-107), Thalidomide and thalidomide analogs, including but not limited to, lenalidomide (CC-5013, REVLIMID®) and CC-4047 (AC-TIMID™), Theratope, Thioguanine (6-thioguanine, 6-TG), Thiotepa (triethylenethiophosphaoramide, Thioplex®), Thymosin alpha I (Zadaxin®, Thymalfasin®), Tiazofurin (Thiazole®), Tirapazamine (SR-259075, SR-4233, Tirazone®, Win-59075), TNP-470 (AGM-1470, Fumagillin), Tocladesine (8-Cl-cAMP), Topotecan (Hycamtin®, SK&F-104864, NSC-609699, Evotopin®), Toremifene (Estrimex®, Fareston®), Tositumomab® (Bexxar®), Tretinoin (Retin-A®, Atragen®, ATRA, Vesanoid®), TriAb® (anti-idiotype antibody immune stimulator), Trilostane (Modrefen®), Triptorelin pamoate (Trelstar Depots, Decapeptyl®), Trimetrexate (Neutrexin®), Troxacitabine (BCH-204, BCH-4556, Troxatyl®), TS-1, UCN-01 (7-hydroxystaurosporine), Valrubicin (Valstar®), Valspodar (PSC 833), Vapreotide® (BMY-41606), Vaxid (B-cell lymphoma DNA vaccine), Vinblastine (Velban®, VLB), Vincristine (Oncovin®), Onco TCS®, VCR, Leurocristine®), Vindesine (Eldisine®, Fildesin®V), Vinorelbine (Navelbine®), Vitaxin® (LM-609, integrin alphavbeta3 antagonistic MAb), WF10 (macrophage regulator), WHI-P131, WT1 Vaccine, XR-5000 (DACA), XR-9576 (XR-9351, P-glycoprotein/MDR inhibitor), ZD-9331, ZD-1839 (IRESSA®), and Zoledronate (Zometa®).

In preferred embodiments, agonists and/or antagonists of the invention are administered in combination with one or more of the above-described therapeutic agents in the treatment, prevention, amelioration and/or cure of cancers and premalignant conditions.

In further specific embodiments, polynucleotides and/or polypeptides of the invention and/or agonists and/or antagonists thereof may be administered in combination with one or more combinations of therapeutic agents useful in the treatment, prevention, amelioration and/or cure of cancers and premalignant conditions including, but not limited to, 9-aminocamptothecin+G-CSF, Adriamycin®+Blenoxane+Vinblastine+Dacarbazine (ABVD), BCNU (Carmustine)+Etoposide+Ara-C (Cytarabine)+Melphalen (BEAM), Bevacizumab®+Leucovorin, Bleomycin+Etoposide+Platinol® (Cisplatin) (BEP), Bleomycin+Etoposide+Adriamycin+Cyclophosphamide+Vincristine+Procarbazine+Prednisone (BEACOPP), Bryostatin+Vincristine, Busulfan+Melphalan, Carboplatin+Cereport®, Carboplatin+Cyclophosphamide, Carboplatin+Paclitaxel, Carboplatin+Etoposide+Bleomycin (CEB), Carboplatin+Etoposide+Thiotepa, Cisplatin+Cyclophosphamide, Cisplatin+Docetaxel, Cisplatin+Doxorubicin, Cisplatin+Etoposide, Cisplatin+Gemcitabine, Cisplatin+Interferon alpha, Cisplatin+Irinotecan, Cisplatin+Paclitaxel, Cisplatin+Teniposide, Cisplatin+Vinblastine, Cisplatin+Vindesine, Cisplatin+Vinorelbine, Cisplatin+Cytarabine+Ifosfamide, Cisplatin+Ifosfamide+Vinblastine, Cisplatin+Vinblastine+Mitomycin C, Cisplatin+Vincristine+Fluorouracil, Cisplatin+Vincristine+Lomustine, Cisplatin+Vinorelbine+Gemcitabine, Cisplatin+Carmustine+Dacarbazine+Tamoxifen, Cisplatin+Cyclophosphamide+Etoposide+Vincristine, Cisplatin (Platinol®)+Oncovin®+Doxorubicin (Adrianycin®)+Etoposide (CODE), Cisplatin+Cytarabine+Ifosfamide+Etoposide+Methotrexate, Cyclophosphamide+Adriamycin® (Doxorubicin), Cyclophosphamide+Melphalan, Cyclophosphamide+SCH 6636, Cyclophosphamide+Adriamycin®+Cisplatin (Platinol®) (CAP), Cyclophosphamide+Adriamycin®+Vincristine (CAV), Cyclophosphamide+Doxorubicin+Teniposide+Prednisone, Cyclophosphamide+Doxorubicin+Teniposide+Prednisone+Interferon alpha, Cyclophosphamide+Epirubicin+Cisplatin (Platinol®) (CEP), Cyclophosphamide+Epirubicin+Fluorouracil, Cyclophosphamide+Methotrexate+Fluoruracil (CMF), Cyclophosphamide+Methotrexate+Vincristine (CMV), Cyclophosphamide+Adriamycing+Methotrexate+Fluorouracil (CAMF), Cyclophosphamide+Adriamycin®+Methotrexate+Procarbazine (CAMP), Cyclophosphamide+Adriamycin®+Vincristine+Etoposide (CAV-E), Cyclophosphamide+Adriamycing+Vincristine+Prednisone (CHOP), Cyclophosphamide+Novantrone® (Mitoxantrone)+Vincristine (Oncovorin)+Prednisone (CNOP), Cyclophosphamide+Adriamycin®+Vincristine+Prednisone+Rituximab (CHOP+Rituximab), Cyclophosphamide+Adriamycin®+Vincristine+Teniposide (CAV-T), Cyclophosphamide+Adriamycin®+Vincristine alternating with Platinol®+Etoposide (CAV/PE), Cyclophosphamide+BCNU (Carmustine)+VP-16 (Etoposide) (CBV), Cyclophosphamide+Vincristine+Prednisone (CVP), Cyclophosphamide+Oncovin®+Methotrexate+Fluorouracil (COMF), Cytarabine+Methotrexate, Cytarabine+Bleomycin+Vincristine+Methotrexate (CytaBOM), Dactinomycin+Vincristine, Dexamethasone+Cytarabine+Cisplatin (DHAP), Dexamethasone+Ifosfamide+Cisplatin+Etoposide (DICE), Docetaxel+Gemcitabine, Docetaxel+Vinorelbine, Doxorubicin+ Vinblastine+Mechlorethamine+Vincristine+Bleomycin+ Etoposide+Prednisone (Stanford V), Epirubicin+ Gemcitabine, Estramustine+Docetaxel, Estramustine+ Navelbine, Estramustine+Paclitaxel, Estramustine+ Vinblastine, Etoposide (Vepesid®)+Ifosfamide+Cisplatin (Platinol®) (VIP), Etoposide+Vinblastine+Adriamycin (EVA), Etoposide (Vepesid®)+Ifosfamide+Cisplatin+Epirubicin (VIC-E), Etoposide+Methylprednisone+Cytarabine+ Cisplatin (ESHAP), Etoposide+Prednisone+Ifosfamide+ Cisplatin (EPIC), Fludarabine+Mitoxantrone+ Dexamethasone (FMD), Fludarabine+Dexamethasone+ Cytarabine (ara-C)+Cisplatin (Platinol®) (FluDAP), Fluorouracil+Bevacizumab®, Fluorouracil+CeaVac®, Fluorouracil+Leucovorin, Fluorouracil+Levamnisole, Fluorouracil+Oxaliplatin, Fluorouracil+Raltitrexed, Fluorouracil+ SCH 6636, Fluorouracil+Trimetrexate, Fluorouracil+ Leucovorin+Bevacizumab®, Fluorouracil+Leucovorin+ Oxaliplatin, Fluorouracil+Leucovorin+Trimetrexate, Fluorouracil+Oncovin®+Mitomycin C (FOMi), Hydrazine+ Adriamycin®+Methotrexate (HAM), Ifosfamide+Docetaxel, Ifosfamide+Etoposide, Ifosfamide+Gemcitabine, Ifosfamide+Paclitaxel, Ifosfamide+Vinorelbine, Ifosfamide+Carboplatin+Etoposide (ICE), Ifosfamide+Cisplatin+ Doxorubicin, Irinotecan+C225 (Cetuximab®), Irinotecan+ Docetaxel, Irinotecan+Etoposide, Irinotecan+Fluorouracil, Irinotecan+Gemcitabine, Mechlorethamine+Oncovin® (Vincristine)+Procarbazine (MOP), Mechlorethamine+Oncovin® (Vincristine)+Procarbazine+Prednisone (MOPP), Mesna+Ifosfamide+Idarubicin+Etoposide (MIZE), Methotrexate+Interferon alpha, Methotrexate+Vinblastine, Methotrexate+Cisplatin, Methotrexate with leucovorin rescue+Bleomycin+Adriamycin+Cyclophosphamide+Oncovorin+ Dexamethasone (m-BACOD), Mitomycin C+Ifosfamide+ Cisplatin (Platinol®) (MIP), Mitomycin C+Vinblastine+ Paraplatin® (MVP), Mitoxantrone+Hydrocortisone, Mitoxantrone+Prednisone, Oncovin®+SCH 6636, Oxaliplatin+Leucovorin, Paclitaxel+Doxorubicin, Paclitaxel+SCH 6636, Paraplatin®+Docetaxel, Paraplatin®V+Etoposide, Paraplatin®+Gemcitabine, Paraplatin®+Interferon alpha, Paraplatin®+Irinotecan, Paraplatin®+Paclitaxel, Paraplatin®)+Vinblastine, Carboplatin (Paraplatin®)+Vincristine, Paraplatin®+Vindesine, Paraplatin®+Vinorelbine, Pemetrexed disodium+Gemcitabine, Platinol® (Cisplatin)+Vinblastine+Bleomycin (PVB), Prednisone+Methotrexate+ Adriamycin+Cyclophosphamide+Etoposide (ProMACE), Procarbazine+Lomustine, Procarbazine+Lomustine+Vincristine, Procarbazine+Lomustine+Vincristine+Thioguanine, Procarbazine+Oncovin®+CCNU®+Cyclophosphamide (POCC), Quinine+Doxorubicin, Quinine+Mitoxantrone+ Cytarabine, Thiotepa+Etoposide, Thiotepa+Busulfan+Cyclophosphamide, Thiotepa+Busulfan+Melphalan, Thiotepa+ Etoposide+Carmustine, Thiotepa+Etoposide+Carboplatin, Topotecan+Paclitaxel, Trimetrexate+Leucovorin, Vinblastine+Doxorubicin+Thiotepa, Vinblastine+Bleomycin+Etoposide+Carboplatin, Vincristine+Lomustine+Prednisone, Vincristine (Oncovin®)+Adriamycin®+Dexamethasone (VAD), Vincristine (Oncovin®)+Adriamycing+Procarbazine (VAP), Vincristine+Dactinomycin+Cyclophosphamide, and Vinorelbine+Gemcitabine.

In preferred embodiments, agonists and/or antagonists of the invention are administered in combination with one or more of the above-described combinations of therapeutic agents in the treatment, prevention, amelioration and/or cure of cancers and premalignant conditions.

Polynucleotides and/or polypeptides of the invention and/ or agonists and/or antagonists thereof may be administered in combination with one or more therapeutic agents described above to treat, prevent, ameliorate and/or cure cancers and premalignant conditions of any tissue known to express DR5 receptor.

In preferred embodiments, agonists and/or antagonists of the invention are administered in combination with one or more therapeutic agents described above to treat, prevent, ameliorate and/or cure cancers and premalignant conditions of any tissue known to express DR5 receptor.

Tissues known to express DR5 receptor include, but are not limited to, heart, placenta, lung, liver, skeletal muscle, pancreas, spleen, thymus, prostate, testis, uterus, ovary, small intestine, colon, brain kidney, bone marrow, skin, pituitary, cartilage and blood.

In specific embodiments polynucleotides and/or polypeptides of the invention and/or agonists and/or antagonists thereof may be administered in combination with one or more therapeutic agents, as described above, in the treatment, prevention, amelioration and/or cure of solid tissue cancers (e.g., skin cancer, prostate cancer, pancreatic cancer, hepatic cancer, lung cancer, ovarian cancer, colorectal cancer, head and neck tumors, breast tumors, endothelioma, osteoblastoma, osteoclastoma, Ewing's sarcoma, and Kaposi's sarcoma), as well as hematological cancers (e.g., leukemia, acute lymphocytic leukemia, chronic lymphocytic leukemia, non-Hodgkin's lymphoma, multiple myeloma).

In preferred embodiments, agonists and/or antagonists of the invention are administered in combination with one or more therapeutic agents, as described above, in the treatment, prevention, amelioration and/or cure of solid tissue cancers (e.g., skin cancer, prostate cancer, pancreatic cancer, hepatic cancer, lung cancer, ovarian cancer, colorectal cancer, head and neck tumors, breast tumors, endothelioma, osteoblastoma, osteoclastoma, Ewing's sarcoma, and Kaposi's sarcoma), as well as hematological cancers (e.g., leukemia, acute lymphocytic leukemia, chronic lymphocytic leukemia, non-Hodgkin's lymphoma, multiple myeloma).

In specific embodiments polynucleotides and/or polypeptides of the invention and/or agonists and/or antagonists thereof may be used to treat, ameliorate and/or prevent skin cancers including, but not limited to, basal cell carcinoma, squamous cell carcinoma and malignant melanoma. Polynucleotides and/or polypeptides of the invention and/or agonists and/or antagonists thereof may be used in combination with one or more surgical and/or radiological procedures and/or therapeutic agents to treat, ameliorate and/or prevent skin cancers.

In preferred embodiments agonists and/or antagonists of the present invention are used to treat, ameliorate and/or prevent skin cancers including, but not limited to, basal cell carcinoma, squamous cell carcinoma and malignant melanoma. Agonists and/or antagonists of the present invention may be used in combination with one or more surgical and/or radiological procedures and/or therapeutic agents to treat, ameliorate and/or prevent skin cancers.

Polynucleotides and/or polypeptides of the invention and/ or agonists and/or antagonists thereof may be administered in combination with one or more therapeutic agents useful in the treatment of skin cancers and premalignant conditions including, but not limited to, Bleomycin (Blenoxane®), Cannustine (DTI-015, BCNU, BiCNU, Gliadel Wafer®), Cisplatin (Platinol®, CDDP), Dacarbazine (DTIC), Interferon alpha 2b (Intron A®), Interleukin-2 (ProleiukinR®), Tamoxifen (Nolvadex®, Temozolamide (Temodar®, NSC 362856), Vinblastine (Velban®, VLB), Vincristine (Oncovin®, Onco TCS®, VCR, Leurocristine®), and Vindesine (Eldisine®, Fildesin®).

In preferred embodiments, agonists and/or antagonists of the invention are administered in combination with one or more of the above-described therapeutic agents in the treatment, amelioration and/or prevention of skin cancers and premalignant conditions.

Preferred combinations of therapeutic agents useful in the treatment of skin cancers and premalignant conditions which may be administered in combination with polynucleotides and/or polypeptides of the invention and/or agonists and/or antagonists thereof include, but are not limited to, Cisplatin+ Carmustine+Dacarbazine+Tamoxifen.

In preferred embodiments, agonists and/or antagonists of the invention are administered in combination with one or more of the above-described therapeutic agent combinations in the treatment, amelioration and/or prevention of skin cancers and premalignant conditions.

In further specific embodiments, polynucleotides and/or polypeptides of the invention and/or agonists and/or antagonists thereof are used to treat, ameliorate and/or prevent head and neck cancers including brain cancers. Polynucleotides and/or polypeptides of the invention and/or agonists and/or antagonists thereof may be used in combination with one or more surgical and/or radiological procedures and/or therapeutic agents to treat, ameliorate and/or prevent head and neck cancers including brain cancers. Brain cancers which may be treated using polynucleotides and/or polypeptides of the invention and/or agonists and/or antagonists thereof include, but are not limited to, gliomas such as astrocytomas and oligodendromas, non-glial tumors such as neuronal, meningeal, ependymal and choroid plexus cell tumors, and metastatic brain tumors such as those originating as breast, lung, prostate and skin cancers.

In preferred embodiments, agonists and/or antagonists of the present invention are used to treat, ameliorate and/or prevent head and neck cancers including brain cancers. Agonists and/or antagonists of the present invention may be used in combination with one or more surgical and/or radiological procedures and/or therapeutic agents to treat, ameliorate and/or prevent head and neck cancers including brain cancers. Brain cancers which may be treated using agonists and/or antagonists of the present invention include, but are not limited to, gliomas such as astrocytomas and oligodendromas, non-glial tumors such as neuronal, meningeal, ependymal and choroid plexus cell tumors, and metastatic brain tumors such as those originating as breast, lung, prostate and skin cancers.

In preferred embodiments, agonists and/or antagonists of the invention are used to treat brain tumors. In one preferred embodiment, agonists of the invention are used to treat glioblastoma multiforme.

Polynucleotides and/or polypeptides of the invention and/ or agonists and/or antagonists thereof may be administered in combination with one or more radiological procedures useful in the treatment of brain cancers including, but not limited to, external beam radiation therapy, stereotactic radiation therapy, conformal radiation therapy, intensity-modulated radiation therapy (IMRT), and radiosurgery.

In preferred embodiments, agonists and/or antagonists of the invention are administered in combination with one or more radiological procedures useful in the treatment of brain cancers including, but not limited to, external beam radiation therapy, stereotactic radiation therapy, conformal radiation therapy, intensity-modulated radiation therapy (IMRT), and radiosurgery.

Polynucleotides and/or polypeptides of the invention and/ or agonists and/or antagonists thereof may be administered in combination with one or more therapeutic agents useful in the treatment of brain cancers and premalignant conditions, including, but not limited to, Bleomycin (Blenoxane®), Busulfan (Busulfex®, Myleran®), Carboplatin (Paraplatin®, CBDCA), Carmustine (DTI-015, BCNU, BiCNU, Gliadel Wafer®), Cisplatin (Platinol®, CDDP), Cisplatin-epinephrine gel (IntraDose®, FocaCist®), Cyclophosphamide (Cytoxan®, CTX), Cytarabine (Cytosar-U®, ara-C, cytosine arabinoside, DepoCyt®), Dacarbazine (DTIC®), Dactinomycin (Cosmegen®), Daunorubicin (Daunomycin, DaunoXome®, Daunorubicin®, Cerubidine®), Docetaxel (Taxotere®, Taxane®), Dexamethasone (Decadron®), Etoposide phosphate (Etopophos®), Etoposide (VP-16, Vepesid®), Fluorouracil (5-FU, Adrucil®), Hydroxyurea (Hydrea®), Ifosfamide (IFEX®), Lomustine (CCNU®, CeeNU®), Melphalan (L-PAM, Alkeran®, Phenylalanine mustard), Mercaptopurine (6-mercaptopurine, 6-MP), Methchlorethamine (Nitrogen Mustard, $HN_2$, Mustargen®), Methotrexate®(MTX, Mexate®, Folex®), Paclitaxel (Paxene®, Taxol®), Paclitaxel-DHA (Taxoprexin®), Procarbazine (Matulane®), Temozolamide (Temodar®, NSC 362856), Teniposide (VM-26, Vumon®), Thioguanine (6-thioguanine, 6-TG), Thiotepa (triethylenethiophosphaoramide), Topotecan (Hycamtin®, SK&F-104864, NSC-609699, Evotopin®), and Vincristine (Oncovin®, Onco TCS®, VCR, Leurocristine®).

In preferred embodiments, agonists and/or antagonists of the invention are administered in combination with one or more of the above-described therapeutic agents in the treatment, amelioration and/or prevention of brain cancers and premalignant conditions.

Further examples of therapeutic agents useful in the treatment of brain cancers and premalignant conditions which may be administered in combination with polynucleotides and/or polypeptides of the invention and/or agonists and/or antagonists thereof include, but are not limited to, 81C6 (Anti-tenascin monoclonal antibody), BIBX-1382, Cereport® (Lobradimil®, RMP-7), Cilengitide® (EMD-121974, integrin alphavbeta3 antagonist), CMT-3 (Metastat®), Cotara® (chTNT-1/B, [$^{131}$I]-chTNT-1/B), CP IL-4-toxin (IL-4 fusion toxin), Fenretinide® (4HPR), Fotemustine (Muphoran®, Mustophoran®), Gemcitabine (Gemto®, Gemzar®), Hypericin® (VIMRxyn®), Imatinib mesylate (STI-571, Imatinib®, Glivec®, Gleevec®, Abl tyrosine kinase inhibitor), Irinotecan (Camptosar®, CPT-11, Topotecin®, CaptoCPT-1), Leflunomide (SU-101, SU-0200), Mivobulin isethionate (CI-980), 06-benzylguanine (BG, Procept®), Prinomastat® (AG-3340, MMP inhibitor), R115777 (Zarnestra®), SU6668 (PDGF-TK inhibitor), T-67 (T-138067, T-607), Tamoxifen (Nolvadex®), Tf-CRM107 (Transferrin-CRM-107), Thalidomide and thalidomide analogs, including but not limited to, lenalidomide (CC-5013, REVLIMID®) and CC-4047 (ACTIMID™), Tiazofurin (Thiazole®), Vapreotide® (BMY-41606), Vinorelbine (Navelbine®), and XR-5000 (DACA).

In preferred embodiments, agonists and/or antagonists of the invention are administered in combination with one or more of the above-described therapeutic agents in the treatment, amelioration and/or prevention of brain cancers and premalignant conditions.

Preferred combinations of therapeutic agents useful in the treatment of brain cancers and premalignant conditions which may be administered in combination with polynucleotides and/or polypeptides of the invention and/or agonists and/or antagonists thereof include, but are not limited to, Busulfan+Melphalan, Carboplatin+ Cereport®, Carboplatin+ Etoposide, Carboplatin+ Etoposide+ Thiotepa, Cisplatin+ Etoposide, Cisplatin+ Cytarabine+ Ifosfamide, Cisplatin+ Vincristine+Lomustine, Cisplatin+

Cyclophosphamide+Etoposide+Vincristine, Cisplatin+Cytarabine+Ifosfamide+Etoposide+Methotrexate, Cyclophosphamide+Melphalan, Cytarabine+Methotrexate, Dactinomycin+Vincristine, Mechlorethamine+Oncovin® (Vincristine)+Procarbazine (MOP), Mechlorethamine+Oncovin® (Vincristine)+Procarbazine+Prednisone (MOPP), Carboplatin (Paraplatin®)+Etoposide, Carboplatin (Paraplatin®)+Vincristine, Procarbazine+Lomustine, Procarbazine+Lomustine+Vincristine, Procarbazine+Lomustine+Vincristine+Thioguanine, Thiotepa+Etoposide, Thiotepa+Etoposide+Carmustine, Thiotepa+Etoposide+Carboplatin, Vinblastine+Bleomycin+Etoposide+Carboplatin, and Vincristine+Lomustine+Prednisone.

In preferred embodiments, agonists and/or antagonists of the invention are administered in combination with one or more of the above-described combinations of therapeutic agents in the treatment, amelioration and/or prevention of brain cancers and premalignant conditions.

In further particular embodiments, polynucleotides and/or polypeptides of the invention and/or agonists and/or antagonists thereof are used to treat, ameliorate and/or prevent breast cancer and premalignant conditions. Polynucleotides and/or polypeptides of the invention and/or agonists and/or antagonists thereof may be used in combination with one or more surgical and/or radiological procedures and/or therapeutic agents to treat, ameliorate and/or prevent breast cancer. Breast cancers which may be treated using polynucleotides and/or polypeptides of the invention and/or agonists and/or antagonists thereof include, but are not limited to, ductal carcinoma, stage 1, stage 11, stage III and stage 1V breast cancers as well as invasive breast cancer and metastatic breast cancer.

In preferred embodiments, agonists and/or antagonists of the present invention are used to treat, ameliorate and/or prevent breast cancer and premalignant conditions. Agonists and/or antagonists of the present invention may be used, in combination with one or more surgical and/or radiological procedures and/or therapeutic agents to treat, ameliorate and/or prevent breast cancer and premalignant conditions. Breast cancers which may be treated using agonists and/or antagonists of the present invention include, but are not limited to, ductal carcinoma, stage I, stage 11, stage III and stage 1V breast cancers as well as invasive breast cancer and metastatic breast cancer.

In preferred embodiment, agonists and/or antagonists of the invention are used to treat metastatic breast cancer.

In other preferred embodiments, agonists and/or antagonists of the present invention are administered in combination with one or more surgical and/or radiological procedures useful in the treatment of breast cancer and premalignant conditions.

Polynucleotides and/or polypeptides of the invention and/or agonists and/or antagonists thereof may be administered in combination with one or more therapeutic agents useful in the treatment of breast cancer and premalignant conditions, including, but not limited to, Amifostine (Ethyol®), Aminoglutethimide (Cytadren®), Anastrozole (Arimidex®), Bleomycin (Blenoxane®), Capecitabine (Xeloda®, Doxifluridine®, oral 5-FU), Cisplatin (Platinol®, CDDP), Cisplatin-epinephrine gel (IntraDose®, FocaCist®), Cyclophosphamide (Cytoxan®, Neosar®, CTX), Docetaxel (Taxotere®, Taxane®), Doxorubicin (Adriamycin®, Doxil®, Rubex®), Epirubicin (Ellence®, EPI, 4' epi-doxorubicin), Exemestane (Aromasin®, Nikidess®R), Fadrozole (Afema®, Fadrozole hydrochloride, Arensin®), Fluorouracil (5-FU, Adrucil®, Fluoroplex®, Efudex®), Herceptin® (Trastuzumab®, Anti-HER-2 monoclonal antibody, Anti-EGFR-2 MAb), Ifosfamide (IFEX®), Letrozole (Femara®), Leucovorin (Leucovorin®, Wellcovorin®), Mechlorethamine (Nitrogen Mustard, $HN_2$, Mustargen®), Megestrol acetate (Megace®, Pallace®), Melphalan (L-PAM, Alkeran®, Phenylalanine mustard), Methotrexate® (MTX, Mexate®, Folex®), Methyltestosterone (Android-10®, Testred®, Virilon®), Mitomycin C (Mitomycin®, Mutamycin®, Mito Extra®), Orzel® (Tegafur+Uracil+Leucovorin), Paclitaxel (Paxene®, Taxol®), Sobuzoxane (MST-16, Perazolin®), Tamoxifen (Nolvadex®, Testosterone (Andro®, Androderm®, Testoderm TTS®, Testoderm®, Depo-Testosterone®, Androgel®, depoAndro®), Vinblastine (Velban®, VLB), Vincristine (Oncovin®, Onco TCS®, VCR, Leurocristine®), and Vinorelbine (Navelbine®).

In preferred embodiments, agonists and/or antagonists of the invention are administered in combination with one or more of the above-described therapeutic agents in the treatment, amelioration and/or prevention of breast cancers and premalignant conditions.

Further examples of therapeutic agents useful in the treatment of breast cancer and premalignant conditions which may be administered in combination with polynucleotides and/or polypeptides of the invention and/or agonists and/or antagonists thereof include, but are not limited to, Aldesleukin (IL-2, Proleukin®), Altretamine (Hexylen®, hexamethylmelamine, Hexastat®), Angiostatin, Annamycin (AR-522, annamycin LF, Aronex®)), Biricodar dicitrate (Incel®, Incel MDR Inhibitor), Boronated Protoporphyrin Compound (PDIT, Photodynamic Immunotherapy), Bryostatin-1 (Bryostatin, BMY-45618, NSC-339555), Busulfan (Busulfex®, Myleran®), Carmustine (DTI-015, BCNU, BiCNU, Gliadel Wafer®), D-limonene, Dacarbazine (DTIC), Daunorubicin (Daunomycin, DaunoXome®, Daunorubicin®, Cerubidine®), Dolastatin-10 (DOLA-10, NSC-376128), DPPE, DX-8951f (DX-8951), EMD-121974, Endostatin, EO9 (EO1, EO4, EO68, EO70, EO72), Etoposide phosphate (Etopophos®), Etoposide (VP-16, Vepesid®), Fluasterone, Fludarabine (Fludara®V, FAMP), Flutamide (Eulexin®), Formestane (Lentaron®), Fulvestrant (Faslodex®), Galarubicin hydrochloride (DA-125), Gemcitabine (Gemto®, Gemzar®), Her-2/Neu vaccine, Hydroxyurea (Hydrea®), Idarubicin (Idamycin®, DMDR, IDA), Interferon alpha 2a (Intron A®), Interferon gamma (Gamma-interferon, Gamma 100®, Gamma-IF), Irinotecan (Camptosar®, CPT-11, Topotecin®, CaptoCPT-1), Ketoconazole (Nizoral®), KRN-8602 (MX, MY-5, NSC-619003, MX-2), L-asparaginase (Elspar®), Leuprolide acetate (Viadur®, Lupron®), Lomustine (CCNU®, CeeNU®), LY-335979, Mannan-MUC1 vaccine, 2-Methoxyestradiol (2-ME, 2-ME2), Mitoxantrone (Novantrone®, DHAD), Motexafin Lutetium (Lutrin®, Optrin®, Lu-Tex®, lutetium texaphyrin, Lucyn®, Antrin®), MPV-2213ad (Finrozole®), MS-209, Muc-1 vaccine, NaPro Paclitaxel, Perillyl alcohol (perilla alcohol, perillic alcohol, perillol, NSC-641066), Pirarubicin (THP), Procarbazine (Matulane®), Providence Portland Medical Center Breast Cancer Vaccine, Pyrazoloacridine (NSC-366140, PD-115934), Raloxifene hydrochloride (Evista®, Keoxifene hydrochloride), Raltitrexed (Tomudex®, ZD-1694), Rebeccamycin, Streptozocin (Zanosar®), Temozolamide (Temodar®, NSC 362856), Theratope, Thiotepa (triethylenethiophosphaoramide, Thioplex®), Topotecan (Hycamtin®, SK&F-104864, NSC-609699, Evotopin®), Toremifene (Estrimex®, Fareston®), Trilostane (Modrefen®), and XR-9576 (XR-9351, P-glycoprotein/MDR inhibitor).

In preferred embodiments, agonists and/or antagonists of the invention are administered in combination with one or more of the above-described therapeutic agents in the treatment, amelioration and/or prevention of breast cancers and premalignant conditions.

Preferred combinations of therapeutic agents useful in the treatment of breast cancer which may be administered in combination with polynucleotides and/or polypeptides of the invention and/or agonists and/or antagonists thereof include, but are not limited to, Cyclophosphamide+Adriamycin® (Doxorubicin), Cyclophosphamide+Epirubicin+Fluorouracil, Cyclophosphamide+Methotrexate+Fluorouracil (CMF), Paclitaxel+Doxorubicin, and Vinblastine+Doxorubicin+Thiotepa.

In preferred embodiments, agonists and/or antagonists of the invention are administered in combination with one or more of the above-described therapeutic agent combinations in the treatment, amelioration and/or prevention of breast cancers and premalignant conditions.

In further specific embodiments, polynucleotides and/or polypeptides of the invention and/or agonists and/or antagonists thereof are used to treat, ameliorate and/or prevent lung cancer and premalignant conditions. Polynucleotides and/or polypeptides of the invention and/or agonists and/or antagonists thereof may be used in combination with one or more surgical and/or radiological procedures and/or therapeutic agents to treat, ameliorate and/or prevent lung cancer. Lung cancer which may be treated using polynucleotides and/or polypeptides of the invention and/or agonists and/or antagonists thereof includes, but is not limited to, non-small cell lung cancer (NSCLC) including early stage NSCLC (i.e., Stage IA/IB and Stage IIA/IIB), Stage IIIA NSCLC, Stage IIA (unresectable)/IIIB NSCLC and Stage IV NSCLC, small cell lung cancer (SCLC) including limited stage SCLC and extensive stage SCLC as well as Malignant Pleural Mesothelioma.

In preferred embodiments, agonists and/or antagonists of the present invention are used to treat, ameliorate and/or prevent lung cancer and premalignant conditions. Agonists and/or antagonists of the present invention may be used in combination with one or more surgical and/or radiological procedures and/or therapeutic agents to treat, ameliorate and/ or prevent lung cancer and premalignant conditions. Lung cancer which may be treated using agonists and/or antagonists of the present invention includes, but is not limited to, non-small cell lung cancer (NSCLC) including early stage NSCLC (i.e., Stage IA/IB and Stage IIA/IIB), Stage IIIA NSCLC, Stage IIA (unresectable)/IIIB NSCLC and Stage IV NSCLC, small cell lung cancer (SCLC) including limited stage SCLC and extensive stage SCLC as well as Malignant Pleural Mesothelioma.

In preferred embodiments, agonists and/or antagonists of the invention are used to treat non-small cell lung cancers.

Polynucleotides and/or polypeptides of the invention and/ or agonists and/or antagonists thereof may be administered in combination with one or more therapeutic agents useful in the treatment of lung cancer and premalignant conditions, including, but not limited to, BAY 43-9006 (Raf kinase inhibitor), Carboplatin (Paraplatin®, CBDCA), Chlorambucil (Leukeran®), Cisplatin (Platinol®, CDDP), Cisplatin-epinephrine gel (IntraDose®, FocaCist®), Cyclophosphamide (Cytoxan®, Neosar®, CTX), Docetaxel (Taxotere®, Taxane®), Doxorubicin (Adriamycin®, Doxil®, Rubex®), Edatrexate, Epirubicin (Ellence®, EPI, 4' epi-doxorubicin), Etoposide phosphate (Etopophos®), Etoposide (VP-16, Vepesid®), Gemcitabine (Gemto®, Gemzar®), Herceptin® (Trastuzumab®, Anti-HER-2 monoclonal antibody, Anti-EGFR-2 MAb), Ifosfamide (IFEX®), Irinotecan (Camptosar®, CPT-11, Topotecin®, CaptoCPT-1), Lomustine (CCNU®, CeeNU®), Mechlorethamine (Nitrogen Mustard, HN$_2$, Mustargen®), Melphalan (L-PAM, Alkeran®, Phenylalanine mustard), Methotrexate® (MTX, Mexate®, Folex®), Mitomycin C (Mitomycin®, Mutamycin®, Mito Extra®), Paclitaxel (Paxene®, Taxol®), Paclitaxel-DHA (Taxoprexin®), Porfimer sodium (Photofrin®), Procarbazine (Matulane®), SKI-2053R(NSC-D644591), Teniposide (VM-26, Vumon®), Topotecan (Hycamtin®, SK&F-104864, NSC-609699, Evotopin®), Vinblastine (Velban®, VLB), Vincristine (Oncovin®, Onco TCS®, VCR, Leurocristine®), Vindesine (Eldisine®, Fildesin®), and Vinorelbine (Navelbine®).

In preferred embodiments, agonists and/or antagonists of the invention are administered in combination with one or more of the above-described therapeutic agents in the treatment, amelioration and/or prevention of lung cancers and premalignant conditions.

Further examples of therapeutic agents useful in the treatment of lung cancer and premalignant conditions which may be administered in combination with polynucleotides and/or polypeptides of the invention and/or agonists and/or antagonists thereof include, but are not limited to, ABX-EGF (anti-EGFr MAb), Acetyldinaline (CI-994), AG-2034 (AG-2024, AG-2032, GARFT [glycinamide ribonucleoside transformylase] inhibitor), Alanosine, Aminocamptothecin (9-AC, 9-Aminocamptothecin, NSC 603071), Angiostatin, Aplidine (Aplidin®, Aplidina®), BBR 3464, Bexarotene (Targretin®, LGD1069), BIBH-1 (Anti-FAP MAb), BIBX-1382, BLP-25 (MUC-1 peptide), Bryostatin-1 (Bryostatin®V, BMY-45618, NSC-339555), Budesonide (Rhinocort®), C225 (IMC-225, EGFR inhibitor, Anti-EGFr MAb, Cetuximab®), Capecitabine (Xeloda®, Doxifluridine®, oral 5-FU), Carboxyamidotriazole (NSC 609974, CAI, L-651582), CEA-cide® (Labetuzumab®, Anti-CEA monoclonal antibody, hMN-14), Cereport® (Lobradimil®, RMP-7), CI-1033 (Pan-erbB RTK inhibitor), Cilengitide® (EMD-121974, integrin alphavbeta3 antagonist), 9-cis retinoic acid (9-cRA), Cisplatin-liposomal (SPI-077), CMB-401 (Anti-PEM MAb/calicheamycin), CMT-3 (Metastat®), CP-358774 (Tarceva®, OSI-774, EGFR inhibitor), CT-2584 (Apra®), DAB389-EGF (EGF fusion toxin), DeaVac® (CEA anti-idiotype vaccine), Decitabine (5-aza-2'-deoxyytidine), Diethylnorspermine (DENSPM), Dihydro-5-azacytidine, EGF-P64k Vaccine, Endostatin, Etanidazole (Radinyl®), Exetecan mesylate (DX-8951, DX-8951f), Exisulind (SAAND, Aptosyn®, cGMP-PDE2 and 5 inhibitor), FK-317 (FR-157471, FR-70496), Flavopiridol (HMR-1275), Fotemustine (Muphoran®, Mustophoran®), G3139 (Genasense®, GentaAnticode®, Bcl-2 antisense), Gadolinium texaphyrin (Motexafin gadolinium, Gd-Tex®, Xcytrin®), GBC-590, GL331, Galarubicin hydrochloride (DA-125), Glufosfamide® (O-D-glucosyl-isofosfamide mustard, D19575, INN), GVAX (GM-CSF gene therapy), INGN-101 (p53 gene therapy/retrovirus), INGN-201 (p53 gene therapy/adenovirus), Irofulven (MGI-114), ISIS-2053, ISIS-3521 (PKC-alpha antisense), ISIS-5132 (K-ras/raf antisense), Isotretinoin (13-CRA, 13-cis retinoic acid, Accutane®), Lometrexol (T-64, T-904064), Marimastat® (BB-2516, TA-2516, MMP inhibitor), MDX-447 (BAB-447, EMD-82633, H-447, anti-EGFr/FcGammaR1r), MGV, Mitumomab® (BEC-2, EMD-60205), Mivobulin isethionate (CI-980), Neovastat® (AE-941, MMP inhibitor), NPI-0052 (proteasome inhibitor), Onconase (Ranpirnase®), Onyx-015 (p53 gene therapy), Pemetrexed disodium (Alimta®, MTA, multitargeted antifolate, LY 231514), Pivaloyloxymethyl butyrate (AN-9, Pivanex®), Prinomastat® (AG-3340, MMP inhibitor), PS-341 (LDP-341, 26S proteasome inhibitor), Pyrazoloacridine (NSC-366140, PD-115934), R115777 (Zamestra®), Raltitrexed (Tomudex®, ZD-1694), R-flurbiprofen (Flurizan®, E-7869, MPC-7869), RFS-2000 (9-nitrocamptothecan, 9-NC, Rubitecan®), RSR-13 (GSJ-61), Satraplatin (BMS-182751, JM-216), SCH-66336, Sizofilan® (SPG, Sizofuran®, Schizophyllan®, Sonifilan®), Squalamine (MSI-1256F), SR-49059 (vasopressin receptor inhibitor, Vla), SU5416 (Semaxanib®), VEGF inhibitor), Taurolidine (Taurolin®), Temozolamide (Temodar®, NSC 362856), Thalidomide and thalidomide analogs, including but not limited to, lenalidomide (CC-5013, REVLIMID®) and CC-4047 (ACTIMID™), Thymosin alpha I (Zadaxin®, Thymalfasin®), Tirapazamine (SR-259075, SR-4233, Tirazone®, Win-59075), TNP-470 (AGM-1470), TriAb® (anti-idiotype antibody immune stimulator), Tretinoin (Retin-A®, Atragen®, ATRA, Vesanoid®), Troxacitabine (BCH-204, BCH-4556, Troxatyl®D), Vitaxin®D (LM-609, integrin alphavbeta3 antagonistic MAb), XR-9576 (P-glycoprotein/MDR inhibitor), and ZD-1839 (IRESSA®).

In preferred embodiments, agonists and/or antagonists of the invention are administered in combination with one or more of the above-described therapeutic agents in the treatment, amelioration and/or prevention of lung cancers and premalignant conditions.

Preferred combinations of therapeutic agents useful in the treatment of lung cancer and premalignant conditions which may be administered in combination with polynucleotides and/or polypeptides of the invention and/or agonists and/or antagonists thereof include, but are not limited to, Cisplatin+Docetaxel, Cisplatin+Etoposide, Cisplatin+Gemcitabine, Cisplatin+Interferon alpha, Cisplatin+Irinotecan, Cisplatin+Paclitaxel, Cisplatin+Teniposide, Cisplatin+Vinblastine, Cisplatin+Vindesine, Cisplatin+Vinorelbine, Cisplatin+Vinblastine+Mitomycin C, Cisplatin+Vinorelbine+Gemcitabine, Cisplatin (Platinol®)+Oncovin®+Doxorubicin (Adriamycin®)+Etoposide (CODE), Cyclophosphamide+Adriamycing+Cisplatin (Platinol®) (CAP), Cyclophosphamide+Adriamycing+Vincristine (CAV), Cyclophosphamide+Epirubicin+Cisplatin (Platinol®) (CEP), Cyclophosphamide+Methotrexate+Vincristine (CMV), Cyclophosphamide+Adriamycin®, Methotrexate+Fluorouracil (CAMF), Cyclophosphamide+Adriamycin®, Methotrexate+Procarbazine (CAMP), Cyclophosphamide+Adriamycin®, Vincristine+Etoposide (CAV-E), Cyclophosphamide+Adriamycin®, Vincristine+Teniposide (CAV-T), Cyclophosphamide+Oncovin®, Methotrexate+Fluorouracil (COMF), Cyclophosphamide+Adriamycin®+Vincristine, alternating with Cisplatin+Etoposide (CAV/PE), Docetaxel+Gemcitabine, Docetaxel+Vinorelbine, Etoposide (Vepesid®)+Ifosfamide+Cisplatin (Platinol®) (VIP), Etoposide (Vepesid®)+Ifosfamide, Cisplatin+Epirubicin (VIC-E), Fluorouracil+Oncovin®+Mitomycin C (FOMi), Hydrazine+Adriamycin®+Methotrexate (HAM), Ifosfamide+Docetaxel, Ifosfamide+Etoposide, Ifosfamide+Gemcitabine, Ifosfamide+Paclitaxel, Ifosfamide+Vinorelbine, Ifosfamide+Carboplatin+Etoposide (ICE), Irinotecan+Docetaxel, Irinotecan+Etoposide, Irinotecan+Gemcitabine, Methotrexate+Cisplatin, Methotrexate+Interferon alpha, Methotrexate+Vinblastine, Mitomycin C+Ifosfamide+Cisplatin (Platinol®) (MIP), Mitomycin C+Vinblastine+Paraplatin® (MVP), Paraplatin®+Docetaxel, Paraplatin®+Etoposide, Paraplatin®+Gemcitabine, Paraplatin®+Interferon alpha, Paraplatin®+Irinotecan, Paraplatin®+Paclitaxel, Paraplatin®)+Vinblastine, Paraplatin®+Vindesine, Paraplatin®+Vinorelbine, Procarbazine+Oncovin®+CCNU® (Lomustine)+Cyclophosphamide (POCC), Vincristine (Oncovin®)+Adriamycin®+Procarbazine (VAP), and Vinorelbine+Gemcitabine.

In preferred embodiments, agonists and/or antagonists of the invention are administered in combination with one or more of the above-described therapeutic agent combinations in the treatment, amelioration and/or prevention of lung cancers and premalignant conditions.

In further particular embodiments, polynucleotides and/or polypeptides of the invention and/or agonists and/or antagonists thereof are used to treat, ameliorate and/or prevent colorectal cancer and premalignant conditions. Polynucleotides and/or polypeptides of the invention and/or agonists and/or antagonists thereof may be used in combination with one or more surgical and/or radiological procedures and/or therapeutic agents to treat, ameliorate and/or prevent colorectal cancer and premalignant conditions. Colorectal cancers which may be treated using polynucleotides and/or polypeptides of the invention and/or agonists and/or antagonists thereof include, but are not limited to, colon cancer (e.g., early stage colon cancer (stage I and II), lymph node positive colon cancer (stage III), metastatic colon cancer (stage 1V)) and rectal cancer.

In preferred embodiments, agonists and/or antagonists of the present invention are used to treat, ameliorate and/or prevent colorectal cancer and premalignant conditions. Agonists and/or antagonists of the present invention may be used in combination with one or more surgical and/or radiological procedures and/or therapeutic agents to treat, ameliorate and/or prevent colorectal cancer and premalignant conditions. Colorectal cancers which may be treated using agonists and/or antagonists of the present invention include, but are not limited to, colon cancer (e.g., early stage colon cancer (stage I and II), lymph node positive colon cancer (stage III), metastatic colon cancer (stage 1V)) and rectal cancer.

In preferred embodiments, agonists and/or antagonists of the invention are used to treat colon cancer and premalignant conditions.

Polynucleotides and/or polypeptides of the invention and/or agonists and/or antagonists thereof may be administered in combination with one or more therapeutic agents useful in the treatment of colorectal cancer and premalignant conditions, including, but not limited to, Capecitabine (Xeloda®, Doxifluridine®, oral 5-FU), Fluorouracil (5-FU, Adrucil®, Fluoroplex®, Efudex®), Irinotecan (Camptosar®, CPT-11, Topotecin®, CaptoCPT-1), Leucovorin (Leucovorin®, Welicovorin®), and Levamisole (Ergamisol®).

In preferred embodiments, agonists and/or antagonists of the invention are administered in combination with one or more of the above-described therapeutic agents in the treatment, amelioration and/or prevention of colorectal cancers and premalignant conditions.

Preferred combinations of therapeutic agents useful in the treatment of colorectal cancer and premalignant conditions which may be administered in combination with polynucleotides and/or polypeptides of the invention and/or agonists and/or antagonists thereof include, but are not limited to, Fluorouracil+Leucovorin and Fluorouracil+Levamisole.

In preferred embodiments, agonists and/or antagonists of the invention are administered in combination with one or more of the above-described therapeutic agent combinations in the treatment, amelioration and/or prevention of colorectal cancers and premalignant conditions.

Further examples of therapeutic agents useful in the treatment of colorectal cancer and premalignant conditions which may be administered in combination with polynucleotides and/or polypeptides of the invention and/or agonists and/or antagonists thereof include, but are not limited to, Aminocamptothecin (9-AC, 9-Aminocamptothecin, NSC 603071), Aplidine (Aplidin®, Aplidina®), Bevacizumab® (Anti-VEGF monoclonal antibody, rhuMAb-VEGF), C225 (IMC-225, EGFR inhibitor, Anti-EGFr MAb, Cetuximab®), C242-DM1 (huC242-DM1), CC49-zeta gene therapy, CEAcide® (Labetuzumab®, Anti-CEA monoclonal antibody, hMN-14), CeaVac® (MAb 3H1), CP-609754, CTP-37 (Avicine®, hCG blocking vaccine), Declopramide (Oxi-104), Eniluracil (776c85), F19 (Anti-FAP monoclonal antibody, iodinated anti-FAP MAb), FMdC (KW-2331, MDL-101731), FUDR (Floxuridine®), Gemcitabine (Gemto®, Gemzar®), Herceptin®(Trastuzumab®, Anti-HER-2 monoclonal antibody, Anti-EGFR-2 MAb), Intoplicine (RP 60475), L-778123 (Ras inhibitors), Leuvectin® (cytofectin+ IL-2 gene, IL-2 gene therapy), MN-14 (Anti-CEA immunoradiotherapy, $^{131}$I-MN-14, $^{188}$Re-MN-14), OncoVAX-CL, OncoVAX-CL-Jenner (GA-733-2 vaccine) Orzel® (Tegafur+Uracil+Leucovorin), Oxaliplatin (Eloxatine®, Eloxatin®), Paclitaxel-DHA (Taxoprexin®), Pemetrexed disodium (Alimta®, MTA, multitargeted antifolate, LY 231514), R115777 (Zarnestra®), Raltitrexed (Tomudex®, ZD-1694), SCH 66336, SU5416 (Semaxanib®, VEGF inhibitor), Tocladesine (8-Cl-cAMP), Trimetrexate (Neutrexin®), TS-1, and ZD-9331.

In preferred embodiments, agonists and/or antagonists of the invention are administered in combination with one or more of the above-described therapeutic agents in the treatment, amelioration and/or prevention of colorectal cancers and premalignant conditions.

Further exemplary combinations of therapeutic agents useful in the treatment of colorectal cancer and premalignant conditions which may be administered in combination with polynucleotides and/or polypeptides of the invention and/or agonists and/or antagonists thereof include, but are not limited to, Aminocamptothecin+G-CSF, Bevacizumab®+Fluorouracil, Bevacizumab®+Leucovorin, Bevacizumab®+Fluorouracil+Leucovorin, Cyclophosphamide+SCH 6636, Fluorouracil+CeaVac®, Fluorouracil+Oxaliplatin, Fluorouracil+Raltitrexed, Fluorouracil+SCH 6636, Fluorouracil+Trimetrexate, Fluorouracil+Leucovorin+Oxaliplatin, Fluorouracil+Leucovorin+Trimetrexate, Irinotecan+C225 (Cetuximab®), Oncovin®+SCH 6636, Oxaliplatin+Leucovorin, Paclitaxel+SCH 6636, Pemetrexed disodium+Gemcitabine, and Trimetrexate+Leucovorin.

In preferred embodiments, agonists and/or antagonists of the invention are administered in combination with one or more of the above-described therapeutic agent combinations in the treatment, amelioration and/or prevention of colorectal cancers and premalignant conditions.

In further specific embodiments, polynucleotides and/or polypeptides of the invention and/or agonists and/or antagonists thereof are used to treat, ameliorate and/or prevent prostate cancer and premalignant conditions. Polynucleotides and/or polypeptides of the invention and/or agonists and/or antagonists thereof may be used in combination with one or more surgical and/or radiological procedures and/or therapeutic agents to treat, ameliorate and/or prevent prostate cancer and premalignant conditions. Prostate cancer which may be treated using polynucleotides and/or polypeptides of the invention and/or agonists and/or antagonists thereof includes, but is not limited to, benign prostatic hyperplasia, malignant prostate cancer (e.g., stage 1, stage 11, stage III or stage 1V) and metastatic prostate cancer.

In preferred embodiments, agonists and/or antagonists of the present invention are used to treat, ameliorate and/or prevent prostate cancer and premalignant conditions. Agonists and/or antagonists of the present invention may be used in combination with one or more surgical and/or radiological procedures and/or therapeutic agents to treat, ameliorate and/or prevent prostate cancer and premalignant conditions. Prostate cancer which may be treated using polynucleotides and/or polypeptides of the invention and/or agonists and/or antagonists thereof includes, but is not limited to, benign prostatic hyperplasia, malignant prostate cancer (e.g., stage 1, stage 11, stage III or stage 1V) and metastatic prostate cancer.

In preferred embodiments, agonists and/or antagonists of the invention are used to treat malignant prostate cancer. In other preferred embodiments, agonists and/or antagonists of the invention are used to treat metastatic prostate cancer.

Polynucleotides and/or polypeptides of the invention and/or agonists and/or antagonists thereof may be administered in combination with one or more surgical, radiological and/or hormonal procedures useful in the treatment of prostate cancer and premalignant conditions including, but not limited to, prostatectomy (e.g., radical retropubic prostatectomy), external beam radiation therapy, brachytherapy, orchiectomy and hormone treatment (e.g., LHRH agonists, androgen receptor inhibitors).

In preferred embodiments, agonists and/or antagonists of the present invention may be administered in combination with one or more surgical, radiological and/or hormonal procedures useful in the treatment of prostate cancer and premalignant conditions including, but not limited to, prostatectomy (e.g., radical retropubic prostatectomy), external beam radiation therapy, brachytherapy, orchiectomy and hormone treatment (e.g., LHRH agonists, androgen receptor inhibitors).

Polynucleotides and/or polypeptides of the invention and/or agonists and/or antagonists thereof may be administered in combination with one or more therapeutic agents useful in the treatment of prostate cancer and premalignant conditions including, but not limited to, Aminoglutethimide (Cytadren®), Biclutamide (Casodex®), Cyclophosphamide (Cytoxan®g, Neosar®, CTX), Diethylstilbestrol (DES), Doxorubicin (Adriamycin®, Doxil®, Rubex®), Flutamide (Eulexin®), Hydrocortisone, Ketoconazole (Nizoral®), Leuprolide acetate (Viadur®, Lupron®, Leuprogel®, Eligard®), Mitoxantrone (Novantrone®, DHAD), Nilutamide (Nilandron®), Paclitaxel (Paxene®, Taxol®), Paclitaxel-DHA (Taxoprexin®), PC SPES, Prednisone, Triptorelin pamoate (Trelstar Depot®, Decapeptyl®), and Vinblastine (Velban®, VLB).

In preferred embodiments, agonists and/or antagonists of the invention are administered in combination with one or more of the above-described therapeutic agents in the treatment, amelioration and/or prevention of prostate cancers and premalignant conditions.

Further examples of therapeutic agents useful in the treatment of prostate cancer and premalignant conditions which may be administered in combination with polynucleotides and/or polypeptides of the invention and/or agonists and/or antagonists thereof include, but are not limited to, Abarelix®) (Abarelix-Depot-M®, PPI-149, R-3827); Abiraterone Acetate® (CB-7598, CB-7630), ABT-627 (ET-1 inhibitor), APC-8015 (Provenge®, Dendritic cell therapy), Avorelin® (Meterelin®, MF-6001, EP-23904), CEP-701 (KT-5555), CN-706, CT-2584 (Apra®, CT-2583, CT-2586, CT-3536), GBC-590, Globo H hexasaccharide (Globo H-KLH®), Interferon alpha 2a (Intron A®), Liarozole (Liazal, Liazol, R-75251, R-85246, Ro-85264), MDX-447 (MDX-220, BAB-447, EMD-82633, H-447, anti-EGFr/FcGammaR1r), NPI-0052 (proteasome inhibitor), OncoVAX-P (OncoVAX-PrPSA), PROSTVAC, PS-341 (LDP-341, 26S proteasome inhibitor), PSMA MAb (Prostate Specific Membrane Antigen monoclonal antibody), and R-flurbiprofen (Flurizan®, E-7869, MPC-7869).

In preferred embodiments, agonists and/or antagonists of the invention are administered in combination with one or more of the above-described therapeutic agents in the treatment, amelioration and/or prevention of prostate cancers and premalignant conditions.

Preferred combinations of therapeutic agents useful in the treatment of prostate cancer and premalignant conditions which may be administered in combination with polynucleotides and/or polypeptides of the invention and/or agonists and/or antagonists thereof include, but are not limited to, Docetaxel+Estramustine, Mitoxantrone+Hydrocortisone, Mitoxantrone+Prednisone, Navelbine+Estramustine, Paclitaxel+Estramustine, and Vinblastine+Estramustine.

In preferred embodiments, agonists and/or antagonists of the invention are administered in combination with one or more of the above-described therapeutic agent combinations in the treatment, amelioration and/or prevention of prostate cancers and premalignant conditions.

In further specific embodiments, polynucleotides and/or polypeptides of the invention and/or agonists and/or antagonists thereof are used to treat, ameliorate and/or prevent pancreatic cancer and premalignant conditions. Polynucleotides and/or polypeptides of the invention and/or agonists and/or antagonists thereof may be used in combination with one or more surgical and/or radiological procedures and/or therapeutic agents to treat, ameliorate and/or prevent pancreatic cancer and premalignant conditions. Pancreatic cancers which may be treated using polynucleotides and/or polypeptides of the invention and/or agonists and/or antagonists thereof include, but are not limited to, adenocarcinoma, endocrine (islet cell) tumors, tumors confined to the pancreas, locally advanced pancreatic cancer and metastatic pancreatic cancer.

In preferred embodiments, agonists and/or antagonists of the present invention are used to treat, ameliorate and/or prevent pancreatic cancer and premalignant conditions. Agonists and/or antagonists of the present invention may be used in combination with one or more surgical and/or radiological procedures and/or therapeutic agents to treat, ameliorate and/or prevent pancreatic cancer and premalignant conditions. Pancreatic cancers which may be treated using agonists and/or antagonists of the present invention include, but are not limited to, adenocarcinoma, endocrine (islet cell) tumors, tumors confined to the pancreas, locally advanced pancreatic cancer and metastatic pancreatic cancer.

In preferred embodiments, agonists and/or antagonists of the invention are used to treat locally advanced pancreatic cancer. In other preferred embodiments, agonists and/or antagonists of the invention are used to treat metastatic pancreatic cancer and premalignant conditions.

Polynucleotides and/or polypeptides of the invention and/or agonists and/or antagonists thereof may be administered: in combination with one or more surgical and/or radiological procedures useful in the treatment of pancreatic cancer and premalignant conditions including, but not limited to, pancreaticoduodenumectomy (Whipple resection).

In preferred embodiments, agonists and/or antagonists of the present invention may be administered in combination with one or more surgical and/or radiological procedures useful in the treatment of pancreatic cancer and premalignant conditions including, but not limited to, pancreaticoduodenumectomy (Whipple resection).

Polynucleotides and/or polypeptides of the invention and/ or agonists and/or antagonists thereof may be administered in combination with one or more therapeutic agents useful in the treatment of pancreatic cancer and premalignant conditions including, but not limited to, Capecitabine (Xeloda®, Doxifluridine®, oral 5-FU), Cisplatin (Platinol®, CDDP), Fluorouracil (5FU, Adrucil®, Fluoroplex®, Efudex®), Gemcitabine (Gemto®, Gemzar®), and Irinotecan (Camptosar®, CPT-11, Topotecin®, CaptoCPT-1).

In preferred embodiments, agonists and/or antagonists of the invention are administered in combination with one or more of the above-described therapeutic agents in the treatment, amelioration and/or prevention of pancreatic cancers.

Preferred combinations of therapeutic agents useful in the treatment of pancreatic cancer and premalignant conditions which may be administered in combination with polynucleotides and/or polypeptides of the invention and/or agonists and/or antagonists thereof include, but are not limited to, Cisplatin+Gemcitabine, CP-358774+Gemcitabine, Docetaxel+Gemcitabine, Irinotecan+Fluorouracil, Irinotecan+Gemcitabine, and Paclitaxel+Gemcitabine.

In preferred embodiments, agonists and/or antagonists of the invention are administered in combination with one or more of the above-described therapeutic agent combinations in the treatment, amelioration and/or prevention of pancreatic cancers and premalignant conditions.

Further examples of therapeutic agents useful in the treatment of pancreatic cancer and premalignant conditions which may be administered in combination with polynucleotides and/or polypeptides of the invention and/or agonists and/or antagonists thereof include, but are not limited to, ABX-EGF (anti-EGFr MAb), Acetyldinaline (CI-994, GOE-5549, GOR-5549, PD-130636), BMS-214662 (BMS-192331, BMS-193269, BMS-206635), BNP-1350 (BNPI-1100, Karenitecins), C225 (IMC-225, EGFR inhibitor, Anti-EGFr MAb, Cetuximab®), C242-DM1 (huC242-DM1, SB-408075), Carbendazin®(FB-642), Carmustine (DTI-015, BCNU, BiCNU, Gliadel Wafer®), CMT-3 (COL-3, Metastat®), CP-358774 (Tarceva®, OSI-774, EGFR inhibitor), Docetaxel (Taxotere®, Taxane®), Exetecan mesylate (DX-8951, DX-8951f), Flavopiridol (HMR-1275), Gastrimmune® (Anti-gastrin-17 immunogen, anti-g17), GBC-590, Herceptin® (Trastuzumab®, Anti-HER-2 monoclonal antibody, Anti-EGFR-2 MAb), HSPPC-96 (HSP cancer vaccine, gp96 heat shock protein-peptide complex), Irofulven (MGI-114), ISIS-2503 (Ras antisense), Onyx-015 (p53 gene therapy), Paclitaxel (Paxene®), Taxol®), Pemetrexed disodium (Alimta®, MTA, multitargeted antifolate, LY 231514), Perillyl alcohol (perilla alcohol, perillic alcohol, perillol, NSC-641066), RFS-2000 (9-nitrocamptothecan, 9-NC, Rubitecan®), and Rituximab® (Rituxan®, anti-CD20 MAb).

In preferred embodiments, agonists and/or antagonists of the invention are administered in combination with one or more of the above-described therapeutic agents in the treatment, amelioration and/or prevention of pancreatic cancers and premalignant conditions.

In further particular embodiments, polynucleotides and/or polypeptides of the invention and/or agonists and/or antagonists thereof are used to treat, ameliorate and/or prevent hepatic cancer and premalignant conditions. Polynucleotides and/or polypeptides of the invention and/or agonists and/or antagonists thereof may be used in combination with one or more surgical and/or radiological procedures and/or therapeutic agents to treat, ameliorate and/or prevent hepatic cancer and premalignant conditions. Hepatic cancers which may be treated using polynucleotides and/or polypeptides of the invention and/or agonists and/or antagonists thereof include, but are not limited to, hepatocellular carcinoma, malignant hepatoma, cholangiocarcinoma, mixed hepatocellular cholangiocarcinoma or hepatoblastoma.

In preferred embodiments, agonists and/or antagonists of the present invention are used to treat, ameliorate and/or prevent hepatic cancer and premalignant conditions. Agonists and/or antagonists of the present invention may be used in combination with one or more surgical and/or radiological procedures and/or therapeutic agents to treat, ameliorate and/or prevent hepatic cancer and premalignant conditions. Hepatic cancers which may be treated using agonists and/or antagonists of the present invention include, but are not limited to, hepatocellular carcinoma, malignant hepatoma, cholangiocarcinoma, mixed hepatocellular cholangiocarcinoma or hepatoblastoma.

In preferred embodiments, agonists and/or antagonists of the invention are used to treat hepatoblastoma. In other preferred embodiments, agonists and/or antagonists of the invention are used to treat hepatocellular carcinoma.

Polynucleotides and/or polypeptides of the invention and/or agonists and/or antagonists thereof may be administered in combination with one or more surgical and/or radiological procedures useful in the treatment of hepatic cancers and premalignant conditions including, but not limited to, partial hepatectomy, liver transplant, radiofrequency ablation, laser therapy, microwave therapy, cryosurgery, percutaneous ethanol injection, hepatic arterial infusion, hepatic artery ligation, chemoembolization and external beam radiation therapy.

In preferred embodiments, agonists and/or antagonists of the present invention may be administered in combination with one or more surgical and/or radiological procedures useful in the treatment of hepatic cancers and premalignant conditions including, but not limited to, partial hepatectomy, liver transplant, radiofrequency ablation, laser therapy, microwave therapy, cryosurgery, percutaneous ethanol injection, hepatic arterial infusion, hepatic artery ligation, chemoembolization and external beam radiation therapy.

Polynucleotides and/or polypeptides of the invention and/or agonists and/or antagonists thereof may be administered in combination with one or more therapeutic agents useful in the treatment of hepatic cancer and premalignant conditions including, but not limited to, Aldesleukin (IL-2, Proleukin®), Cisplatin (Platinol®, CDDP), Doxorubicin (Adriamycin®, Doxil®, Rubex®), Etoposide phosphate (Etopophos®), Etoposide (VP-16, Vepesid®), Fluorouracil (5-FU, Adrucil®, Fluoroplex®, Efudex®), I-131 Lipidiol®, Ifosfamide (IFEX®), Megestrol acetate (Megace®, Pallace®), Pravastatin sodium (Pravachol®), and Vincristine (Oncovin®, Onco TCS®, VCR, Leurocristine®).

In preferred embodiments, agonists and/or antagonists of the invention are administered in combination with one or more of the above-described therapeutic agents in the treatment, amelioration and/or prevention of hepatic cancers and premalignant conditions.

Preferred combinations of therapeutic agents useful in the treatment of hepatic cancer and premalignant conditions which may be administered in combination with polynucleotides and/or polypeptides of the invention and/or agonists and/or antagonists thereof include, but are not limited to, Cisplatin+Doxorubicin, Cisplatin+Etoposide, Cisplatin+Vincristine+Fluorouracil, and Ifosfamide+Cisplatin+Doxorubicin.

In preferred embodiments, agonists and/or antagonists of the invention are administered in combination with one or more of the above-described therapeutic agent combinations in the treatment, amelioration and/or prevention of hepatic cancers and premalignant conditions.

In further particular embodiments, polynucleotides and/or polypeptides of the invention and/or agonists and/or antagonists thereof are used to treat, ameliorate and/or prevent ovarian cancer and premalignant conditions. Polynucleotides and/or polypeptides of the invention and/or agonists and/or antagonists thereof may be used in combination with one or more surgical and/or radiological procedures and/or therapeutic agents to treat, ameliorate and/or prevent ovarian cancer and premalignant conditions. Ovarian cancers which may be treated using polynucleotides and/or polypeptides of the invention and/or agonists and/or antagonists thereof include, but are not limited to, epithelial carcinoma, germ cell tumors and stromal tumors.

In preferred embodiments, agonists and/or antagonists of the present invention are used to treat, ameliorate and/or prevent ovarian cancer and premalignant conditions. Agonists and/or antagonists of the present invention may be used in combination with one or more surgical and/or radiological procedures and/or therapeutic agents to treat, ameliorate and/or prevent ovarian cancer and premalignant conditions. Ovarian cancers which may be treated using agonists and/or antagonists of the present invention include, but are not limited to, epithelial carcinoma, germ cell tumors and stromal tumors.

In preferred embodiments, agonists and/or antagonists of the invention are used to treat germ cell tumors and premalignant conditions. In other preferred embodiments, agonists and/or antagonists of the invention are used to treat epithelial carcinoma and premalignant conditions.

Polynucleotides and/or polypeptides of the invention and/or agonists and/or antagonists thereof may be administered in combination with one or more surgical and/or radiological procedures useful in the treatment of ovarian cancer and premalignant conditions including, but not limited to, hysterectomy, oophorectomy, hysterectomy with bilateral salpingo-oophorectomy, omentectomy, tumor debulking, external beam radiation therapy and intraperitoneal radiation therapy.

In preferred embodiments, agonists and/or antagonists of the invention are administered in combination with one or more of the above-described surgical and/or radiological procedures in the treatment, amelioration and/or prevention of ovarian cancers and premalignant conditions.

Polynucleotides and/or polypeptides of the invention and/or agonists and/or antagonists thereof may be administered in combination with one or more therapeutic agents useful in the treatment of ovarian cancer and premalignant conditions including, but not limited to, Altretamine (Hexylen®, hexamethylmelamine, Hexastat®), Bleomycin (Blenoxane®), Carboplatin (Paraplatin®, CBDCA), Cisplatin (Platinol®, CDDP), Cyclophosphamide (Cytoxan®, Neosar®, CTX), Dactinomycin (Cosmegen®), Doxorubicin (Adriamycin®, Doxil®, Rubex®), Etoposide phosphate (Etopophos®), Etoposide (VP-16, Vepesid®), Fluorouracil (5-FU, Adrucil®, Fluoroplex®, Efudex®), Gemcitabine (Gemto®, Gemzar®), Ifosfamide (IFEX®), Irinotecan (Camptosar®, CPT-11, Topotecin®, CaptoCPT-1), Leucovorin (Leucovorin®, Wellcovorin®), Melphalan (L-PAM, Alkeran®, Phenylalanine mustard), Paclitaxel (Paxene®, Taxol®), Tamoxifen (Nolvadex®, Vinblastine (Velban®, VLB) and Vincristine (Oncovin®, Onco TCS®, VCR, Leurocristine®).

In preferred embodiments, agonists and/or antagonists of the invention are administered in combination with one or more of the above-described therapeutic agents in the treatment, amelioration and/or prevention of ovarian cancers and premalignant conditions.

Preferred combinations of therapeutic agents useful in the treatment of ovarian cancer and premalignant conditions which may be administered in combination with polynucleotides and/or polypeptides of the invention and/or agonists and/or antagonists thereof include, but are not limited to, Bleomycin+Etoposide+Platinol® (Cisplatin) (BEP), Carboplatin+Cyclophosphamide, Carboplatin+Paclitaxel, Carboplatin+Etoposide+Bleomycin (CEB), Cisplatin+Cyclophosphamide, Cisplatin+Etoposide, Cisplatin+Paclitaxel, Cisplatin+Ifosfamide+Vinblastine, Fluorouracil+Leucovorin, Platinol® (Cisplatin)+Vinblastine+Bleomycin (PVB), and Vincristine+Dactinomycin+Cyclophosphamide.

In preferred embodiments, agonists and/or antagonists of the invention are administered in combination with one or more of the above-described therapeutic agent combinations in the treatment, amelioration and/or prevention of ovarian cancers and premalignant conditions.

In further particular embodiments, polynucleotides and/or polypeptides of the invention and/or agonists and/or antagonists thereof are used to treat, ameliorate and/or prevent Ewing's sarcoma. Polynucleotides and/or polypeptides of the invention and/or agonists and/or antagonists thereof may be used in combination with one or more surgical and/or radiological procedures and/or therapeutic agents to treat, ameliorate and/or prevent Ewing's sarcoma. Ewing's sarcoma family tumors which may be treated using polynucleotides and/or polypeptides of the invention and/or agonists and/or antagonists thereof include, but are not limited to, Ewing's tumor of bone (ETB), extraosseus Ewing's (EOE), primitive neuroectodermal tumors (PNET or peripheral neuroepithelioma) and Askin's tumor.

In preferred embodiments, agonists and/or antagonists of the present invention are used to treat, ameliorate and/or prevent Ewing's sarcoma. Agonists and/or antagonists of the present invention may be used in combination with one or more surgical and/or radiological procedures and/or therapeutic agents to treat, ameliorate and/or prevent Ewing's sarcoma. Ewing's sarcoma family tumors which may be treated using agonists and/or antagonists of the present invention include, but are not limited to, Ewing's tumor of bone (ETB), extraosseus Ewing's (EOE), primitive neuroectodermal tumors (PNET or peripheral neuroepithelioma) and Askin's tumor.

In preferred embodiments, agonists and/or antagonists of the invention are used to treat Ewing's tumor of bone. In other preferred embodiments, agonists and/or antagonists of the invention are used to treat peripheral neuroepithelioma.

Polynucleotides and/or polypeptides of the invention and/or agonists and/or antagonists thereof may be administered in combination with one or more surgical and/or radiological procedures useful in the treatment of Ewing's sarcoma family tumors.

In preferred embodiments, agonists and/or antagonists of the invention are administered in combination with one or more surgical and/or radiological procedures useful in the treatment of Ewing's sarcoma family tumors.

Polynucleotides and/or polypeptides of the invention and/or agonists and/or antagonists thereof may be administered in combination with one or more therapeutic agents useful in the treatment of Ewing's sarcoma family tumors including, but not limited to, Cyclophosphamide (Cytoxan®, Neosar®, CTX), Doxorubicin (Adriamycin®, Doxil®, Rubex®), Etoposide phosphate (Etopophos®), Etoposide (VP-16, Vepesid®), Filgrastim (Neupogen®, G-CSF), Ifosfamide (IFEX®), Topotecan (Hycamtin®, SK&F-104864, NSC-609699, Evotopin®), and Vincristine (Oncovin®, Onco TCS®, VCR, Leurocristine®).

In preferred embodiments, agonists and/or antagonists of the invention are administered in combination with one or more of the above-described therapeutic agents in the treatment, amelioration and/or prevention of Ewing's sarcoma family tumors.

Preferred combinations of therapeutic agents useful in the treatment of Ewing's sarcoma family tumors which may be administered in combination with polynucleotides and/or polypeptides of the invention and/or agonists and/or antagonists thereof include, but are not limited to, Cyclophosphamide+Topotecan, Cyclophosphamide+Doxorubicin+Vincristine, Cyclophosphamide+Doxorubicin+Vincristine, alternating with Ifosfamide+Etoposide andcyclophosphamide+Doxorubicin+Vincristine, alternating with Filgrastim+Ifosfamide+Etoposide.

In preferred embodiments, agonists and/or antagonists of the invention are administered in combination with one or more of the above-described therapeutic agent combinations in the treatment, amelioration and/or prevention of Ewing's sarcoma family tumors.

In further specific embodiments, polynucleotides and/or polypeptides of the invention and/or agonists and/or antagonists thereof are used to treat, ameliorate and/or prevent hematological cancers and premalignant conditions. Polynucleotides and/or polypeptides of the invention and/or agonists and/or antagonists thereof may be used in combination with one or more surgical and/or radiological procedures and/or therapeutic agents to treat, ameliorate and/or prevent hematological cancers and premalignant conditions. Hematological cancers which may be treated using polynucleotides and/or polypeptides of the invention and/or agonists and/or antagonists thereof include, but are not limited to, non-Hodgkin's lymphoma (e.g., small lymphocytic lymphoma, follicular center cell lymphoma, lymphoplasmacytoid lymphoma, marginal zone lymphoma, mantle cell lymphoma, immunoblastic lymphoma, burkitt's lymphoma, lymphoblastic lymphoma, peripheral T-cell lymphoma, anaplastic large cell lymphoma and intestinal T-cell lymphoma), leukemia, acute lymphocytic leukemia, chronic lymphocytic leukemia and plasma cell neoplasms including multiple myeloma.

In preferred embodiments, agonists and/or antagonists of the present invention are used to treat, ameliorate and/or prevent hematological cancers and premalignant conditions. Agonists and/or antagonists of the present invention may be used in combination with one or more surgical and/or radiological procedures and/or therapeutic agents to treat, ameliorate and/or prevent hematological cancers and premalignant conditions. Hematological cancers which may be treated using agonists and/or antagonists of the present invention include, but are not limited to, non-Hodgkin's lymphoma (e.g., small lymphocytic lymphoma, follicular center cell lymphoma, lymphoplasmacytoid lymphoma, marginal zone lymphoma, mantle cell lymphoma, immunoblastic lymphoma, burkitt's lymphoma, lymphoblastic lymphoma, peripheral T-cell lymphoma, anaplastic large cell lymphoma and intestinal T-cell lymphoma), leukemia, acute lymphocytic leukemia, chronic lymphocytic leukemia and plasma cell neoplasms including multiple myeloma.

In preferred embodiments, agonists and/or antagonists of the invention are used to treat plasma cell neoplasms. In certain preferred embodiments, that plasma cell neoplasm is multiple myeloma.

In other preferred embodiment, agonists and/or antagonists of the invention are used to treat non-Hodgkin's lymphoma.

In other preferred embodiments, agonists and/or antagonists of the invention are used to treat leukemia. In certain preferred embodiments, that leukemia is acute lymphocytic leukemia. In certain preferred embodiments, that leukemia is chronic lymphocytic leukemia.

Polynucleotides and/or polypeptides of the invention and/or agonists and/or antagonists thereof may be administered in combination with one or more surgical and/or radiological procedures useful in the treatment of hematological cancer and premalignant conditions including, but not limited to, bone marrow transplantation, external beam radiation and total body irradiation.

In specific embodiments, agonists and/or antagonists of the invention are administered in combination with one or more surgical and/or radiological procedures useful in the treatment of hematological cancer and premalignant conditions including, but not limited to, bone marrow transplantation, external beam radiation and total body irradiation.

In preferred embodiments, agonists and/or antagonists of the present invention may be administered in combination with one or more surgical and/or radiological procedures useful in the treatment of multiple myeloma including, but not limited to, allogeneic bone marrow transplantation and peripheral stem cell support.

In other preferred embodiments, agonists and/or antagonists of the present invention may be administered in combination with one or more surgical and/or radiological procedures useful in the treatment of non-Hodgkin's lymphoma including, but not limited to, allogeneic bone marrow transplantation and peripheral stem cell support.

In other preferred embodiments, agonists and/or antagonists of the present invention may be administered in combination with one or more surgical and/or radiological procedures useful in the treatment of leukemia including, but not limited to, allogeneic bone marrow transplantation and peripheral stem cell support. In specific embodiments, agonists and/or antagonists of the invention are used to treat acute lymphocytic leukemia (ALL). In other specific embodiments, agonists and/or antagonists of the invention are used to treat chronic lymphocytic leukemia (CLL).

Polynucleotides and/or polypeptides of the invention and/or agonists and/or antagonists thereof may be administered in combination with one or more therapeutic agents useful in the treatment of multiple myeloma including, but not limited to, Alkylating agents, Anthracyclines, Carmustine (DTI-015, BCNU, BiCNU, Gliadel Wafer®), Cyclophosphamide (Cytoxan®, Neosar®, CTX), Dexamethasone (Decadron®), Doxorubicin (Adriamycin®, Doxil®, Rubex®), Melphalan (L-PAM, Alkeran®, Phenylalanine mustard), Prednisone, Thalidomide and thalidomide analogs, including but not limited to, lenalidomide (CC-5013, REVLIMID®) and CC-4047 (ACTIMID™), and Vincristine (Oncovorin®, Onco TCS®, VCR, Leurocristine®).

In preferred embodiments, agonists and/or antagonists of the invention are administered in combination with one or more of the above-described therapeutic agents in the treatment, amelioration and/or prevention of multiple myeloma.

Preferred combinations of therapeutic agents useful in the treatment of multiple myeloma which may be administered in combination with polynucleotides and/or polypeptides of the invention and/or agonists and/or antagonists thereof include, but are not limited to, Cyclophosphamide+Prednisone, Melphalan+Prednisone (MP), Vincristine+Adriamycin®+Dexamethasone (VAD), Vincristine+Carmustine+Melphalan+Cyclophosphamide+Prednisone (VBMCP; the M2 protocol), and Vincristine+Melphalan+Cyclophosphamide+Prednisone alternating with Vincristine+Carmustine+Doxorubicin+Prednisone (VMCP/VBAP).

In preferred embodiments, agonists and/or antagonists of the invention are administered in combination with one or more of the above-described therapeutic agent combinations in the treatment, amelioration and/or prevention of multiple myeloma.

Polynucleotides and/or polypeptides of the invention and/or agonists and/or antagonists thereof may be administered in combination with one or more therapeutic agents useful in the treatment of non-Hodgkin's lymphoma including, but not limited to, 2-chlorodeoxyadenosine, Amifostine (Ethyol®, Ethiofos®, WR-272), Bexarotene (Targretin®, Targretin Gel®, Targretin Oral®, LGD1069), Bleomycin (Blenoxane®), Busulfan (Busulfex®, Myleran®), Carboplatin (Paraplatin®, CBDCA), Carmustine (DTI-015, BCNU, BiCNU, Gliadel Wafer®), Chlorambucil (Leukeran®), Cisplatin (Platinol®, CDDP), Cladribine (2-CdA, Leustatin®), Cyclophosphamide (Cytoxan®, Neosar®, CTX), Cytarabine (Cytosar-U®, ara-C, cytosine arabinoside, DepoCyt®), Dacarbazine (DTIC), Daunorubicin (Daunomycin, DaunoXome®, Daunorubicin®, Cerubidine®), Denileukin diftitox (Ontak®), Dexamethasone (Decadron®), Dolasetron mesylate (Anzemet®), Doxorubicin (Adriamycin®, Doxil®, Rubex®), Erythropoietin (EPO®, Epogen®, Procrit®), Etoposide phosphate (Etopophos®), Etoposide (VP-16, Vepesid®), Fludarabine (Fludara®, FAMP), Granisetron (Kytril®), Hydrocortisone, Idarubicin (Idamycin®, DMDR, IDA), Ifosfamide (IFEX®), Interferon alpha (Alfaferone®, Alpha-IF®), Interferon alpha 2a (Intron A®), Mechlorethamine (Nitrogen Mustard, $HN_2$, Mustargen®), Melphalan (L-PAM, Alkeran®, Phenylalanine mustard), Methotrexate® (MTX, Mexate®, Folex®), Methylprednisolone (Solumedrol®), Mitoxantrone (Novantrone®, DHAD), Ondansetron (Zofran®), Pentostatin (Nipent®, 2-deoxycoformycin), Perfosfamide (4-hydroperoxycyclophosphamide, 4-HC), Prednisone, Procarbazine (Matulane®), Rituximab® (Rituxan®, anti-CD20 MAb), Thiotepa (triethylenethiophosphaoramide, Thioplex®), Topotecan (Hycamtin®, SK&F-104864, NSC-609699, Evotopin®), Vinblastine (Velban®, VLB), Vincristine (Oncovin®, Onco TCS®, VCR, Leurocristine®) and Vindesine (Eldisine®, Fildesin®).

In preferred embodiments, agonists and/or antagonists of the invention are administered in combination with one or more of the above-described therapeutic agents in the treatment, amelioration and/or prevention of non-Hodgkin's lymphoma.

Preferred combinations of therapeutic agents useful in the treatment of non-Hodgkin's lymphoma which may be administered in combination with polynucleotides and/or polypeptides of the invention and/or agonists and/or antagonists thereof include, but are not limited to, Adriamycin®+Blenoxane+Vinblastine+Dacarbazine (ABVD), Anti-idiotype therapy (BsAb)+Interferon alpha, Anti-idiotype therapy (BsAb)+Chlorambucil, Anti-idiotype therapy (BsAb)+Interleukin-2, BCNU (Carmustine)+Etoposide+Ara-C (Cytarabine)+Melphalen (BEAM), Bleomycin+Etoposide+Adriamycin+Cyclophosphamide+Vincristine+Procarbazine+Prednisone (BEACOPP), Bryostatin+Vincristine, Cyclophosphamide+BCNU (Carmustine)+VP-16 (Etoposide) (CBV), Cyclophosphamide+Vincristine+Prednisone (CVP), Cyclophosphamide+Adriamycin® (Hydroxyldaunomycin)+Vincristine (Oncovorin)+Prednisone (CHOP), Cyclophosphamide+Novantrone® (Mitoxantrone)+Vincristine (Oncovorin)+Prednisone (CNOP), Cyclophosphamide+Doxorubicin+Teniposide+Prednisone, Cyclophosphamide+Adriamycin® (Hydroxyldaunomycin)+Vincristine (Oncovorin)+Prednisone+Rituximab (CHOP+Rituximab), Cyclophosphamide+Doxorubicin+Teniposide+Prednisone+Interferon alpha, Cytarabine+Bleomycin+Vincristine+Methotrexate (CytaBOM), Dexamethasone+Cytarabine+Cisplatin (DHAP), Dexamethasone+Ifosfamide+Cisplatin+Etoposide (DICE), Doxorubicin+Vinblastine+Mechlorethamine+Vincristine+Bleomycin+Etoposide+Prednisone (Stanford V), Etoposide+Vinblastine+Adriamycin (EVA), Etoposide+Methylprednisone+Cytarabine+Cisplatin (ESHAP), Etoposide+Prednisone+Ifosfamide+Cisplatin (EPIC), Fludarabine, Mitoxantrone+Dexamethasone (FMD), Fludarabine, Dexamethasone, Cytarabine (ara-C), +Cisplatin (Platinol®) (FluDAP), Ifosfamide+Cisplatin+Etoposide (ICE), Mechlorethamine+Oncovin® (Vincristine)+Procarbazine+Prednisone (MOPP), Mesna+Ifosfamide+Idarubicin+Etoposide (MIZE), Methotrexate with leucovorin rescue+Bleomycin+Adriamycin+Cyclophosphamide+Oncovorin+Dexamethasone (m-BACOD), Prednisone+Methotrexate+Adriamycin+Cyclophosphamide+Etoposide (ProMACE), Thiotepa+Busulfan+Cyclophosphamide, Thiotepa+Busulfan+Melphalan, Topotecan+Paclitaxel, and Vincristine (Oncovin®)+Adriamycin®+Dexamethasone (VAD).

In preferred embodiments, agonists and/or antagonists of the invention are administered in combination with one or more of the above-described therapeutic agent combinations in the treatment, amelioration and/or prevention of non-Hodgkin's lymphoma.

Further examples of therapeutic agents useful in the treatment of non-Hodgkin's lymphoma which may be administered in combination with polynucleotides and/or polypeptides of the invention and/or agonists and/or antagonists thereof include, but are not limited to, A007 (4-4'-dihydroxybenzophenone-2,4-dinitrophenylhydrazone), AG-2034 (AG-2024, AG-2032, GARFT [glycinamide ribonucleoside transformylase] inhibitor), Aldesleukin (IL-2, Proleukin®), Alemtuzumab (Campath®), Alitretinoin (Panretin®, LGN-1057), Altretamine (Hexylen®, hexamethylmelamine, Hexastat®), Aminocamptothecin (9-AC, 9-Aminocamptothecin, NSC 603071), Anti-CD19/CD3 MAb (anti-CD19/CD3 scFv, anti-NHL MAb), Anti-idiotype therapy (BsAb), Arabinosylguanine (Ara-G, GW506U78), Arsenic trioxide (Trisenox®, ATO), B43-Genistein (anti-CD19 Ab/genistein conjugate), B7 antibody conjugates, Betathine (Beta-LT), BLyS antagonists, Bryostatin-1 (Bryostatin®, BMY-45618, NSC-339555), CHML (Cytotropic Heterogeneous Molecular Lipids), Clofarabine (chloro-fluoro-araA), Daclizumab (Zenapax®), Depsipeptide (FR901228, FK228), Dolastatin-10 (DOLA-10, NSC-376128), Epirubicin (Ellence®, EPI, 4' epidoxorubicin), Epratuzumab (Lymphocide®, humanized anti-CD22, HAT), Fly3/flk2 ligand (Mobista®), G3139 (Genasense®, GentaAnticode®, Bcl-2 antisense), HuID10 (anti-HLA-DR MAb, SMART ID 10), HumaLYM (anti-CD20 MAb), Ibritumomab tiuxetan (Zevalin®), Interferon gamma (Gamma-interferon, Gamma 100®, Gamma-IF), Irinotecan (Camptosar®, CPT-11, Topotecin®, CaptoCPT-1), ISIS-2053, ISIS-3521 (PKC-alpha antisense), Lmb-2 immunotoxin (anti-CD25 recombinant immuno toxin, anti-Tac(Fv)-PE38), Leuvectin®(cytofectin+IL-2 gene, IL-2 gene therapy), Lym-1(131-I LYM-1), Lymphoma vaccine (Genitope), Nelarabine (Compound 506, U78), Neugene compounds (Oncomyc-NG®, Resten-NG®, myc antisense), NovoMAb-G2 scFv (NovoMAb-G2 IgM), 06-benzylguanine (BG, Procept®), Oxaliplatin (Eloxatine®, Eloxatin®), Paclitaxel (Paxene®, Taxol®), Paclitaxel-DHA (Taxoprexin®), Peldesine (BCX-34, PNP inhibitor), Rebeccamycin and Rebeccamycin analogues, SCH-66336, Sobuzoxane (MST-16, Perazolin®), SU5416 (Semaxanib®, VEGF inhibitor), TER-286, Thalidomide and thalidomide analogs, including but not limited to, lenalidomide (CC-5013, REVLIMID®) and CC4047 (ACTIMID™), TNP-470 (AGM-1470), Tositumomab (Bexxar®), Valspodar (PSC 833), Vaxid (B-cell lymphoma DNA vaccine), Vinorelbine (Navelbine®), WF10 (macrophage regulator) and XR-9576 (XR-9351, P-glycoprotein/MDR inhibitor).

In preferred embodiments, agonists and/or antagonists of the invention are administered in combination with one or more of the above-described therapeutic agents in the treatment, amelioration and/or prevention of non-Hodgkin's lymphoma.

Polynucleotides and/or polypeptides of the invention and/or agonists and/or antagonists thereof may be administered in combination with one or more therapeutic agents useful in the treatment of acute lymphocytic leukemia including, but not limited to, Amsacrine, Carboplatin (Paraplatin®, CBDCA), Carmustine (DTI-015, BCNU, BiCNU, Gliadel Wafer®), Cholecaliferol, Cyclophosphamide (Cytoxan®, Neosar®, CTX), Cytarabine (Cytosar-U®, ara-C, cytosine arabinoside, DepoCyt®), Daunorubicin (Daunomycin, DaunoXome®, Daunorubicin®, Cerubidine®), Dexamethasone (Decadron®), Doxorubicin (Adriamycin®, Doxil®, Rubex®), Etoposide (VP-16, Vepesid®), Filgrastam® (Neupogen®, G-CSF, Leukine®), Fludarabine (Fludara®, FAMP), Idarubicin (Idamycin®, DMDR, IDA), Ifosfamide (IFEX®), Imatinib mesylate (STI-571, Imatinib®), Glivec®, Gleevec®, Ab1 tyrosine kinase inhibitor), Interferon gamma (Gamma-interferon, Gamma 100®, Gamma-IF), L-asparaginase (Elspar®, Crastinin®, Asparaginase Medac®, Kidrolase®), Mercaptopurine (6-mercaptopurine, 6-MP), Methotrexate® (MTX, Mexate®, Folex®), Mitoxantrone (Novantrone®, DHAD), Pegaspargase® (Oncospar®), Prednisone, Retinoic acid, Teniposide (VM-26, Vumon®), Thioguanine (6-thioguanine, 6-TG), Topotecan (Hycamtin®, SK&F-104864, NSC-609699, Evotopin®), Tretinoin (Retin-A®, Atragen®), ATRA, Vesanoid®) and Vincristine (Oncovorin®, Onco TCS®, VCR, Leurocristine®).

In preferred embodiments, agonists and/or antagonists of the invention are administered in combination with one or more of the above-described therapeutic agents in the treatment, amelioration and/or prevention of acute lymphocytic leukemia.

Further examples of therapeutic agents useful in the treatment of acute lymphocytic leukemia which may be administered in combination with polynucleotides and/or polypeptides of the invention and/or agonists and/or antagonists thereof include, but are not limited to, Aminocamptothecin (9-AC, 9-Aminocamptothecin, NSC 603071), Aminopterin, Annamycin (AR-522, annamycin LF, Aronex®), Arabinosylguanine (Ara-G, GW506U78, Nelzarabine®), Arsenic trioxide (Trisenox®, ATO, Atrivex®), B43-Genistein (anti-CD19 Ab/genistein conjugate), B43-PAP (anti-CD19 Ab/pokeweed antiviral protein conjugate), Cordycepin, CS-682, Decitabine (5-aza-2'-deoxyytidine), Dolastatin-10 (DOLA-10, NSC-376128), G3139 (Genasense®, GentaAnticode®, Bcl-2 antisense), Irofulven (MGI-114, Ivofulvan, Acylfulvene analogue), MS-209, Phenylbutyrate, Quinine, TNP-470 (AGM-1470, Fumagillin), Trimetrexate (Neutrexin®), Troxacitabine (BCH-204, BCH-4556, Troxatyl®), UCN-01 (7-hydroxystaurosporine), WHI-P131 and WT1 Vaccine.

In preferred embodiments, agonists and/or antagonists of the invention are administered in combination with one or more of the above-described therapeutic agents in the treatment, amelioration and/or prevention of acute lymphocytic leukemia.

Preferred combinations of therapeutic agents useful in the treatment of acute lymphocytic leukemia which may be administered in combination with polynucleotides and/or polypeptides of the invention and/or agonists and/or antagonists thereof include, but are not limited to, Carboplatin+Mitoxantrone, Carmustine+Cyclophosphamide+Etoposide, Cytarabine+Daunorubicin, Cytarabine+Doxorubicin, Cytarabine+Idarubicin, Cytarabine+Interferon gamma, Cytarabine+L-asparaginase, Cytarabine+Mitoxantrone, Cytarabine+Fludarabine and Mitoxantrone, Etoposide+Cytarabine, Etoposide+Ifosfamide, Etoposide+Mitoxantrone, Ifosfamide+Etoposide+Mitoxantrone, Ifosfamide+Teniposide, Methotrexate+Mercaptopurine, Methotrexate+Mercaptopurine+Vincristine+Prednisone, Phenylbutyrate+Cytarabine, Phenylbutyrate+Etoposide, Phenylbutyrate+Topotecan, Phenylbutyrate+Tretinoin, Quinine+Doxorubicin, Quinine+Mitoxantrone+Cytarabine, Thioguanine+Cytarabine+Amsacrine, Thioguanine+Etoposide+Idarubicin, Thioguanine+Retinoic acid+Cholecaliferol, Vincristine+Prednisone, Vincristine+Prednisone and L-asparaginase, Vincristine+Dexamethasone/Prednisone+Asparaginase+Daunorubicin/Doxorubicin, Vincristine+Dexamethasone/Prednisone+Asparaginase+Daunorubicin/Doxorubicin+Filgrastim, Vincristine+Dexamethasone/Prednisone+Asparaginase+Daunorubicin/Doxorubicin+Cyclophosphamide+Methotrexate, and Vincristine+Dexamethasone/Prednisone+Asparaginase+Daunorubicin/Doxorubicin+Cyclophosphamide+Methotrexate+Filgrastim.

In preferred embodiments, agonists and/or antagonists of the invention are administered in combination with one or more of the above-described therapeutic agent combinations in the treatment, amelioration and/or prevention of acute lymphocytic leukemia.

Polynucleotides and/or polypeptides of the invention and/or agonists and/or antagonists thereof may be administered in combination with one or more therapeutic agents useful in the treatment of chronic lymphocytic leukemia including, but not limited to, Chlorambucil (Leukeran®), Cladribine (2-CdA, Leustatin®), Cyclophosphamide (Cytoxan®, Neosar®, CTX), Cytarabine (Cytosar-U®, ara-C, cytosine arabinoside, DepoCyt®, cytarabine ocfosfate, ara-CMP), Doxorubicin (Adriamycin®, Doxil®, Rubex®), Fludarabine (Fludara®, FAMP), Pentostatin (Nipent®, 2-deoxycoformycin), Prednisone and Vincristine (Oncovorin®, Onco TCS®, VCR, Leurocristine®).

In preferred embodiments, agonists and/or antagonists of the invention are administered in combination with one or more of the above-described therapeutic agents in the treatment, amelioration and/or prevention of chronic lymphocytic leukemia.

Further examples of therapeutic agents useful in the treatment of chronic lymphocytic leukemia which may be administered in combination with polynucleotides and/or polypeptides of the invention and/or agonists and/or antagonists thereof include, but are not limited to, Alemtuzumab (Campath®), Aminocamptothecin (9-AC, 9-Aminocamptothecin, NSC 603071), Aminopterin, Annamycin (AR-522, annamycin LF, Aronex®), Arabinosylguanine (Ara-G, GW506U78, Nelzarabine®, Compound 506U78), Arsenic trioxide (Trisenox®, ATO, Atrivex®), Bryostatin-1 (Bryostatin®, BMY-45618, NSC-339555), CS-682, Dolastatin-10 (DOLA-10, NSC-376128), Filgrastim (Neupogen®, G-CSF, Leukine), Flavopiridol (NSC-649890, HMR-1275), G3139 (Genasense®, GentaAnticode®, Bcl-2 antisense), Irofulven (MGI-114, Ivofulvan, Acylfulvene analogue), MS-209, Phenylbutyrate, Rituximab®(Rituxan®, anti-CD20 MAb), Thalidomide and thalidomide analogs, including but not limited to, lenalidomide (CC-5013, REVLIMID®) and CC-4047 (ACTIMID™), Theophylline, TNP-470 (AGM-1470, Fumagillin), UCN-01 (7-hydroxystaurosporine) and WHI-P131.

In preferred embodiments, agonists and/or antagonists of the invention are administered in combination with one or more of the above-described therapeutic agents in the treatment, amelioration and/or prevention of chronic lymphocytic leukemia.

Preferred combinations of therapeutic agents useful in the treatment of chronic lymphocytic leukemia which may be administered in combination with polynucleotides and/or polypeptides of the invention and/or agonists and/or antagonists thereof include, but are not limited to, Fludarabine+Prednisone, and Cyclophosphamide+Doxorubicin+Vincristine+Prednisone (CHOP).

In preferred embodiments, agonists and/or antagonists of the invention are administered in combination with one or more of the above-described therapeutic agent combinations in the treatment, amelioration and/or prevention of chronic lymphocytic leukemia.

Diseases associated with increased apoptosis include AIDS; neurodegenerative disorders (such as Alzheimer's disease, Parkinson's disease, Amyotrophic lateral sclerosis, Retinitis pigmentosa, Cerebellar degeneration); and brain tumor or prior associated disease); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia. In preferred embodiments, DR4 polynucleotides, polypeptides and/or agonists are used to treat the diseases and disorders listed above.

Many of the pathologies associated with HIV are mediated by apoptosis, including HIV-induced nephropathy and HIV encephalitis. Thus, in additional preferred embodiments, DR4 polynucleotides, polypeptides, and/or DR4 agonists of the invention are used to treat and/or prevent AIDS and pathologies associated with AIDS. Another embodiment of the present invention is directed to the use of DR4 to reduce TRAIL-mediated death of T-cells in HIV-infected patients.

The state of immunodeficiency that defines AIDS is secondary to a decrease in the number and function of CD4+ T-lymphocytes. Recent reports estimate the daily loss of CD4+ T-cells to be between $3.5 \times 10^7$ and $2 \times 10^9$ cells (Wei X., et al., *Nature* 373:117-122 (1995)). One cause of CD4+ T-cell depletion in the setting of HIV infection is believed to be HIV-induced apoptosis (see, for example, Meyaard et al., *Science* 257:217-219, (1992); Groux et al., *J Exp. Med.,* 175: 331, (1992); and Oyaizu et al., in *Cell Activation and Apoptosis in HIV Infection*, Andrieu and Lu, Eds., Plenum Press, New York, 1995, pp. 101-114). Indeed, HIV-induced apoptotic cell death has been demonstrated not only in vitro but also, more importantly, in infected individuals (Ameisen, J. C., *AIDS* 8:1197-1213 (1994); Finkel, T. H., and Banda, N. K., *Curr. Opin. Immunol.* 6:605-615 (1995); Muro-Cacho, C. A. et al., *J. Immunol.* 154:5555-5566 (1995)). Furthermore, apoptosis and CD4+ T-lymphocyte depletion is tightly correlated in different animal models of AIDS (Brunner, T., et al., *Nature* 373:441-444 (1995); Gougeon, M. L., et al., *AIDS Res. Hum. Retroviruses* 9:553-563 (1993)) and, apoptosis is not observed in those animal models in which viral replication does not result in AIDS (Gougeon, M. L. et al., AIDS Res. Hum. Retroviruses 9:553-563 (1993)). Further data indicates that uninfected but primed or activated T lymphocytes from HIV-infected individuals undergo apoptosis after encountering the TNF-family ligand FasL. Using monocytic cell lines that result in death following HIV infection, it has been demonstrated that infection of U937 cells with HIV results in the de novo expression of FasL and that FasL mediates HIV-induced apoptosis (Badley, A. D. et al., *J. Virol.* 70:199-206 (1996)). Further the TNF-family ligand was detectable in uninfected macrophages and its expression was upregulated following HIV infection resulting in selective killing of uninfected CD4 T-lymphocytes (Badley, A. D et al., *J. Virol.* 70:199-206 (1996)). Further, additional studies have implicated Fas-mediated apoptosis in the loss of T-cells in HIV individuals (Katsikis et al., *J. Exp. Med.* 181:2029-2036 (1995)). It is also possible that T-cell apoptosis occurs through multiple mechanisms. Further, at least some of the T-cell death seen in HIV patients may be mediated by TRAIL.

Thus, by the invention, a method for treating and/or preventing HIV$^+$ individuals is provided which involves administering DR4, DR4 polypeptides, polynucleotides, antagonists, and/or agonists of the present invention to reduce selective killing of CD4$^+$ T-lymphocytes. While not wanting to be bound by theory, activated human T-cells are believed to be induced to undergo programmed cell death (apoptosis) upon triggering through the CD3/T-cell receptor complex, a process termed activated-induced cell death (AICD). AICD of CD4$^+$ T-cells isolated from HIV-Infected asymptomatic individuals has been reported (Groux et al., supra). Thus, AICD may play a role in the depletion of CD4$^+$ T-cells and the progression to AIDS in HIV-infected individuals. Thus, the present invention provides a method of inhibiting TRAIL-mediated T-cell death in HIV patients, comprising administering a DR4 polypeptide of the invention (preferably, a soluble DR4 polypeptide) and/or DR4 antagonist of the invention to the patients. Modes of administration and dosages are discussed in detail below. In one embodiment, the patient is asymptomatic when treatment with DR4 commences. If desired, prior to treatment, peripheral blood T-cells may be extracted from an HIV patient, and tested for susceptibility to TRAIL-mediated cell death by procedures known in the art. In one embodiment, a patient's blood or plasma is contacted with DR4 polypeptides of the invention ex vivo. The DR4 polypeptides of the invention may be bound to a suitable chromatography matrix by procedures known in the art. The patient's blood or plasma flows through a chromatography column containing DR4 bound to the matrix, before being returned to the patient. The immobilized DR4 polypeptide binds TRAIL, thus removing TRAIL protein from the patient's blood.

In additional embodiments a DR4 polypeptide and/or antagonist of the invention is administered in combination with other inhibitors of T-cell apoptosis. For example, as discussed above, Fas-mediated apoptosis also has been implicated in loss of T-cells in HIV individuals (Katsikis et al., *J. Exp. Med.* 181:2029-2036, 1995). Thus, a patient susceptible to both Fas ligand mediated and TRAIL mediated T-cell death may be treated with both an agent that blocks TRAIL/TRAIL receptor interactions and an agent that blocks Fas-ligand/Fas interactions. Suitable agents for blocking binding of Fas-ligand to Fas include, but are not limited to, soluble Fas polypeptides; multimeric forms of soluble Fas polypeptides (e.g., dimers of sFas/Fc); anti-Fas antibodies that bind Fas without transducing the biological signal that results in apoptosis; anti-Fas-ligand antibodies that block binding of Fas-ligand to Fas; and muteins of Fas-ligand that bind Fas but do not transduce the biological signal that results in apoptosis. Preferably, the antibodies employed according to this method are monoclonal antibodies. Examples of suitable agents for blocking Fas-ligand/Fas interactions, including blocking anti-Fas monoclonal antibodies, are described in International application publication number WO 95/10540, hereby incorporated by reference.

Suitable agents, which also block binding of TRAIL to a TRAIL receptor that may be administered with the polynucleotides and/or polypeptides of the present invention include, but are not limited to, soluble TRAIL receptor polypeptides (e.g., a soluble form of OPG, TR5 (International application publication number WO 98/30693); DR5 (International application publication number WO 98/41629); and TR10 (International application publication number WO 98/54202)); multimeric forms of soluble TRAIL receptor polypeptides; and TRAIL receptor antibodies that bind the TRAIL receptor without transducing the biological signal that results in apoptosis, anti-TRAIL antibodies that block binding of TRAIL to one or more TRAIL receptors, and muteins of TRAIL that bind TRAIL receptors but do not transduce the biological signal that results in apoptosis. Preferably, the antibodies employed according to this method are monoclonal antibodies.

In rejection of an allograft, the immune system of the recipient animal has not previously been primed to respond because the immune system for the most part is only primed by environmental antigens. Tissues from other members of the same species have not been presented in the same way that, for example, viruses and bacteria have been presented. In the case of allograft rejection, immunosuppressive regimens are designed to prevent the immune system from reaching the effector stage. However, the immune profile of xenograft rejection may resemble disease recurrence more that allograft rejection. In the case of disease recurrence, the immune system has already been activated, as evidenced by destruction of the native islet cells. Therefore, in disease recurrence the immune system is already at the effector stage. DR4 polynucleotides, polypeptides and/or agonists of the present invention are able to suppress the immune response to both allografts and xenografts because lymphocytes activated and differentiated into effector cells will express the DR4 polypeptide, and thereby are susceptible to compounds which enhance apoptosis. Thus, the present invention further provides a method for creating immune privileged tissues. Antagonist of the invention can further be used in the treatment and/or prevention of Inflammatory Bowel-Disease.

DR4 antagonists or agonists of the invention may be useful for treating and/or preventing inflammatory diseases, such as rheumatoid arthritis, osteoarthritis, psoriasis, septicemia, and inflammatory bowel disease.

In addition, due to lymphoblast expression of DR4, soluble DR4, agonist or antagonist monoclonal antibodies may be used to treat and/or prevent this form of cancer. Further, soluble DR4 or neutralizing monoclonal antibodies may be used to treat and/or prevent various chronic and acute forms of inflammation such as rheumatoid arthritis, osteoarthritis, psoriasis, septicemia, and inflammatory bowel disease.

In one embodiment, DR4 polypeptides, polynucleotides, and/or antagonists of the invention may be used to treat and/or prevent cardiovascular disorders, including peripheral artery disease, such as limb ischemia.

Cardiovascular disorders include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular disorders also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

In one embodiment, DR4 polynucleotides, polypeptides and/or antagonists of the invention is used to treat and/or prevent thrombotic microangiopathies. One such disorder is thrombotic thrombocytopenic purpura (TTP) (Kwaan, H. C., *Semin. Hematol.* 24:71 (1987); Thompson et al., *Blood* 80:1890 (1992)). Increasing TTP-associated mortality rates have been reported by the U.S. Centers for Disease Control (Torok et al., *Am. J. Hematol.* 50:84 (1995)). Plasma from patients afflicted with TTP (including HIV+ and HIV− patients) induces apoptosis of human endothelial cells of dermal microvascular origin, but not large vessel origin (Laurence et al., *Blood* 87:3245 (1996)). Plasma of TTP patients thus is thought to contain one or more factors that directly or indirectly induce apoptosis. As described in International patent application number WO 97/01633 (hereby incorporated by reference), TRAIL is present in the serum of TTP patients, and is likely to play a role in inducing apoptosis of microvascular endothelial cells. Another thrombotic microangiopathy is hemolytic-uremic syndrome (HUS) (Moake, J. L., *Lancet,* 343:393 (1994); Melnyk et al., (*Arch. Intern. Med.,* 155:2077 (1995); Thompson et al., supra). Thus, in one embodiment, the invention is directed to use of DR4 to treat and/or prevent the condition that is often referred to as "adult HUS" (even though it can strike children as well). A disorder known as childhood/diarrhea-associated HUS differs in etiology from adult HUS. In another embodiment, conditions characterized by clotting of small blood vessels may be treated and/or prevented using DR4. Such conditions include, but are not limited to, those described herein. For example, cardiac problems seen in about 5-10% of pediatric AIDS patients are believed to involve clotting of small blood vessels. Breakdown of the microvasculature in the heart has been reported in multiple sclerosis patients. As a further example, treatment and/or prevention of systemic lupus erythematosus (SLE) is contemplated. In one embodiment, a patient's blood or plasma is contacted with DR4 polynucleotides and/or polypeptides of the invention ex vivo. The DR4 polynucleotides and/or polypeptides of the invention may be bound to a suitable chromatography matrix by procedures known in the art. According to this embodiment, the patient's blood or plasma flows through a chromatography column containing DR4 polynucleotides and/or polypeptides of the invention bound to the matrix, before being returned to the patient. The immobilized DR4 binds TRAIL, thus removing TRAIL protein from the patient's blood. Alternatively, DR4 polynucleotides and/or polypeptides of the invention may be administered in vivo to a patient afflicted with a thrombotic microangiopathy. In one embodiment, a soluble form of DR4 polypeptide of the invention is administered to the patient. Thus, the present invention provides a method for treating and/or preventing a thrombotic microangiopathy, involving use of an effective amount of DR4. A DR4 polypeptide may be employed in in vivo or ex vivo procedures, to inhibit TRAIL-mediated damage to (e.g., apoptosis of) microvascular endothelial cells.

DR4 polynucleotides and/or polypeptides of the invention may be employed in combination with other agents useful in treating and/or preventing a particular disorder. For example, in an in vitro study reported by Laurence et al. (*Blood* 87:3245 (1996)), some reduction of TTP plasma-mediated apoptosis of microvascular endothelial cells was achieved by using an anti-Fas blocking antibody, aurintricarboxylic acid, or normal plasma depleted of cryoprecipitate. Thus, a patient may be treated with a polynucleotide and/or polypeptide of the invention in combination with an agent that inhibits Fas-ligand-mediated apoptosis of endothelial cells, such as, for example, an agent described above. In one embodiment, DR4 polynucleotides and/or polypeptides of the invention and an anti-FAS blocking antibody are both administered to a patient afflicted with a disorder characterized by thrombotic microangiopathy, such as TTP or HUS. Examples of blocking monoclonal antibodies directed against Fas antigen (CD95) are described in International patent application publication number WO 95/10540, hereby incorporated by reference.

The naturally occurring balance between endogenous stimulators and inhibitors of angiogenesis is one in which inhibitory influences predominate (Rastinejad et al., *Cell* 56:345-355 (1989)). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., *Biotech.* 9:630-634 (1991); Folkman et al., *N. Engl. J. Med.,* 333:1757-1763 (1995); Auerbach et al., *J Microvasc. Res.* 29:401-411 (1985); Folkman, *Advances in Cancer Research*, eds. Klein and Weinhouse, Academic Press, New York, pp. 175-203 (1985); Patz, *Am. J. Opthalmol.* 94:715-743 (1982); and Folkman et al., *Science* 221:719-725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442-447 (1987).

The present invention provides for treatment and/or prevention of diseases or disorders associated with neovascularization by administration of the DR4 polynucleotides and/or polypeptides of the invention (including DR4 agonists and/or antagonists). Malignant and metastatic conditions which can be treated and/or prevented with the polynucleotides and polypeptides of the invention include, but are not limited to those malignancies, solid tumors, and cancers described herein and otherwise known in the art (for a review of such disorders, see Fishman et al., *Medicine,* 2d Ed., J. B. Lippincott Co., Philadelphia (1985)).

Additionally, ocular disorders associated with neovascularization which can be treated and/or prevented with the DR4 polynucleotides and polypeptides of the present invention (including DR4 agonists and DR4 antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704-710 (1978) and Gartner et al., *Surv. Ophthal.* 22:291-312 (1978).

Additionally, disorders which can be treated and/or prevented with the DR4 polynucleotides and polypeptides of the present invention (including DR4 agonists and DR4 antagonists) include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Polynucleotides and/or polypeptides of the invention and/or agonists and/or antagonists thereof are useful in the diagnosis, prognosis, treatment and/or prevention of a wide range of diseases and/or conditions. Such diseases and conditions include, but are not limited to, cancer (e.g., immune cell related cancers, breast cancer, prostate cancer, ovarian cancer, follicular lymphoma, cancer associated with mutation or alteration of p53, brain tumor, bladder cancer, uterocervical cancer, colon cancer, colorectal cancer, non-small cell carcinoma of the lung, small cell carcinoma of the lung, stomach cancer, etc.), lymphoproliferative disorders (e.g., lymphadenopathy), microbial (e.g., viral, bacterial, etc.) infection (e.g., HIV-1 infection, HIV-2 infection, herpesvirus infection (including, but not limited to, HSV-1, HSV-2, CMV, VZV, HHV-6, HHV-7, EBV), adenovirus infection, poxvirus infection, human papilloma virus infection, hepatitis infection (e.g., HAV, HBV, HCV, etc.), *Helicobacter pylori* infection, invasive Staphylococcia, etc.), parasitic infection, nephritis, bone disease (e.g., osteoporosis), atherosclerosis, pain, cardiovascular disorders (e.g., neovascularization, hypovascularization or reduced circulation (e.g., ischemic disease (e.g., myocardial infarction, stroke, etc.))), AIDS, allergy, inflammation, neurodegenerative disease (e.g., Alzheimer's disease, Parkinson's disease, amyotrophic lateral sclerosis, pigmentary retinitis, cerebellar degeneration, etc.), graft rejection (acute and chronic), graft vs. host disease, diseases due to osteomyelodysplasia (e.g., aplastic anemia, etc.), joint tissue destruction in rheumatism, liver disease (e.g., acute and chronic hepatitis, liver injury, and cirrhosis), autoimmune disease (e.g., multiple sclerosis, rheumatoid arthritis, systemic lupus erythematosus, immune complex glomerulonephritis, autoimmune diabetes, autoimmune thrombocytopenic purpura, Grave's disease, Hashimoto's thyroiditis, etc.), cardiomyopathy (e.g., dilated cardiomyopathy), diabetes, diabetic complications (e.g., diabetic nephropathy, diabetic neuropathy, diabetic retinopathy), influenza, asthma, psoriasis, glomerulonephritis, septic shock, and ulcerative colitis.

Polynucleotides and/or polypeptides of the invention and/or agonists and/or antagonists thereof are useful in promoting angiogenesis, wound healing (e.g., wounds, burns, and bone fractures).

DR4 polynucleotides or polypeptides, or agonists of DR4, can be used in the treatment and/or prevention of infectious agents. For example, by increasing the immune response, particularly increasing the proliferation and differentiation of B-cells in response to an infectious agent, infectious diseases may be treated and/or prevented. The immune response may be increased by either enhancing an existing immune response, or by initiating a new immune response. Alternatively, DR4 polynucleotides or polypeptides, or agonists or antagonists of DR4, may also directly inhibit the infectious agent, without necessarily eliciting an immune response.

Viruses are one example of an infectious agent that can cause disease or symptoms that can be treated and/or prevented by DR4 polynucleotides or polypeptides, or agonists of DR4. Examples of viruses, include, but are not limited to the following DNA and RNA viruses and viral families: Arbovirus, Adenoviridae, Arenaviridae, Arterivirus, Bimaviridae, Bunyaviridae, Caliciviridae, Circoviridae, Coronaviridae, Dengue virus, HIV-1, HIV-2, Flaviviridae, Hepadnaviridae (e.g., hepatitis B virus), Herpesviridae (e.g., cytomegalovirus, herpes simplex viruses 1 and 2, varicella-zoster virus, Epstein-Barr virus (EBV), herpes B virus, and human herpes viruses 6, 7, and 8), Morbillivirus, Rhabdoviridae (e.g., rabies virus), Orthomyxoviridae (e.g., influenza A virus, and influenza B), Paramyxoviridae (e.g., parainfluenza virus), papilloma virus, Papovaviridae, Parvoviridae, Picornaviridae (e.g., EMCV and poliovirus), Poxyiridae (e.g., areola or vaccinia virus), Reoviridae (e.g., rotavirus), Retroviridae (HTLV-I, HTLV-II, Lentivirus), and Togaviridae (e.g., Rubivirus). These viruses and virus families can cause a variety of diseases or symptoms, including, but not limited to: arthritis, bronchiollitis, respiratory diseases, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, smallpox, opportunistic infections (e.g., AIDS, Kaposi's sarcoma), pneumonia, Burkitt's lymphoma, chickenpox, zoster, hemorrhagic fever, measles, mumps, parainfluenza, rabies, the common cold, polio, leukemia, rubella, sexually transmitted diseases, skin diseases (e.g., Kaposi's, warts), and viremia. DR4 polynucleotides or polypeptides, or agonists or antagonists of DR4, can be used to treat, prevent, and/or detect any of these symptoms or diseases.

In specific embodiments, DR4 polynucleotides, polypeptides, or agonists and/or antagonists are used to treat and/or prevent: meningitis, Dengue, EBV, and/or hepatitis.

In an additional specific embodiment DR4 polynucleotides, polypeptides, or agonists and/or antagonists are used to treat patients non-responsive to one or more other commercially available hepatitis vaccines.

In a further specific embodiment, DR4 polynucleotides, polypeptides, or agonists and/or antagonists are used to treat AIDS.

Similarly, bacteria and fungi that can cause disease or symptoms and that can be treated and/or prevented by DR4 polynucleotides or polypeptides, or agonists or antagonists of DR4, include, but are not limited to the following organisms.

Bacteria include, but are not limited to *Actinomyces, Bacillus* (e.g., *B. anthracis*), *Bacteroides, Bordetella, Bartonella, Borrelia* (e.g., *B. burgdorferi*), *Brucella, Campylobacter, Capnocytophaga, Chlamydia, Clostridium, Corynebacterium, Coxiella, Dermatophilus, Enterococcus, Ehrlichia, Escherichia* (e.g., Enterotoxigenic *E. coli* and Enterohemorrhagic *E. coli*), *Francisella, Fusobacterium, Haemobartonella, Haemophilus* (e.g., *H. influenzae* type b), *Helicobacter, Klebsiella*, L-form bacteria, *Legionella, Leptospira, Listeria, Mycobacteria* (e.g., *M. leprae* and *M. tuberculosis*), *Mycoplasma, Neisseria* (e.g., *N. gonorrheae* and *N. meningitidis*), *Neorickettsia, Nocardia, Pasteurella, Peptococcus, Peptostreptococcus, Pneumococcus, Proteus, Pseudomonas, Rickettsia, Rochalimaea, Salmonella* (e.g., *S. typhimurium* and *S. typhi*), *Serratia, Shigella, Staphylococcus* (e.g., *S. aureus*), *Streptococcus* (e.g., *S. pyogenes, S. pneumoniae*, and Group B *streptococcus*), *Streptomyces, Treponema, Vibrio* (e.g., *Vibrio cholerae*) and *Yersinia* (e.g., *Y. pestis*). Fungi include, but are not limited to: *Absidia, Acremonium, Alternaria, Aspergillus, Basidiobolus, Bipolaris, Blastomyces, Candida* (e.g., *C. albicans*), *Coccidioides, Conidiobolus, Cryptococcus* (e.g., *C. neoformans*), *Curvalaria, Erysipelothrix, Epidermophyton, Exophiala, Geotrichum, Histoplasma, Madurella, Malassezia, Microsporum, Moniliella, Mortierella, Mucor, Paecilomyces, Penicillium, Phialemonium, Phialophora, Prototheca, Pseudallescheria, Pseudomicrodochium, Pythium, Rhinosporidium, Rhizopus, Scolecobasidium, Sporothrix, Stemphylium, Trichophyton, Trichosporon*, and *Xylohypha*. These and other bacteria or fungi can cause diseases or symptoms including, but not limited to: bacteremia, endocarditis, eye infections (conjunctivitis, uveitis), gingivitis, opportunistic infections (e.g., AIDS related infections), paronychia, prosthesis-related infections, Reiter's Disease, respiratory tract infections, such as whooping cough or emphysema, sepsis, Lyme Disease, cat-scratch disease, dysentery, paratyphoid fever, food poisoning, typhoid, pneumonia, gonorrhea, meningitis, chlamydia, syphilis, diphtheria, leprosy, paratuberculosis, tuberculosis, lupus, botulism, gangrene, tetanus, impetigo, rheumatic fever, scarlet fever, sexually transmitted diseases, skin diseases (e.g., cellulitis, dermatocycoses), toxemia, urinary tract infections, and wound infections. DR4 polynucleotides or polypeptides, or agonists or antagonists of DR4, can be used to treat, prevent and/or detect any of these symptoms or diseases.

In specific embodiments, DR4 polynucleotides, polypeptides, or agonists and/or antagonists thereof are used to treat and/or prevent: tetanus, diphtheria, botulism, and/or meningitis type B.

Moreover, parasites causing parasitic diseases or symptoms that can be treated and/or prevented by DR4 polynucleotides or polypeptides, or agonists of DR4, include, but are not limited to: protozoan parasites including, but not limited to, *Babesia, Balantidium, Besnoitia, Cryptosporidium, Eimeria, Encephalitozoon, Entamoeba, Giardia, Hammondia, Hepatozoon, Isospora, Leishmania, Microsporidia, Neospora, Nosema, Pentatrichomonas, Plasmodium* (e.g., *Plasmodium virax, Plasmodium falciparium, Plasmodium malariae* and *Plasmodium ovale*), *Pneumocystis, Sarcocystis, Schistosoma, Theileria, Toxoplasma*, and *Trypanosoma*; and helminth parasites including, but not limited to, *Acanthocheilonema, Aelurostrongylus, Ancylostoma, Angiostrongylus, Ascaris, Brugia, Bunostomum, Capillaria, Chabertia, Cooperia, Crenosoma, Dictyocaulus, Dioctophyme, Dipetalonema, Diphyllobothrium, Diplydium, Dirofilaria, Dracunculus, Enterobius, Filaroides, Haemonchus, Lagochilascaris, Loa, Mansonella, Muellerius, Nanophyetus, Necator, Nematodirus, Oesophagostomum, Onchocerca,*

*Opisthorchis, Ostertagia, Parafilaria, Paragonimus, Parascaris, Physaloptera, Protostrongylus, Setaria, Spirocerca, Spirometra, Stephanofilaria, Strongyloides, Strongylus, Thelazia, Toxascaris, Toxocara, Trichinella, Trichostrongylus, Trichuris, Uncinaria,* and *Wuchereria*. These parasites can cause a variety of diseases or symptoms, including, but not limited to: scabies, trombiculiasis, eye infections (e.g., river blindness), elephantiasis, intestinal disease (e.g., dysentery, giardiasis), liver disease, lung disease, opportunistic infections (e.g., AIDS related), malaria, pregnancy complications, and toxoplasmosis. DR4 polynucleotides or polypeptides, or agonists or antagonists of DR4, can be used to treat, prevent and/or detect any of these symptoms or diseases.

In specific embodiments, DR4 polynucleotides, polypeptides, or agonists and/or antagonists thereof are used to treat and/or prevent malaria.

Polynucleotides and/or polypeptides of the invention and/or agonists and/or antagonists thereof are also useful as an adjuvant to enhance immune responsiveness to specific antigen, tumor-specific responses, and/or anti-viral immune responses.

An adjuvant to enhance anti-viral immune responses. Anti-viral immune responses that may be enhanced using the compositions of the invention as an adjuvant, include virus and virus associated diseases or symptoms described herein or otherwise known in the art. In specific embodiments, the compositions of the invention are used as an adjuvant to enhance an immune response to a virus, disease, or symptom selected from the group consisting of: AIDS, meningitis, Dengue, EBV, and hepatitis (e.g., hepatitis B). In another specific embodiment, the compositions of the invention are used as an adjuvant to enhance an immune response to a virus, disease, or symptom selected from the group consisting of: HIV/AIDS, Respiratory syncytial virus, Dengue, Rotavirus, Japanese B encephalitis, Influenza A and B, Parainfluenza, Measles, Cytomegalovirus, Rabies, Junin, Chikungunya, Rift Valley fever, Herpes simplex virus, and yellow fever.

Anti-bacterial or anti-fungal immune responses that may be enhanced using the compositions of the invention as an adjuvant, include bacteria or fungus and bacteria or fungus associated diseases or symptoms described herein or otherwise known in the art. In specific embodiments, the compositions of the invention are used as an adjuvant to enhance an immune response to a bacterium or fungus, disease, or symptom selected from the group consisting of: tetanus, diphtheria, botulism, and meningitis type B. In another specific embodiment, the compositions of the invention are used as an adjuvant to enhance an immune response to a bacteria selected from the group consisting of: *Vibrio cholerae, Mycobacterium leprae, Salmonella typhi, Salmonella paratyphi, Neisseria meningitidis, Streptococcus pneumoniae,* Group B streptococcus, *Shigella* spp., Enterotoxigenic *E. coli*, Enterohemorrhagic *E. coli,* and *Borrelia burgdorferi*.

Anti-parasitic immune responses that may be enhanced using the compositions of the invention as an adjuvant, include parasite and parasite associated diseases or symptoms described herein or otherwise known in the art. In specific embodiments, the compositions of the invention are used as an adjuvant to enhance an immune response to a parasite. In another specific embodiment, the compositions of the invention are used as an adjuvant to enhance an immune response to *Plasmodium* spp. (malaria).

More generally, polynucleotides and/or polypeptides of the invention and/or agonists and/or antagonists thereof are useful in regulating (i.e., elevating or reducing) immune response. For example, polynucleotides and/or polypeptides of the invention may be useful in preparation or recovery from surgery, trauma, radiation therapy, chemotherapy, and transplantation, or may be used to boost immune response and/or recovery in the elderly and immunocompromised individuals. Alternatively, polynucleotides and/or polypeptides of the invention and/or agonists and/or antagonists thereof are useful as immunosuppressive agents, for example in the treatment and/or prevention of autoimmune disorders. In specific embodiments, polynucleotides and/or polypeptides of the invention are used to treat and/or prevent chronic inflammatory, allergic or autoimmune conditions, such as those described herein or are otherwise known in the art.

In one embodiment, DR4 polynucleotides and/or polypeptides of the invention and/or agonists or antagonists thereof may be used as an immune system enhancer prior to, during, or after bone marrow transplant and/or other transplants (e.g., allogenic or xenogenic organ transplantation). With respect to transplantation, compositions of the invention may be administered prior to, concomitant with, and/or after transplantation. In a specific embodiment, compositions of the invention are administered after transplantation, prior to the beginning of recovery of T-cell populations. In another specific embodiment, compositions of the invention are first administered after transplantation after the beginning of recovery of T-cell populations, but prior to full recovery of B-cell populations.

In another embodiment, DR4 polynucleotides and/or polypeptides of the invention and/or agonists or antagonists thereof may be used as an agent to boost immunoresponsiveness among B-cell immunodeficient individuals. B-cell immunodeficiencies that may be ameliorated or treated and/or prevented by administering the DR4 polypeptides or polynucleotides of the invention, or agonists or antagonists thereof, include, but are not limited to, severe combined immune deficiency (SCID), congenital agammaglobulinemia, common variable immunodeficiency, Wiskott-Aldrich Syndrome, and X-linked immunodeficiency with hyper IgM.

Additionally, DR4 polynucleotides and/or polypeptides of the invention and/or agonists or antagonists thereof may be used as an agent to boost immunoresponsiveness among individuals having an acquired loss of B-cell function. Conditions resulting in an acquired loss of B-cell function that may be ameliorated, treated, and/or prevented by administering the DR4 polypeptides or polynucleotides of the invention, or agonists or antagonists thereof, include, but are not limited to, HIV Infection, AIDS, bone marrow transplant, and B-cell chronic lymphocytic leukemia (CLL).

Furthermore, DR4 polynucleotides and/or polypeptides of the invention and/or agonists or antagonists thereof may be used as an agent to boost immunoresponsiveness among individuals having a temporary immune deficiency. Conditions resulting in a temporary immune deficiency that may be ameliorated, treated, and/or prevented by administering the DR4 polypeptides or polynucleotides of the invention, and/or agonists or antagonists thereof, include, but are not limited to, recovery from viral infections (e.g., influenza), conditions associated with malnutrition, recovery from infectious mononucleosis, or conditions associated with stress, recovery from measles, recovery from blood transfusion, recovery from surgery.

DR4 polynucleotides and/or polypeptides of the invention and/or agonists or antagonists thereof may also be used as a regulator of antigen presentation by monocytes, dendritic cells, and/or B-cells. In one embodiment, DR4 (in soluble, membrane-bound or transmembrane forms) enhances antigen presentation or antagonizes antigen presentation in vitro or in vivo.

In related embodiments, said enhancement or antagonization of antigen presentation may be useful as an anti-tumor treatment or to modulate the immune system. For example, DR4 polynucleotides and/or polypeptides of the invention and/or agonists or antagonists thereof may be used as an agent to direct an individual's immune system towards development of a humoral response (i.e. TH2) as opposed to a TH1 cellular response. Also, DR4 polynucleotides and/or polypeptides of the invention and/or agonists or antagonists thereof may be used as a stimulator of B-cell production in pathologies such as AIDS, chronic lymphocyte disorder and/or Common Variable Immunodeficiency.

In another embodiment, DR4 polynucleotides and/or polypeptides of the invention and/or agonists or antagonists thereof may be used as a means to induce tumor proliferation and thus make the tumor more susceptible to anti-neoplastic agents. For example, multiple myeloma is a slowly dividing disease and is thus refractory to virtually all anti-neoplastic regimens. If these cells were forced to proliferate more rapidly their susceptibility profile would likely change.

Other embodiments where DR4 polynucleotides and/or polypeptides of the invention and/or agonists or antagonists thereof may be used include, but are not limited to: as a stimulator of B-cell production in pathologies such as AIDS, chronic lymphocyte disorder and/or Common Variable Immunodeficiency; as a therapy for generation and/or regeneration of lymphoid tissues following surgery, trauma or genetic defect; as a gene-based therapy for genetically inherited disorders resulting in immuno-incompetence such as observed among SCID patients; as an antigen for the generation of antibodies to inhibit or enhance DR5 mediated responses; as a means of activating T-cells; as pretreatment of bone marrow samples prior to transplant (such treatment would increase B-cell representation and thus accelerate recovery); as a means of regulating secreted cytokines that are elicited by DR4; to modulate IgE concentrations in vitro or in vivo; and to treat and/or prevent IgE-mediated allergic reactions including, but are not limited to, asthma, rhinitis, and eczema.

Alternatively, DR4 polynucleotides and/or polypeptides of the invention and/or agonists and/or antagonists thereof are useful as immunosuppressive agents, for example in the treatment and/or prevention of autoimmune disorders. In specific embodiments, polynucleotides and/or polypeptides of the invention are used to treat and/or prevent chronic inflammatory, allergic or autoimmune conditions, such as those described herein or are otherwise known in the art.

Preferably, treatment using DR4 polynucleotides or polypeptides, or agonists or antagonists of DR4, could either be by administering an effective amount of DR4 polypeptide to the patient, or by removing cells from the patient, supplying the cells with DR4 polynucleotide, and returning the engineered cells to the patient (ex vivo therapy). Moreover, as further discussed herein, the DR4 polypeptide or polynucleotide can be used as an adjuvant in a vaccine to raise an immune response against infectious disease.

Additional preferred embodiments of the invention include, but are not limited to, the use of DR4 polypeptides and functional agonists or antagonists in the following applications: administration to an animal (e.g., mouse, rat, rabbit, hamster, guinea pig, pigs, micro-pig, chicken, camel, goat, horse, cow, sheep, dog, cat, non-human primate, and human, most preferably human) to boost the immune system to produce increased quantities of one or more antibodies (e.g., IgG, IgA, IgM, and IgE), to induce higher affinity antibody production (e.g., IgG, IgA, IgM, and IgE), and/or to increase an immune response; or administration to an animal (including, but not limited to, those listed above, and also including transgenic animals) incapable of producing functional endogenous antibody molecules or having an otherwise compromised endogenous immune system, but which is capable of producing human immunoglobulin molecules by means of a reconstituted or partially reconstituted immune system from another animal (see, e.g., published PCT Application Nos. WO98/24893, WO96/34096, WO96/33735, and WO91/10741.

Antagonists of DR4 include binding and/or inhibitory antibodies, antisense nucleic acids, ribozymes or soluble forms of the DR4 receptor(s). These would be expected to reverse many of the activities of herein, as well as find clinical or practical application including, but not limited to the following applications. DR4 antagonists may be used as a means of blocking various aspects of immune responses to foreign agents or self, for example, autoimmune disorders such as lupus, and arthritis, as well as immunoresponsiveness to skin allergies, inflammation, bowel disease, injury and pathogens. Although our current data speaks directly to the potential role of DR4 in B-cell and T-cell related pathologies, it remains possible that other cell types may gain expression or responsiveness to DR4. Thus, DR4 may, like CD40 and its ligand, may be regulated by the status of the immune system and the microenvironment in which the cell is located. DR4 antagonists may be used as a therapy for preventing the B-cell proliferation and Ig secretion associated with autoimmune diseases such as idiopathic thrombocytopenic purpura, systemic lupus erythematosus and; as an inhibitor of graft versus host disease or transplant rejection; as a therapy for B-cell malignancies such as ALL, Hodgkin's disease, non-Hodgkin's lymphoma, Chronic lymphocyte leukemia, plasmacytomas, multiple myeloma, Burkitt's lymphoma, and EBV-transformed diseases; as a therapy for chronic hypergammaglobulinemeia evident in such diseases as monoclonalgammopathy of undetermined significance (MGUS), Waldenstrom's disease, related idiopathic monoclonalgammopathies, and plasmacytomas; as a therapy for decreasing cellular proliferation of Large B-cell Lymphomas; as a means of decreasing the involvement of B-cells and Ig associated with Chronic Myelogenous Leukemia; or as an immunosuppressive agent.

Furthermore, DR4 polypeptides or polynucleotides of the invention, or antagonists thereof may be used to modulate IgE concentrations in vitro or in vivo, or to treat and/or prevent IgE-mediated allergic reactions including, but not limited to, asthma, rhinitis, and eczema.

All of the therapeutic applications of DR4 polynucleotides and/or polypeptides of the invention and/or agonists and/or antagonists thereof described herein may, in addition to their uses in human medicine, be used in veterinary medicine. The present invention includes treatment of companion animals, including, but not limited to dogs, cats, ferrets, birds, and horses; food animals, including, but not limited to cows, pigs, chickens, and sheep; and exotic animals, e.g., zoo animals.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human, primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

DR4 polynucleotides and/or polypeptides of the invention and/or agonists and/or antagonists thereof described herein may be employed in a composition with a pharmaceutically acceptable carrier, e.g., as described herein.

In one aspect, the present invention is directed to a method for enhancing apoptosis induced by a TNF-family ligand, which involves administering to a cell which expresses the DR4 polypeptide an effective amount of DR4 ligand, analog or an agonist capable of increasing DR4 mediated signaling. Preferably, DR4 mediated signaling is increased to treat and/or prevent a disease wherein decreased apoptosis or decreased cytokine and adhesion molecule expression is exhibited. An agonist can include soluble forms of DR4 and monoclonal antibodies directed against the DR4 polypeptide.

In a further aspect, the present invention is directed to a method for inhibiting apoptosis induced by a TNF-family ligand, which involves administering to a cell which expresses the, DR4 polypeptide an effective amount of an antagonist capable of decreasing DR4 mediated signaling. Preferably, DR4 mediated signaling is decreased to treat and/or prevent a disease wherein increased apoptosis or NF-kB expression is exhibited. An antagonist can include soluble forms of DR4 (e.g., polypeptides containing all or a portion of the DR4 extracellular domain) and monoclonal antibodies directed against the DR4 polypeptide.

By "agonist" is intended naturally occurring and synthetic compounds capable of enhancing or potentiating apoptosis (e.g., stimulating DR4 activities). By "antagonist" is intended naturally occurring and synthetic compounds capable of inhibiting apoptosis (e.g., inhibiting DR4 activities). Whether any candidate "agonist" or "antagonist" of the present invention can enhance or inhibit apoptosis can be determined using art-known TNF-family ligand/receptor cellular response assays, including those described in more detail below.

The present invention further encompasses methods and compositions for killing of cells expressing DR4 on their surface, comprising, or alternatively consisting of, contacting agonists of the invention with such cells expressing DR4 on their surface.

In preferred embodiments, the present invention further encompasses methods and compositions for killing of cells expressing DR4 on their surface, comprising, or alternatively consisting of, contacting agonistic anti-DR4 antibodies of the invention with such cells expressing DR4 on their surface.

In specific embodiments, the present invention encompasses methods and compositions for inducing apoptosis in cells expressing DR4 on their surface, comprising, or alternatively consisting of, contacting agonists of the invention with such cells expressing DR4 on their surface.

In preferred embodiments, the present invention encompasses methods and compositions for inducing apoptosis in cells expressing DR4 on their surface, comprising, or alternatively consisting of, contacting agonistic anti-DR4 antibodies of the invention with such cells expressing DR4 on their surface.

In further specific embodiments, the present invention encompasses methods and compositions for inducing apoptosis in cells expressing a polypeptide comprising amino acids about 52 to about 184 of SEQ ID NO:2 on their surface, comprising, or alternatively consisting of, contacting agonists of the invention with such cells expressing said polypeptide on their surface.

In preferred embodiments, the present invention encompasses methods and compositions for inducing apoptosis in cells expressing a polypeptide comprising amino acids about 52 to about 184 of SEQ ID NO:2 on their surface, comprising, or alternatively consisting of, contacting agonistic anti-DR4 antibodies of the invention with such cells expressing said polypeptide on their surface.

In further specific embodiments, the present invention encompasses methods and compositions for inducing apoptosis in cells expressing a polypeptide comprising the extracellular domain of the polypeptide encoded by the cDNA clone contained in ATCC Deposit No. 97920 on their surface, comprising, or alternatively consisting of, contacting agonists of the invention with such cells expressing said polypeptide on their surface.

In preferred embodiments, the present invention encompasses methods and compositions for inducing apoptosis in cells expressing a polypeptide comprising the extracellular domain of the polypeptide encoded by the cDNA clone contained in ATCC Deposit No. 97920 on their surface, comprising, or alternatively consisting of, contacting agonistic anti-DR4 antibodies of the invention with such cells expressing said polypeptide on their surface.

The present invention further encompasses methods and compositions for killing of cells expressing DR4 on their surface, comprising, or alternatively consisting of, administering to an animal, agonists of the invention in an amount effective to kill such DR4 expressing cells.

In preferred embodiments, the present invention further encompasses methods and compositions for killing of cells expressing DR4 on their surface, comprising, or alternatively consisting of, administering to an animal, agonistic anti-DR4 antibodies of the invention in an amount effective to kill such DR4 expressing cells.

In specific embodiments, the present invention encompasses methods and compositions for inducing apoptosis in cells expressing DR4 on their surface, comprising, or alternatively consisting of, administering to an animal, agonists of the invention in an amount effective to induce apoptosis in such DR4 expressing cells.

In preferred embodiments, the present invention encompasses methods and compositions for inducing apoptosis in cells expressing DR4 on their surface, comprising, or alternatively consisting of, administering to an animal, agonistic anti-DR4 antibodies of the invention in an amount effective to induce apoptosis in such DR4 expressing cells.

In further specific embodiments, the present invention encompasses methods and compositions for inducing apoptosis in cells expressing a polypeptide comprising amino acids about 52 to about 184 of SEQ ID NO:2 on their surface, comprising; or alternatively consisting of, administering to an animal, agonists of the invention in an amount effective to induce apoptosis in such cells expressing said polypeptide on their surface.

In preferred embodiments, the present invention encompasses methods and compositions for inducing apoptosis in cells expressing a polypeptide comprising amino acids about 52 to about 184 of SEQ ID NO:2 on their surface, comprising, or alternatively consisting of, administering to an animal, agonistic anti-DR4 antibodies of the invention in an amount effective to induce apoptosis in such cells expressing said polypeptide on their surface.

In further specific embodiments, the present invention encompasses methods and compositions for inducing apoptosis in cells expressing a polypeptide comprising the extracellular domain of the polypeptide encoded by the cDNA clone contained in ATCC Deposit No. 97920 on their surface, comprising, or alternatively consisting of, administering to an animal, agonists of the invention in an amount effective to induce apoptosis in such cells expressing said polypeptide on their surface.

In preferred embodiments, the present invention encompasses methods and compositions for inducing apoptosis in cells expressing a polypeptide comprising the extracellular domain of the polypeptide encoded by the cDNA clone contained in ATCC Deposit No. 97920 on their surface, comprising, or alternatively consisting of, administering to an animal, agonistic anti-DR4 antibodies of the invention in an amount effective to induce apoptosis in such cells expressing said polypeptide on their surface.

One such screening procedure involves the use of melanophores which are transfected to express the receptor of the present invention. Such a screening technique is described in PCT WO 92/01810, published Feb. 6, 1992. Such an assay may be employed, for example, for screening for a compound which inhibits (or enhances) activation of the receptor polypeptide of the present invention by contacting the melanophore cells which encode the receptor with both a TNF-family ligand and the candidate antagonist (or agonist). Inhibition or enhancement of the signal generated by the ligand indicates that the compound is an antagonist or agonist of the ligand/receptor signaling pathway.

Other screening techniques include the use of cells which express the receptor (for example, transfected CHO cells) in a system which measures extracellular pH changes caused by receptor activation, for example, as described in *Science* 246: 181-296 (October 1989). For example, compounds may be contacted with a cell which expresses the receptor polypeptide of the present invention and a second messenger response, e.g., signal transduction or pH changes, may be measured to determine whether the potential compound activates or inhibits the receptor.

Another such screening technique involves introducing RNA encoding the receptor into *Xenopus* oocytes to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another screening technique involves expressing in cells a construct wherein the receptor is linked to a phospholipase C or D. Such cells include endothelial cells, smooth muscle cells, embryonic kidney cells, etc. The screening may be accomplished as herein above described by detecting activation of the receptor or inhibition of activation of the receptor from the phospholipase signal.

Another method involves screening for compounds which inhibit activation of the receptor polypeptide of the present invention antagonists by determining inhibition of binding of labeled ligand to cells which have the receptor on the surface thereof. Such a method involves transfecting a eukaryotic cell with DNA encoding the receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

Further screening assays for agonist and antagonist of the present invention are described in Tartaglia, L. A., and Goeddel, D. V., *J. Biol. Chem.* 267(7):4304-4307 (1992).

Thus, in a further aspect, a screening method is provided for determining whether a candidate agonist or antagonist is capable of enhancing or inhibiting a cellular response to a TNF-family ligand. The method involves contacting cells which express the DR4 polypeptide with a candidate compound and a TNF-family ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By "assaying a cellular response" is intended qualitatively or quantitatively measuring a cellular response to a candidate compound and/or a TNF-family ligand (e.g., determining or estimating an increase or decrease in T-cell proliferation or tritiated thymidine labeling). By the invention, a cell expressing the DR4 polypeptide can be contacted with either an endogenous or exogenously administered TNF-family ligand.

Agonist according to the present invention include naturally occurring and synthetic compounds such as, for example, TNF family ligand peptide fragments, transforming growth factor, neurotransmitters (such as glutamate, dopamine, N-methyl-D-aspartate), tumor suppressors (p53), cytolytic T-cells and antimetabolites. Preferred agonist include chemotherapeutic drugs such as, for example, cisplatin, doxorubicin, bleomycin, cytosine arabinoside, nitrogen mustard, methotrexate and vincristine. Others include ethanol and β-amyloid peptide. (*Science* 267:1457-1458 (1995)). Further preferred agonist include polyclonal and monoclonal antibodies raised against the DR4 polypeptide, or a fragment thereof. Such agonist antibodies raised against a TNF-family receptor are disclosed in Tartaglia, L. A., et al., *Proc. Natl. Acad. Sci. USA* 88:9292-9296 (1991); and Tartaglia, L. A., and Goeddel, D. V., *J. Biol. Chem.* 267 (7):4304-4307 (1992). See, also, PCT Application WO 94/09137.

Antagonist according to the present invention include naturally occurring and synthetic compounds such as, for example, the CD40 ligand, neutral amino acids, zinc, estrogen, androgens, viral genes (such as Adenovirus ElB, Baculovirus p35 and IAP, Cowpox virus crmA, Epstein-Barr virus BHRF1, LMP-1, African swine fever virus LMW5-HL, and Herpesvirus yl 34.5), calpain inhibitors, cysteine protease inhibitors, and tumor promoters (such as PMA, Phenobarbital, and hexachlorocyclohexanes (e.g., ∀-, ∃-, or (-hexachlorocyclohexane).

Other potential antagonists include antisense molecules. Antisense technology can be used to control gene expression through antisense DNA or RNA or through triple-helix formation. Antisense techniques are discussed, for example, in Okano, *J. Neurochem.* 56:560 (1991); *Oligodeoxynucleotides as Antisense Inhibitors of Gene Expression*, CRC Press, Boca Raton, Fla. (1988). Triple helix formation is discussed in, for instance Lee et al., *Nucleic Acids Research* 6:3073 (1979); Cooney et al., Science 241:456 (1988); and Dervan et al., *Science* 251:1360 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide. The oligonucleotides described above can also be delivered to cells such that the antisense RNA or DNA may be expressed in vivo to inhibit production of the DR4 receptor.

In one embodiment, the DR4 antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the DR4 antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding DR4, or fragments thereof, can be by any promoter known in the art to act in vertebrate, preferably human cells. Such promoters can be inducible or constitutive. Such promoters include, but are not limited to, the SV40 early promoter region (Bernoist and Chambon, *Nature* 29:304-310 (1981), the promoter contained in the 3' long terminal repeat of Rous sarcoma virus (Yamamoto et al., Cell 22:787-797 (1980), the herpes thymidine promoter (Wagner et al., *Proc. Natl. Acad. Sci. U.S.A.* 78:1441-1445 (1981), the regulatory sequences of the metallothionein gene (Brinster et al., *Nature* 296:39-42 (1982)), etc.

The antisense nucleic acids of the invention comprise a sequence complementary to at least a portion of an RNA transcript of a DR4 gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded DR4 antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with a DR4RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., *Nature* 372:333-335 (1994). Thus, oligonucleotides complementary to either the 5'- or 3'-non-translated, non-coding regions of the DR4 shown in SEQ ID NO:1 could be used in an antisense approach to inhibit translation of endogenous DR4 mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of DR4 mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., *Proc. Natl. Acad. Sci. U.S.A.* 86:6553-6556 (1989); Lemaitre et al., *Proc. Nail. Acad. Sci.* 84:648-652 (1987); PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., *BioTechniques* 6:958-976 (1988)) or intercalating agents. (See, e.g., Zon, *Pharm. Res.* 5:539-549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual D-units, the strands run parallel to each other (Gautier et al., *Nucl. Acids Res.* 15:6625-6641 (1987)). The oligonucleotide is a 2'-O-methylribonucleotide (Inoue et al., *Nucl. Acids Res.* 15:6131-6148 (1987)), or a chimeric RNA-DNA analogue (Inoue et al., *FEBS Lett.* 215:327-330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (*Nucl. Acids Res.* 16:3209 (1988)), methylphosphonate oligonucleotides can be prepared by use of controlled pore glass polymer supports (Sarin et al., *Proc. Natl. Acad. Sci. U.S.A.* 85:7448-7451 (1988)), etc.

While antisense nucleotides complementary to the DR4 coding region sequence could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, *Science* 247:1222-1225 (1990). While ribozymes that cleave mRNA at site specific recognition sequences can be used to destroy DR4 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585-591 (1988). There are numerous potential hammerhead ribozyme cleavage sites within the nucleotide sequence of DR4 (SEQ ID NO:2). Preferably, the ribozyme is engineered so that the cleavage recognition site is located near the 5' end of the DR4 mRNA; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express DR4 in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous DR4 messages and inhibit translation. Since ribozymes, unlike antisense molecules are catalytic, a lower intracellular concentration is required for efficiency.

Endogenous gene expression can also be reduced by inactivating or "knocking out" the DR4 gene and/or its promoter using targeted homologous recombination. (e.g., see Smithies et al., Nature 317:230-234 (1985); Thomas & Capecchi, Cell 51:503-512 (1987); Thompson et al., Cell 5:313-321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi (1987) and Thompson (1989), supra). However this approach can be routinely adapted for use in humans provided the recombinant DNA constructs are directly administered or targeted to the required site in vivo using appropriate viral vectors that will be apparent to those of skill in the art. The contents of each of the documents recited in this paragraph is herein incorporated by reference in its entirety.

Further antagonist according to the present invention include soluble forms of DR4, i.e., DR4 fragments that include the ligand binding domain from the extracellular region of the full length receptor. Such soluble forms of the receptor, which may be naturally occurring or synthetic, antagonize DR4 mediated signaling by competing with the cell surface DR4 for binding to TNF-family ligands. Thus, soluble forms of the receptor that include the ligand binding domain are novel cytokines capable of inhibiting apoptosis induced by TNF-family ligands. These are preferably expressed as dimers or trimers, since these have been shown to be superior to monomeric forms of soluble receptor as antagonists, e.g., IgGFc-TNF receptor family fusions. Other such cytokines are known in the art and include Fas B (a soluble form of the mouse Fas receptor) that acts physiologically to limit apoptosis induced by Fas ligand (Hughes, D. P. and Crispe, I. N., J. Exp. Med. 182:1395-1401 (1995)).

The experiments set forth in Example 5 demonstrates that DR4 is a death domain-containing molecule capable of triggering apoptosis which is important in the regulation of the immune system. In addition, the experiments set forth below demonstrate that DR4-induced apoptosis was blocked by the inhibitors of ICE-like proteases, CrmA and z-VAD-fink. Thus, inhibitors of ICE-like proteases, FADD-DN and FLICE-DN/MACHal C360S could also be used as antagonists for DR4 activity.

As discussed above, the term "antibody" (Ab) or "monoclonal antibody" (mAb) as used herein is meant to include intact molecules as well as fragments thereof (such as, for example, Fab and F(ab')$_2$ fragments) which are capable of binding an antigen. Fab and F (ab')$_2$ fragments lack the Fc fragment of intact antibody, clear more rapidly from the circulation, and may have less non-specific tissue binding of an intact antibody (Wahl et al., J Nucl. Med. 24:316-325 (1983)).

Antibodies according to the present invention may be prepared by any of a variety of methods using DR4 immunogens of the present invention. As indicated, such DR4 immunogens include the full length (complete) DR4 polypeptide (which may or may not include the leader sequence) and DR4 polypeptide fragments such as the ligand binding domain, the transmembrane domain, the intracellular domain and the death domain.

Proteins and other compounds which bind the DR4 domains are also candidate agonist and antagonist according to the present invention. Such binding compounds can be "captured" using the yeast two-hybrid system (Fields and Song, Nature 340:245-246 (1989)). A modified version of the yeast two-hybrid system has been described by Roger Brent and his colleagues (Gyuris, J. et al., Cell 75:791-803 (1993); Zervos, A. S. et al., Cell 72:223-232 (1993)). Preferably, the yeast two-hybrid system is used according to the present invention to capture compounds which bind to either the DR4 ligand binding domain or to the DR4 intracellular domain. Such compounds are good candidate agonist and antagonist of the present invention.

By a "TNF-family ligand" is intended naturally occurring, recombinant, and synthetic ligands that are capable of binding to a member of the TNF receptor family and inducing and/or blocking the ligand/receptor signaling pathway. Members of the TNF ligand family include, but are not limited to, DR4 ligands, TRAIL, TNF-α, TNF-β-∀, lymphotoxin-α (LT-α, also known as TNF-β), LT-β (found in complex heterotrimer LT-α2-β), FasL, VEGI (International Publication No. WO 96/14328), AIM-I (International Publication No. WO 97/33899), AIM-II (International Publication No. WO 97/34911), APRIL (J. Exp. Med. 188(6):1185-1190), endokine-alpha (International Publication No. WO 98/07880), neutrokine-alpha (International Publication No. WO 98/18921), CD40L, CD27L, CD30L, 4-IBBL, OX40L and nerve growth factor (NGF).

Gene Therapy

In a specific embodiment, nucleic acids comprising sequences encoding antibodies or functional derivatives thereof, are administered to treat, inhibit and/or prevent a disease or disorder associated with aberrant expression and/ or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11(5): 155-215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody nucleic acids (Koller and Smithies, 1989, Proc. Natl. Acad. Sci. USA 86:8932-8935; Zijlstra et al., 1989, Nature 342:435-438). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262:4429-4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932-8935; Zijlstra et al., 1989, Nature 342:435-438).

In a specific embodiment, viral vectors that contains nucleic acid sequences encoding an antibody of the invention are used. For example, a retroviral vector can be used (see Miller et al., 1993, Meth. Enzymol. 217:581-599). These retroviral vectors have been to delete retroviral sequences that are not necessary for packaging of the viral genome and integration into host cell DNA. The nucleic acid sequences encoding the antibody to be used in gene therapy are cloned into one or more vectors, which facilitates delivery of the gene into a patient. More detail about retroviral vectors can be found in Boesen et al., 1994, Biotherapy 6:291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499-503 present a review of adenovirus-based gene therapy. Bout et al., 1994, Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al., 1991, Science 252:431-434; Rosenfeld et al., 1992, Cell 68:143-155; Mastrangeli et al., 1993, J. Clin. Invest. 91:225-234; PCT Publication WO94/12649; and Wang et al., 1995, Gene Therapy 2:775-783. In a preferred embodiment, adenovirus vectors are used.

Adeno-associated virus (AAV) has also been proposed for use in gene therapy (Walsh et al., 1993, Proc. Soc. Exp. Biol. Med. 204:289-300; U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, 1993, *Meth. Enzymol.* 217:599-618; Cohen et al., 1993, *Meth. Enzymol.* 217:618-644; Cline, 1985, *Pharmac. Ther.* 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T-lymphocytes, B-lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see, e.g., PCT Publication WO 94/08598, dated Apr. 28, 1994; Stemple and Anderson, 1992, *Cell* 71:973-985; Rheinwald, 1980, *Meth. Cell Bio.* 21A:229; and Pittelkow and Scott, 1986, *Mayo Clinic Proc.* 61:771).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Modes of Administration

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

The agonist or antagonists described herein can be administered in vitro, ex vivo, or in vivo to cells which express the receptor of the present invention. By administration of an "effective amount" of an agonist or antagonist is intended an amount of the compound that is sufficient to enhance or inhibit a cellular response to a TNF-family ligand and include polypeptides. In particular, by administration of an "effective amount" of an agonist or antagonists is intended an amount effective to enhance or inhibit DR4 mediated apoptosis. Of course, where apoptosis is to be enhanced, an agonist according to the present invention can be co-administered with a TNF-family ligand. One of ordinary skill will appreciate that effective amounts of an agonist or antagonist can be determined empirically and may be employed in pure form or in pharmaceutically acceptable salt, ester or prodrug form. The agonist or antagonist may be administered in compositions in combination with one or more pharmaceutically acceptable excipients.

It will be understood that, when administered to a human patient, the total daily usage of the compounds and compositions of the present invention will be decided by the attending physician within the scope of sound medical judgment. The specific therapeutically effective dose level for any particular patient will depend upon factors well known in the medical arts.

As a general proposition, the total pharmaceutically effective amount of DR4 polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the DR4 agonists or antagonists is typically administered at a dose rate of about 1 µg/kg/hour to about 50 µg/kg/hour, either by 1-4 injections per day or by continuous subcutaneous infusions, for example, using a mini-pump. An intravenous bag solution may also be employed.

Dosaging may also be arranged in a patient specific manner to provide a predetermined concentration of an agonist or antagonist in the blood, as determined by the RIA technique. Thus patient dosaging may be adjusted to achieve regular on-going trough blood levels, as measured by RIA, on the order of from 50 to 1000 ng/ml, preferably 150 to 500 ng/ml.

Pharmaceutical compositions of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use.

In addition to soluble DR4 polypeptides, DR4 polypeptide containing the transmembrane region can also be used when appropriately solubilized by including detergents, such as CHAPS or NP-40, with buffer.

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

The present invention also provides pharmaceutical compositions. Such compositions comprise a therapeutically effective amount of a compound, and a pharmaceutically acceptable carrier. In particular embodiments, pharmaceutical compositions are provided comprising an agonist or antagonist and a pharmaceutically acceptable carrier or excipient, which may be administered orally, rectally, parenterally, intracisternally, intravaginally, intraperitoneally, topically (as by powders, ointments, drops or transdermal patch), bucally, or as an oral or nasal spray. Importantly, by co-administering an agonist and a TNF-family ligand, clinical side effects can be reduced by using lower doses of both the ligand and the agonist. It will be understood that the agonist can be "co-administered" either before, after, or simultaneously with the TNF-family ligand, depending on the exigencies of a particular therapeutic application. By "pharmaceutically acceptable carrier" is meant a non-toxic solid, semisolid or liquid filler, diluent, encapsulating material or formulation auxiliary of any type. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "parenteral" as used herein refers to modes of administration which include intravenous, intramuscular, intraperitoneal, intrasternal, subcutaneous and intraarticular injection and infusion. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

As indicated above, the compositions of the invention may be administered alone or in combination with other therapeutic agents. Therapeutic agents that may be administered in combination with the compositions of the invention, include but are not limited to, other members of the TNF family, chemotherapeutic agents, antibiotics, steroidal and non-steroidal anti-inflammatories, conventional immunotherapeutic agents, cytokines, chemokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the compositions of the invention are administered in combination with other members of the TNF family. TNF, TNF-related or TNF-like molecules that may be administered with the compositions of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), (International Publication No. WO 96/14328), TNF-(-∀, TNF-(-∃ (International Publication No. WO 00/08139), TRAIL, AIM-II (International Publication No. WO 97/34911), APRIL (J. Exp. Med. 188(6):1185-1190), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), and TR12, AIM-I (International Publication No. WO 97/33899), and soluble forms CD154, CD70, and CD153.

In another embodiment, the compositions of the invention are administered in combination with CD40 ligand (CD40L), a soluble form of CD40L (e.g., AVRENDTA), biologically active fragments, variants, or derivatives of CD40L, anti-CD40L antibodies (e.g., agonistic or antagonistic antibodies), and/or anti-CD40 antibodies (e.g., agonistic or antagonistic antibodies).

In yet another embodiment, the compositions of the invention are administered in combination with one, two, three, four, five, or more of the following compositions: tacrolimus (Fujisawa), thalidomide (e.g., Celgene), anti-Tac(Fv)-PE40 (e.g., Protein Design Labs), inolimomab (Biotest), MAK-195F (Knoll), ASM-981 (Novartis), interleukin-1 receptor (e.g., Immunex), interleukin-4 receptor (e.g., Immunex), ICM3 (ICOS), BMS-188667 (Bristol-Myers Squibb), anti-TNF Ab (e.g., Therapeutic antibodies), CG-1088 (Celgene), anti-B7 monoclonal antibody (e.g., Innogetics), MEDI-507 (BioTransplant), ABX-CBL (Abgenix).

According to the invention, a patient susceptible to both Fas ligand (Fas-L) mediated and TRAIL mediated cell death may be treated with both an agent that inhibits TRAIL/TRAIL-R interactions and an agent that inhibits Fas-L/Fas interactions. Suitable agents for blocking binding of Fas-L to Fas include, but are not limited to, soluble Fas polypeptides; oligomeric forms of soluble Fas polypeptides (e.g., dimers of sFas/Fc); anti-Fas antibodies that bind Fas without transducing the biological signal that results in apoptosis; anti-Fas-L antibodies that block binding of Fas-L to Fas; and muteins of Fas-L that bind Fas but do not transduce the biological signal that results in apoptosis. Preferably, the antibodies employed according to this method are monoclonal antibodies. Examples of suitable agents for blocking Fas-L/Fas interactions, including blocking anti-Fas monoclonal antibodies, are described in WO 95/10540, hereby incorporated by reference.

In certain embodiments, compositions of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the compositions of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lanivudine). Non-nucleoside reverse transcriptase inhibitors that may be administered in combination with the compositions of the invention, include, but are not limited to, VIRAMUNE™ (nevirapine), RESCRIPTOR™ (delavirdine), and SUSTIVA™ (efavirenz). Protease inhibitors that may be administered in combination with the compositions of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with compositions of the invention to treat AIDS and/or to prevent or treat HIV infection.

In other embodiments, compositions of the invention may be administered in combination with anti-opportunistic infection agents. Anti-opportunistic agents that may be administered in combination with the compositions of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, compositions of the invention are used in any combination with TRIMETHOPRIM-SULFAMETHOXAZOLE™, DAPSONE™, PENTAMIDINE™, and/or ATOVAQUONE™ to prophylactically treat and/or prevent an opportunistic *Pneumocystis carinii* pneumonia infection. In another specific embodiment, compositions of the invention are used in any combination with ISONIAZID™, RIFAMPIN™, PYRAZINAMIDE™, and/or ETHAMBUTOL™ to prophylactically treat and/or prevent an opportunistic *Mycobacterium avium* complex infection. In another specific embodiment, compositions of the invention are used in any combination with RIFABUTIN™, CLARITHROMYCIN™, and/or AZITHROMYCIN™ to prophylactically treat and/or prevent an opportunistic *Mycobacterium tuberculosis* infection. In another specific embodiment, compositions of the invention are used in any combination with GANCICLOVIR™, FOSCARNET™, and/or CIDOFOVIR™ to prophylactically treat and/or prevent an opportunistic cytomegalovirus infection. In another specific embodiment, compositions of the invention are used in any combination with FLUCONAZOLE™, ITRACONAZOLE™, and/or KETOCONAZOLE™ to prophylactically treat and/or prevent an opportunistic fungal infection. In another specific embodiment, compositions of the invention are used in any combination with ACYCLOVIR™ and/or FAMCICOLVIR™ to prophylactically treat and/or prevent an opportunistic herpes simplex virus type I and/or type II infection. In another specific embodiment, compositions of the invention are used in any combination with PYRIMETHAMINE™ and/or LEUCOVORIN™ to prophylactically treat and/or prevent an opportunistic *Toxoplasma gondii* infection. In another specific embodiment, compositions of the invention are used in any combination with LEUCOVORIN™ and/or NEUPOGEN™ to prophylactically treat and/or prevent an opportunistic bacterial infection.

In a further embodiment, the compositions of the invention are administered in combination with an antiviral agent. Antiviral agents that may be administered with the compositions of the invention include, but are not limited to, acyclovir, ribavirin, amantadine, and remantidine.

In a further embodiment, the compositions of the invention are administered in combination with an antibiotic agent. Antibiotic agents that may be administered with the compositions of the invention include, but are not limited to, amoxicillin, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the compositions of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T-cells.

In specific embodiments, compositions of the invention are administered in combination with immunosuppressants. Immunosuppressants preparations that may be administered with the compositions of the invention include, but are not limited to, ORTHOCLONE™ (OKT3), SANDIMMUNE™/ NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In an additional embodiment, compositions of the invention are administered alone or in combination with one or more intravenous immune globulin preparations. Intravenous immune globulin preparations that may be administered with the compositions of the invention include, but not limited to, GAMMAR™, IVEEGAM™, SANDOGLOBULIN™, GAMMAGARD S/D™, and GAMIMUNE™. In a specific embodiment, compositions of the invention are administered in combination with intravenous immune globulin preparations in transplantation therapy (e.g., bone marrow transplant).

In a further embodiment, the compositions of the invention are administered in combination with an antibiotic agent. Antibiotic agents that may be administered with the compositions of the invention include, but are not limited to, tetracycline, metronidazole, amoxicillin, beta-lactamases, aminoglycosides, macrolides, quinolones, fluoroquinolones, cephalosporins, erythromycin, ciprofloxacin, and streptomycin.

In an additional embodiment, the compositions of the invention are administered alone or in combination with an anti-inflammatory agent. Anti-inflammatory agents that may be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In one embodiment, the compositions of the invention are administered in combination with steroid therapy. Steroids that may be administered in combination with the compositions of the invention, include, but are not limited to, oral corticosteroids, prednisone, and methylprednisolone (e.g., IV methylprednisolone). In a specific embodiment, compositions of the invention are administered in combination with prednisone. In a further specific embodiment, the compositions of the invention are administered in combination with prednisone and an immunosuppressive agent. Immunosuppressive agents that may be administered with the compositions of the invention and prednisone are those described herein, and include, but are not limited to, azathioprine, cyclophosphamide, and cyclophosphamide IV. In a another specific embodiment, compositions of the invention are administered in combination with methylprednisolone. In a further specific embodiment, the compositions of the invention are administered in combination with methylprednisolone and an immunosuppressive agent. Immunosuppressive agents that may be administered with the compositions of the invention and methylprednisolone are those described herein, and include, but are not limited to, azathioprine, cyclophosphamide, and cyclophosphamide IV.

In another embodiment, the compositions of the invention are administered in combination with an antimalarial. Antimalarials that may be administered with the compositions of the invention include, but are not limited to, hydroxychloroquine, chloroquine, and/or quinacrine.

In yet another embodiment, the compositions of the invention are administered in combination with an NSAID.

In a nonexclusive embodiment, the compositions of the invention are administered in combination with one, two, three, four, five, ten, or more of the following drugs: NRD-101 (Hoechst Marion Roussel), diclofenac (Dimethaid), oxaprozin potassium (Monsanto), mecasermin (Chiron), T-614 (Toyama), pemetrexed disodium (Eli Lilly), atreleuton (Abbott), valdecoxib (Monsanto), eltenac (Byk Gulden), campath, AGM-1470 (Takeda), CDP-571 (Celltech Chiroscience), CM-101 (CarboMed), ML-3000 (Merckle), CB-2431 (KS Biomedix), CBF-BS2 (KS Biomedix), IL-1 Ra gene therapy (Valentis), JTE-522 (Japan Tobacco), paclitaxel (Angiotech), DW-166HC (Dong Wha), darbufelone mesylate (Warner-Lambert), soluble TNF receptor 1 (synergen; Amgen), IPR-6001 (Institute for Pharmaceutical Research), trocade (Hoffman-La Roche), EF-5 (Scotia Pharmaceuticals), BIIL-284 (Boehringer Ingelheim), BIIF-1149 (Boehringer Ingelheim), LeukoVax (Inflammatics), MK-663 (Merck), ST-1482 (Sigma-Tau), and butixocort propionate (WarnerLambert).

In yet another embodiment, the compositions of the invention are administered in combination with one, two, three, four, five or more of the following drugs: methotrexate, sulfasalazine, sodium aurothiomalate, auranofin, cyclosporine, penicillamine, azathioprine, an antimalarial drug (e.g., as described herein), cyclophosphamide, chlorambucil, gold, ENBREL™ (Etanercept), anti-TNF antibody, and prednisolone. In a more preferred embodiment, the compositions of the invention are administered in combination with an antimalarial, methotrexate, anti-TNF antibody, ENBREL™ and/ or suflasalazine.

In one embodiment, the compositions of the invention are administered in combination with methotrexate. In another embodiment, the compositions of the invention are administered in combination with anti-TNF antibody. In another embodiment, the compositions of the invention are administered in combination with methotrexate and anti-TNF antibody. In another embodiment, the compositions of the invention are administered in combination with suflasalazine. In another specific embodiment, the compositions of the invention are administered in combination with methotrexate, anti-TNF antibody, and suflasalazine. In another embodiment, the compositions of the invention are administered in combination ENBREL™. In another embodiment, the compositions of the invention are administered in combination with ENBREL™ and methotrexate. In another embodiment, the compositions of the invention are administered in combination with ENBREL™, methotrexate and suflasalazine. In another embodiment, the compositions of the invention are administered in combination with ENBREL™, methotrexate and suflasalazine. In other embodiments, one or more antimalarials is combined with one of the above-recited combinations. In a specific embodiment, the compositions of the invention are administered in combination with an antimalarial (e.g., hydroxychloroquine), ENBREL™, methotrexate and suflasalazine. In another specific embodiment, the compositions of the invention are administered in combination with an antimalarial (e.g., hydroxychloroquine), sulfasalazine, anti-TNF antibody, and methotrexate.

In another embodiment, compositions of the invention are administered in combination with a chemotherapeutic agent.

Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); triterpenoids (e.g. oleanic acid and urosolic acid); cyclohexamide; casein kinase inhibitors; and others (e.g., dicarbazine, asparaginase, mitotane, vincristine sulfate, vinblastine sulfate, and etoposide).

In specific embodiments, compositions of the present invention are administered in combination with one or more chemotherapeutic agents including, but not limited to, 81C6 (Anti-tenascin monoclonal antibody), 2-chlorodeoxyadenosine, A007 (4-4'-dihydroxybenzophenone-2,4-dinitrophenylhydrazone), Abarelix® (Abarelix-Depot-M®, PPI-149, R-3827); Abiraterone Acetate® (CB-7598, CB-7630), ABT-627 (ET-1 inhibitor), ABX-EGF (anti-EGFr MAb), Acetyldinaline (CI-994, GOE-5549, GOR-5549, PD-130636), AG-2034 (AG-2024, AG-2032, GARFT [glycinamide ribonucleoside transformylase] inhibitor), Alanosine, Aldesleukin (IL-2, Proleukin®), Alemtuzumab® (Campath®), Alitretinoin (Panretin®, LGN-1057), Allopurinol (Aloprim®, Zyloprim®), Altretamine (Hexylen®, hexamethylmelamine, Hexastat®), Amifostine (Ethyol®), Aminocamptothecin (9-AC, 9-Aminocamptothecin, NSC 603071), Aminoglutethimide (Cytadren®), Aminolevulinic acid (Levulan®, Kerastick®), Aminopterin, Amsacrine, Anastrozole (Arimidex®), Angiostatin, Annamycin (AR-522, annamycin LF, Aronex®), Anti-idiotype therapy (BsAb), Anti-CD19/CD3 MAb (anti-CD19/CD3 scFv, anti-NHL MAb), APC-8015 (Provenge®, Dendritic cell therapy), Aplidine (Aplidin®, Aplidina®), Arabinosylguanine (Ara-G, GW506U78, Nelzarabine®, Compound 506U78), Arsenic trioxide (Trisenox®, ATO, Atrivex®), Avorelin®(Meterelin®, MF-6001, EP-23904), B43-Genistein (anti-CD19 Ab/genistein conjugate), B43-PAP (anti-CD19 Ab/pokeweed antiviral protein conjugate), B7 antibody conjugates, BAY 43-9006 (Raf kinase inhibitor), BBR 3464, Betathine (Beta-LT), Bevacizumab® (Anti-VEGF monoclonal antibody, rhuMAb-VEGF), Bexarotene (Targretin®, LGD1069), BIBH-1 (Anti-FAP MAb), BIBX-1382, Biclutamide (Casodex®), Biricodar dicitrate (Incel®, Incel MDR Inhibitor), Bleomycin (Blenoxane®), BLP-25 (MUC-1 peptide), BLyS antagonists, BMS-214662 (BMS-192331, BMS-193269, BMS-206635), BNP-1350 (BNPI-1100, Karenitecins), Boronated Protoporphyrin Compound (PDIT, Photodynamic Immunotherapy), Bryostatin-1 (Bryostatin®, BMY-45618, NSC-339555), Budesonide (Rhinocort®), Busulfan (Busulfex®, Mylaran®), C225 (IMC-225, EGFR inhibitor, Anti-EGFr MAb, Cetuximab®), C242-DM1 (huC242-DM1), Cabergoline (Dostinex®), Capecitabine (Xeloda®, Doxifluridine®, oral 5-FU), Carbendazin® (FB-642), Carboplatin (Paraplatin®, CBDCA), Carboxyamidotriazole (NSC 609974, CAI, L-651582), Carmustine (DTI-015, BCNU, BiCNU, Gliadel Wafer®), CC49-zeta gene therapy, CEAcide® (Labetuzumab®, Anti-CEA monoclonal antibody, hMN-14), CeaVac® (MAb 3H1), Celecoxib (Celebrex®), CEP-701 (KT-5555), Cereport® (Lobradimil®, RMP-7), Chlorambucil (Leukeran®), CHML (Cytotropic Heterogeneous Molecular Lipids), Cholecaliferol, CI-1033 (Pan-erbB RTK inhibitor), Cilengitide (EMD-121974, integrin alphavbeta3 antagonist), Cisplatin (Platinol®, CDDP), Cisplatin-epinephrine gel (IntraDose®, FocaCist®), Cisplatin-liposomal (SPI-077), 9-cis retinoic acid (9-cRA), Cladribine (2-CdA, Leustatin®), Clofarabine (chloro-fluoro-araA), Clonadine hydrochloride (Duraclon®), CMB-401 (Anti-PEM MAb/calicheamycin), CMT-3 (COL-3, Metastat®), Cordycepin, Cotara® (chTNT-1/B, [$^{131}$I]-chTNT-1/B), CN-706, CP-358774 (Tarceva®, OSI-774, EGFR inhibitor), CP-609754, CP IL-4-toxin (IL-4 fusion toxin), CS-682, CT-2584 (Apra®, CT-2583, CT-2586, CT-3536), CTP-37 (Avicine®, hCG blocking vaccine), Cyclophosphamide (Cytoxan®, Neosar®, CTX), Cytarabine (Cytosar-U®, ara-C, cytosine arabinoside, DepoCyt®), D-limonene, DAB389-EGF (EGF fusion toxin), Dacarbazine (DTIC), Daclizumab® (Zenapax®), Dactinomycin (Cosmegen®), Daunomycin (Daunorubicin®, Cerubidine®), Daunorubicin (DaunoXome®, Daunorubicin®, Cerubidine®), DeaVac® (CEA anti-idiotype vaccine), Decitabine (5-aza-2'-deoxyytidine), Declopramide (Oxi-104), Denileukin diftitox (Ontak®), Depsipeptide (FR901228, FK228), Dexamethasone (Decadron®), Dexrazoxane (Zinecard®), Diethylnorspermine (DENSPM), Diethylstilbestrol (DES), Dihydro-5-azacytidine, Docetaxel (Taxotere®, Taxane®), Dolasetron mesylate (Anzemet®), Dolastatin-10 (DOLA-10, NSC-376128), Doxorubicin (Adriamycin®, Doxil®, Rubex®), DPPE, DX-8951f (DX-8951), Edatrexate, EGF-P64k Vaccine, Elliott's B Solution®, EMD-121974, Endostatin, Eniluracil (776c85), EO9 (EO1, EO4, EO68, EO70, EO72), Epirubicin (Ellence®, EPI, 4' epi-doxorubicin), Epratuzumab® (Lymphocide®, humanized anti-CD22, HAT), Erythropoietin (EPO®, Epogen®, Procrit®), Estramustine (Emcyt®), Etanidazole (Radinyl®), Etoposide phosphate (Etopophos®), Etoposide (VP-16, Vepesid®), Exemestane (Aromasin®, Nikidess®), Exetecan mesylate (DX-8951, DX-8951f), Exisulind (SAAND, Aptosyn®, cGMP-PDE2 and 5 inhibitor), F19 (Anti-FAP monoclonal antibody, iodinated anti-FAP MAb), Fadrozole (Afema®, Fadrozole hydrochloride, Arensin®), Fenretinide® (4HPR), Fentanyl citrate (Actiq®), Filgrastim (Neupogen®, G-CSF), FK-317 (FR-157471, FR-70496), Flavopiridol (HMR-1275), Fly3/flk2 ligand (Mobista®), Fluasterone, Fludarabine (Fludara®, FAMP), Fludeoxyglucose (F-18®), Fluorouracil (5-FU, Adrucil®, Fluoroplex®, Efudex®), Flutamide (Eulexin®), FMdC (KW-2331, MDL-101731), Formestane (Lentaron®), Fotemustine (Muphoran®, Mustophoran®), FUDR (Floxuridine®), Fulvestrant (Faslodex®), G3139 (Genasense®, GentaAnticode®, Bcl-2 antisense), Gadolinium texaphyrin (Motexafin gadolinium, Gd-Tex®, Xcytrin®), Galarubicin hydrochloride (DA-125), GBC-590, Gastrimmune® (Anti-gastrin-17 immunogen, anti-g17), Gemcitabine (Gemto®, Gemzar®), Gentuzumab-ozogamicin (Mylotarg®), GL331, Globo H hexasaccharide (Globo H-KLH®), Glufosfamide® (β-D-glucosyl-isofosfamide mustard, D19575, INN), Goserelin acetate (Zoladex®), Granisetron (Xcytrin®), GVAX (GM-CSF gene therapy), Her-2/Neu vaccine, Herceptin® (Trastuzumab®, Anti-HER-2 monoclonal antibody, Anti-EGFR-2 MAb), HSPPC-96 (HSP cancer vaccine, gp96 heat shock protein-peptide complex), Hu1D10 (anti-HLA-DR MAb, SMART ID10), HumaLYM (anti-CD20 MAb), Hydrocortisone, Hydroxyurea (Hydrea®), Hypericin®(VIM-Rxyn®), 1-131 Lipidiol®, Ibritumomab® tiuxetan (Zevalin®), Idarubicin (Idamycin®, DMDR, IDA), Ifosfamide (IFEX®), Imatinib mesylate (STI-571, Imatinib®, Glivec®, Gleevec®, Ab1 tyrosine kinase inhibitor), INGN-101 (p53 gene therapy/retrovirus), INGN-201 (p53 gene therapy/adenovirus), Interferon alpha (Alfaferone®, Alpha-IF®), Interferon alpha 2a (Intron A®), Interferon gamma (Gamma-interferon, Gamma 100®, Gamma-IF), Interleukin-2 (ProleiukinR®), Intoplicine (RP 60475), Irinotecan (Camptosar®, CPT-11, Topotecin®, CaptoCPT-1), Irofulven (MGI-114, Ivofulvan, Acylfulvene analogue), ISIS-2053 (PKC-alpha antisense), ISIS-2503 (Ras antisense), ISIS-3521 (PKC-alpha antisense), ISIS-5132 (K-ras/raf antisense), Isotretinoin (13-CRA, 13-cis retinoic acid, Accutane®V), Ketoconazole (Nizoral®), KRN-8602 (MX, MY-5, NSC-619003, MX-2), L-778123 (Ras inhibitors), L-asparaginase (Elspar®, Crastinin®, Asparaginase Medac®, Kidrolase®), Leflunomide (SU-101, SU-0200), Letrozole (Femara®), Leucovorin (Leucovorin®, Welicovorin®), Leuprolide acetate (Viadur®, Lupron®, Leuprogel®, Eligard®), Leuvectin® (cytofectin+IL-2 gene, IL-2 gene therapy), Levamisole (Ergamisol®), Liarozole (Liazal, Liazol, R-75251, R-85246, Ro-85264), Lmb-2 immunotoxin (anti-CD25 recombinant immuno toxin, anti-Tac(Fv)-PE38), Lometrexol (T-64, T-904064), Lomustine (CCNU®, CeeNU®), LY-335979, Lym-1 (131-1 LYM-1), Lymphoma vaccine (Genitope), Mannan-MUC1 vaccine, Marimastat® (BB-2516, TA-2516, MMP inhibitor), MDX-447 (MDX-220, BAB-447, EMD-82633, H-447, anti-EGFr/FcGammaR1r), Mechlorethamine (Nitrogen Mustard, $HN_2$, Mustargen®), Megestrol acetate (Megace®, Pallace®), Melphalan (L-PAM, Alkeran®, Phenylalanine mustard), Mercaptopurine (6-mercaptopurine, 6-MP), Mesna (Mesnex®), Methotrexate® (MTX, Mexate®, Folex®), Methoxsalen (Uvadex®), 2-Methoxyestradiol (2-ME, 2-ME2), Methylprednisolone (Solumedrol®), Methyltestosterone (Android-10®, Testred®, Virilon®), MGV, Mitomycin C (Mitomycin®, Mutamycin®, Mito Extra®), Mitoxantrone (Novantrone®, DHAD), Mitumomab® (BEC-2, EMD-60205), Mivobulin isethionate (CI-980), MN-14 (Anti-CEA immunoradiotherapy, $^{131}$I-MN-14, $^{188}$Re-MN-14), Motexafin Lutetium (Lutrin®, Optrin®, Lu-Tex®, lutetium texaphyrin, Lucyn®, Antrin®), MPV-2213ad (Finrozole®), MS-209, Muc-1 vaccine, NaPro Paclitaxel, Nelarabine (Compound 506, U78), Neovastat® (AE-941, MMP inhibitor), Neugene compounds (Oncomyc-NG, Resten-NG, myc antisense), Nilutamide (Nilandron®), NovoMAb-G2 scFv (NovoMAb-G2 IgM), NPI-0052 (proteasome inhibitor), 06-benzylguanine (BG, Procept®), Octreotide acetate (Sandostatin LAR® Depot), Odansetron (Zofran®), Onconase (Ranpimase®), OncoVAX-CL, OncoVAX-CL Jenner (GA-733-2 vaccine), OncoVAX-P (OncoVAX-PrPSA), Onyx-015 (p53 gene therapy), Oprelvekin (Neumage®), Orzel (Tegafur+Uracil+Leucovorin), Oxaliplatin (Eloxatine®, Eloxatin®), Pacis® (BCG, live), Paclitaxel (Paxene®, Taxol®), Paclitaxel-DHA (Taxoprexin®), Pamidronate (Aredia®), PC SPES, Pegademase (Adagen®, Pegademase bovine), Pegaspargase®(Oncospar®), Peldesine (BCX-34, PNP inhibitor), Pemetrexed disodium (Alimta®, MTA, multitargeted antifolate, LY 231514), Pentostatin (Nipent®, 2-deoxycoformycin), Perfosfamide (4-hydroperoxycyclophosphamide, 4-HC), Perillyl alcohol (perilla alcohol, perillic alcohol, perillol, NSC-641066), Phenylbutyrate, Pirarubicin (THP), Pivaloyloxymethyl butyrate (AN-9, Pivanex®), Porfimer sodium (Photofrin®), Prednisone, Prinomastat® (AG-3340, MMP inhibitor), Procarbazine (Matulane®), PROSTVAC, Providence Portland Medical Center Breast Cancer Vaccine, PS-341 (LDP-341, 26S proteasome inhibitor), PSMA MAb (Prostate Specific Membrane Antigen monoclonal antibody), Pyrazoloacridine (NSC-366140, PD-115934), Quinine, R115777 (Zamestra®), Raloxifene hydrochloride (Evista®, Keoxifene hydrochloride), Raltitrexed (Tomudex®, ZD-1694), Rebeccamycin, Retinoic acid, R-flurbiprofen (Flurizan®, E-7869, MPC-7869), RFS-2000 (9-nitrocamptothecan, 9-NC, Rubitecan®), Rituximab®(Rituxan®, anti-CD20 MAb), RSR-13 (GSJ-61), Satraplatin (BMS-182751, JM-216), SCH 6636, SCH-66336, Sizofilan® (SPG, Sizofuran®, Schizophyllan®, Sonifilan®), SKI-2053R(NSC-D644591), Sobuzoxane (MST-16, Perazolin®), Squalamine (MSI-1256F), SR-49059 (vasopressin receptor inhibitor, V1a), Streptozocin (Zanosar®), SU5416 (Semaxanib®, VEGF inhibitor), SU6668 (PDGF-TK inhibitor), T-67 (T-138067, T-607), Talc (Sclerosol®), Tamoxifen (Nolvadex®), Taurolidine (Taurolin®), Temozolamide (Temodar®, NSC 362856), Teniposide (VM-26, Vumon®)), TER-286, Testosterone (Andro®, Androderm®, Testoderm TTS®, Testoderm®, Depo-Testosterone®, Androgel®, depoAndro®), Tf-CRM107 (Transferrin-CRM-107), Thalidomide and thalidomide analogs, including but not limited to, lenalidomide (CC-5013, REVLIMID®) and CC-4047 (AC-TIMID™), Theratope, Thioguanine (6-thioguanine, 6-TG), Thiotepa (triethylenethiophosphaoramide, Thioplex®), Thymosin alpha I (Zadaxin®, Thymalfasin®), Tiazofurin (Thiazole®), Tirapazamine (SR-259075, SR-4233, Tirazone®, Win-59075), TNP-470 (AGM-1470, Fumagillin), Tocladesine (8-Cl-cAMP), Topotecan (Hycamtin®, SK&F-104864, NSC-609699, Evotopin®), Toremifene (Estrimex®, Fareston®), Tositumomab®g (Bexxar®), Tretinoin (Retin-A®, Atragen®, ATRA, Vesanoid®), TriAb® (anti-idiotype antibody immune stimulator), Trilostane (Modrefen®), Triptorelin pamoate (Trelstar Depot®, Decapeptyl®), Trimetrexate (Neutrexin®), Troxacitabine (BCH-204, BCH-4556, Troxatyl®), TS-1, UCN-01 (7-hydroxystaurosporine), Valrubicin (Valstar®), Valspodar (PSC 833), Vapreotide® (BMY-41606), Vaxid (B-cell lymphoma DNA vaccine), Vinblastine (Velban®V, VLB), Vincristine (Oncovin®, Onco TCS®, VCR, Leurocristine®), Vindesine (Eldisine®g, Fildesin®), Vinorelbine (Navelbine®), Vitaxin® (LM-609, integrin alphavbeta3 antagonist MAb), WF10 (macrophage regulator), WHI-P131, WT1 Vaccine, XR-5000 (DACA), XR-9576 (XR-9351, P-glycoprotein/MDR inhibitor), ZD-9331, ZD-1839 (IRESSA®), and Zoledronate (Zometa®).

In a specific embodiment, compositions of the invention are administered in combination with CHOP (cyclophosphamide, doxorubicin, vincristine, and prednisone) or any combination of the components of CHOP. In another embodiment, compositions of the invention are administered in combination with Rituximab. In a further embodiment, compositions of the invention are administered with Rituximab and CHOP, or Rituximab and any combination of the components of CHOP.

In further specific embodiments, compositions of the present invention are administered in combination with one or more combinations of chemotherapeutic agents including, but not limited to, 9-aminocamptothecin+G-CSF, Adriamycin®+Blenoxane+Vinblastine+Dacarbazine (ABVD), BCNU (Carmustine)+Etoposide+Ara-C (Cytarabine)+Melphalen (BEAM), Bevacizumab®+Leucovorin, Bleomycin+Etoposide+Platinol® (Cisplatin) (BEP), Bleomycin+Etoposide+Adriamycin+Cyclophosphamide+Vincristine+Procarbazine+Prednisone (BEACOPP), Bryostatin+Vincristine, Busulfan+Melphalan, Carboplatin+Cereport®, Carboplatin+Cyclophosphamide, Carboplatin+Paclitaxel, Carboplatin+Etoposide+Bleomycin (CEB), Carboplatin+Etoposide+Thiotepa, Cisplatin+Cyclophosphamide, Cisplatin+Docetaxel, Cisplatin+Doxorubicin, Cisplatin+Etoposide, Cisplatin+Gemcitabine, Cisplatin+Interferon alpha, Cisplatin+Irinotecan, Cisplatin+Paclitaxel, Cisplatin+Teniposide, Cisplatin+Vinblastine, Cisplatin+Vindesine, Cisplatin+Vinorelbine, Cisplatin+Cytarabine+Ifosfamide, Cisplatin+Ifosfamide+Vinblastine, Cisplatin+Vinblastine+Mitomycin C, Cisplatin+Vincristine+Fluorouracil, Cisplatin+Vincristine+Lomustine, Cisplatin+Vinorelbine+Gemcitabine, Cisplatin+Carmustine+Dacarbazine+Tamoxifen, Cisplatin+Cyclophosphamide+Etoposide+Vincristine, Cisplatin (Platinol®)+Oncovin®+Doxorubicin (Adriamycin®)+Etoposide (CODE), Cisplatin+Cytarabine+Ifosfamide+Etoposide+Methotrexate, Cyclophosphamide+Adriamycin® (Doxorubicin), Cyclophosphamide+Melphalan, Cyclophosphamide+SCH 6636, Cyclophosphamide+Adriamycin®+Cisplatin (Platinol®) (CAP), Cyclophosphamide+Adriamycing+Vincristine (CAV), Cyclophosphamide+Doxorubicin+Teniposide+Prednisone, Cyclophosphamide+Doxorubicin+Teniposide+Prednisone+Interferon alpha, Cyclophosphamide+Epirubicin+Cisplatin (Platinol®) (CEP), Cyclophosphamide+Epirubicin+Fluorouracil, Cyclophosphamide+Methotrexate+Fluoruracil (CMF), Cyclophosphamide+Methotrexate+Vincristine (CMV), Cyclophosphamide+Adriamycin®+Methotrexate+Fluorouracil (CAMF), Cyclophosphamide+Adriamycing+Methotrexate+Procarbazine (CAMP), Cyclophosphamide+Adriamycin®+Vincristine+Etoposide (CAV-E), Cyclophosphamide+Adriamycin®+Vincristine+Prednisone (CHOP), Cyclophosphamide+Novantrone® (Mitoxantrone)+Vincristine (Oncovirin)+Prednisone (CNOP), Cyclophosphamide+Adriamycin®+Vincristine+Prednisone+Rituximab (CHOP+Rituximab), Cyclophosphamide+Adriamycing+Vincristine+Teniposide (CAV-T), Cyclophosphamide+Adriamycin®&+Vincristine alternating with Platinol®+Etoposide (CAV/PE), Cyclophosphamide+BCNU (Carmustine)+VP-16 (Etoposide) (CBV), Cyclophosphamide+Vincristine+Prednisone (CVP), Cyclophosphamide+Oncovin®+Methotrexate+Fluorouracil (COMF), Cytarabine+Methotrexate, Cytarabine+Bleomycin+Vincristine+Methotrexate (CytaBOM), Dactinomycin+Vincristine, Dexamethasone+Cytarabine+Cisplatin (DHAP), Dexamethasone+Ifosfamide+Cisplatin+Etoposide (DICE), Docetaxel+Gemcitabine, Docetaxel+Vinorelbine, Doxorubicin+Vinblastine+Mechlorethamine+Vincristine+Bleomycin+Etoposide+Prednisone (Stanford V), Epirubicin+Gemcitabine, Estramustine+Docetaxel, Estramustine+Navelbine, Estramustine+Paclitaxel, Estramustine+Vinblastine, Etoposide (Vepesid®)+Ifosfamide+Cisplatin (Platinol®) (VIP), Etoposide+Vinblastine+Adriamycin (EVA), Etoposide (Vepesid®)+Ifosfamide+Cisplatin+Epirubicin (VIC-E), Etoposide+Methylprednisone+Cytarabine+Cisplatin (ESHAP), Etoposide+Prednisone+Ifosfamide+Cisplatin (EPIC), Fludarabine+Mitoxantrone+Dexamethasone (FMD), Fludarabine+Dexamethasone+Cytarabine (ara-C)+Cisplatin (Platinol™) (FluDAP), Fluorouracil+Bevacizumab®, Fluorouracil+CeaVac®, Fluorouracil+Leucovorin, Fluorouracil+Levamisole, Fluorouracil+Oxaliplatin, Fluorouracil+Raltitrexed, Fluorouracil+SCH 6636, Fluorouracil+Trimetrexate, Fluorouracil+Leucovorin+Bevacizumab®, Fluorouracil+Leucovorin+Oxaliplatin, Fluorouracil+Leucovorin+Trimetrexate, Fluorouracil+Oncovin®+Mitomycin C (FOMi), Hydrazine+Adriamycin®+Methotrexate (HAM), Ifosfamide+Docetaxel, Ifosfamide+Etoposide, Ifosfamide+Gemcitabine, Ifosfamide+Paclitaxel, Ifosfamide+Vinorelbine, Ifosfamide+Carboplatin+Etoposide (ICE), Ifosfamide+Cisplatin+Doxorubicin, Irinotecan+C225 (Cetuximab®), Irinotecan+Docetaxel, Irinotecan+Etoposide, Irinotecan+Fluorouracil, Irinotecan+Gemcitabine, Mechlorethamine+Oncovin® (Vincristine)+Procarbazine (MOP), Mechlorethamine+Oncovin® (Vincristine)+Procarbazine+Prednisone (MOPP), Mesna+Ifosfamide+Idarubicin+Etoposide (MIZE), Methotrexate+Interferon alpha, Methotrexate+Vinblastine, Methotrexate+Cisplatin, Methotrexate with leucovorin rescue+Bleomycin+Adriamycin+Cyclophosphamide+Oncovorin+Dexamethasone (m-BACOD), Mitomycin C+Ifosfamide+Cisplatin (Platinol®) (MIP), Mitomycin C+Vinblastine+Paraplatin® (MVP), Mitoxantrone+Hydrocortisone, Mitoxantrone+Prednisone, Oncovin®+SCH 6636, Oxaliplatin+Leucovorin, Paclitaxel+Doxorubicin, Paclitaxel+SCH 6636, Paraplatin®g+Docetaxel, Paraplatin®+Etoposide, Paraplatin®+Gemcitabine, Paraplatin®+Interferon alpha, Paraplatin®+Irinotecan, Paraplatin®+Paclitaxel, Paraplatin®)+Vinblastine, Carboplatin (Paraplatin®)+Vincristine, Paraplatin®+Vindesine, Paraplatin®+Vinorelbine, Pemetrexed disodium+Gemcitabine, Platinol® (Cisplatin)+Vinblastine+Bleomycin (PVB), Prednisone+Methotrexate+Adriamycin+Cyclophosphamide+Etoposide (ProMACE), Procarbazine+Lomustine, Procarbazine+Lomustine+Vincristine, Procarbazine+Lomustine+Vincristine+Thioguanine, Procarbazine+Oncovin®+CCNU®+Cyclophosphamide (POCC), Quinine+Doxorubicin, Quinine+Mitoxantrone+Cytarabine, Thiotepa+Etoposide, Thiotepa+Busulfan+Cyclophosphamide, Thiotepa+Busulfan+Melphalan, Thiotepa+Etoposide+Cannustine, Thiotepa+Etoposide+Carboplatin, Topotecan+Paclitaxel, Trimetrexate+Leucovorin, Vinblastine+Doxorubicin+Thiotepa, Vinblastine+Bleomycin+Etoposide+Carboplatin, Vincristine+Lomustine+Prednisone, Vincristine (Oncovin®)+Adriamycin®+Dexamethasone (VAD), Vincristine (Oncovin®)+Adriamycing+Procarbazine (VAP), Vincristine+Dactinomycin+Cyclophosphamide, and Vinorelbine+Gemcitabine.

In an additional embodiment, the compositions of the invention are administered in combination with cytokines. Cytokines that may be administered with the compositions of the invention include, but are not limited to, IL-2, IL-3, IL-4, IL-5, IL-6, IL-7, IL-10, IL-12, IL-13, IL-15, anti-CD40, CD40L, IFN-gamma and TNF-alpha.

In an additional embodiment, the compositions of the invention are administered in combination with angiogenic proteins. Angiogenic proteins that may be administered with the compositions of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (P1GF), as disclosed in International Publication Number WO 92/06194; Placental Growth Factor-2 (P1GF-2), as disclosed in Hauser et al., Growth Factors, 4:259-268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B-186 (VEGF-B 186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the compositions of the invention are administered in combination with Fibroblast Growth Factors. Fibroblast Growth Factors that may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the compositions of the invention are administered in combination with other therapeutic or prophylactic regimens, such as, for example, radiation therapy.

In one embodiment, the compositions of the invention are administered in combination with one or more chemokines. In specific embodiments, the compositions of the invention are administered in combination with an α(C×C) chemokine selected from the group consisting of gamma-interferon inducible protein-10 (γIP-10), interleukin-8 (IL-8), platelet factor-4 (PF4), neutrophil activating protein (NAP-2), GRO-α, GRO-β, GRO-γ, neutrophil-activating peptide (ENA-78), granulocyte chemoattractant protein-2 (GCP-2), and stromal cell-derived factor-1 (SDF-1, or pre-B-cell stimulatory factor (PBSF)); and/or a β (CC) selected from the group consisting of: RANTES (regulated on activation, normal T expressed and secreted), macrophage inflammatory protein-1 alpha (MIP-1α), macrophage inflammatory protein-1 beta (MIP-1β), monocyte chemotactic protein-1 (MCP-1), monocyte chemotactic protein-2 (MCP-2), monocyte chemotactic protein-3 (MCP-3), monocyte chemotactic protein-4 (MCP-4) macrophage inflammatory protein-1 gamma (MIP-1γ), macrophage inflammatory protein-3 alpha (MIP-3α), macrophage inflammatory protein-3 beta (MIP-3 β), macrophage inflammatory protein-4 (MIP-4/DC-CK-1/PARC), eotaxin, Exodus, and 1-309; and/or the γ(C) chemokine, lymphotactin.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, 1987, CRC Crit. Ref Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (1990, Science 249:1527-1533).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides.

Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

In one embodiment, the invention provides a method of delivering compositions containing the polypeptides of the invention (e.g., compositions containing DR4 polypeptides or anti-DR4 antibodies associated with heterologous polypeptides, heterologous nucleic acids, toxins, or prodrugs) to targeted cells, expressing the membrane-bound form of DR4 on their surface. DR4 polypeptides or anti-DR4 antibodies of the invention may be associated with heterologous polypeptides, heterologous nucleic acids, toxins, or prodrugs via hydrophobic, hydrophilic, ionic and/or covalent interactions.

In one embodiment, the invention provides a method for the specific delivery of compositions of the invention to cells by administering polypeptides of the invention (e.g., DR4 or anti-DR4 antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., DR4 polypeptides or anti-DR4 antibodies) in association with toxins or cytotoxic prodrugs.

In a specific embodiment, the invention provides a method for the specific destruction of cells expressing DR4 receptors on their surface (e.g., activated T-cells, cancer cells, or leukemic cells) by administering DR4 polypeptides in association with toxins or cytotoxic prodrugs.

In another specific embodiment, the invention provides a method for the specific destruction of cells expressing the membrane-bound form of DR4 on their surface (e.g., spleen, bone marrow, kidney and PBLs) by administering anti-DR4 antibodies in association with toxins or cytotoxic prodrugs.

By "toxin" is meant compounds that bind and activate endogenous cytotoxic effector systems, radioisotopes, holotoxins, modified toxins, catalytic subunits of toxins, cytotoxins (cytotoxic agents), or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, Pseudomonas exotoxin A, diphtheria toxin, saporin, momordin, gelonin, pokeweed antiviral protein, alpha-sarcin and cholera toxin. "Toxin" also includes a cytostatic or cytocidal agent, a therapeutic agent or a radioactive metal ion, e.g., alpha-emitters such as, for example, $^{213}$Bi, or other radioisotopes such as, for example, $^{103}$Pd, $^{133}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Yttrium, $^{117}$Tin, $^{186}$Rhenium, $^{166}$Holmium, and $^{188}$Rhenium; luminescent labels, such as luminol; and fluorescent labels, such as fluorescein and rhodamine, and biotin.

Techniques known in the art may be applied to label proteins (including antibodies) of the invention. Such techniques include, but are not limited to, the use of bifunctional conjugating agents (see, e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety). A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubicin, and phenoxyacetamide derivatives of doxorubicin.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, M. et al., *J. Cell. Biol.* 101:976-985 (1985); Jalkanen, M. et al., *J. Cell. Biol.* 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{112}$In), and technetium ($^{99}$Tc); luminescent labels, such as luminol; and fluorescent labels, such as fluorescein and rhodamine, and biotin.

One aspect of the invention is the detection and diagnosis of a disease or disorder associated with aberrant expression of a polypeptide of the interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982)).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Chromosome Assays

The sequences of the present invention are also valuable for chromosome identification. The sequence is specifically targeted to and can hybridize with a particular location on an individual human chromosome. The mapping of DNAs to chromosomes according to the present invention is an important first step in correlating those sequences with genes associated with disease.

In certain preferred embodiments in this regard, the cDNA herein disclosed is used to clone genomic DNA of a DR4 gene. This can be accomplished using a variety of well known techniques and libraries, which generally are available commercially. The genomic DNA the is used for in situ chromosome mapping using well known techniques for this purpose.

In addition, sequences can be mapped to chromosomes by preparing PCR primers (preferably 15-25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA to a metaphase chromosomal spread can be used to provide a precise chromosomal location in one step. This technique can be used with cDNA as short as 50 or 60. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance in Man*, available on line through Johns Hopkins University, Welch Medical Library. The relationship between genes and diseases that have been mapped to the same chromosomal region are then identified through linkage analysis (coinheritance of physically adjacent genes)).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1

Expression and Purification in *E. coli*

The deposited cDNA encoding the mature DR4 protein (ATCC No. 97853) is amplified using PCR oligonucleotide primers specific to the amino terminal sequences of the DR4 protein and to vector sequences 3' to the gene. Additional nucleotides containing restriction sites to facilitate cloning are added to the 5' and 3' sequences respectively.

The following primers are used for expression of DR4 extracellular domain in *E. coli*. 5' primer 5'-GCG GCATGCATGATCAATCAATTGGCAC-3' (SEQ ID NO:8) contains the underlined SphI site. 3' primer: 5'-GCG AAGCTTTCAATTATGTCCATTGCCTG-3' (SEQ ID NO:9) contains the underlined HindIII site. Vector is pQE60.

The restriction sites are convenient to restriction enzyme sites in the bacterial expression vector pQE60, which are used for bacterial expression in these examples. (Qiagen, Inc. 9259 Eton Avenue, Chatsworth, Calif., 91311). pQE60 encodes ampicillin antibiotic resistance ("Ampr") and contains a bacterial origin of replication ("ori"), an IPTG inducible promoter, a ribosome binding site ("RBS").

The amplified DR4DNA and the vector pQE60 both are digested with SphI and HindIII and the digested DNAs are then ligated together. Insertion of the DDCR protein DNA into the restricted pQE60 vector places the DR4 protein coding region downstream of and operably linked to the vector's IPTG-inducible promoter and in-frame with an initiating AUG/appropriately positioned for translation of DR4 protein.

The ligation mixture is transformed into competent *E. coli* cells using standard procedures. Such procedures are described in Sambrook et al., Molecular Cloning: a Laboratory Manual, 2nd Ed.; Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kan'"), is used in carrying out the illustrative example described herein. This strain, which is only one of many that are suitable for expressing DR4 protein, is available commercially from Qiagen.

Transformants are identified by their ability to grow on LB plates in the presence of ampicillin and kanamycin. Plasmid DNA is isolated from resistant colonies and the identity of the cloned DNA confirmed by restriction analysis.

Clones containing the desired constructs are grown overnight ("O/N") in liquid culture in LB media supplemented with both ampicillin (100 µg/ml) and kanamycin (25 µg/ml).

The O/N culture is used to inoculate a large culture, at a dilution of approximately 1:100 to 1:250. The cells are grown to an optical density at 600 nm ("OD600") of between 0.4 and 0.6. Isopropyl-B-D-thiogalactopyranoside ("IPTG") is then added to a final concentration of 1 mM to induce transcription from lac repressor sensitive promoters, by inactivating the lad repressor. Cells subsequently are incubated further for 3 to 4 hours. Cells then are harvested by centrifugation and disrupted, by standard methods. Inclusion bodies are purified from the disrupted cells using routine collection techniques, and protein is solubilized from the inclusion bodies into 8M urea. The 8M urea solution containing the solubilized protein is passed over a PD-10 column in 2× phosphate-buffered saline ("PBS"), thereby removing the urea, exchanging the buffer and refolding the protein. The protein is purified by a further step of chromatography to remove endotoxin. Then, it is sterile filtered. The sterile filtered protein preparation is stored in 2×PBS at a concentration of 95 µg/ml.

Example 2

Expression in Mammalian Cells

Most of the vectors used for the transient expression of a given gene sequence in mammalian cells carry the SV40 origin of replication. This allows the replication of the vector to high copy numbers in cells (e.g., COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g. RSV, HTLVI, HIVI and the early promoter of the cytomegalovirus (CMV). However, also cellular signals can be used (e.g., human actin, promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12M1 (ATCC67109). Mammalian host cells that could be used include, human HeLa, 283, H9 and Jurkat cells, mouse NIH3T3 and C127 cells, Cos 1, Cos 7 and CV1 African green monkey cells, quail QC1-3 cells, mouse L cells and Chinese hamster ovary cells.

Alternatively, a gene of interest can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Using this marker, the mammalian cells are grown in increasing amounts of methotrexate for selection and the cells with the highest resistance are selected. These cell lines contain the amplified gene(s) integrated into a chromosome. Chinese hamster ovary (CHO) cells are often used for the production of proteins.

The expression vectors pCI and pC4 contain the strong promoter (LTR) of the Rous Sarcoma Virus (Cullen et al., *Molecular and Cellular Biology* 438:44701 (1985)), plus a fragment of the CMV-enhancer (Boshart et al., *Cell* 41:521-530 (1985)). Multiple cloning sites, e.g. with the restriction enzyme cleavage sites BamHI, XbaI and Asp718, facilitate the cloning of the gene of interest. The vectors contain in addition the 3' intron, the polyadenylation and termination signal of the rat preproinsulin gene.

Cloning and Expression in CHO Cells

The vector pC4 is used for the expression of DR4 polypeptide. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., et al., *J. Biol. Chem.* 253:1357-1370 (1978); Hamlin, J. L. and Ma, C. *Biochem. et Biophys. Acta,* 1097:107-143 (1990); Page, M. J. and Sydenham, M. A. *Biotechnology* 9:64-68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, et al., *Molecular and Cellular Biology*, March 1985:438-447) plus a fragment isolated from the enhancer of the immediate early gene of human cytomegalovirus (CMV) (Boshart et al., Cell 41:521-530 (1985)). Downstream of the promoter are the following single restriction enzyme cleavage sites that allow the integration of the genes: BamHI, Xba I, and ASP718. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the DR4 polypeptide in a regulated way in mammalian cells (Goshen, M., & Bujard, H. *Proc. Natl. Acad. Sci. USA* 89:5547-5551 (1992)). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzyme BamHI and then dephosphorylated using calf intestinal phosphates by procedures known in the art. The vector is then isolated from a 1% agarose gel.

The DNA sequence encoding the complete polypeptide is amplified using PCR oligonucleotide primers corresponding to the 5' and 3' sequences of the desired portion of the gene. The 5' primer containing the underlined BamHI site, a Kozak sequence, and an AUG start codon, has the following sequence: 5' GCGGGATCCGCCATCATGGC GCCAC-CACCAGCTAGA 3' (SEQ ID NO:10). The 3' primer, containing the underlined BamHI site, has the following sequence: 5' GCGGGATCCTCACTCCAAGGACAC GGCAGAGCC 3' (SEQ ID NO:11).

The amplified fragment is digested with the endonuclease BamHI and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five μg of the expression plasmid pC4 is cotransfected with 0.5 μg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of Methotrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100-200 μM. Expression of the desired gene product is analyzed, for instance, by SDS-PAGE and Western blot or by reversed phase HPLC analysis.

Example 3

Protein Fusions of DR4

DR4 polypeptides of the invention are optionally fused to other proteins. These fusion proteins can be used for a variety of applications. For example, fusion of DR4 polypeptides to His-tag, HA-tag, protein A, IgG domains, and maltose binding protein facilitates purification. (See EP A 394,827; Traunecker, et al., *Nature* 331:84-86 (1988)). Similarly, fusion to IgG-1, IgG-3, and albumin increases the half-life time in vivo. Nuclear localization signals fused to DR4 polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made using techniques known in the art or by using or routinely modifying the following protocol, which outlines the fusion of a polypeptide to an IgG molecule.

Briefly, the human Fc portion of the IgG molecule can be PCR amplified, using primers that span the 5' and 3' ends of the sequence described in SEQ ID NO:13. These primers also preferably contain convenient restriction enzyme sites that will facilitate cloning into an expression vector, preferably a mammalian expression vector.

For example, if the pC4 (Accession No. 209646) expression vector is used, the human Fc portion can be ligated into the BamHI cloning site. Note that the 3' BamHI site should be destroyed. Next, the vector containing the human Fc portion is re-restricted with BamHI, linearizing the vector, and DR4 polynucleotide, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Example 4

Cloning and Expression of the Soluble Extracellular Domain of DR4 in a Baculovirus Expression System The deposited cDNA encoding the soluble extracellular domain of DR4 protein (ATCC No. 97853) is amplified using PCR oligonucleotide primers corresponding to the 5' and 3' sequences of the gene:

The 5' primer for DR4 has the sequence: 5' GCG GGATCCGCCATCATG GCGCCACCACCAGCTAGA 3' (SEQ ID NO: 10) containing the underlined BamHI restriction enzyme site. Inserted into an expression vector, as described below, the 5' end of the amplified fragment encoding DR4 provides an efficient cleavage signal peptide. An efficient signal for initiation of translation in eukaryotic cells, as described by Kozak, M., *J. Mol. Biol.* 196:947-950 (1987) is appropriately located in the vector portion of the construct.

The 3' primer for both DR4 has the sequence: 5' GCG GGATCCTCA ATTATGTCCATTGCCTG 3' (SEQ ID NO:12) containing the underlined BamHI restriction followed by nucleotides complementary to the DR4 nucleotide sequence set out in SEQ ID NO:1, followed by the stop codon.

The amplified fragment is isolated from a 1% agarose gel using a commercially available kit ("Geneclean," BIO 101 Inc., La Jolla, Calif.) The fragment then is digested with BamHI and Asp718 and again is purified on a 1% agarose gel.

The vector pA2 is used to express the DR4 protein in the baculovirus expression system, using standard methods, such as those described in Summers et al., *A Manual of Methods for Baculovirus Vectors and Insect Cell Culture Procedures*, Texas Agricultural Experimental Station Bulletin No. 1555 (1987). This expression vector contains the strong polyhedron promoter of the Autograph californica nuclear polyhedrosis virus (ACMNPV) followed by convenient restriction sites. For an easy selection of recombinant virus the beta-galactosidase gene from *E. coli* is inserted in the same orientation as the polyhedron promoter and is followed by the polyadenylation signal of the polyhedron gene. The polyhedron sequences are flanked at both sides by viral sequences for cell-mediated homologous recombination with wild-type viral DNA to generate viable virus that express the cloned polynucleotide.

Many other baculovirus vectors could be used in place of pA2, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., *Virology* 170:31-39, among others.

The plasmid is digested with the restriction enzyme BamHI and then is dephosphorylated using calf intestinal phosphatase, using routine procedures known in the art. The DNA is then isolated from a 1% agarose gel using a commercially available kit ("Geneclean" BIO 101 Inc., La Jolla, Calif.).

Fragment and the dephosphorylated plasmid are ligated together with T4 DNA ligase. *E. coli* HB101 cells are transformed with ligation mix and spread on culture plates. Bacteria are identified that contain the plasmid with the human DDCR gene by digesting DNA from individual colonies using BamHI and then analyzing the digestion product by gel electrophoresis. The sequence of the cloned fragment is confirmed by DNA sequencing. This plasmid is designated herein pBac DR4.

5 μg of the plasmid pBac DR4 is co-transfected with 1.0 μg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84:7413-7417 (1987). 1 μg of BaculoGold™ virus DNA and 5 μg of the plasmid pBac DR4 are mixed in a sterile well of a microliter plate containing 50 μl of serum free Grace's medium (Life Technologies Inc., Gaithersburg, Md.). Afterwards 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27 E C. After 5 hours the transfection solution is removed from the plate and 1 ml of Grace's insect medium supplemented with 10% fetal calf serum is added. The plate is put back into an incubator and cultivation is continued at 27 E C for four days.

After four days the supernatant is collected and a plaque assay is performed, as described by Summers and Smith, cited above. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9-10).

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculovirus is used to infect Sf9 cells seeded in 35 mm dishes. Four days later the supernatants of these culture dishes are harvested and then they are stored at 4 E C. A clone containing properly inserted DR4 is identified by DNA analysis including restriction mapping and sequencing. This is designated herein as V-DR4.

Sf9 cells are grown in Grace's medium supplemented with 10% heat-inactivated FBS. The cells are infected with the recombinant baculovirus V-DR4 at a multiplicity of infection ("MOI") of about 2 (about 1 to about 3). Six hours later the medium is removed and is replaced with SF900 II medium minus methionine and cysteine (available from Life Technologies Inc., Gaithersburg). 42 hours later, 5 μCi of $^{35}$S-methionine and 5 μCi $^{35}$S cysteine (available from Amersham) are added. The cells are further incubated for 16 hours and then they are harvested by centrifugation, lysed and the labeled proteins are visualized by SDS-PAGE and autoradiography.

Example 5

DR4 Induced Apoptosis in Mammalian Cells

Overexpression of Fas/APO-1 and TNFR-1 in mammalian cells mimics receptor activation (M. Muzio, et al., *Cell* 85, 817-827 (1996); M. P. Boldin, et al, *Cell* 85, 803-815 (1996)). Thus, this system was utilized to study the functional role of DR4. Transient expression of DR4 in MCF7 human breast carcinoma cells and 293 human embryonic kidney cells induced rapid apoptosis.

Cell death assays are performed essentially as previously described (A. M. Chinnaiyan, et al., *Cell* 81, 505-12 (1995); M. P. Boldin, et al, *J Biol Chem* 270, 7795-8 (1995); F. C. Kischkel, et al., *EMBO* 14, 5579-5588 (1995); A. M. Chinnaiyan, et al., *J Biol Chem* 271, 4961-4965 (1996)). Briefly, MCF-7 human breast carcinoma clonal cell lines stably transfected with either vector alone or a CrmA expression construct (M. Tewari, et al., *J Biol Chem* 270, 3255-60 (1995)), are transiently transfected with pCMV-DR4-galactosidase (or pCMV-DR4-galactosidase (lacking the death domain)) in the presence of a ten-fold excess of pcDNA3 expression constructs encoding the indicated proteins using lipofectamine (GIBCO-BRL). 293 cells are likewise transfected using the CaPO$_4$ method. The ICE family inhibitor z-VAD-fmk (Enzyme Systems Products, Dublin, Calif.) is added to the cells at a concentration of 10 μM, 5 hrs after transfection. 32 hours following transfection, cells are fixed and stained with X-Gal as previously described (A. M. Chinnaiyan, et al., *Cell* 81, 505-12 (1995); M. P. Boldin, et al., *J Biol Chem* 270, 7795-8 (1995); F. C. Kischkel, et al., *EMBO* 14, 5579-5588 (1995)).

The cells displayed morphological alterations typical of cells undergoing apoptosis, becoming rounded, condensed and detaching from the dish. Similar to TNFR-1 and Fas/APO-1 (M. Muzio, et al., *Cell* 85, 817-827 (1996); M. P. Boldin, et al., *Cell* 85, 803-815 (1996); M. Tewari, et al., *J Biol Chem* 270, 3255-60 (1995)), DR4-induced apoptosis was blocked by the inhibitors of ICE-like proteases, CrmA and z-VAD-fmk.

Example 6

The Extracellular Domain of DR4 Binds the Cytotoxic Ligand, TRAIL, and Blocks TRAIL-Induced Apoptosis This example shows that the present receptor, DR4, binds TRAIL. The soluble extracellular ligand binding domain of DR4 was expressed as a fusion to the Fc portion of human immunoglobulin (IgG). cDNA encoding the extracellular domain of DR4 (amino acids 110 to 239) was obtained by polymerase chain reaction and cloned into a modified pCMV1FLAG vector that allowed for in-frame fusion with the Fc portion of human IgG.

As shown in FIGS. 6A and 6B, DR4-Fc specifically bound TRAIL, but not the related cytotoxic ligand TNFα. In this experiment, we transfected 293 cells with constructs encoding the Fc-extracellular domains of DR4, TNFR1, or Fas, and the corresponding ligands, and the conditioned media was harvested 72 to 80 hours later, clarified by centrifugation, divided, and stored at −80° C. For binding assays, equal amounts of receptor-Fc- and ligand containing conditioned media were mixed in buffer containing 50 mM Hepes, pH 7.0, 150 mM NaCl, 1 mM EDTA, 0.5% NP-40, and a protease inhibitor mixture, and the sample was incubated at 4° C. with continuous rotation for 4 hours. Receptor-Fc-ligand complexes were precipitated with protein G-Sepharose, extensively washed with the above buffer, boiled in SDS sample buffer, and resolved on a 12% SDS-polyacrylamide gel and co-precipitated soluble ligands were detected by immunoblotting with anti-Flag (Babco) or anti-myc-HRP (BMB) or to FasL (Pharmingen).

Additionally, DR4-Fc blocked the ability of TRAIL to induce apoptosis (FIG. 6A). MCF7 cells were treated with soluble TRAIL (400 ng/ml) in the presence of equal amounts of Fc-fusions or Fc alone. Five hours later cells were fixed with formaldehyde, and the nuclei were stained with 4',6'-diamidino-2-phenylindole (DAPI) and examined by fluorescence microscopy with a fluorescein isothiocyanate range barrier filter cube. The data (mean 6±SD) shown in FIG. 6A are the percentage of apoptotic nuclei among total nuclei counted (n=3).

Finally, DR4-Fc had no effect on apoptosis TNFα-induced cell death under conditions where TNFR1-Fc completely abolished TNFα killing (FIG. 6B). MCF7 cells were treated with TNFα (40 ng/ml; Genentech, Inc.) in the presence of equal amounts of Fc-fusions or Fc alone. Nuclei were stained and examined 15 to 18 hours later.

Example 7

Assays to Detect Stimulation or Inhibition of B-cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B-cell responsiveness including IL-2, IL-4, IL-5, IL6, IL-7, IL-10, IL-13, IL-14 and IL-15. Interestingly, these signals are by themselves weak effectors but can, in combination with various co-stimulatory proteins, induce activation, proliferation, differentiation, homing, tolerance and death among B-cell populations. One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

Experimental Procedure

In Vitro assay-Purified DR4 protein, or truncated forms thereof, is assessed for its ability to induce activation, proliferation, differentiation or inhibition and/or death in B-cell populations and their precursors. The activity of DR4 protein on purified human tonsillar B-cells, measured qualitatively over the dose range from 0.1 to 10,000 ng/mL, is assessed in a standard B-lymphocyte co-stimulation assay in which purified tonsillar B-cells are cultured in the presence of either formalin-fixed *Staphylococcus aureus* Cowan I (SAC) or immobilized anti-human IgM antibody as the priming agent.

Second signals such as IL-2 and IL-15 synergize with SAC and IgM crosslinking to elicit B-cell proliferation as measured by tritiated-thymidine incorporation. Novel synergizing agents can be readily identified using this assay. The assay involves isolating human tonsillar B-cells by magnetic bead (MACS) depletion of CD3-positive cells. The resulting cell population is greater than 95% B-cells as assessed by expression of CD45R(B220). Various dilutions of each sample are placed into individual wells of a 96-well plate to which are added $10^5$ B-cells suspended in culture medium (RPMI 1640 containing 10% FBS, $5\times10^{-5}$ M βME, 100 U/ml penicillin, 10 μg/ml streptomycin, and $10^{-5}$ dilution of SAC) in a total volume of 150 μl. Proliferation or inhibition is quantitated by a 20 hour pulse (1 μCi/well) with $^3$H-thymidine (6.7 Ci/mM) beginning 72 hour post factor addition. The positive and negative controls are IL-2 and medium respectively.

In Vivo assay-BALB/c mice are injected (i.p.) twice per day with buffer only, or 2 mg/Kg of DR4 protein, or truncated forms thereof. Mice receive this treatment for 4 consecutive days, at which time they are sacrificed and various tissues and serum collected for analyses. Comparison of H&E sections from normal and DR4 protein-treated spleens identify the results of the activity of DR4 protein on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B-cell marker, anti-CD45R (B220), are used to determine whether any physiological changes to splenic cells, such as splenic disorganization, are due to increased B-cell representation within loosely defined B-cell zones that infiltrate established T-cell regions.

Flow cytometric analyses of the spleens from DR4 protein-treated mice is used to indicate whether DR4 protein specifically increases the proportion of ThB+, CD45R(B220)dull B-cells over that which is observed in control mice.

Likewise, a predicted consequence of increased mature B-cell representation in vivo is a relative increase in serum Ig titers. Accordingly, serum IgM and IgA levels are compared between buffer and DR4 protein-treated mice.

The studies described in this example test the activity in DR4 protein. However, one skilled in the art could easily modify the exemplified studies to test the activity of DR4 polynucleotides (e.g., gene therapy), agonists, and/or antagonists of DR4.

Example 8

T-Cell Proliferation Assay

A CD3-induced proliferation assay is performed on PBMCs and is measured by the uptake of $^3$H-thymidine. The assay is performed as follows. Ninety-six well plates are coated with 100 μl/well of monoclonal antibody to CD3 (HIT3a, Pharmingen) or isotype-matched control monoclonal antibody (B33.1) overnight at 4° C. (1 μg/ml in 0.05M bicarbonate buffer, pH 9.5), then washed three times with PBS. PBMC are isolated by F/H gradient centrifugation from human peripheral blood and added to quadruplicate wells ($5\times10^4$/well) of monoclonal antibody coated plates in RPMI containing 10% FCS and P/S in the presence of varying concentrations of DR4 protein (total volume 200 iμl). Relevant protein buffer and medium alone are controls. After 48 hours culture at 37° C., plates are spun for 2 minutes at 1000 rpm and 100 μl of supernatant is removed and stored −20° C. for measurement of IL-2 (or other cytokines) if effect on proliferation is observed. Wells are supplemented with 100 µl of medium containing 0.5 µCi of $^3$H-thymidine and cultured at 37° C. for 18-24 hr. Wells are harvested and incorporation of $^3$H-thymidine used as a measure of proliferation. Anti-CD3 alone is the positive control for proliferation. IL-2 (100 U/ml) is also used as a control which enhances proliferation. Control antibody which does not induce proliferation of T-cells is used as the negative controls for the effects of DR4 proteins.

The studies described in this example test the activity in DR4 protein. However, one skilled in the art could easily modify the exemplified studies to test the activity of DR4 polynucleotides (e.g., gene therapy), agonists, and/or antagonists of DR4.

Example 9

Effect of DR4 on the Expression of MHC Class II, Costimulatory and Adhesion Molecules and Cell Differentiation of monocytes and Monocyte-Derived Human Dendritic Cells Dendritic cells are generated by the expansion of proliferating precursors found in the peripheral blood: adherent PBMC or elutriated monocytic fractions are cultured for 7-10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-α, causes a rapid change in surface phenotype (increased expression of MHC class I and II, costimulatory and adhesion molecules, downregulation of FCγRII, upregulation of CD83). These changes correlate with increased antigen-presenting capacity and with functional maturation of the dendritic cells.

FACS analysis of surface antigens is performed as follows. Cells are treated 1-3 days with increasing concentrations of DR4 or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Effect on the Production of Cytokines

Cytokines generated by dendritic cells, in particular IL-12, are important in the initiation of T-cell dependent immune responses. IL-12 strongly influences the development of Th1 helper T-cell immune response, and induces cytotoxic T and NK cell function. An ELISA is used to measure the IL-12 release as follows. Dendritic cells ($10^6$/ml) are treated with increasing concentrations of DR4 for 24 hours. LPS (100 ng/ml) is added to the cell culture as positive control. Supernatants from the cell cultures are then collected and analyzed for IL-12 content using commercial ELISA kit (e.g., R & D Systems (Minneapolis, Minn.)). The standard protocols provided with the kits are used.

Effect on the Expression of MHC Class II, Costimulatory and Adhesion Molecules

Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T-cell activation. Increase expression of Fc receptors may correlate with improved monocyte cytotoxic activity, cytokine release and phagocytosis.

FACS analysis is used to examine the surface antigens as follows. Monocytes are treated 1-5 days with increasing concentrations of DR4 or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Monocyte Activation and/or Increased Survival:

Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. DR4, agonists, or antagonists of DR4 can be screened using the three assays described below. For each of these assays, Peripheral blood mononuclear cells (PBMC) are purified from single donor leukopacks (American Red Cross, Baltimore, Md.) by centrifugation through a Histopaque gradient (Sigma). Monocytes are isolated from PBMC by counterflow centrifugal elutriation.

1. Monocyte Survival Assay. Human peripheral blood monocytes progressively lose viability when cultured in absence of serum or other stimuli. Their death results from internally regulated process (apoptosis). Addition to the culture of activating factors, such as TNF-alpha dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of DR4. Cells are suspended at a concentration of $2 \times 10^6$/ml in PBS containing PI at a final concentration of 5 µg/ml, and then incubated at room temperature for 5 minutes before FAC Scan analysis. PI uptake has been demonstrated to correlate with DNA fragmentation in this experimental paradigm.

2. Effect on cytokine release. An important function of monocytes/macrophages is their regulatory activity on other cellular populations of the immune system through the release of cytokines after stimulation. An ELISA to measure cytokine release is performed as follows. Human monocytes are incubated at a density of $5 \times 10^5$ cells/ml with increasing concentrations of DR4 and under the same conditions, but in the absence of DR4. For IL-12 production, the cells are primed overnight with IFN-γ (100 U/ml) in presence of DR4. LPS (10 ng/ml) is then added. Conditioned media are collected after 24 h and kept frozen until use. Measurement of TNF-α, IL-10, MCP-1 and IL-8 is then performed using a commercially available ELISA kit (e.g., R & D Systems (Minneapolis, Minn.)) applying the standard protocols provided with the kit.

3. Oxidative burst. Purified monocytes are plated in 96-well plate at $2-1 \times 10^5$ cell/well. Increasing concentrations of DR4 are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 nM PMA). The plates are incubated at 37° C. for 2 hours and the reaction is stopped by adding 20 µl 1N NaOH per well. The absorbance is read at 610 nm. To calculate the amount of $H_2O_2$ produced by the macrophages, a standard curve of a $H_2O_2$ solution of known molarity is performed for each experiment.

The studies described in this example test the activity in DR4 protein. However, one skilled in the art could easily modify the exemplified studies to test the activity of DR4 polynucleotides (e.g., gene therapy), agonists, and/or antagonists of DR4.

Example 10

The Effect of DR4 on the Growth of Vascular Endothelial Cells

On day 1, human umbilical vein endothelial cells (HUVEC) are seeded at $2$–$5 \times 10^4$ cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium is replaced with M199 containing 10% FBS, 8 units/ml heparin. DR4 protein of SEQ ID NO. 2, and positive controls, such as VEGF and basic FGF (bFGF) are added, at varying concentrations. On days 4 and 6, the medium is replaced. On day 8, cell number is determined with a Coulter Counter.

An increase in the number of HUVEC cells after treatment with DR4 indicates that DR4 may proliferate vascular endothelial cells.

The studies described in this example test the activity in DR4 protein. However, one skilled in the art could easily modify the exemplified studies to test the activity of DR4 polynucleotides (e.g., gene therapy), agonists, and/or antagonists of DR4.

Example 11

Stimulatory Effect of DR4 on the Proliferation of Vascular Endothelial Cells

For evaluation of mitogenic activity of growth factors, the colorimetric MTS (3-(4,5-dimethylthiazol-2-yl)-5-(3-carboxymethoxyphenyl)-2-(4-sulfophenyl)$_2$H-tetrazolium) assay with the electron coupling reagent PMS (phenazine methosulfate) was performed (CellTiter 96 AQ, Promega). Cells are seeded in a 96-well plate (5,000 cells/well) in 0.1 ml serum-supplemented medium and are allowed to attach overnight. After serum-starvation for 12 hours in 0.5% FBS, conditions (bFGF, VEGF$_{165}$ or DR4 in 0.5% FBS) with or without Heparin (8 U/ml) are added to wells for 48 hours. 20 mg of MTS/PMS mixture (1:0.05) are added per well and allowed to incubate for 1 hour at 37° C. before measuring the absorbance at 490 nm in an ELISA plate reader. Background absorbance from control wells (some media, no cells) is subtracted, and seven wells are performed in parallel for each condition. See, Leak et al. In Vitro *Cell. Dev. Biol.* 30A:512-518 (1994).

The studies described in this example test the activity in DR4 protein. However, one skilled in the art could easily modify the exemplified studies to test the activity of DR4 polynucleotides (e.g., gene therapy), agonists, and/or antagonists of DR4.

Example 12

Inhibition of PDGF-induced Vascular Smooth Muscle Cell Proliferation Stimulatory Effect HAoSMC proliferation can be measured, for example, by BrdUrd incorporation. Briefly, subconfluent, quiescent cells grown on the 4-chamber slides are transfected with CRP or FITC-labeled AT2-3LP. Then, the cells are pulsed with 10% calf serum and 6 mg/ml BrdUrd. After 24 hours, immunocytochemistry is performed by using BrdUrd Staining Kit (Zymed Laboratories). In brief, the cells are incubated with the biotinylated mouse anti-BrdUrd antibody at 4° C. for 2 h after exposing to denaturing solution and then with the streptavidin-peroxidase and diaminobenzidine. After counterstaining with hematoxylin, the cells are mounted for microscopic examination, and the BrdUrd-positive cells are counted. The BrdUrd index is calculated as a percent of the BrdUrd-positive cells to the total cell number. In addition, the simultaneous detection of the BrdUrd staining (nucleus) and the FITC uptake (cytoplasm) is performed for individual cells by the concomitant use of bright field illumination and dark field-UV fluorescent illumination. See, Hayashida et al., *J. Biol. Chem.* 6; 271(36):21985-21992 (1996).

The studies described in this example test the activity in DR4 protein. However, one skilled in the art could easily modify the exemplified studies to test the activity of DR4 polynucleotides (e.g., gene therapy), agonists, and/or antagonists of DR4.

Example 13

Stimulation of Endothelial Migration

This example will be used to explore the possibility that DR4 may stimulate lymphatic endothelial cell migration.

Endothelial cell migration assays are performed using a 48 well microchemotaxis chamber (Neuroprobe Inc., Cabin John, M D; Falk, W., et al., "A 48 well micro chemotaxis assembly for rapid and accurate measurement of leukocyte migration." *J. Immunological Methods* 33:239-247 (1980)). Polyvinylpyrrolidone-free polycarbonate filters with a pore size of 8 μm (Nucleopore Corp. Cambridge, Mass.) are coated with 0.1% gelatin for at least 6 hours at room temperature and dried under sterile air. Test substances are diluted to appropriate concentrations in M199 supplemented with 0.25% bovine serum albumin (BSA), and 25 μl of the final dilution is placed in the lower chamber of the modified Boyden apparatus. Subconfluent, early passage (2-6) HUVEC or BMEC cultures are washed and trypsinized for the minimum time required to achieve cell detachment. After placing the filter between lower and upper chamber, $2.5 \times 10^5$ cells suspended in 50 μl M199 containing 1% FBS are seeded in the upper compartment. The apparatus is then incubated for 5 hours at 37° C. in a humidified chamber with 5% $CO_2$ to allow cell migration. After the incubation period, the filter is removed and the upper side of the filter with the non-migrated cells is scraped with a rubber policeman. The filters are fixed with methanol and stained with a Giemsa solution (Diff-Quick, Baxter, McGraw Park, Ill.). Migration is quantified by counting cells of three random high-power fields (40×) in each well, and all groups are performed in quadruplicate.

The studies described in this example test the activity in DR4 protein. However, one skilled in the art could easily modify the exemplified studies to test the activity of DR4 polynucleotides (e.g., gene therapy), agonists, and/or antagonists of DR4.

Example 14

Stimulation of Nitric Oxide Production by Endothelial Cells

Nitric oxide released by the vascular endothelium is believed to be a mediator of vascular endothelium relaxation.

Thus, DR4 activity can be assayed by determining nitric oxide production by endothelial cells in response to DR4. Nitric oxide is measured in 96-well plates of confluent microvascular endothelial cells after 24 hours starvation and a subsequent 4 hr exposure to various levels of a positive control (such as VEGF-1) and DR4. Nitric oxide in the medium is determined by use of the Griess reagent to measure total nitrite after reduction of nitric oxide-derived nitrate by nitrate reductase. The effect of DR4 on nitric oxide release is examined on HUVEC.

Briefly, NO release from cultured HUVEC monolayer is measured with a NO-specific polarographic electrode connected to a NO meter (Iso-NO, World Precision Instruments Inc.). Calibration of the NO element is performed according to the following equation:

$$2KNO_2 + 2KI + 2H_2SO_4 \rightarrow 2NO + I_2 + 2H_2O + 2K_2SO_4$$

The standard calibration curve is obtained by adding graded concentrations of $KNO_2$ (0, 5, 10, 25, 50, 100, 250, and 500 nmol/L) into the calibration solution containing $K_1$ and $H_2SO_4$. The specificity of the Iso-NO electrode to NO is previously determined by measurement of NO from authentic NO gas. The culture medium is removed and HUVECs are washed twice with Dulbecco's phosphate buffered saline. The cells are then bathed in 5 ml of filtered Krebs-Henseleit solution in 6-well plates, and the cell plates are kept on a slide warmer (Lab Line Instruments Inc.) to maintain the temperature at 37° C. The NO sensor probe is inserted vertically into the wells, keeping the tip of the electrode 2 mm under the surface of the solution, before addition of the different conditions. S-nitroso acetyl penicillamin (SNAP) is used as a positive control. The amount of released NO is expressed as picomoles per $1 \times 10^6$ endothelial cells. All values reported are means of four to six measurements in each group (number of cell culture wells). See, Leak et al. *Biochem. and Biophys. Res. Comm.* 217:96-105 (1995).

The studies described in this example test the activity in DR4 protein. However, one skilled in the art could easily modify the exemplified studies to test the activity of DR4 polynucleotides (e.g., gene therapy), agonists, and/or antagonists of DR4.

Example 15

Effect of DR4 on Cord Formation in Angiogenesis

Another step in angiogenesis is cord formation, marked by differentiation of endothelial cells. This bioassay measures the ability of microvascular endothelial cells to form capillary-like structures (hollow structures) when cultured in vitro.

CADMEC (microvascular endothelial cells) are purchased from Cell Applications, Inc. as proliferating (passage 2) cells and are cultured in Cell Applications' CADMEC Growth Medium and used at passage 5. For the in vitro angiogenesis assay, the wells of a 48-well cell culture plate are coated with Cell Applications' Attachment Factor Medium (200 µl/well) for 30 minutes at 37° C. CADMEC are seeded onto the coated wells at 7,500 cells/well and cultured overnight in Growth Medium. The Growth Medium is then replaced with 300 µg Cell Applications Chord Formation Medium containing control buffer or DR4 (0.1 to 100 ng/ml) and the cells are cultured for an additional 48 hr. The numbers and lengths of the capillary-like chords are quantitated through use of the Boeckeler VIA-170 video image analyzer. All assays are done in triplicate.

Commercial (R&D) VEGF (50 ng/ml) is used as a positive control. b-estradiol (1 ng/ml) is used as a negative control. The appropriate buffer (without protein) is also utilized as a control.

The studies described in this example test the activity in DR4 protein. However, one skilled in the art could easily modify the exemplified studies to test the activity of DR4 polynucleotides (e.g., gene therapy), agonists, and/or antagonists of DR4.

Example 16

Angiogenic Effect on Chick Chorioallantoic Membrane

Chick chorioallantoic membrane (CAM) is a well-established system to examine angiogenesis. Blood vessel formation on CAM is easily visible and quantifiable. The ability of DR4 to stimulate angiogenesis in CAM can be examined.

Fertilized eggs of the White Leghorn chick (*Gallus gallus*) and the Japanese quail (*Coturnix coturnix*) are incubated at 37.8° C. and 80% humidity. Differentiated CAM of 16-day-old chick and 13-day-old quail embryos is studied with the following methods.

On Day 4 of development, a window is made into the eggshell of chick eggs. The embryos are checked for normal development and the eggs sealed with cellotape. They are further incubated until Day 13. Thermanox coverslips (Nunc, Naperville, Ill.) are cut into disks of about 5 mm in diameter. Sterile and salt-free growth factors, and DR4, are dissolved in distilled water and about 3.3 mg/5 ml are pipetted on the disks. After air-drying, the inverted disks are applied on CAM. After 3 days, specimens are fixed in 3% glutaraldehyde and 2% formaldehyde and rinsed in 0.12 M sodium cacodylate buffer. They are photographed with a stereo microscope [Wild M8] and embedded for semi- and ultrathin sectioning as described above. Controls are performed with carrier disks alone.

The studies described in this example test the activity in DR4 protein. However, one skilled in the art could easily modify the exemplified studies to test the activity of DR4 polynucleotides (e.g., gene therapy), agonists, and/or antagonists of DR4.

Example 17

Angiogenesis Assay Using a Matrigel Implant in Mouse

In order to establish an in vivo model for angiogenesis to test DR4 protein activities, mice and rats are implanted subcutaneously with methylcellulose disks containing either 20 mg of BSA (negative control), 1 mg of DR4, or 0.5 mg of VEGF-1 (positive control). The negative control disks should contain little vascularization, while the positive control disks should show signs of vessel formation.

The studies described in this example test the activity in DR4 protein. However, one skilled in the art could easily modify the exemplified studies to test the activity of DR4 polynucleotides (e.g., gene therapy), agonists, and/or antagonists of DR4.

Example 18

Rescue of Ischemia in Rabbit Lower Limb Model

To study the in vivo effects of DR4 on ischemia, a rabbit hind-limb ischemia model is created by surgical removal of one femoral arteries as described previously (Takeshita, S. et al., *Am J Pathol* 147:1649-1660 (1995)). The excision of the femoral artery results in retrograde propagation of thrombus and occlusion of the external iliac artery. Consequently, blood flow to the ischemic limb is dependent upon collateral vessels originating from the internal iliac artery (Takeshita, S. et al., *Am J Pathol* 47:1649-1660 (1995)). An interval of 10 days is allowed for post-operative recovery of rabbits and development of endogenous collateral vessels. At 10 day post-operatively (day 0), after performing a baseline angiogram, the internal iliac artery of the ischemic limb is transfected with 500 mg naked DR4 expression plasmid by arterial gene transfer technology using a hydrogel-coated balloon catheter as described (Riessen, R. et al., *Hum Gene Ther.* 4:749-758 (1993); Leclerc, G. et al., *J. Clin. Invest.* 90: 936-944 (1992)). When DR4 is used in the treatment, a single bolus of 500 mg DR4 protein or control is delivered into the internal iliac artery of the ischemic limb over a period of 1 minute through an infusion catheter. On day 30, various parameters are measured in these rabbits: (a) BP ratio—The blood pressure ratio of systolic pressure of the ischemic limb to that of normal limb; (b) Blood Flow and Flow Reserve—Resting FL: the blood flow during undilated condition and Max FL: the blood flow during fully dilated condition (also an indirect measure of the blood vessel amount) and Flow Reserve is reflected by the ratio of max FL: resting FL; (c) Angiographic Score—This is measured by the angiogram of collateral vessels. A score is determined by the percentage of circles in an overlaying grid that with crossing opacified arteries divided by the total number m in the rabbit thigh; (d) Capillary density—The number of collateral capillaries determined in light microscopic sections taken from hind-limbs.

The studies described in this example test the activity in DR4 protein. However, one skilled in the art could easily modify the exemplified studies to test the activity of DR4 polynucleotides (e.g., gene therapy), agonists, and/or antagonists of DR4.

Example 19

Diabetic Mouse and Glucocorticoid-Impaired Wound Healing Models

A. Diabetic db+/db+ Mouse Model

To demonstrate that DR4 accelerates the healing process, the genetically diabetic mouse model of wound healing is used. The full thickness wound healing model in the db+/db+ mouse is a well-characterized, clinically relevant and reproducible model of impaired wound healing. Healing of the diabetic wound is dependent on formation of granulation tissue and re-epithelialization rather than contraction (Gartner, M. H. et al., *J. Surg. Res.* 52:389 (1992); Greenhalgh, D. G. et al., *Am. J. Pathol.* 136:1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+) mice have a single autosomal recessive mutation on chromosome 4 (db+) (Coleman et al. *Proc. Natl. Acad. Sci. USA* 77:283-293 (1982)). Animals show polyphagia, polydipsia and polyuria. Mutant diabetic mice (db+/db+) have elevated blood glucose, increased or normal insulin levels, and suppressed cell-mediated immunity (Mandel et al., *J. Immunol.* 120:1375 (1978); Debray-Sachs, M. et al., *Clin. Exp. Immunol.* 51(1):1-7 (1983); Leiter et al., *Am. J. of Pathol.* 114:46-55 (1985)). Peripheral neuropathy, myocardial complications, and microvascular lesions, basement membrane thickening and glomerular filtration abnormalities have been described in these animals (Norido, F. et al., *Exp. Neurol.* 83(2):221-232 (1984); Robertson et al., Diabetes 29(1):60-67; (1980); Giacomelli et al., *Lab Invest.* 40(4):460-473 (1979); Coleman, D. L., *Diabetes* 31 (Suppl): 1-6 (1982)). These homozygous diabetic mice develop hyperglycemia that is resistant to insulin analogous to human type II diabetes (Mandel et al., *J. Immunol.* 120:1375-1377 (1978)).

The characteristics observed in these animals suggests that healing in this model may be similar to the healing observed in human diabetes (Greenhalgh, et al., *Am. J. of Pathol.* 136: 1235-1246 (1990)).

Genetically diabetic female C57BL/KsJ (db+/db+) mice and their non-diabetic (db+/+m) heterozygous littermates are used in this study (Jackson Laboratories). The animals are purchased at 6 weeks of age and were 8 weeks old at the beginning of the study. Animals are individually housed and received food and water ad libitum. All manipulations are performed using aseptic techniques. The experiments are conducted according to the rules and guidelines of Human Genome Sciences, Inc. Institutional Animal Care and Use Committee and the Guidelines for the Care and Use of Laboratory Animals.

Wounding protocol is performed according to previously reported methods (Tsuboi, R. and Rifkin, D. B., *J. Exp. Med.* 172:245-251 (1990)). Briefly, on the day of wounding, animals are anesthetized with an intraperitoneal injection of Avertin (0.01 mg/mL), 2,2,2-tribromoethanol and 2-methyl-2-butanol dissolved in deionized water. The dorsal region of the animal is shaved and the skin washed with 70% ethanol solution and iodine. The surgical area is dried with sterile gauze prior to wounding. An 8 mm full-thickness wound is then created using a Keyes tissue punch. Immediately following wounding, the surrounding skin is gently stretched to eliminate wound expansion. The wounds are left open for the duration of the experiment. Application of the treatment is given topically for 5 consecutive days commencing on the day of wounding. Prior to treatment, wounds are gently cleansed with sterile saline and gauze sponges.

Wounds are visually examined and photographed at a fixed distance at the day of surgery and at two day intervals thereafter. Wound closure is determined by daily measurement on days 1-5 and on day 8. Wounds are measured horizontally and vertically using a calibrated Jameson caliper. Wounds are considered healed if granulation tissue is no longer visible and the covered by a continuous epithelium.

DR4 is administered using at a range different doses of DR4, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology and immunohistochemistry. Tissue specimens are placed in 10% neutral buffered formalin in tissue cassettes between biopsy sponges for further processing.

Three groups of 10 animals each (5 diabetic and 5 non-diabetic controls) are evaluated: 1) Vehicle placebo control, 2) DR4, 3) positive control.

Wound closure is analyzed by measuring the area in the vertical and horizontal axis and obtaining the total square area of the wound. Contraction is then estimated by establishing the differences between the initial wound area (day 0) and that of post treatment (day 8). The wound area on day I was 64 mm², the corresponding size of the dermal punch. Calculations were made using the following formula:

[Open area on day 8]−[Open area on day 1]/[Open area on day 1]

Specimens are fixed in 10% buffered formalin and paraffin embedded blocks are sectioned perpendicular to the wound surface (5 mm) and cut using a Reichert-Jung microtome. Routine hematoxylin-eosin (H&E) staining is performed on cross-sections of sections of bisected wounds. Histologic examination of the wounds are used to assess whether the healing process and the morphologic appearance of the repaired skin is altered by treatment with DR4. This assessment included verification of the presence of cell accumulation, inflammatory cells, capillaries, fibroblasts, re-epithelialization and epidermal maturity (Greenhalgh, D. G. et al., *Am. J. Pathol.* 136:1235 (1990)). A calibrated lens micrometer is used by a blinded observer.

Tissue sections are also stained immunohistochemically with a polyclonal rabbit anti-human keratin antibody using ABC Elite detection system. Human skin is used as a positive tissue control while non-immune IgG is used as a negative control. Keratincyte growth is determined by evaluating the extent of reepithelialization of the wound using a calibrated lens micrometer.

Proliferating cell nuclear antigen/cyclin (PCNA) in skin specimens is demonstrated by using anti-PCNA antibody (1:50) with an ABC Elite detection system. Human colon cancer served as a positive tissue control and human brain tissue is used as a negative tissue control. Each specimen included a section with omission of the primary antibody and substitution with non-mouse immune mouse IgG. Ranking of these sections is based on the extent of proliferation on a scale of 0-8, the lower side of the scale reflecting slight proliferation to the higher side reflecting intense proliferation.

Experimental data are analyzed using an unpaired t test. A p value of <0.05 is considered significant.

B. Steroid Impaired Rat Model

The inhibition of wound healing by steroids has been well documented in various in vitro and in vivo systems (Wahl, S. M. *Glucocorticoids and Wound healing*. In: Anti-Inflammatory Steroid Action: Basic and Clinical Aspects. 280-302 (1989); Wahl, S. M. et al., *J. Immunol.* 115: 476-481 (1975); Werb, Z. et al., *J. Exp. Med.* 147:1684-1694 (1978)). Glucocorticoids retard wound healing by inhibiting angiogenesis, decreasing vascular permeability (Ebert, R. H., et al., *An. Intern. Med.* 37:701-705 (1952)), fibroblast proliferation, and collagen synthesis (Beck, L. S. et al., *Growth Factors.* 5:295-304 (1991); Haynes, B. F. et al., *J. Clin. Invest.* 61: 703-797 (1978)) and producing a transient reduction of circulating monocytes (Haynes, B. F., et al., *J. Clin. Invest.* 1:703-797 (1978); Wahl, S. M., *Glucocorticoids and wound healing*, In: Anti-inflammatory Steroid Action: Basic and Clinical Aspects, Academic Press, New York, pp. 280-302 (1989)). The systemic administration of steroids to impaired wound healing is a well establish phenomenon in rats (Beck, L. S. et al., *Growth Factors.* 5:295-304 (1991); Haynes, B. F., et al., *J. Clin. Invest* 1:703-797 (1978); Wahl, S. M., *Glucocorticoids and wound healing*, In: Anti-inflammatory Steroid Action: Basic and Clinical Aspects, Academic Press, New York, pp. 280-302 (1989); Pierce, K. F. et al., *Proc. Natl. Acad. Sci. USA* 86: 2229-2233 (1989)).

To demonstrate that DR4 can accelerate the healing process, the effects of multiple topical applications of DR4 on full thickness excisional skin wounds in rats in which healing has been impaired by the systemic administration of methylprednisolone is assessed.

Young adult male Sprague Dawley rats weighing 250-300 g (Charles River Laboratories) are used in this example. The animals are purchased at 8 weeks of age and were 9 weeks old at the beginning of the study. The healing response of rats is impaired by the systemic administration of methylprednisolone (17 mg/kg/rat intramuscularly) at the time of wounding. Animals are individually housed and received food and water ad libitum. All manipulations are performed using aseptic techniques. This study is conducted according to the rules and guidelines of Human Genome Sciences, Inc. Institutional Animal Care and Use Committee and the Guidelines for the Care and Use of Laboratory Animals.

The wounding protocol is followed according to section A, above. On the day of wounding, animals are anesthetized with an intramuscular injection of ketamine (50 mg/kg) and xylazine (5 mg/kg). The dorsal region of the animal is shaved and the skin washed with 70% ethanol and iodine solutions. The surgical area is dried with sterile gauze prior to wounding. An 8 mm full-thickness wound is created using a Keyes tissue punch. The wounds are left open for the duration of the experiment. Applications of the testing materials are given topically once a day for 7 consecutive days commencing on the day of wounding and subsequent to methylprednisolone administration. Prior to treatment, wounds are gently cleansed with sterile saline and gauze sponges.

Wounds are visually examined and photographed at a fixed distance at the day of wounding and at the end of treatment. Wound closure is determined by daily measurement on days 1-5 and on day 8. Wounds are measured horizontally and vertically using a calibrated Jameson caliper. Wounds are considered healed if granulation tissue was no longer visible and the wound is covered by a continuous epithelium.

DR4 is administered using at a range different doses of DR4, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology. Tissue specimens are placed in 10% neutral buffered formalin in tissue cassettes between biopsy sponges for further processing.

Four groups of 10 animals each (5 with methylprednisolone and 5 without glucocorticoid) were evaluated: 1) Untreated group 2) Vehicle placebo control 3) DR4 treated groups.

Wound closure is analyzed by measuring the area in the vertical and horizontal axis and obtaining the total area of the wound. Closure is then estimated by establishing the differences between the initial wound area (day 0) and that of post treatment (day 8). The wound area on day 1 was 64 mm², the corresponding size of the dermal punch. Calculations were made using the following formula:

[Open area on day 8]−[Open area on day 1]/[Open area on day 1]

Specimens are fixed in 10% buffered formalin and paraffin embedded blocks are sectioned perpendicular to the wound surface (5 mm) and cut using an Olympus microtome. Routine hematoxylin-eosin (H&E) staining was performed on cross-sections of bisected wounds. Histologic examination of the wounds allows assessment of whether the healing process and the morphologic appearance of the repaired skin was improved by treatment with DR4. A calibrated lens micrometer is used by a blinded observer to determine the distance of the wound gap.

Experimental data are analyzed using an unpaired t test. A p value of <0.05 is considered significant.

The studies described in this example test the activity in DR4 protein. However, one skilled in the art could easily modify the exemplified studies to test the activity of DR4 polynucleotides (e.g., gene therapy), agonists, and/or antagonists of DR4.

Example 20

Lymphadema Animal Model

The purpose of this experimental approach is to create an appropriate and consistent lymphedema model for testing the therapeutic effects of DR4 in lymphangiogenesis and re-establishment of the lymphatic circulatory system in the rat hind limb. Effectiveness is measured by swelling volume of the affected limb, quantification of the amount of lymphatic vasculature, total blood plasma protein, and histopathology. Acute lymphedema is observed for 7-10 days. Perhaps more importantly, the chronic progress of the edema is followed for up to 3-4 weeks.

Prior to beginning surgery, blood sample is drawn for protein concentration analysis. Male rats weighing approximately ~350 g are dosed with Pentobarbital. Subsequently, the right legs are shaved from knee to hip. The shaved area is swabbed with gauze soaked in 70% ethanol. Blood is drawn for serum total protein testing. Circumference and volumetric measurements are made prior to injecting dye into paws after marking 2 measurement levels (0.5 cm above heel, at mid-pt of dorsal paw). The intradermal dorsum of both right and left paws are injected with 0.05 ml of 1% Evan's Blue. Circumference and volumetric measurements are then made following injection of dye into paws.

Using the knee joint as a landmark, a mid-leg inguinal incision is made circumferentially allowing the femoral vessels to be located. Forceps and hemostats are used to dissect and separate the skin flaps. After locating the femoral vessels, the lymphatic vessel that runs along side and underneath the vessel(s) is located. The main lymphatic vessels in this area are then electrically coagulated or suture ligated.

Using a microscope, muscles in back of the leg (near the semitendinosis and adductors) are bluntly dissected. The popliteal lymph node is then located. The 2 proximal and 2 distal lymphatic vessels and distal blood supply of the popliteal node are then located and ligated by suturing. The popliteal lymph node, and any accompanying adipose tissue, is then removed by cutting connective tissues.

Care is taken to control any mild bleeding resulting from this procedure. After lymphatics are occluded, the skin flaps are sealed by using liquid skin (Vetbond) (A J Buck). The separated skin edges are sealed to the underlying muscle tissue while leaving a gap of ~0.5 cm around the leg. Skin also may be anchored by suturing to underlying muscle when necessary.

To avoid infection, animals are housed individually with mesh (no bedding). Recovering animals are checked daily through the optimal edematous peak, which typically occurred by day 5-7. The plateau edematous peak are then observed. To evaluate the intensity of the lymphedema, the circumference and volumes of 2 designated places on each paw before operation and daily for 7 days are measured. The effect plasma proteins on lymphedema is determined and whether protein analysis is a useful testing perimeter is also investigated. The weights of both control and edematous limbs are evaluated at 2 places. Analysis is performed in a blind manner.

Circumference Measurements: Under brief gas anesthetic to prevent limb movement, a cloth tape is used to measure limb circumference. Measurements are done at the ankle bone and dorsal paw by 2 different people then those 2 readings are averaged. Readings are taken from both control and edematous limbs.

Volumetric Measurements: On the day of surgery, animals are anesthetized with pentobarbital and are tested prior to surgery. For daily volumetrics animals are under brief halothane anesthetic (rapid immobilization and quick recovery), both legs are shaved and equally marked using waterproof marker on legs. Legs are first dipped in water, then dipped into instrument to each marked level then measured by Buxco edema software (Chen/Victor). Data is recorded by one person, while the other is dipping the limb to marked area.

Blood-plasma protein measurements: Blood is drawn, spun, and serum separated prior to surgery and then at conclusion for total protein and Ca2+ comparison.

Limb Weight Comparison: After drawing blood, the animal is prepared for tissue collection. The limbs were amputated using a quillitine, then both experimental and control legs were cut at the ligature and weighed. A second weighing is done as the tibio-cacaneal joint was disarticulated and the foot was weighed.

Histological Preparations: The transverse muscle located behind the knee (popliteal) area is dissected and arranged in a metal mold, filled with freezeGel, dipped into cold methylbutane, placed into labeled sample bags at −80 EC until sectioning. Upon sectioning, the muscle was observed under fluorescent microscopy for lymphatics. Other immuno/histological methods are currently being evaluated.

The studies described in this example test the activity in DR4 protein. However, one skilled in the art could easily modify the exemplified studies to test the activity of DR4 polynucleotides (e.g., gene therapy), agonists, and/or antagonists of DR4.

Example 21

Production of an Antibody

A. Hybridoma Technology

The antibodies of the present invention can be prepared by a variety of methods. (See, Current Protocols, Chapter 2.) As one example of such methods, cells expressing DR4 are administered to an animal to induce the production of sera containing polyclonal antibodies. In a preferred method, a preparation of DR4 protein is prepared and purified to render it substantially free of natural contaminants. Such a preparation is then introduced into an animal in order to produce polyclonal antisera of greater specific activity.

Monoclonal antibodies specific for protein DR4 are prepared using hybridoma technology. (Kohler et al., Nature 256:495 (1975); Kohler et al., *Eur. J. Immunol.* 6:511 (1976); Kohler et al., *Eur. J. Immunol.* 6:292 (1976); Hammerling et al., in: Monoclonal Antibodies and T-Cell Hybridomas, Elsevier, N.Y., pp. 563-681 (1981)). In general, an animal (preferably a mouse) is immunized with DR4 polypeptide or, more preferably, with a secreted DR4 polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al. (Gastroenterology 80:225-232 (1981). The hybridoma cells obtained through such a selection are then assayed to identify clones which secrete antibodies capable of binding the DR4 polypeptide.

Alternatively, additional antibodies capable of binding to DR4 polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the DR4 protein-specific antibody can be blocked by DR4. Such antibodies comprise anti-idiotypic antibodies to the DR4 protein-specific antibody and are used to immunize an animal to induce formation of further DR4 protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed infra. (See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).)

Isolation of Antibody Fragments Directed Against DR4-V1 and DR4 from a Library of scFvs Naturally occurring V-genes isolated from human PBLs are constructed into a large library of antibody fragments which contain reactivities against polypeptides of the present invention to which the donor may or may not have been exposed (see, e.g., U.S. Pat. No. 5,885,793 incorporated herein in its entirety by reference).

Rescue of the Library

A library of scFvs is constructed from the RNA of human PBLs as described in WO92/01047. To rescue phage displaying antibody fragments, approximately $10^9$ *E. coli* harboring the phagemid are used to inoculate 50 ml of 2×TY containing 1% glucose and 100 µg/ml of ampicillin (2×TY-AMP-GLU) and grown to an O.D. of 0.8 with shaking. Five ml of this culture is used to innoculate 50 ml of 2×TY-AMP-GLU, 2×10⁸ TU of delta gene 3 helper phage (M13 gene 111, see WO92/01047) are added and the culture incubated at 37° C. for 45 minutes without shaking and then at 37° C. for 45 minutes with shaking. The culture is centrifuged at 4000 r.p.m. for 10 minutes and the pellet resuspended in 2 liters of 2×TY containing 100 µg/ml ampicillin and 50 µg/ml kanamycin and grown overnight. Phage are prepared as described in WO92/01047.

M13 gene III is prepared as follows: M13 gene III helper phage does not encode gene III protein, hence the phage(mid) displaying antibody fragments have a greater avidity of binding to antigen. Infectious M13 gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are pelleted (IEC-Centra 8, 4000 revs/min for 10 min), resuspended in 300 ml 2×TY broth containing 100 µg ampicillin/ml and 25 µg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 µm filter (Minisart NML; Sartorius) to give a final concentration of approximately 1013 transducing units/ml (ampicillin-resistant clones).

Panning of the Library

Immunotubes (Nunc) are coated overnight in PBS with 4 ml of either 100 mg/ml or 10 mg/ml of a polypeptide of the present invention. Tubes are blocked with 2% Marvel-PBS for 2 hours at 37° C. and then washed 3 times in PBS. Approximately $10^{13}$ TU of phage are applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log *E. coli* TG1 by incubating eluted phage with bacteria for 30 minutes at 37° C. The *E. coli* are then plated on TYE plates containing 1% glucose and 100 µg/ml ampicillin. The resulting bacterial library is then rescued with M13 gene III helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders

Eluted phage from the 3rd and 4th rounds of selection are used to infect *E. coli* HB 2151 and soluble scFv is produced (Marks, et al., 1991) from single colonies for assay. ELISAs are performed with microtiter plates coated with either 10 pg/ml of the polypeptide of the present invention in 50 mM bicarbonate pH 9.6. Clones positive in ELISA are further characterized by PCR fingerprinting (see e.g., WO92/01047) and then by sequencing.

Example 22

Tissue distribution of DR4 Gene Expression

Northern blot analysis is carried out to examine DR4 gene (ATCC No. 97853) expression in human tissues, using methods described by, among others, Sambrook et al., cited above. A cDNA probe containing the entire nucleotide sequence of the DR4 protein (SEQ ID NO:1) is labeled with $^{32}$P using the Rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for DR4 mRNA.

Multiple Tissue Northern (MTN) blots containing various human tissues (H) or human immune system tissues (IM) are obtained from Clontech and are examined with labeled probe using ExpressHyb™ hybridization solution (Clontech) according to manufacturer's protocol number PT1190-1. Following hybridization and washing, the blots are mounted and exposed to film at −70<C overnight, and films developed according to standard procedures. Expression of DR4 was detected in tissues enriched in lymphocytes including amniotic cells, heart, liver cancer, kidney, peripheral blood leukocytes, activated T-cell, K562 plus PMA, W138 cells, Th2 cells, human tonsils, and CD34 depleted buffy coat (cord blood). It can be envisaged that DR4 plays a role in lymphocyte homeostasis.

Example 23

Method of Determining Alterations in the DR4 Gene

RNA is isolated from entire families or individual patients presenting with a phenotype of interest (such as a disease). cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95° C. for 30 seconds; 60-120 seconds at 52-58° C.; and 60-120 seconds at 70° C., using buffer solutions described in Sidransky, D., et al., *Science* 252:706 (1991).

PCR products are then sequenced using primers labeled at their 5' end with T4 polynucleotide kinase, employing SequiTherm Polymerase. (Epicentre Technologies). The intron-exon borders of selected exons of DR4 are also determined and genomic PCR products analyzed to confirm the results. PCR products harboring suspected mutations in DR4 is then cloned and sequenced to validate the results of the direct sequencing.

PCR products of DR4 are cloned into T-tailed vectors as described in Holton, T. A. and Graham, M. W., *Nucleic Acids Research*, 19:1156 (1991) and sequenced with T7 polymerase (United States Biochemical). Affected individuals are identified by mutations in DR4 not present in unaffected individuals.

Genomic rearrangements are also observed as a method of determining alterations in the DR4 gene. Genomic clones isolated using techniques known in the art are nick-translated with digoxigenindeoxy-uridine 5'-triphosphate (Boehringer Manheim), and FISH performed as described in Johnson, C. et al., *Methods Cell Biol.* 35:73-99 (1991). Hybridization with the labeled probe is carried out using a vast excess of human cot-1 DNA for specific hybridization to the DR4 genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, C. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region of DR4 (hybridized by the probe) are identified as insertions, deletions, and translocations. These DR4 alterations are used as a diagnostic marker for an associated disease.

Example 24

Method of Detecting Abnormal Levels of DR4 in a Biological Sample

DR4 polypeptides can be detected in a biological sample, and if an increased or decreased level of DR4 is detected, this polypeptide is a marker for a particular phenotype. Methods of detection are numerous, and thus, it is understood that one skilled in the art can modify the following assay to fit their particular needs.

For example, antibody-sandwich ELISAs are used to detect DR4 in a sample, preferably a biological sample. Wells of a microtiter plate are coated with specific antibodies to DR4, at a final concentration of 0.2 to 10 µg/ml. The antibodies are either monoclonal or polyclonal and are produced using technique known in the art. The wells are blocked so that non-specific binding of DR4 to the well is reduced.

The coated wells are then incubated for >2 hours at RT with a sample containing DR4. Preferably, serial dilutions of the sample should be used to validate results. The plates are then washed three times with deionized or distilled water to remove unbounded DR4.

Next, 50 µl of specific antibody-alkaline phosphatase conjugate, at a concentration of 25-400 ng, is added and incubated for 2 hours at room temperature. The plates are again washed three times with deionized or distilled water to remove unbounded conjugate.

75 µl of 4-methylumbelliferyl phosphate (MUP) or p-nitrophenyl phosphate (NPP) substrate solution is then added to each well and incubated 1 hour at room temperature to allow cleavage of the substrate and fluorescence. The fluorescence is measured by a microtiter plate reader. A standard curve is prepared using the experimental results from serial dilutions of a control sample with the sample concentration plotted on the X-axis (log scale) and fluorescence or absorbance on the Y-axis (linear scale). The DR4 polypeptide concentration in a sample is then interpolated using the standard curve based on the measured fluorescence of that sample.

Example 25

Method of Treating Decreased Levels of DR4

The present invention relates to a method for treating an individual in need of a decreased level of DR4 biological activity in the body comprising, administering to such an individual a composition comprising a therapeutically effective amount of DR4 antagonist. Preferred antagonists for use in the present invention are DR4-specific antibodies.

Moreover, it will be appreciated that conditions caused by a decrease in the standard or normal expression level of DR4 in an individual can be treated by administering DR4, preferably in a soluble and/or secreted form. Thus, the invention also provides a method of treatment of an individual in need of an increased level of DR4 polypeptide comprising administering to such an individual a pharmaceutical composition comprising an amount of DR4 to increase the biological activity level of DR4 in such an individual.

For example, a patient with decreased levels of DR4 polypeptide receives a daily dose 0.1-100 µg/kg of the polypeptide for six consecutive days. Preferably, the polypeptide is in a soluble and/or secreted form.

Example 26

Method of Treating Increased Levels of DR4

The present invention also relates to a method for treating an individual in need of an increased level of DR4 biological activity in the body comprising administering to such an individual a composition comprising a therapeutically effective amount of DR4 or an agonist thereof.

Antisense technology is used to inhibit production of DR4. This technology is one example of a method of decreasing levels of DR4 polypeptide, preferably a soluble and/or secreted form, due to a variety of etiologies, such as cancer.

For example, a patient diagnosed with abnormally increased levels of DR4 is administered intravenously antisense polynucleotides at 0.5, 1.0, 1.5, 2.0 and 3.0 mg/kg day for 21 days. This treatment is repeated after a 7-day rest period if the is determined to be well tolerated.

Example 27

Method of Treatment Using Gene Therapy—Ex Vivo

One method of gene therapy transplants fibroblasts, which are capable of expressing soluble and/or mature DR4 polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37<C for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., *DNA,* 7:219-25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding DR4 can be amplified using PCR primers which correspond to the 5' and 3' end encoding sequences respectively. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform *E. coli* HB101, which are then plated onto agar containing kanamycin for the purpose of confirming that the vector contains properly inserted DR4.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the DR4 gene is then added to the media and the packaging cells transduced with the vector. The packaging cells now produce infectious viral particles containing the DR4 gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a Millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether DR4 protein is produced.

The engineered fibroblasts are then transplanted onto the host, either alone or after having been grown to confluence on cytodex 3 microcarrier beads.

Example 28

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) DR4 sequences into an animal to increase or decrease the expression of the DR4 polypeptide. The DR4 polynucleotide may be operatively linked to a promoter or any other genetic elements necessary for the expression of the DR4 polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata H. et al., *Cardiovasc. Res.* 35: 470-479 (1997); Chao J. et al., *Pharmacol. Res.* 35:517-522 (1997); Wolff J. A. *Neuromuscul. Disord.* 7:314-318 (1997); Schwartz B. et al., *Gene Ther.* 3:405-411 (1996); Tsurumi Y. et al., *Circulation* 94:3281-3290 (1996) (incorporated herein by reference).

The DR4 polynucleotide constructs may be delivered by any method that delivers injectable materials to the cells of an animal, such as, injection into the interstitial space of tissues (heart, muscle, skin, lung, liver, intestine and the like). The DR4 polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the DR4 polynucleotides may also be delivered in liposome formulations (such as those taught in Felgner P. L. et al. *Ann. NY Acad. Sci.* 772:126-139 (1995) and Abdallah B. et al. *Biol. Cell* 85(1): 1-7 (1995)) which can be prepared by methods well known to those skilled in the art.

The DR4 polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The DR4 polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked DR4 polynucleotide injection, an effective dosage amount of DNA or RNA will be in the range of from about 0.05 μg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked DR4 polynucleotide constructs can be delivered to arteries during angioplasty by the catheter used in the procedure.

The dose response effects of injected DR4 polynucleotide in muscle in vivo is determined as follows. Suitable DR4 template DNA for production of mRNA coding for DR4 polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice anesthetized by intraperitoneal injection with 0.3 ml of 2.5% Avertin. A 1.5 cm incision is made on the anterior thigh, and the quadriceps muscle is directly visualized. The DR4 template DNA is injected in 0.1 ml of carrier in a I cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 μm cross-section of the individual quadriceps muscles is histochemically stained for DR4 protein expression. A time course for DR4 protein expression may be done in a similar fashion except that quadriceps from different mice are harvested at different times. Persistence of DR4 DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using DR4 naked DNA.

Example 29

Sensitive and Specific Immunohistochemical Assays for the Detection of TRAIL Receptors DR4 and DR5

Specific and sensitive assays for the detection of DR4 and DR5 receptors in formalin-fixed, paraffin-embedded human tumor tissues were developed. Affinity purified rabbit polyclonal antibodies, specific for DR4 and DR5, were optimized using a two step assay utilizing the EnVision®+visualization system. The optimal antigen retrieval was determined to be heat induced epitope retrieval (HIER). The optimal antibody concentrations were established while employing an incubation time of 30 minutes for the DR4 assay and 60 minutes for the DR5 assay. The reactions were visualized with 3'3-diaminobenzidine (DAB+).

Sections from formalin-fixed, paraffin-embedded pellets from cell lines previously characterized by flow cytometry for surface expression of DR4 and DR5 demonstrated optimal IHC staining using both assays. Similarly, tumor-enriched xenograft models showed IHC staining with minimal background staining of the surrounding non-reactive mouse tissue. Optimal staining for both DR4 and DR5 was observed on a wide range of human tumor specimens, including colon, lung and breast carcinoma. Staining of the tumor cells was favorable with minimal background staining in the stroma.

Materials

Recombinant DR4 and DR5 Antigens:

DR4 and DR5 were expressed in NSO cells. The proteins were secreted in culture media. DR4 and DR5 were purified by a three-step procedure combining HQ (PerSeptive Biosystems) anion exchange chromatography at pH 8.5 using a salt gradient of 0-1 M NaCl) Hydrophobic Interaction Chromatography on a Phenyl (high sub) Sepharose column (Amersham Bioscience) and a Hydroxyapatite column for final purification and removing high salt. Purified protein is endotoxin free and 99% pure in N-terminal sequencing and HPLC-RPC.

Primary antibody/recombinant antigen preparations in optimal concentrations were mixed for 30 minutes at room temperature prior to application to the specimen.

Antibodies:

Affinity purified rabbit polyclonal antibodies specific for DR4 and DR5 were produced by HGS. Optimal antibody titers were established using control specimens and diluted in Antibody Diluent with background reducing components (DakoCytomation code S3022).

Target Retrieval:

Heat-induced epitope retrieval (HIER) was performed using target retrieval solution, TRS (DakoCytomation code S1700) in a pressure cooker (Farberware Programmable Pressure Cooker #FPC400) for 30 minutes at high pressure.

Detection Reagents:

Immunostaining was performed using the EnVision+visualization system (DakoCytomation code K4011). This detection system utilizes an HRP enzyme labelled polymer backbone conjugated to mouse secondary antibodies. The reactions were visualized with 3'3-diaminobenzidine (DAB+; DakoCytomation code K3468).

Cell Pellet Models:

Approximately one million cells were suspended in 100 L FACS buffer (PBS with 0.1% sodium azide and 0.1% BSA) and incubated with PE-conjugated antibodies directed against DR4 (eBiosciences #12-6644-73), DR5 (eBiosciences #12-9908-73) or isotype matched control (eBiosciences #12-4719-71). Cells were incubated with antibodies for 10 to 20 minutes at room temperature, washed once in FACS buffer and pelleted by centrifugation. The cells were resuspended in 0.5 µg/ml propidium iodide for live/dead discrimination and analyzed on a FACScan using CellQuest software (BD Immunocytometry Systems).

Control cell lines used were as follows: MDA-MB-231 (breast carcinoma), Colo-205 (colon carcinoma), HT1080 (colon carcinoma), H460 (lung carcinoma), H2122 (lung carcinoma) and ST486 (lymphoma). These control cell lines were chosen based upon supportive flow cytometric, mRNA analytical, in vitro cytotoxic response to agonist DR4 and DR5 antibodies and/or protein chemical data to characterize expression of both DR4 and DR5. Four-micron sections of formalin-fixed, paraffin-embedded cell pellet blocks were mounted on silanized slides, deparaffinized with Histo-Clear (National Diagnostics) and rehydrated in graded alcohol.

Xenograft Models:

Colo205 Colon: Female Swiss athymnic mice (7-8 weeks of age, 20 g average body weight) were used for xenograft models. On day 0, 1×107 Colo205 cells (ATCC CCL-222) were implanted subcutaneously in the lower right flank of the mice. Once tumors had grown to approximately 100 mm$^3$ (day 9) tumors were harvested.

MDA-MB-231 Breast: Female Swiss nude mice (7-10 weeks of age) were used for xenograft models. On day 0, 106 MDA-MB-231 cells (HGS stock) were implanted subcutaneously SC lower right mammary area (inguinal area) of the mice. Once tumors had grown to a approximately 25 mm$^3$ (day 6) tumors were harvested. Tumors were excised and placed in 10% neutral buffered formalin (NBF) for 24 hours. Tumors were then trimmed, processed, and embedded in paraffin using routine histologic techniques. Four-micron sections of formalin-fixed, paraffin-embedded xenograft tissue blocks were mounted on silanized slides, deparaffinized with Histo-Clear (National Diagnostics) and rehydrated in graded alcohol.

Human Tissue Specimens: Four-micron sections of formalin-fixed, paraffin-embedded normal and neoplastic human tissue were mounted on silanized slides. The tissue sections were deparaffinized in Histo-Clear (National Diagnostics) and rehydrated in graded alcohols. Some specimens used for the development of these assays used tissue samples provided by the Cooperative Human Tissue Network which is funded by the National Cancer Institute.

In conclusion, two highly specific IHC assays have been developed for the detection of DR4 and DR5 expression in formalin-fixed, paraffin-embedded human tissues. Xenograft and cell pellet controls were used to establish assay specificity. Optimal IHC staining for both DR4 and DR5 was observed on a wide variety of formalin-fixed, paraffin-embedded human tumor tissues, including lung, colon and breast carcinoma. DR5 tumor expression was stronger and more widespread than DR4. Adjacent normal tissues have significantly weaker expression. The observed staining pattern was generally heterogeneous and either membrane or cytoplasmic in appearance. These assays allow for sensitive and specific detection of DR4 and DR5 expression in human tissue samples.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

Further, the Sequence Listing submitted herewith, in both computer and paper forms, is hereby incorporated by reference in its entirety.

Additionally, the disclosures and sequence listings of U.S. Provisional Application No. 60/990,687, filed Nov. 28, 2001, U.S. Provisional Application No. 60/885,971, filed Jan. 22, 2007, U.S. patent application Ser. No. 11/076,187, filed Mar. 10, 2005, U.S. Provisional Application No. 60/608,469, filed Sep. 10, 2004, U.S. Provisional Application No. 60/551,768, filed Mar. 11, 2004, U.S. patent application Ser. No. 10/648,786 filed Aug. 27, 2003, U.S. Provisional Application No. 60/413,861 filed Sep. 27, 2002, U.S. Provisional Application No. 60/406,922 filed Aug. 30, 2002, U.S. patent application Ser. No. 09/565,918 filed May 5, 2000, now U.S. Pat. No. 6,433,137, U.S. patent application Ser. No. 09/448,868 filed Nov. 24, 1999, U.S. Provisional Application No. 60/132,922 filed May 6, 1999, U.S. patent application Ser. No. 09/013,895 filed Jan. 27, 1998, now U.S. Pat. No. 6,342,363, U.S. Provisional Application No. 60/037,829 filed Feb. 5, 1997, and U.S. Provisional Application No. 60/035,722 filed Jan. 28, 1997, are each herein incorporated by reference in their entireties.

What is claimed is:

1. A method for inducing apoptosis of a DR4-expressing cell, comprising contacting said cell with an agonist antibody or fragment thereof that specifically binds to a polypeptide consisting of amino acids 24 to 238 of SEQ ID NO:2 in combination with a second agent selected from the group consisting of:
(a) an alkylating agent;
(b) an antimetabolite;
(c) a farnesyl transferase inhibitor;
(d) a mitotic spindle inhibitor;
(e) a topoisomerase inhibitor;
(f) a tyrosine kinase inhibitor;
(g) a proteasome inhibitor;
(h) an antibiotic;
(i) a histone deacetylase inhibitor;
(j) a HSP90 inhibitor;
(k) thalidomide;
(l) a thalidomide analog;
(m) a monoclonal antibody;
(n) radiation therapy;
(o) a AKT/mTOR signaling pathway inhibitor; and
(p) a BCL-2 inhibitor.

2. The method of claim 1, wherein said alkylating agent is a nitrogen mustard.

3. The method of claim 1, wherein said alkylating agent is carboplatin.

4. The method of claim 1, wherein said alkylating agent is cisplatin.

5. The method of claim 1, wherein said alkylating agent is oxaliplatin.

6. The method of claim 1, wherein said antimetabolite is methotrexate.

7. The method of claim 1, wherein said antimetabolite is fluorouracil+leucovorin.

8. The method of claim 1, wherein said antimetabolite is cytosine arabinoside.

9. The method of claim 1, wherein said antimetabolite is pemetrexed.

10. The method of claim 1, wherein said antimetabolite is gemcitabine.

11. The method of claim 1, wherein said antimetabolite is capecitabine.

12. The method of claim 1, wherein said mitotic spindle inhibitor is docetaxel.

13. The method of claim 1, wherein said mitotic spindle inhibitor is paclitaxel.

14. The method of claim 1, wherein said mitotic spindle inhibitor is vincristine.

15. The method of claim 1, wherein said mitotic spindle inhibitor is vinblastine.

16. The method of claim 1, wherein said topoisomerase inhibitor is 9-aminocamptothecin.

17. The method of claim 1, wherein said topoisomerase inhibitor is topotecan.

18. The method of claim 1, wherein said topoisomerase inhibitor is irinotecan.

19. The method of claim 1, wherein said topoisomerase inhibitor is etoposide.

20. The method of claim 1, wherein said tyrosine kinase inhibitor is imatinib mesylate.

21. The method of claim 1, wherein said tyrosine kinase inhibitor is BAY 43-9006.

22. The method of claim 1, wherein said proteasome inhibitor is PS-341.

23. The method of claim 1, wherein said proteasome inhibitor is NPI-0052.

24. The method of claim 1, wherein said antibiotic is bleomycin.

25. The method of claim 1, wherein said antibiotic is daunorubicin.

26. The method of claim 1, wherein said antibiotic is doxorubicin.

27. The method of claim 1, wherein said antibiotic is dactinomycin.

28. The method of claim 1, wherein said monoclonal antibody is bevacizumab.

29. The method of claim 1, wherein said monoclonal antibody is rituximab.

30. The method of claim 1, wherein said thalidomide analog is revlimid.

31. A method for treating cancer, comprising administering to a patient therapeutically effective amounts of an agonist antibody or fragment thereof that specifically binds to a polypeptide consisting of amino acids 24 to 238 of SEQ ID NO:2 in combination with a second agent selected from the group consisting of:
(a) a tyrosine kinase inhibitor;
(b) a proteasome inhibitor;
(c) an antibiotic;
(d) a histone deacetylase inhibitor;
(e) a HSP90 inhibitor;
(f) thalidomide;
(g) a thalidomide analog;
(h) a monoclonal antibody;
(i) radiation therapy;
(j) a AKT/mTOR signaling pathway inhibitor; and
(k) a BCL-2 inhibitor.

32. The method of claim 31, wherein said tyrosine kinase inhibitor is BAY 43-9006.

33. The method of claim 31, wherein said proteasome inhibitor is NPI-0052.

34. The method of claim 31, wherein said antibiotic is bleomycin.

35. The method of claim 31, wherein said antibiotic is daunorubicin.

36. The method of claim 31, wherein said antibiotic is doxorubicin.

37. The method of claim 31, wherein said antibiotic is dactinomycin.

38. The method of claim 31, wherein said monoclonal antibody is bevacizumab.

39. The method of claim 31, wherein said monoclonal antibody is rituximab.

40. The method of claim 31, wherein said thalidomide analog is revlimid.

41. A method of treating cancer, comprising administering to a patient a therapeutically effective amount of an agonist antibody or fragment thereof that specifically binds to a polypeptide consisting of amino acids 24 to 238 of SEQ ID NO:2, wherein said cancer is selected from the group consisting of:
   (a) multiple myeloma;
   (b) bile duct cancer;
   (c) hepatoma; and
   (d) non-small cell lung cancer.

42. The method of claim 41, wherein said cancer is multiple myeloma.

43. The method of claim 41, wherein said cancer is bile duct cancer.

44. The method of claim 41, wherein said cancer is a hepatoma.

45. The method of claim 41, wherein said cancer is non-small cell lung cancer.

46. The method of claim 1, wherein said antibody or fragment thereof is a monoclonal antibody.

47. The method of claim 1, wherein said antibody or fragment thereof is selected from the group consisting of:
   (a) a polyclonal antibody;
   (b) a chimeric antibody;
   (c) a human antibody;
   (d) a humanized antibody;
   (e) a single-chain Fv antibody; and
   (f) an Fab antibody fragment.

48. The method of claim 1, wherein said antibody or fragment thereof is pegylated.

49. The method of claim 1, wherein said antibody or fragment thereof is fused to a heterologous polypeptide.

50. The method of claim 1, wherein said cell is contacted by said antibody or fragment thereof and said second agent simultaneously.

51. The method of claim 1, wherein said cell is contacted by said antibody or fragment thereof and said second agent sequentially.

52. The method of claim 1, which is in vitro.

53. The method of claim 1, which is in vivo.

54. The method of claim 1, wherein said cell is a cancer cell.

55. The method of claim 31, wherein said antibody or fragment thereof is a monoclonal antibody.

56. The method of claim 31, wherein said antibody or fragment thereof is selected from the group consisting of:
   (a) a polyclonal antibody;
   (b) a chimeric antibody;
   (c) a human antibody;
   (d) a humanized antibody;
   (e) a single-chain Fv antibody; and
   (f) an Fab antibody fragment.

57. The method of claim 31, wherein said antibody or fragment thereof is pegylated.

58. The method of claim 31, wherein said antibody or fragment thereof is fused to a heterologous polypeptide.

59. The method of claim 31, wherein said antibody or fragment thereof and said second agent are administered to the patient simultaneously.

60. The method of claim 31, wherein said antibody or fragment thereof and said second agent are administered to the patient sequentially.

61. The method of claim 41, wherein said antibody or fragment thereof is a monoclonal antibody.

62. The method of claim 41, wherein said antibody or fragment thereof is selected from the group consisting of:
   (a) a polyclonal antibody;
   (b) a chimeric antibody;
   (c) a human antibody;
   (d) a humanized antibody;
   (e) a single-chain Fv antibody; and
   (f) an Fab antibody fragment.

63. The method of claim 41, wherein said antibody or fragment thereof is pegylated.

64. The method of claim 41, wherein said antibody or fragment thereof is fused to a heterologous polypeptide.

* * * * *

SEQUENCE LISTING

<160> NUMBER OF SEQ ID NOS: 13

<210> SEQ ID NO 1
<211> LENGTH: 2152
<212> TYPE: DNA
<213> ORGANISM: Homo sapiens

<400> SEQUENCE: 1

```
ttcgggcacg agggcaggat ggcgccacca ccagctagag tacatctagg tgcgttcctg      60
gcagtgactc cgaatcccgg gagcgcagcg agtgggacag aggcagccgc ggccacaccc     120
agcaaagtgt ggggctcttc cgcggggagg attgaaccac gaggcgggg  ccgaggagcg     180 ctccctacct ccatgggaca gcacggaccc agtgcccggg cccgggcagg gcgcgcccca     240
ggacccaggc cggcgcggga agccagccct cggctccggg tccacaagac cttcaagttt     300
gtcgtcgtcg gggtcctgct gcaggtcgta cctagctcag ctgcaaccat caaacttcat     360
```

```
gatcaatcaa ttggcacaca gcaatgggaa catagcccctt tgggagagtt gtgtccacca      420
ggatctcata gatcagaacg tcctggagcc tgtaaccggt gcacagaggg tgtgggttac      480
accaatgctt ccaacaattt gtttgcttgc ctcccatgta cagcttgtaa atcagatgaa      540
gaagagagaa gtccctgcac cacgaccagg aacacagcat gtcagtgcaa accaggaact      600
ttccggaatg acaattctgc tgagatgtgc cggaagtgca gcacagggtg ccccagaggg      660
atggtcaagg tcaaggattg tacgccctgg agtgacatcg agtgtgtcca caagaatca       720
ggcaatggac ataatatatg ggtgattttg gttgtgactt tggttgttcc gttgctgttg      780
gtggctgtgc tgattgtctg ttgttgcatc ggctcaggtt gtggagggga ccccaagtgc      840
atggacaggg tgtgtttctg cgcttgggt  ctcctacgag ggcctggggc tgaggacaat      900
gctcacaacg agattctgag caacgcagac tcgctgtcca ctttcgtctc tgagcagcaa      960
atggaaagcc aggagccggc agatttgaca ggtgtcactg tacagtcccc aggggaggca     1020
cagtgtctgc tgggaccggc agaagctgaa gggtctcaga ggaggaggct gctggttcca     1080
gcaaatggtg ctgaccccac tgagactctg atgctgttct ttgacaagtt tgcaaacatc     1140
gtgcccttg  actcctggga ccagctcatg aggcagctgg acctcacgaa aaatgagatc     1200
gatgtggtca gagctggtac agcaggccca ggggatgcct tgtatgcaat gctgatgaaa     1260
tgggtcaaca aaactggacg gaacgcctcg atccacaccc tgctggatgc cttggagagg     1320
atggaagaga gacatgcaaa agagaagatt caggacctct tggtggactc tggaaagttc     1380
atctacttag aagatggcac aggctctgcc gtgtccttgg agtgaaagac tcttttacc      1440
agaggtttcc tcttaggtgt taggagttaa tacatattag gttttttttt ttttttaacat    1500
gtatacaaag taaattctta gccacgtgta ttggctcctg cctgtaatcc catcactttg     1560
ggaggctgac gccggtggat ccacttgagg tccgaagttc aagaccagcc ctgaaccaa      1620
catcgtggaa atgcccgtct tttacaaaaa aataccaaaa attcaactgg aatgtgcatg     1680
gtgtgtgcca tcatttcctc ggctaactac gggaggtctg aggccaggag aatccacttg     1740
aaccccacga aggacagtgt agactgcaga ttgcaccact gcactcccag cctgggaaca     1800
cagagcaaga ctctgtctca agataaaata aaataaactt gaaagaatta ttgcccgact     1860
gaggctcaca tgccaaagga aaatctggtt ctccccctgag ctggcctccg tgtgtttcct    1920
tatcatggtg gtcaattgga ggtgttaatt tgaatggatt aaggaacacc tagaacactg     1980
gtaaggcatt atttctggga cattatttct gggcatgtct tcgagggtgt ttccagaggg     2040
gattggcatg cgatcgggtg gactgagtgg aaaagaccta cccttaattt ggggggggcac   2100
cgtccgacag actggggagc aagatagaag aaaacaaaaa aaaaaaaaaa aa             2152
```

<210> SEQ ID NO 2
<211> LENGTH: 468
<212> TYPE: PRT
<213> ORGANISM: Homo sapiens

<400> SEQUENCE: 2

Met Ala Pro Pro Ala Arg Val His Leu Gly Ala Phe Leu Ala Val
1               5                   10                  15

Thr Pro Asn Pro Gly Ser Ala Ala Ser Gly Thr Glu Ala Ala Ala
                20                  25                  30

Thr Pro Ser Lys Val Trp Gly Ser Ala Gly Arg Ile Glu Pro Arg
            35                  40                  45

Gly Gly Gly Arg Gly Ala Leu Pro Thr Ser Met Gly Gln His Gly Pro
    50                  55                  60

```
Ser Ala Arg Ala Arg Ala Gly Arg Ala Pro Gly Pro Arg Pro Ala Arg
 65                  70                  75                  80

Glu Ala Ser Pro Arg Leu Arg Val His Lys Thr Phe Lys Phe Val Val
                 85                  90                  95

Val Gly Val Leu Leu Gln Val Val Pro Ser Ala Ala Thr Ile Lys
            100                 105                 110

Leu His Asp Gln Ser Ile Gly Thr Gln Gln Trp Glu His Ser Pro Leu
            115                 120                 125

Gly Glu Leu Cys Pro Pro Gly Ser His Arg Ser Glu Arg Pro Gly Ala
            130                 135                 140

Cys Asn Arg Cys Thr Glu Gly Val Gly Tyr Thr Asn Ala Ser Asn Asn
145                 150                 155                 160

Leu Phe Ala Cys Leu Pro Cys Thr Ala Cys Lys Ser Asp Glu Glu Glu
                165                 170                 175

Arg Ser Pro Cys Thr Thr Thr Arg Asn Thr Ala Cys Gln Cys Lys Pro
            180                 185                 190

Gly Thr Phe Arg Asn Asp Asn Ser Ala Glu Met Cys Arg Lys Cys Ser
            195                 200                 205

Thr Gly Cys Pro Arg Gly Met Val Lys Val Lys Asp Cys Thr Pro Trp
210                 215                 220

Ser Asp Ile Glu Cys Val His Lys Glu Ser Gly Asn Gly His Asn Ile
225                 230                 235                 240

Trp Val Ile Leu Val Val Thr Leu Val Val Pro Leu Leu Leu Val Ala
                245                 250                 255

Val Leu Ile Val Cys Cys Cys Ile Gly Ser Gly Cys Gly Gly Asp Pro
            260                 265                 270

Lys Cys Met Asp Arg Val Cys Phe Trp Arg Leu Gly Leu Leu Arg Gly
            275                 280                 285

Pro Gly Ala Glu Asp Asn Ala His Asn Glu Ile Leu Ser Asn Ala Asp
            290                 295                 300

Ser Leu Ser Thr Phe Val Ser Glu Gln Gln Met Glu Ser Gln Glu Pro
305                 310                 315                 320

Ala Asp Leu Thr Gly Val Thr Val Gln Ser Pro Gly Glu Ala Gln Cys
                325                 330                 335

Leu Leu Gly Pro Ala Glu Ala Glu Gly Ser Gln Arg Arg Arg Leu Leu
            340                 345                 350

Val Pro Ala Asn Gly Ala Asp Pro Thr Glu Thr Leu Met Leu Phe Phe
            355                 360                 365

Asp Lys Phe Ala Asn Ile Val Pro Phe Asp Ser Trp Asp Gln Leu Met
            370                 375                 380

Arg Gln Leu Asp Leu Thr Lys Asn Glu Ile Asp Val Val Arg Ala Gly
385                 390                 395                 400

Thr Ala Gly Pro Gly Asp Ala Leu Tyr Ala Met Leu Met Lys Trp Val
                405                 410                 415

Asn Lys Thr Gly Arg Asn Ala Ser Ile His Thr Leu Leu Asp Ala Leu
            420                 425                 430

Glu Arg Met Glu Glu Arg His Ala Lys Glu Lys Ile Gln Asp Leu Leu
            435                 440                 445

Val Asp Ser Gly Lys Phe Ile Tyr Leu Glu Asp Gly Thr Gly Ser Ala
            450                 455                 460

Val Ser Leu Glu
465
```

<210> SEQ ID NO 3
<211> LENGTH: 669
<212> TYPE: PRT
<213> ORGANISM: Homo sapiens

<400> SEQUENCE: 3

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
        195                 200                 205

Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
            260                 265                 270

Gln Lys Val Gln Leu Leu Arg Asn Trp His Gln Leu His Gly Lys Lys
        275                 280                 285

Glu Ala Tyr Asp Thr Leu Ile Lys Asp Leu Lys Lys Ala Asn Leu Cys
    290                 295                 300

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val Met
                325                 330                 335

Leu Gly Ile Trp Thr Leu Leu Pro Leu Val Leu Thr Ser Val Ala Arg
            340                 345                 350

Leu Ser Ser Lys Ser Val Asn Ala Gln Val Thr Asp Ile Asn Ser Lys
        355                 360                 365

Gly Leu Glu Leu Arg Lys Thr Val Thr Thr Val Glu Thr Gln Asn Leu
    370                 375                 380

Glu Gly Leu His His Asp Gly Gln Phe Cys His Lys Pro Cys Pro Pro

```
            385                 390                 395                 400
Gly Glu Arg Lys Ala Arg Asp Cys Thr Val Asn Gly Asp Glu Pro Asp
                405                 410                 415

Cys Val Pro Cys Gln Glu Gly Lys Glu Tyr Thr Asp Lys Ala His Phe
            420                 425                 430

Ser Ser Lys Cys Arg Arg Cys Arg Leu Cys Asp Glu Gly His Gly Leu
        435                 440                 445

Glu Val Glu Ile Asn Cys Thr Arg Thr Gln Asn Thr Lys Cys Arg Cys
    450                 455                 460

Lys Pro Asn Phe Phe Cys Asn Ser Thr Val Cys Glu His Cys Asp Pro
465                 470                 475                 480

Cys Thr Lys Cys Glu His Gly Ile Ile Lys Glu Cys Thr Leu Thr Ser
            485                 490                 495

Asn Thr Lys Cys Lys Glu Glu Gly Ser Arg Ser Asn Leu Gly Trp Leu
        500                 505                 510

Cys Leu Leu Leu Leu Pro Ile Pro Leu Ile Val Val Lys Arg Lys Glu
    515                 520                 525

Val Gln Lys Thr Cys Arg Lys His Arg Lys Glu Asn Gln Gly Ser His
530                 535                 540

Glu Ser Pro Thr Leu Asn Pro Glu Thr Val Ala Ile Asn Leu Ser Asp
545                 550                 555                 560

Val Asp Leu Ser Lys Tyr Ile Thr Thr Ile Ala Gly Val Met Thr Leu
            565                 570                 575

Ser Gln Val Lys Gly Phe Val Arg Lys Asn Gly Val Asn Glu Ala Lys
        580                 585                 590

Ile Asp Glu Ile Lys Asn Asp Asn Val Gln Asp Thr Ala Glu Gln Lys
    595                 600                 605

Val Gln Leu Leu Arg Asn Trp His Gln Leu His Gly Lys Lys Glu Ala
610                 615                 620

Tyr Asp Thr Leu Ile Lys Asp Leu Lys Lys Ala Asn Leu Cys Thr Leu
625                 630                 635                 640

Ala Glu Lys Ile Gln Thr Ile Ile Leu Lys Asp Ile Thr Ser Asp Ser
            645                 650                 655

Glu Asn Ser Asn Phe Arg Asn Glu Ile Gln Ser Leu Val
        660                 665

<210> SEQ ID NO 4
<211> LENGTH: 909
<212> TYPE: PRT
<213> ORGANISM: Homo sapiens

<400> SEQUENCE: 4

Met Gly Leu Ser Thr Val Pro Asp Leu Leu Pro Leu Val Leu Leu Glu
1               5                   10                  15

Leu Leu Val Gly Ile Tyr Pro Ser Gly Val Ile Gly Leu Val Pro His
            20                  25                  30

Leu Gly Asp Arg Glu Lys Arg Asp Ser Val Cys Pro Gln Gly Lys Tyr
        35                  40                  45

Ile His Pro Gln Asn Asn Ser Ile Cys Cys Thr Lys Cys His Lys Gly
    50                  55                  60

Thr Tyr Leu Tyr Asn Asp Cys Pro Gly Pro Gly Gln Asp Thr Asp Cys Arg
65                  70                  75                  80

Glu Cys Glu Ser Gly Ser Phe Thr Ala Ser Glu Asn His Leu Arg His
            85                  90                  95

Cys Leu Ser Cys Ser Lys Cys Arg Lys Glu Met Gly Gln Val Glu Ile
```

```
                100             105             110
Ser Ser Cys Thr Val Asp Arg Asp Thr Val Cys Gly Cys Arg Lys Asn
        115             120             125
Gln Tyr Arg His Tyr Trp Ser Glu Asn Leu Phe Gln Cys Phe Asn Cys
    130             135             140
Ser Leu Cys Leu Asn Gly Thr Val His Leu Ser Cys Gln Glu Lys Gln
145             150             155             160
Asn Thr Val Cys Thr Cys His Ala Gly Phe Phe Leu Arg Glu Asn Glu
                165             170             175
Cys Val Ser Cys Ser Asn Cys Lys Lys Ser Leu Glu Cys Thr Lys Leu
            180             185             190
Cys Leu Pro Gln Ile Glu Asn Val Lys Gly Thr Glu Asp Ser Gly Thr
            195             200             205
Thr Val Leu Leu Pro Leu Val Ile Phe Phe Gly Leu Cys Leu Leu Ser
210             215             220
Leu Leu Phe Ile Gly Leu Met Tyr Arg Tyr Gln Arg Trp Lys Ser Lys
225             230             235             240
Leu Tyr Ser Ile Val Cys Gly Lys Ser Thr Pro Glu Lys Glu Gly Glu
            245             250             255
Leu Glu Gly Thr Thr Thr Lys Pro Leu Ala Pro Asn Pro Ser Phe Ser
            260             265             270
Pro Thr Pro Gly Phe Thr Pro Thr Leu Gly Phe Ser Pro Val Pro Ser
            275             280             285
Ser Thr Phe Thr Ser Ser Ser Thr Tyr Thr Pro Gly Asp Cys Pro Asn
            290             295             300
Phe Ala Ala Pro Arg Arg Glu Val Ala Pro Tyr Gln Gly Ala Asp
305             310             315             320
Pro Ile Leu Ala Thr Ala Leu Ala Ser Asp Pro Ile Pro Asn Pro Leu
            325             330             335
Gln Lys Trp Glu Asp Ser Ala His Lys Pro Gln Ser Leu Asp Thr Asp
            340             345             350
Asp Pro Ala Thr Leu Tyr Ala Val Val Glu Asn Val Pro Pro Leu Arg
        355             360             365
Trp Lys Glu Phe Val Arg Arg Leu Gly Leu Ser Asp His Glu Ile Asp
        370             375             380
Arg Leu Glu Leu Gln Asn Gly Arg Cys Leu Arg Glu Ala Gln Tyr Ser
385             390             395             400
Met Leu Ala Thr Trp Arg Arg Arg Thr Pro Arg Arg Glu Ala Thr Leu
            405             410             415
Glu Leu Leu Gly Arg Val Leu Arg Asp Met Asp Leu Leu Gly Cys Leu
            420             425             430
Glu Asp Ile Glu Glu Ala Leu Cys Gly Pro Ala Ala Leu Pro Pro Ala
        435             440             445
Pro Ser Leu Leu Arg Met Gly Leu Ser Thr Val Pro Asp Leu Leu Leu
        450             455             460
Pro Leu Val Leu Leu Glu Leu Val Gly Ile Tyr Pro Ser Gly Val
465             470             475             480
Ile Gly Leu Val Pro His Leu Gly Asp Arg Glu Lys Arg Asp Ser Val
            485             490             495
Cys Pro Gln Gly Lys Tyr Ile His Pro Gln Asn Asn Ser Ile Cys Cys
            500             505             510
Thr Lys Cys His Lys Gly Thr Tyr Leu Tyr Asn Asp Cys Pro Gly Pro
            515             520             525
```

-continued

Gly Gln Asp Thr Asp Cys Arg Glu Cys Glu Ser Gly Ser Phe Thr Ala
            530                 535                 540

Ser Glu Asn His Leu Arg His Cys Leu Ser Cys Ser Lys Cys Arg Glu
545                 550                 555                 560

Lys Glu Met Gly Gln Val Glu Ile Ser Ser Cys Thr Val Asp Arg Asp
                565                 570                 575

Thr Val Cys Gly Cys Arg Lys Asn Gln Tyr Arg His Tyr Trp Ser Glu
            580                 585                 590

Asn Leu Phe Gln Cys Phe Asn Cys Ser Leu Cys Leu Asn Gly Thr Val
            595                 600                 605

His Leu Ser Cys Gln Glu Lys Gln Asn Thr Val Cys Thr Cys His Ala
610                 615                 620

Gly Phe Phe Leu Arg Glu Asn Glu Cys Val Ser Cys Ser Asn Cys Lys
625                 630                 635                 640

Lys Ser Leu Glu Cys Thr Lys Leu Cys Leu Pro Gln Ile Glu Asn Val
                645                 650                 655

Lys Gly Thr Glu Asp Ser Gly Thr Thr Val Leu Leu Pro Leu Val Ile
            660                 665                 670

Phe Phe Gly Leu Cys Leu Leu Ser Leu Leu Phe Ile Gly Leu Met Tyr
            675                 680                 685

Arg Tyr Gln Arg Trp Lys Ser Asp Leu Tyr Ser Ile Val Cys Gly Lys
690                 695                 700

Ser Thr Pro Glu Lys Glu Gly Glu Leu Glu Gly Thr Thr Thr Lys Pro
705                 710                 715                 720

Leu Ala Pro Asn Pro Ser Phe Ser Pro Thr Pro Gly Phe Thr Pro Thr
                725                 730                 735

Leu Gly Phe Ser Pro Val Pro Ser Ser Thr Phe Thr Ser Ser Ser Thr
            740                 745                 750

Tyr Thr Pro Gly Asp Cys Pro Asn Phe Ala Ala Pro Arg Arg Glu Val
            755                 760                 765

Ala Pro Pro Tyr Gln Gly Ala Asp Pro Ile Leu Ala Thr Ala Leu Ala
770                 775                 780

Ser Asp Pro Ile Pro Asn Pro Leu Gln Lys Trp Glu Asp Ser Ala His
785                 790                 795                 800

Lys Pro Gln Ser Leu Asp Thr Asp Asp Pro Ala Thr Leu Tyr Ala Val
                805                 810                 815

Val Glu Asn Val Pro Pro Leu Arg Trp Lys Glu Phe Val Arg Arg Leu
            820                 825                 830

Gly Leu Ser Pro His Glu Ile Asp Arg Leu Glu Leu Gln Asn Gly Arg
            835                 840                 845

Cys Leu Arg Glu Ala Gln Tyr Ser Met Leu Ala Thr Trp Arg Arg Arg
850                 855                 860

Thr Pro Arg Arg Glu Ala Thr Leu Glu Leu Leu Gly Arg Val Leu Arg
865                 870                 875                 880

Asp Met Asp Leu Leu Gly Cys Leu Glu Asp Ile Glu Glu Ala Leu Cys
                885                 890                 895

Gly Pro Ala Ala Leu Pro Pro Ala Pro Ser Leu Leu Arg
            900                 905

<210> SEQ ID NO 5
<211> LENGTH: 833
<212> TYPE: PRT
<213> ORGANISM: Homo sapiens

<400> SEQUENCE: 5

-continued

```
Met Gln Arg Pro Arg Gly Cys Ala Ala Val Ala Ala Ala Leu Leu
1               5                  10                 15

Leu Val Leu Leu Gly Ala Arg Ala Gln Gly Gly Thr Arg Ser Pro Arg
            20                  25                  30

Cys Asp Cys Ala Gly Asp Phe His Lys Lys Ile Gly Leu Phe Cys Cys
            35                  40                  45

Arg Gly Cys Pro Ala Gly His Tyr Leu Lys Ala Pro Cys Thr Glu Pro
            50                  55                  60

Cys Gly Asn Ser Thr Cys Leu Val Cys Pro Gln Asp Thr Phe Leu Ala
65                  70                  75                  80

Trp Glu Asn His His Asn Ser Glu Cys Ala Arg Cys Gln Ala Cys Asp
                85                  90                  95

Glu Gln Ala Ser Gln Val Ala Leu Glu Asn Cys Ser Ala Val Ala Asp
                100                 105                 110

Thr Arg Cys Gly Cys Lys Pro Gly Trp Phe Val Glu Cys Gln Val Ser
            115                 120                 125

Gln Cys Val Ser Ser Pro Phe Tyr Cys Gln Pro Cys Leu Asp Cys
            130                 135                 140

Gly Ala Leu His Arg His Thr Arg Leu Leu Cys Ser Arg Arg Asp Thr
145                 150                 155                 160

Asp Cys Gly Thr Cys Leu Pro Gly Phe Tyr Glu His Gly Asp Gly Cys
            165                 170                 175

Val Ser Cys Pro Thr Ser Thr Leu Gly Ser Cys Pro Glu Arg Cys Ala
            180                 185                 190

Ala Val Cys Gly Trp Arg Gln Met Phe Trp Val Gln Val Leu Leu Ala
            195                 200                 205

Gly Leu Val Val Pro Leu Leu Leu Gly Ala Thr Leu Thr Tyr Thr Tyr
            210                 215                 220

Arg His Cys Trp Pro His Lys Pro Leu Val Thr Ala Asp Glu Ala Gly
225                 230                 235                 240

Met Glu Ala Leu Thr Pro Pro Ala Thr His Leu Ser Pro Leu Asp
                245                 250                 255

Ser Ala His Thr Leu Leu Ala Pro Pro Asp Ser Ser Glu Lys Ile Cys
            260                 265                 270

Thr Val Gln Leu Val Gly Asn Ser Trp Thr Pro Gly Tyr Pro Glu Thr
            275                 280                 285

Gln Glu Ala Leu Cys Pro Gln Val Thr Trp Ser Trp Asp Gln Leu Pro
            290                 295                 300

Ser Arg Ala Leu Gly Pro Ala Ala Ala Pro Thr Leu Ser Pro Glu Ser
305                 310                 315                 320

Pro Ala Gly Ser Pro Ala Met Met Leu Gln Pro Gly Pro Gln Leu Tyr
            325                 330                 335

Asp Val Met Asp Ala Val Pro Ala Arg Arg Trp Lys Glu Phe Val Arg
            340                 345                 350

Thr Leu Gly Leu Arg Glu Ala Glu Ile Glu Ala Val Glu Val Glu Ile
            355                 360                 365

Gly Arg Phe Arg Asp Gln Gln Tyr Glu Met Leu Lys Arg Trp Arg Gln
            370                 375                 380

Gln Gln Pro Ala Gly Leu Gly Ala Val Tyr Ala Ala Leu Glu Arg Met
385                 390                 395                 400

Gly Leu Asp Gly Cys Val Glu Asp Leu Arg Ser Arg Leu Gln Arg Gly
            405                 410                 415

Pro Met Glu Gln Arg Pro Arg Gly Cys Ala Ala Val Ala Ala Ala Leu
            420                 425                 430
```

Leu Leu Val Leu Leu Gly Ala Arg Ala Gln Gly Gly Thr Arg Ser Pro
                435                 440                 445

Arg Cys Asp Cys Ala Gly Asp Phe His Lys Lys Ile Gly Leu Phe Cys
        450                 455                 460

Cys Arg Gly Cys Pro Ala Gly His Tyr Leu Lys Ala Pro Cys Thr Glu
465                 470                 475                 480

Pro Cys Gly Asn Ser Thr Cys Leu Val Cys Pro Gln Asp Thr Phe Leu
                485                 490                 495

Ala Trp Glu Asn His His Asn Ser Glu Cys Ala Arg Cys Gln Ala Cys
            500                 505                 510

Asp Glu Ala Ser Gln Val Ala Leu Glu Asn Cys Ser Ala Val Ala Asp
            515                 520                 525

Thr Arg Cys Gly Cys Lys Pro Gly Trp Phe Val Glu Cys Gln Val Ser
        530                 535                 540

Gln Cys Val Ser Ser Pro Phe Tyr Cys Gln Pro Cys Leu Asp Cys
545                 550                 555                 560

Gly Ala Leu His Arg His Thr Arg Leu Leu Cys Ser Arg Arg Asp Thr
                565                 570                 575

Asp Cys Gly Thr Cys Leu Pro Gly Phe Tyr Glu His Gly Asp Gly Cys
            580                 585                 590

Val Ser Cys Pro Thr Ser Thr Leu Gly Ser Cys Pro Glu Arg Cys Ala
            595                 600                 605

Ala Val Cys Gly Trp Arg Gln Met Phe Trp Val Gln Val Leu Leu Ala
        610                 615                 620

Gly Leu Val Val Pro Leu Leu Leu Gly Ala Thr Leu Thr Tyr Thr Tyr
625                 630                 635                 640

Arg His Cys Trp Pro His Lys Pro Leu Val Thr Ala Asp Glu Ala Gly
                645                 650                 655

Met Glu Ala Leu Thr Pro Pro Ala Thr His Leu Ser Pro Leu Asp
                660                 665                 670

Ser Ala His Thr Leu Leu Ala Pro Pro Asp Ser Ser Glu Lys Ile Cys
            675                 680                 685

Thr Val Gln Leu Val Gly Asn Ser Trp Thr Pro Gly Tyr Pro Glu Thr
        690                 695                 700

Gln Glu Ala Leu Cys Pro Gln Val Thr Trp Ser Trp Asp Gln Leu Pro
705                 710                 715                 720

Ser Arg Ala Leu Gly Pro Ala Ala Ala Pro Thr Leu Ser Pro Glu Ser
                725                 730                 735

Pro Ala Gly Ser Pro Ala Met Met Leu Gln Pro Gly Pro Gln Leu Tyr
            740                 745                 750

Asp Val Met Asp Ala Val Pro Ala Arg Arg Trp Lys Glu Phe Val Arg
        755                 760                 765

Thr Leu Gly Leu Arg Glu Ala Glu Ile Glu Ala Val Glu Val Glu Ile
770                 775                 780

Gly Arg Phe Arg Asp Gln Gln Tyr Glu Met Leu Lys Arg Trp Arg Gln
785                 790                 795                 800

Gln Gln Pro Ala Gly Leu Gly Ala Val Tyr Ala Ala Leu Glu Arg Met
                805                 810                 815

Gly Leu Asp Gly Cys Val Glu Asp Leu Arg Ser Arg Leu Gln Arg Gly
            820                 825                 830

Pro

<210> SEQ ID NO 6

```
<211> LENGTH: 426
<212> TYPE: DNA
<213> ORGANISM: Homo sapiens
<220> FEATURE:
<221> NAME/KEY: misc_feature
<222> LOCATION: (5)..(5)
<223> OTHER INFORMATION: n equals a, c, g or t
<220> FEATURE:
<221> NAME/KEY: misc_feature
<222> LOCATION: (10)..(10)
<223> OTHER INFORMATION: n equals a, c, g or t
<220> FEATURE:
<221> NAME/KEY: misc_feature
<222> LOCATION: (42)..(42)
<223> OTHER INFORMATION: n equals a, c, g or t
<220> FEATURE:
<221> NAME/KEY: misc_feature
<222> LOCATION: (93)..(93)
<223> OTHER INFORMATION: n equals a, c, g or t
<220> FEATURE:
<221> NAME/KEY: misc_feature
<222> LOCATION: (98)..(98)
<223> OTHER INFORMATION: n equals a, c, g or t
<220> FEATURE:
<221> NAME/KEY: misc_feature
<222> LOCATION: (158)..(158)
<223> OTHER INFORMATION: n equals a, c, g or t
<220> FEATURE:
<221> NAME/KEY: misc_feature
<222> LOCATION: (181)..(181)
<223> OTHER INFORMATION: n equals a, c, g or t
<220> FEATURE:
<221> NAME/KEY: misc_feature
<222> LOCATION: (207)..(207)
<223> OTHER INFORMATION: n equals a, c, g or t
<220> FEATURE:
<221> NAME/KEY: misc_feature
<222> LOCATION: (273)..(273)
<223> OTHER INFORMATION: n equals a, c, g or t
<220> FEATURE:
<221> NAME/KEY: misc_feature
<222> LOCATION: (282)..(282)
<223> OTHER INFORMATION: n equals a, c, g or t
<220> FEATURE:
<221> NAME/KEY: misc_feature
<222> LOCATION: (288)..(288)
<223> OTHER INFORMATION: n equals a, c, g or t
<220> FEATURE:
<221> NAME/KEY: misc_feature
<222> LOCATION: (329)..(329)
<223> OTHER INFORMATION: n equals a, c, g or t
<220> FEATURE:
<221> NAME/KEY: misc_feature
<222> LOCATION: (391)..(391)
<223> OTHER INFORMATION: n equals a, c, g or t
<220> FEATURE:
<221> NAME/KEY: misc_feature
<222> LOCATION: (399)..(399)
<223> OTHER INFORMATION: n equals a, c, g or t
<220> FEATURE:
<221> NAME/KEY: misc_feature
<222> LOCATION: (404)..(404)
<223> OTHER INFORMATION: n equals a, c, g or t
<220> FEATURE:
<221> NAME/KEY: misc_feature
<222> LOCATION: (425)..(425)
<223> OTHER INFORMATION: n equals a, c, g or t

<400> SEQUENCE: 6
ggcanaggtn cgtacctagc tcacctgcaa ccatcaaact tnatgatcaa tcaattggca      60
cacagcaatg ggaaacatag cccctttggaa ganttgtntc caccaggatc tcatagatca    120
aaacatcctg ggagcctgtt aaccggtgcc ccaaaggntg gtcaaggtca aggaattgtt    180
ncgccctgga agtgaacatc gagtgtntcc acaaaggatt caggcaatgg gacataaata    240
tatgggtgaa ttttggttgt gaactttggt tgntcccgtt gntgttgntg gctgtgctga    300
```

```
ttgtttgttg ttgcatcggc ttcaggtttnt ggaggggggac ccaagtgcat ggacagggtg    360
tgtttctggg gtttgggtct cttagagggc ntgggttang gcangttcac aagggttta     420 gcaang                                                                426
```

<210> SEQ ID NO 7
<211> LENGTH: 339
<212> TYPE: DNA
<213> ORGANISM: Homo sapiens
<220> FEATURE:
<221> NAME/KEY: misc_feature
<222> LOCATION: (23)..(23)
<223> OTHER INFORMATION: n equals a, c, g or t
<220> FEATURE:
<221> NAME/KEY: misc_feature
<222> LOCATION: (45)..(45)
<223> OTHER INFORMATION: n equals a, c, g or t
<220> FEATURE:
<221> NAME/KEY: misc_feature
<222> LOCATION: (49)..(49)
<223> OTHER INFORMATION: n equals a, c, g or t
<220> FEATURE:
<221> NAME/KEY: misc_feature
<222> LOCATION: (67)..(67)
<223> OTHER INFORMATION: n equals a, c, g or t
<220> FEATURE:
<221> NAME/KEY: misc_feature
<222> LOCATION: (70)..(70)
<223> OTHER INFORMATION: n equals a, c, g or t
<220> FEATURE:
<221> NAME/KEY: misc_feature
<222> LOCATION: (205)..(205)
<223> OTHER INFORMATION: n equals a, c, g or t
<220> FEATURE:
<221> NAME/KEY: misc_feature
<222> LOCATION: (215)..(217)
<223> OTHER INFORMATION: n equals a, c, g or t
<220> FEATURE:
<221> NAME/KEY: misc_feature
<222> LOCATION: (257)..(257)
<223> OTHER INFORMATION: n equals a, c, g or t
<220> FEATURE:
<221> NAME/KEY: misc_feature
<222> LOCATION: (268)..(268)
<223> OTHER INFORMATION: n equals a, c, g or t
<220> FEATURE:
<221> NAME/KEY: misc_feature
<222> LOCATION: (294)..(294)
<223> OTHER INFORMATION: n equals a, c, g or t
<220> FEATURE:
<221> NAME/KEY: misc_feature
<222> LOCATION: (320)..(320)
<223> OTHER INFORMATION: n equals a, c, g or t
<220> FEATURE:
<221> NAME/KEY: misc_feature
<222> LOCATION: (334)..(334)
<223> OTHER INFORMATION: n equals a, c, g or t

<400> SEQUENCE: 7

```
tggggctgag gacaatgctg acnacgagat tctgagcaac gcagnactng ctgtccactt    60
tcgtctntgn gcagcaaatg aaagccagg agccggcaga tttgacaggt gtcactgtac    120
agtccccagg ggaggcacag tgtctgctgg tgagttgggg acaggccctt gcaagacctt    180
gtgaggcagg gggtgaaggc catgnctcgg cttcnnntgg tcaaagggga agtgagcct    240 gagggagatg ggacttnagg gggacggngc tgcgtgggga aaaagcagcc accntttgac    300 aaggggaca ggcattttn caaatgtgtg cttnttggt                           339
```

<210> SEQ ID NO 8
<211> LENGTH: 28
<212> TYPE: DNA
<213> ORGANISM: Artificial sequence
<220> FEATURE:

<223> OTHER INFORMATION: Primer

<400> SEQUENCE: 8
gcggcatgca tgatcaatca attggcac                                          28

<210> SEQ ID NO 9
<211> LENGTH: 36
<212> TYPE: DNA
<213> ORGANISM: Artificial sequence
<220> FEATURE:
<223> OTHER INFORMATION: Primer

<400> SEQUENCE: 9
gcgggatccg ccatcatggc gccaccacca gctaga                                 36

<210> SEQ ID NO 10
<211> LENGTH: 33
<212> TYPE: DNA
<213> ORGANISM: Artificial sequence
<220> FEATURE:
<223> OTHER INFORMATION: Primer

<400> SEQUENCE: 10
gcgggatcct cactccaagg acacggcaga gcc                                    33

<210> SEQ ID NO 11
<211> LENGTH: 29
<212> TYPE: DNA
<213> ORGANISM: Artificial sequence
<220> FEATURE:
<223> OTHER INFORMATION: Primer

<400> SEQUENCE: 11
gcgggatcct caattatgtc cattgcctg                                         29

<210> SEQ ID NO 12
<211> LENGTH: 29
<212> TYPE: DNA
<213> ORGANISM: Artificial sequence
<220> FEATURE:
<223> OTHER INFORMATION: Primer

<400> SEQUENCE: 12
gcgggatcct caattatgtc cattgcctg                                         29

<210> SEQ ID NO 13
<211> LENGTH: 733
<212> TYPE: DNA
<213> ORGANISM: Homo sapiens

<400> SEQUENCE: 13
gggatccgga gcccaaatct tctgacaaaa ctcacacatg cccaccgtgc ccagcacctg        60
aattcgaggg tgcaccgtca gtcttcctct tccccccaaa acccaaggac accctcatga      120
tctcccggac tcctgaggtc acatgcgtgg tggtggacgt aagccacgaa gaccctgagg      180
tcaagttcaa ctggtacgtg gacggcgtgg aggtgcataa tgccaagaca aagccgcggg      240
aggagcagta caacagcacg taccgtgtgg tcagcgtcct caccgtcctg caccaggact      300
ggctgaatgg caaggagtac aagtgcaagg tctccaacaa agcccteccaa accccccatcg      360 agaaaaccat ctccaaagcc aaagggcagc ccgagaacc acaggtgtac accctgcccc       420
catcccggga tgagctgacc aagaaccagg tcagcctgac ctgcctggtc aaaggcttct      480
atccaagcga catcgccgtg gagtgggaga gcaatgggca gccggagaac aactacaaga      540

```
                                       -continued
ccacgcctcc cgtgctggac tccgacggct ccttcttcct ctacagcaag ctcaccgtgg    600
acaagagcag gtggcagcag gggaacgtct tctcatgctc cgtgatgcat gaggctctgc    660
acaaccacta cacgcagaag agcctctccc tgtctccggg taaatgagtg cgacggccgc    720
gactctagag gat                                                      733
```